US012186550B2

(12) United States Patent
Manicka

(10) Patent No.: US 12,186,550 B2
(45) Date of Patent: *Jan. 7, 2025

(54) RESILIENT BODY COMPONENT CONTACT FOR A SUBCUTANEOUS DEVICE

(71) Applicant: Manicka Institute LLC, Woodbury, MN (US)

(72) Inventor: Yatheendhar D. Manicka, Woodbury, MN (US)

(73) Assignee: Manicka Institute LLC, Woodbury, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/088,421

(22) Filed: Dec. 23, 2022

(65) Prior Publication Data

US 2023/0130587 A1 Apr. 27, 2023

Related U.S. Application Data

(60) Continuation of application No. 17/139,740, filed on Dec. 31, 2020, now Pat. No. 11,660,444, which is a
(Continued)

(51) Int. Cl.
*A61N 1/05* (2006.01)
*A61B 5/283* (2021.01)
(Continued)

(52) U.S. Cl.
CPC ............ *A61N 1/0504* (2013.01); *A61B 5/283* (2021.01); *A61B 5/349* (2021.01);
(Continued)

(58) Field of Classification Search
CPC .. A61N 1/0504; A61N 1/059; A61N 1/37518; A61N 1/3956; A61B 5/283; A61B 5/349
See application file for complete search history.

(56) References Cited

U.S. PATENT DOCUMENTS

| 3,923,060 A | 12/1975 | Ellinwood, Jr. |
| 4,030,509 A | 6/1977 | Heilman et al. |
(Continued)

FOREIGN PATENT DOCUMENTS

| CA | 2592940 A1 | 1/2008 |
| CN | 101125226 A | 2/2008 |
(Continued)

OTHER PUBLICATIONS

International Search Report and Written Opinion for PCT/US2019/028373, dated Aug. 19, 2019, 15 pages.
(Continued)

*Primary Examiner* — Paula J Stice
(74) *Attorney, Agent, or Firm* — Kinney & Lange, P.A.

(57) ABSTRACT

A subcutaneously implantable device is implantable into a body of a patient, and includes a prong and an electrode. The prong has a contact portion at or adjacent to a distal end thereof that is configured to contact an organ. The prong is constructed to apply pressure to the organ with spring action so as to maintain contact between the contact portion and the organ without fixing the contact portion to the organ. The electrode is provided at the contact portion of the prong, is configured to contact the organ, and is electrically coupled or couplable with circuitry that is configured to provide monitoring, therapeutic, and/or diagnostic capabilities with respect to the organ.

28 Claims, 106 Drawing Sheets

Related U.S. Application Data continuation of application No. 17/105,447, filed on Nov. 25, 2020, now Pat. No. 11,433,233, and a continuation-in-part of application No. 16/355,236, filed on Mar. 15, 2019, now Pat. No. 10,894,155, which is a division of application No. 16/051,451, filed on Jul. 31, 2018, now Pat. No. 10,471,251.

(51) Int. Cl.
| | |
|---|---|
| *A61B 5/349* | (2021.01) |
| *A61B 17/3211* | (2006.01) |
| *A61M 5/142* | (2006.01) |
| *A61N 1/372* | (2006.01) |
| *A61N 1/375* | (2006.01) |
| *A61N 1/39* | (2006.01) |

(52) U.S. Cl.
CPC ..... *A61B 17/3211* (2013.01); *A61M 5/14276* (2013.01); *A61N 1/059* (2013.01); *A61N 1/37211* (2013.01); *A61N 1/37252* (2013.01); *A61N 1/37518* (2017.08); *A61N 1/3956* (2013.01)

(56) References Cited

U.S. PATENT DOCUMENTS

| | | |
|---|---|---|
| 4,256,115 A | 3/1981 | Bilitch |
| 4,291,707 A | 9/1981 | Heilman et al. |
| 4,643,202 A | 2/1987 | Roche |
| 4,683,895 A | 8/1987 | Pohndorf |
| 4,817,634 A | 4/1989 | Holleman et al. |
| 4,827,932 A | 5/1989 | Ideker et al. |
| 4,971,070 A | 11/1990 | Holleman et al. |
| 4,991,578 A | 2/1991 | Cohen |
| 5,042,463 A | 8/1991 | Lekholm |
| 5,243,977 A | 9/1993 | Trabucco et al. |
| 5,247,945 A | 9/1993 | Heinze et al. |
| 5,327,909 A | 7/1994 | Kiser et al. |
| 5,496,362 A | 3/1996 | Kenknight et al. |
| 5,509,924 A | 4/1996 | Paspa et al. |
| 5,545,202 A | 8/1996 | Dahl et al. |
| 5,674,259 A | 10/1997 | Gray |
| 5,792,208 A | 8/1998 | Gray |
| 5,897,586 A | 4/1999 | Molina |
| 5,916,243 A | 6/1999 | Kenknight et al. |
| 5,954,757 A | 9/1999 | Gray |
| 6,044,300 A | 3/2000 | Gray |
| 6,152,955 A | 11/2000 | Kenknight et al. |
| 6,169,922 B1 | 1/2001 | Alferness et al. |
| 6,411,845 B1 | 6/2002 | Mower |
| 6,564,094 B2 | 5/2003 | Alferness et al. |
| 6,567,699 B2 | 5/2003 | Alferness et al. |
| 6,647,292 B1 | 11/2003 | Bardy et al. |
| 6,662,035 B2 | 12/2003 | Sochor |
| 6,689,053 B1 | 2/2004 | Shaw et al. |
| 7,054,692 B1 | 5/2006 | Whitehurst et al. |
| 7,085,606 B2 | 8/2006 | Flach et al. |
| 7,146,226 B2 | 12/2006 | Lau et al. |
| 7,155,295 B2 | 12/2006 | Lau et al. |
| 7,158,839 B2 | 1/2007 | Lau |
| 7,164,952 B2 | 1/2007 | Lau et al. |
| 7,197,362 B2 | 3/2007 | Westlund |
| 7,225,036 B2 | 5/2007 | Lau et al. |
| 7,239,918 B2 | 7/2007 | Strother et al. |
| 7,272,448 B1 | 9/2007 | Morgan et al. |
| 7,288,096 B2 | 10/2007 | Chin |
| 7,346,391 B1 | 3/2008 | Osorio et al. |
| 7,460,911 B2 | 12/2008 | Cosendai et al. |
| 7,512,441 B2 | 3/2009 | Zhang et al. |
| 7,526,342 B2 | 4/2009 | Chin et al. |
| 7,558,631 B2 | 7/2009 | Cowan et al. |
| 7,587,238 B2 | 9/2009 | Moffitt et al. |
| 7,610,092 B2 | 10/2009 | Cowan et al. |
| 7,765,012 B2 | 7/2010 | Gerber |
| 7,813,797 B2 | 10/2010 | Bardy et al. |
| 7,899,537 B1 | 3/2011 | Kroll et al. |
| 8,036,757 B2 | 10/2011 | Worley |
| 8,060,219 B2 | 11/2011 | Ross et al. |
| 8,131,362 B2 | 3/2012 | Moffitt et al. |
| 8,315,701 B2 | 11/2012 | Cowan et al. |
| 8,359,094 B2 | 1/2013 | Bonner et al. |
| 8,386,050 B2 | 2/2013 | Donoghue et al. |
| 8,433,412 B1 | 4/2013 | Westlund et al. |
| 8,469,874 B2 | 6/2013 | Forsell |
| 8,475,355 B2 | 7/2013 | Forsell |
| 8,483,841 B2 | 7/2013 | Sanghera et al. |
| 8,506,474 B2 | 8/2013 | Chin et al. |
| 8,509,894 B2 | 8/2013 | Forsell |
| 8,630,710 B2 | 1/2014 | Kumar et al. |
| 8,688,211 B2 | 4/2014 | Libbus et al. |
| 8,696,745 B2 | 4/2014 | Forsell |
| 8,731,663 B2 | 5/2014 | Bianchi et al. |
| 8,886,311 B2 | 11/2014 | Anderson et al. |
| 9,005,104 B2 | 4/2015 | Forsell |
| 9,008,776 B2 | 4/2015 | Cowan et al. |
| 9,079,035 B2 | 7/2015 | Sanghera et al. |
| 9,180,235 B2 | 11/2015 | Forsell |
| 9,216,285 B1 | 12/2015 | Boling et al. |
| 9,364,595 B2 | 6/2016 | Forsell |
| 9,393,407 B2 | 7/2016 | Bar-Cohen et al. |
| 9,398,901 B2 | 7/2016 | Tischendorf et al. |
| 9,457,137 B2 | 10/2016 | Forsell |
| 9,492,669 B2 | 11/2016 | Demmer et al. |
| 9,511,233 B2 | 12/2016 | Sambelashvili |
| 9,597,514 B2 | 3/2017 | Khairkhahan et al. |
| 9,656,009 B2 | 5/2017 | Kheradvar et al. |
| 9,717,898 B2 | 8/2017 | Thompson-Nauman et al. |
| 9,717,923 B2 | 8/2017 | Thompson-Nauman et al. |
| 9,731,055 B2 | 8/2017 | Forsell |
| 9,789,319 B2 | 10/2017 | Sambelashvili |
| 9,884,194 B2 | 2/2018 | Legay et al. |
| 9,925,318 B2 | 3/2018 | Forsell |
| 10,086,206 B2 | 10/2018 | Sambelashvili |
| 10,092,745 B2 | 10/2018 | Tockman et al. |
| 10,226,618 B2 | 3/2019 | Reddy et al. |
| 10,279,170 B2 | 5/2019 | Syed et al. |
| 10,471,251 B1 | 11/2019 | Manicka |
| 10,556,047 B2 | 2/2020 | Forsell |
| 10,596,383 B2 | 3/2020 | Ghosh |
| 10,603,487 B2 | 3/2020 | Tockman et al. |
| 10,639,483 B2 | 5/2020 | Manicka |
| 10,661,080 B2 | 5/2020 | Tholakanahalli et al. |
| 10,716,511 B2 | 7/2020 | Manicka |
| 10,765,858 B2 | 9/2020 | Marshall et al. |
| 10,980,481 B2 | 4/2021 | Manicka |
| 10,981,002 B2 | 4/2021 | Rys |
| 11,179,571 B2 | 11/2021 | Manicka |
| 11,478,650 B2 | 10/2022 | Manicka |
| 2002/0095139 A1 | 7/2002 | Keogh et al. |
| 2002/0123674 A1 | 9/2002 | Plicchi et al. |
| 2004/0015204 A1 | 1/2004 | Whitehurst et al. |
| 2004/0054391 A1 | 3/2004 | Wildon |
| 2004/0153098 A1 | 8/2004 | Chin et al. |
| 2004/0215280 A1 | 10/2004 | Dublin et al. |
| 2004/0230273 A1 | 11/2004 | Cates et al. |
| 2005/0010259 A1 | 1/2005 | Gerber |
| 2005/0080443 A1 | 4/2005 | Fallin et al. |
| 2005/0113901 A1 | 5/2005 | Coe et al. |
| 2005/0137673 A1 | 6/2005 | Lau et al. |
| 2005/0171589 A1 | 8/2005 | Lau et al. |
| 2005/0228470 A1 | 10/2005 | Osypka |
| 2005/0288563 A1 | 12/2005 | Feliss et al. |
| 2005/0288600 A1 | 12/2005 | Zhang et al. |
| 2005/0288715 A1 | 12/2005 | Lau et al. |
| 2006/0004398 A1 | 1/2006 | Binder et al. |
| 2006/0009675 A1 | 1/2006 | Meyer |
| 2006/0009831 A1 | 1/2006 | Lau et al. |
| 2006/0041276 A1 | 2/2006 | Chan |
| 2006/0116743 A1* | 6/2006 | Gibson ............ A61N 1/36036 607/57 |
| 2006/0116746 A1 | 6/2006 | Chin |
| 2006/0155180 A1 | 7/2006 | Brister et al. |
| 2006/0247748 A1 | 11/2006 | Wahlstrand et al. |

(56) References Cited

U.S. PATENT DOCUMENTS

| | | |
|---|---|---|
| 2006/0287682 A1 | 12/2006 | Cohen et al. |
| 2006/0293740 A1 | 12/2006 | Heil et al. |
| 2007/0004979 A1 | 1/2007 | Wojciechowicz et al. |
| 2007/0043394 A1 | 2/2007 | Zhang et al. |
| 2007/0043416 A1 | 2/2007 | Callas et al. |
| 2007/0055091 A1 | 3/2007 | Lau et al. |
| 2007/0055310 A1 | 3/2007 | Lau |
| 2007/0106359 A1 | 5/2007 | Schaer et al. |
| 2007/0112390 A1 | 5/2007 | Lau et al. |
| 2007/0123923 A1 | 5/2007 | Lindstrom et al. |
| 2007/0173915 A1 | 7/2007 | Westlund |
| 2007/0197859 A1 | 8/2007 | Schaer et al. |
| 2007/0255295 A1 | 11/2007 | Starkebaum et al. |
| 2007/0265669 A1 | 11/2007 | Roline et al. |
| 2008/0132915 A1 | 6/2008 | Buckman et al. |
| 2008/0132981 A1 | 6/2008 | Gerber |
| 2008/0132982 A1 | 6/2008 | Gerber |
| 2008/0243217 A1 | 10/2008 | Wildon |
| 2008/0243220 A1 | 10/2008 | Barker |
| 2008/0298608 A1 | 12/2008 | Wilcox |
| 2008/0312712 A1 | 12/2008 | Penner |
| 2008/0319503 A1 | 12/2008 | Honeck et al. |
| 2009/0030469 A1 | 1/2009 | Meiry |
| 2009/0082828 A1 | 3/2009 | Ostroff |
| 2009/0209986 A1 | 8/2009 | Stewart et al. |
| 2009/0275998 A1 | 11/2009 | Burnes et al. |
| 2009/0275999 A1 | 11/2009 | Burnes et al. |
| 2009/0287266 A1 | 11/2009 | Zdeblick |
| 2009/0299447 A1 | 12/2009 | Jensen et al. |
| 2010/0019985 A1 | 1/2010 | Bashyam et al. |
| 2010/0022873 A1 | 1/2010 | Hunter et al. |
| 2010/0042108 A1 | 2/2010 | Hibino |
| 2010/0100079 A1 | 4/2010 | Berkcan et al. |
| 2010/0114287 A1 | 5/2010 | Privitera et al. |
| 2010/0152798 A1 | 6/2010 | Sanghera et al. |
| 2010/0198288 A1* | 8/2010 | Ostroff ............... A61N 1/3756 607/9 |
| 2010/0241181 A1 | 9/2010 | Savage et al. |
| 2010/0268041 A1 | 10/2010 | Kraemer et al. |
| 2010/0274313 A1* | 10/2010 | Boling ............... A61N 1/37217 607/116 |
| 2011/0034219 A1 | 2/2011 | Filson et al. |
| 2011/0190692 A1 | 8/2011 | Manda |
| 2011/0196193 A1 | 8/2011 | Forsell |
| 2011/0196483 A1 | 8/2011 | Forsell |
| 2011/0196484 A1 | 8/2011 | Forsell |
| 2011/0257504 A1* | 10/2011 | Hendricks ............... A61N 1/05 607/45 |
| 2012/0029335 A1 | 2/2012 | Sudam et al. |
| 2012/0172892 A1 | 7/2012 | Grubac et al. |
| 2012/0330123 A1 | 12/2012 | Doerr |
| 2013/0073003 A1 | 3/2013 | Pless et al. |
| 2013/0085513 A1 | 4/2013 | North |
| 2013/0116529 A1* | 5/2013 | Min ....................... A61B 5/283 600/375 |
| 2013/0138173 A1 | 5/2013 | Bianchi et al. |
| 2013/0218195 A1 | 8/2013 | Kleshinski et al. |
| 2013/0238067 A1* | 9/2013 | Baudino ............... A61N 1/0504 607/116 |
| 2013/0310706 A1 | 11/2013 | Stone et al. |
| 2014/0074093 A9 | 3/2014 | Nelson et al. |
| 2014/0081154 A1 | 3/2014 | Toth |
| 2014/0081158 A1 | 3/2014 | Bodecker et al. |
| 2014/0088611 A1 | 3/2014 | Richardson |
| 2014/0114371 A1 | 4/2014 | Westlund et al. |
| 2014/0128935 A1 | 5/2014 | Kumar et al. |
| 2014/0163579 A1 | 6/2014 | Tischendorf et al. |
| 2014/0309683 A1 | 10/2014 | Bagwell et al. |
| 2014/0309699 A1 | 10/2014 | Houff |
| 2014/0330248 A1 | 11/2014 | Thompson-Nauman et al. |
| 2014/0330287 A1 | 11/2014 | Thompson-Nauman et al. |
| 2014/0330325 A1 | 11/2014 | Thompson-Nauman et al. |
| 2014/0330326 A1 | 11/2014 | Thompson-Nauman et al. |
| 2014/0330327 A1 | 11/2014 | Thompson-Nauman et al. |
| 2014/0330329 A1 | 11/2014 | Thompson-Nauman et al. |
| 2014/0330331 A1 | 11/2014 | Thompson-Nauman et al. |
| 2015/0025591 A1 | 1/2015 | Sunagawa et al. |
| 2015/0057563 A1 | 2/2015 | Kowalski et al. |
| 2015/0126833 A1 | 5/2015 | Anderson et al. |
| 2015/0142070 A1 | 5/2015 | Sambelashvili |
| 2015/0151026 A1 | 6/2015 | Gibson |
| 2015/0257755 A1 | 9/2015 | North |
| 2015/0305639 A1 | 10/2015 | Greenhut et al. |
| 2015/0306377 A1 | 10/2015 | Brantigan |
| 2015/0321016 A1 | 11/2015 | O'Brien et al. |
| 2015/0342627 A1 | 12/2015 | Thompson-Nauman et al. |
| 2015/0343176 A1 | 12/2015 | Asleson et al. |
| 2015/0343197 A1 | 12/2015 | Gardeski et al. |
| 2015/0359513 A1 | 12/2015 | Caluser |
| 2015/0366556 A1* | 12/2015 | Khairkhahan ..... A61B 17/0487 606/232 |
| 2016/0067478 A1 | 3/2016 | McGeehan et al. |
| 2016/0067479 A1 | 3/2016 | Marcovecchio et al. |
| 2016/0067480 A1 | 3/2016 | Sanghera et al. |
| 2016/0067488 A1 | 3/2016 | Sanghera et al. |
| 2016/0121106 A1 | 5/2016 | Marshall et al. |
| 2016/0129169 A1 | 5/2016 | Forsell |
| 2016/0129263 A1 | 5/2016 | Demmer et al. |
| 2016/0144192 A1 | 5/2016 | Sanghera et al. |
| 2016/0158567 A1 | 6/2016 | Marshall et al. |
| 2016/0175580 A1 | 6/2016 | Marshall et al. |
| 2016/0228713 A1 | 8/2016 | Bar-Cohen et al. |
| 2017/0020551 A1 | 1/2017 | Reddy et al. |
| 2017/0021159 A1 | 1/2017 | Reddy et al. |
| 2017/0043173 A1 | 2/2017 | Sharma et al. |
| 2017/0164939 A1 | 6/2017 | Ryshkus et al. |
| 2017/0224995 A1 | 8/2017 | Sanghera et al. |
| 2017/0304019 A1 | 10/2017 | Sanghera et al. |
| 2017/0304634 A1* | 10/2017 | Sanghera ............. A61N 1/0504 |
| 2017/0319863 A1 | 11/2017 | Thompson-Nauman et al. |
| 2018/0021572 A1 | 1/2018 | McGeehan et al. |
| 2018/0036547 A1 | 2/2018 | Reddy |
| 2018/0050199 A1 | 2/2018 | Sanghera et al. |
| 2018/0085593 A1 | 3/2018 | Fayram et al. |
| 2018/0117307 A1 | 5/2018 | Whitman et al. |
| 2018/0133494 A1 | 5/2018 | Reddy |
| 2018/0193060 A1 | 7/2018 | Reddy et al. |
| 2018/0235353 A1 | 8/2018 | Chen et al. |
| 2018/0243570 A1 | 8/2018 | Malinowski et al. |
| 2018/0272122 A1 | 9/2018 | Rys |
| 2018/0361145 A1 | 12/2018 | Mahapatra et al. |
| 2019/0105489 A1 | 4/2019 | Thompson-Nauman et al. |
| 2019/0117959 A1 | 4/2019 | Reddy |
| 2019/0224477 A1 | 7/2019 | Syed et al. |
| 2019/0254771 A1 | 8/2019 | Swift et al. |
| 2019/0321624 A1 | 10/2019 | De Kock et al. |
| 2019/0374695 A1 | 12/2019 | Kheradvar |
| 2020/0023177 A1 | 1/2020 | Sanghera et al. |
| 2020/0038649 A1 | 2/2020 | Manicka |
| 2020/0078584 A1 | 3/2020 | Manicka |
| 2020/0129755 A1 | 4/2020 | Thompson-Nauman et al. |
| 2020/0139108 A1 | 5/2020 | Strommer et al. |
| 2020/0147365 A1 | 5/2020 | Marshall et al. |
| 2020/0147403 A1 | 5/2020 | Manicka |
| 2020/0197205 A1 | 6/2020 | Gage et al. |
| 2020/0215320 A1 | 7/2020 | Tockman et al. |
| 2020/0261735 A1 | 8/2020 | Manicka |
| 2021/0038276 A1 | 2/2021 | Schwagli et al. |
| 2021/0069491 A1 | 3/2021 | Grubac et al. |
| 2021/0121684 A1 | 4/2021 | Manicka |
| 2021/0146122 A1 | 5/2021 | Manicka |

FOREIGN PATENT DOCUMENTS

| | | |
|---|---|---|
| CN | 101610722 A | 12/2009 |
| CN | 102209492 A | 10/2011 |
| CN | 104470580 A | 3/2015 |
| CN | 104797291 A | 7/2015 |
| CN | 105078522 A | 11/2015 |
| CN | 105102060 A | 11/2015 |
| CN | 105377364 A | 3/2016 |
| CN | 106362288 A | 2/2017 |
| CN | 107233665 A | 10/2017 |

(56) References Cited

FOREIGN PATENT DOCUMENTS

| | | | |
|---|---|---|---|
| CN | 107847751 A | 3/2018 | |
| CN | 207654280 U | 7/2018 | |
| EP | 458265 A2 | 11/1991 | |
| EP | 280564 B1 | 6/1993 | |
| EP | 602356 A2 | 6/1994 | |
| EP | 627237 A1 | 12/1994 | |
| EP | 460324 B1 | 3/1996 | |
| EP | 2281600 A1 | 2/2011 | |
| EP | 2119471 B1 | 8/2011 | |
| EP | 2069012 B1 | 5/2017 | |
| EP | 2349381 B1 | 12/2019 | |
| EP | 2349382 B1 | 12/2019 | |
| EP | 2349385 B1 | 12/2019 | |
| JP | 2010502274 A | 1/2010 | |
| JP | 2012509155 A | 4/2012 | |
| JP | 2014054549 A | 3/2014 | |
| JP | 2016517772 A | 6/2016 | |
| WO | 8202664 A1 | 8/1982 | |
| WO | 9220402 A1 | 11/1992 | |
| WO | 9408657 A1 | 4/1994 | |
| WO | 0028918 A1 | 5/2000 | |
| WO | 0191850 A1 | 12/2001 | |
| WO | 02054937 A2 | 7/2002 | |
| WO | 02087688 A1 | 11/2002 | |
| WO | 2004028348 A2 | 4/2004 | |
| WO | 2004073506 A2 | 9/2004 | |
| WO | 2005046789 A1 | 5/2005 | |
| WO | 2005092431 A1 | 10/2005 | |
| WO | 2006083617 A2 | 8/2006 | |
| WO | 2006107590 A2 | 10/2006 | |
| WO | 2007005641 A2 | 1/2007 | |
| WO | 2007103262 A2 | 9/2007 | |
| WO | 2007133947 A2 | 11/2007 | |
| WO | 2008051926 A1 | 5/2008 | |
| WO | 2010014472 A1 | 2/2010 | |
| WO | 2010042014 A1 | 4/2010 | |
| WO | 2010042016 A1 | 4/2010 | |
| WO | 2010042017 A1 | 4/2010 | |
| WO | 2010042018 A1 | 4/2010 | |
| WO | 2010132254 A1 | 11/2010 | |
| WO | 2013152259 A1 | 10/2013 | |
| WO | 2018009913 A1 | 1/2018 | |
| WO | 2018104476 A1 | 6/2018 | |
| WO | 2019084182 A1 | 5/2019 | |
| WO | 2020027888 A1 | 2/2020 | |
| WO | 2020102331 A1 | 5/2020 | |

OTHER PUBLICATIONS

Invitation to Pay Additional Fees and, Where Applicable, Protest Fee for PCT Application No. PCT/US2019/028373, dated Jun. 6, 2019, 2 pages.
International Search Report and Written Opinion for PCT Application No. PCT/US2020/059732 mailed Feb. 4, 2021, 10 pages.
International Search Report and Written Opinion for PCT Application No. PCT/US2020/059733, dated Feb. 5, 2021, 7 pages.
International Search Report and Written Opinion for PCT Application No. PCT/US2021/029151, dated Aug. 17, 2021, 8 pages.
International Search Report and Written Opinion for PCT Application No. PCT/US21/60627, dated Feb. 7, 2022, 12 pages.
International Search Report and Written Opinion for PCT Application No. PCT/US21/60621, dated Feb. 8, 2022, 12 pages.
International Search Report and Written Opinion for PCT Application No. PCT/US21/60625, dated Feb. 18, 2022, 20 pages.
International Search Report and Written Opinion for PCT Application No. PCT/US21/60623, dated Feb. 22, 2022, 7 pages.
International Search Report and Written Opinion for PCT Application No. PCT/US2022/011029, dated Mar. 24, 2022, 11 pages.
Extended European Search Report for European Patent Application No. 19843134.8, dated Apr. 25, 2022, 6 pages.
International Search Report and Written Opinion for PCT Application No. PCT/US2022/026160, dated Jul. 8, 2022, 12 pages.
First Review of the Opinion Circular for Chinese Application No. 2019800003911.0, dated Feb. 16, 2023, 26 pages.
First Review of the Opinion Circular for Chinese Application No. 202011196767.8, dated Mar. 11, 2023, 17 pages.
First Review of the Opinion Circular for Chinese Application No. 202011192123.1, dated Mar. 9, 2023, 17 pages.
First Review of the Opinion Circular for Chinese Application No. 202011192209.4, dated Mar. 10, 2023, 24 pages.
Notice of Reasons for Refusal for Japanese Patent Application No. 2021529225, dated Mar. 15, 2023, 17 pages.
Second Chinese Office Action for Chinese Application No. 202011192209.4, dated Aug. 25, 2023, 18 pages.
Second Chinese Office Action for Chinese Application No. 201980003911.0, dated Oct. 23, 2023, 17 pages.
Indian First Examination Report for Indian Patent Application No. 202117003908, dated Mar. 3, 2023, 7 pages.
Extended European Search Report for European Patent Application No. 20887687.0, dated Nov. 15, 2023, 6 pages.
Extended European Search Report for European Patent Application No. 20887104.6, dated Nov. 15, 2023, 5 pages.
Chinese Office Action for Chinese Application No. 202011192192.2, dated Feb. 2, 2024, 24 pages.
Notice of Decision of Refusal for Japanese Patent Application No. 2021-529225, dated Jan. 10, 2024, 11 pages.
Notification of Registration Procedures for Chinese Application No. 202011192209.4, dated Jan. 24, 2024, 11 pages.
Notification of Registration Procedures for Chinese Application No. 201980003911.0, dated Jan. 18, 2024, 9 pages.
First Chinese Office Action for Chinese Application No. 202011196782.2, dated Feb. 22, 2024, 21 pages.
First Chinese Office Action for Chinese Patent Application No. 202011192203.7, dated Feb. 22, 2024, 17 pages.
First Chinese Office Action for Chinese Patent Application No. 202080084846.1, dated May 10, 2024, 37 pages.
Australian Examination Report for Australian Patent Application No. 2019315780, dated May 21, 2024, 4 pages.
Japanese Office Action for Japanese Patent Application No. 2022-526731, dated Jul. 24, 2024, 18 pages.
Japanese Office Action for Japanese Patent Application No. 2022-526733, dated Jul. 24, 2024, 30 pages.
Extended European Search Report for European Patent Application No. 21867287.1, dated Aug. 6, 2024, 8 pages.
Extended European Search Report for European Patent Application No. 21899050.5, dated Sep. 13, 2024, 7 pages.

* cited by examiner

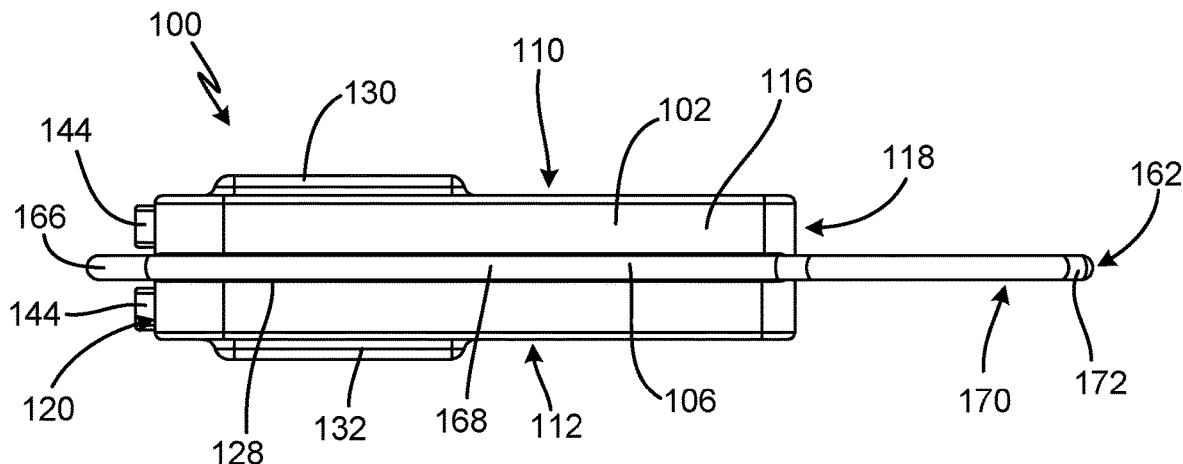
Fig. 6C
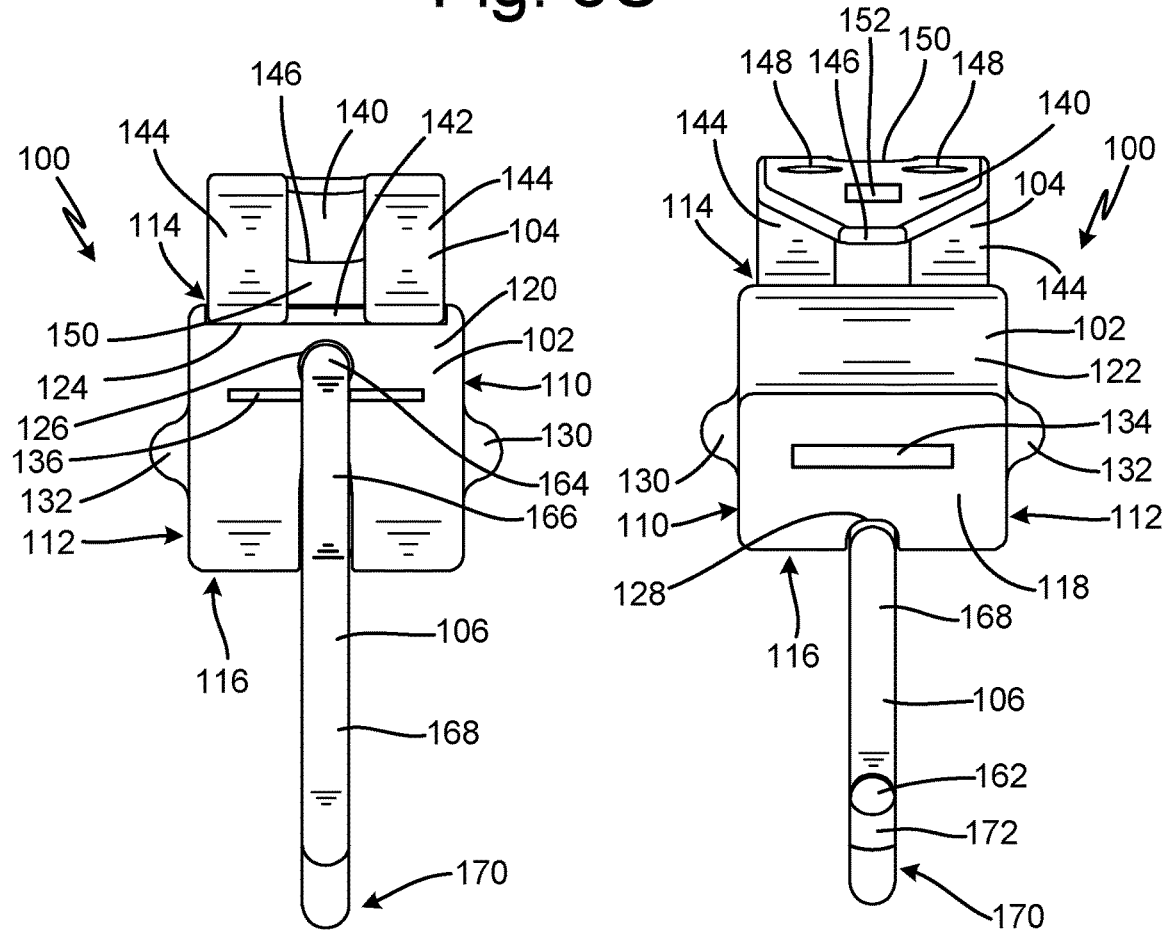
Fig. 6D
Fig. 6E

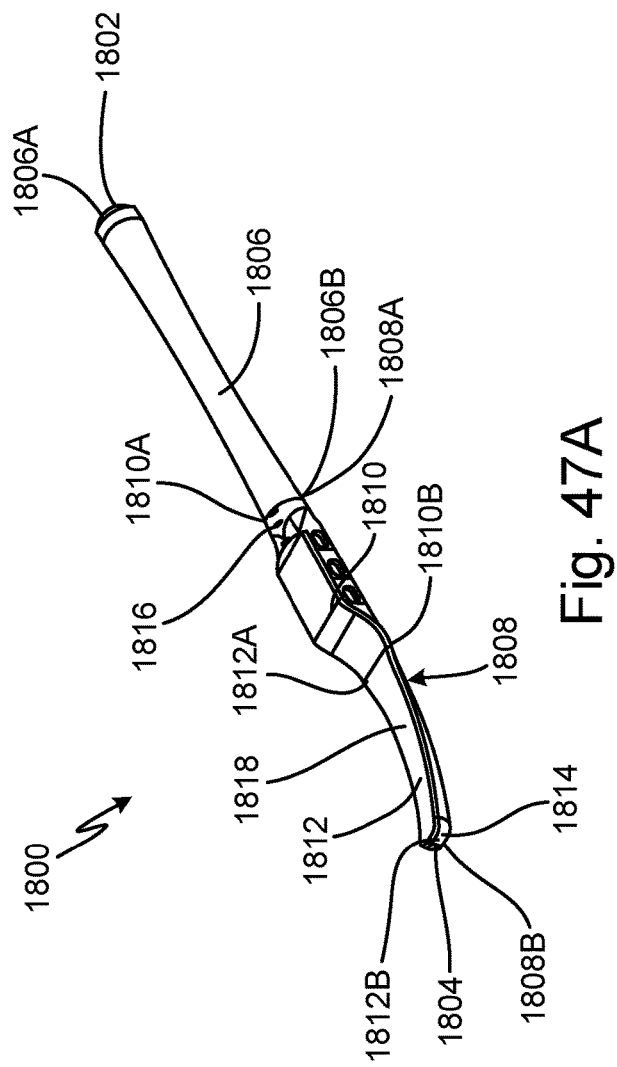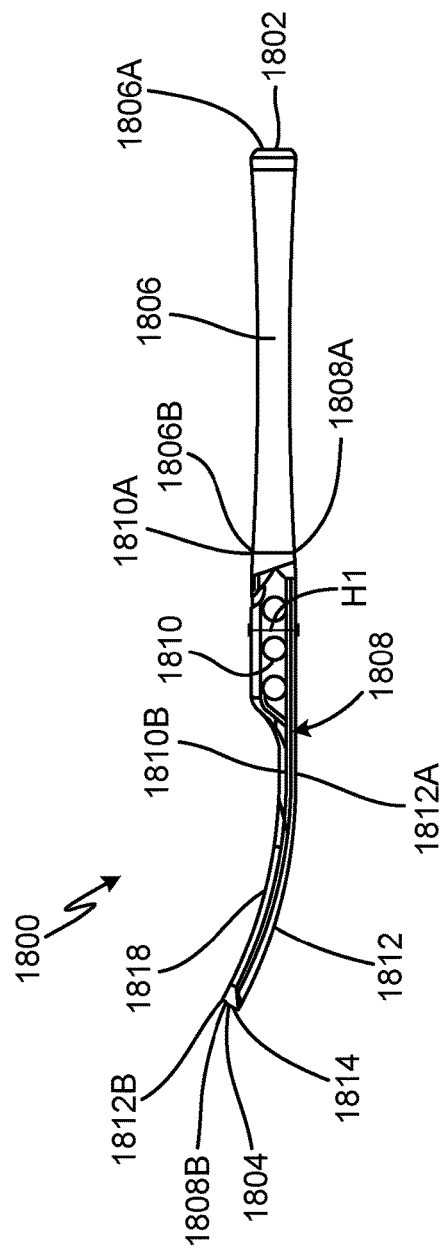
Fig. 47A
Fig. 47B

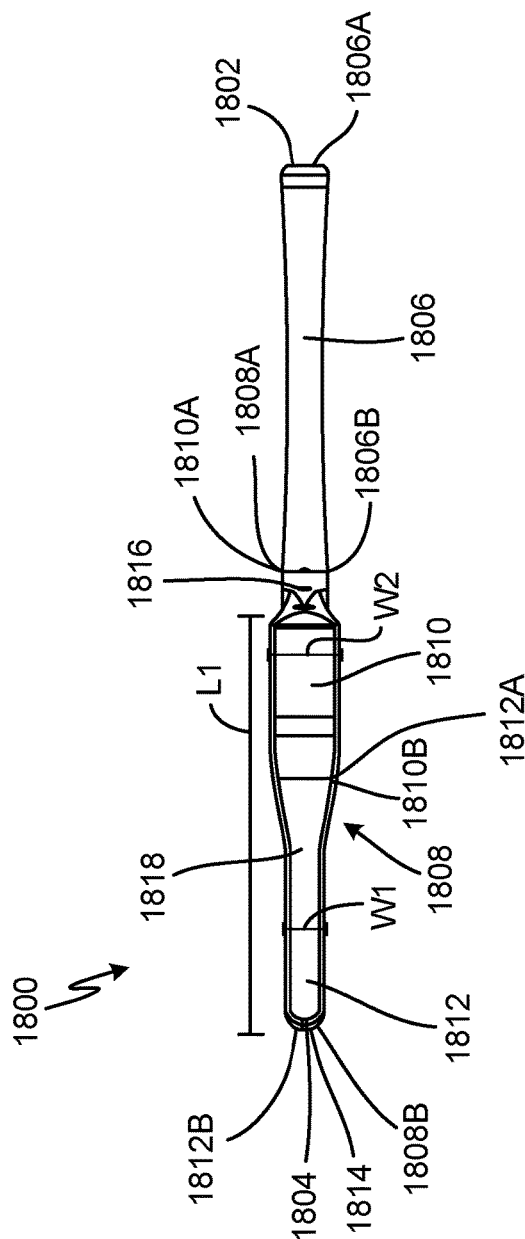
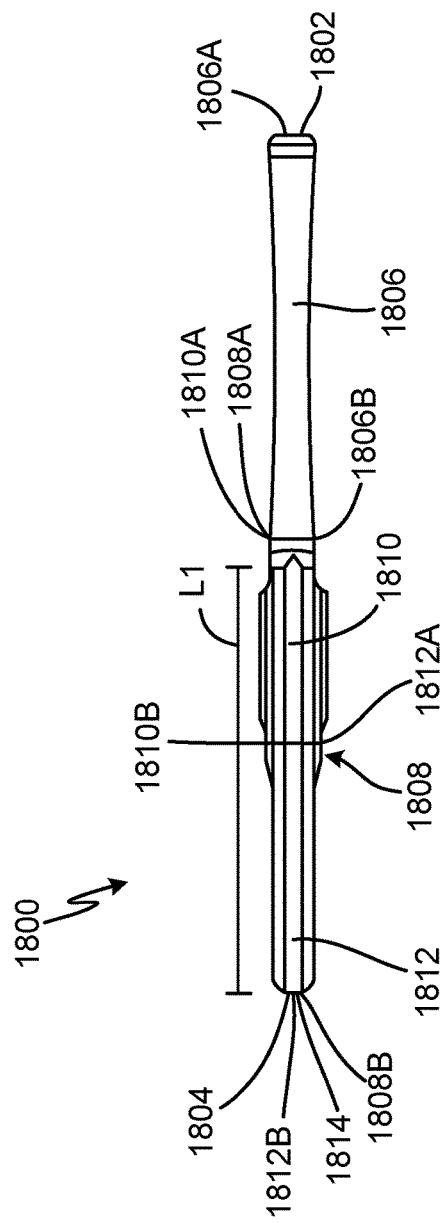
Fig. 47C
Fig. 47D

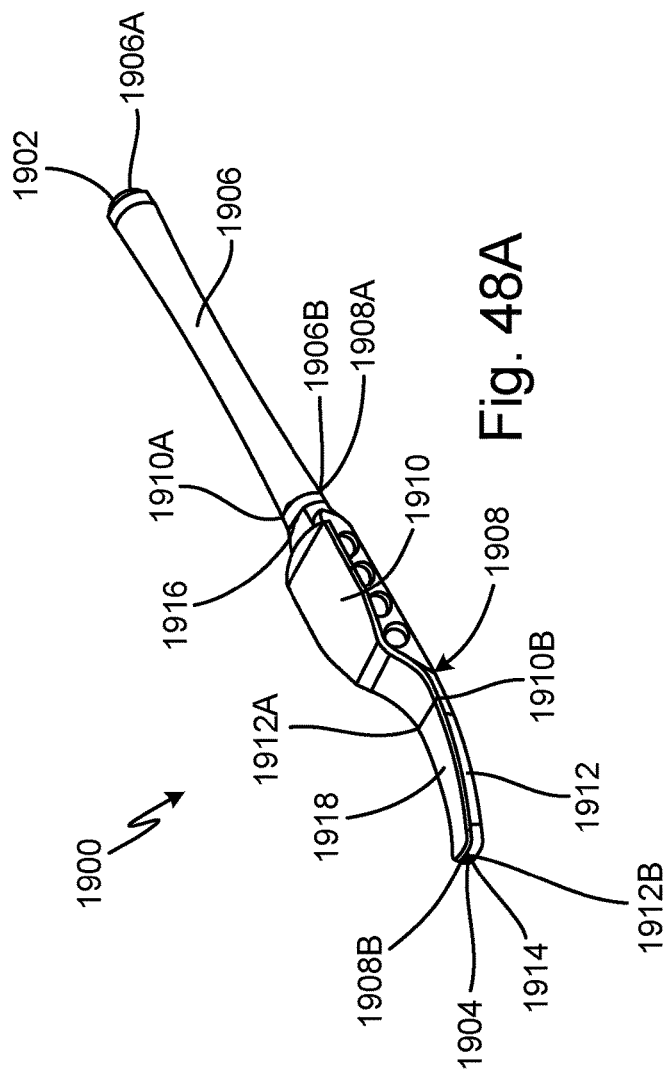
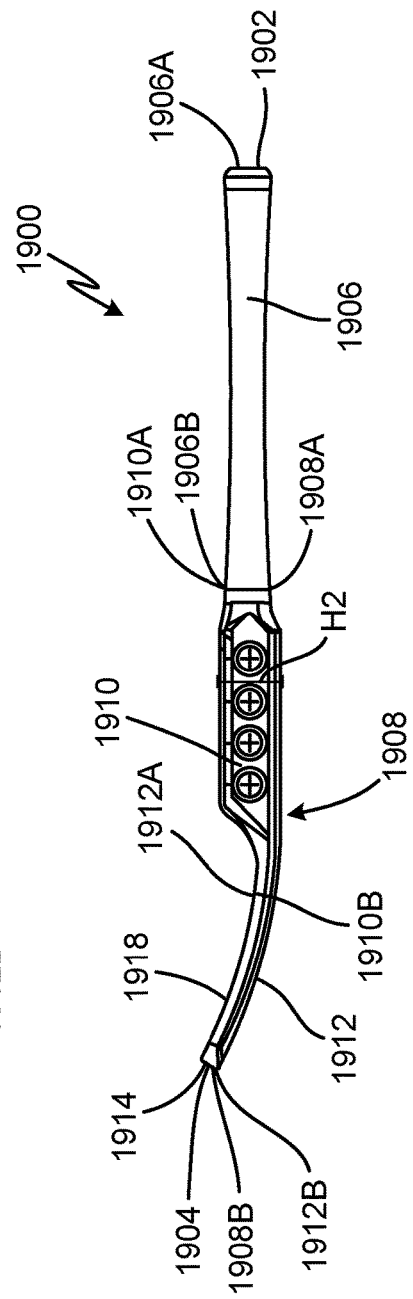
Fig. 48A
Fig. 48B

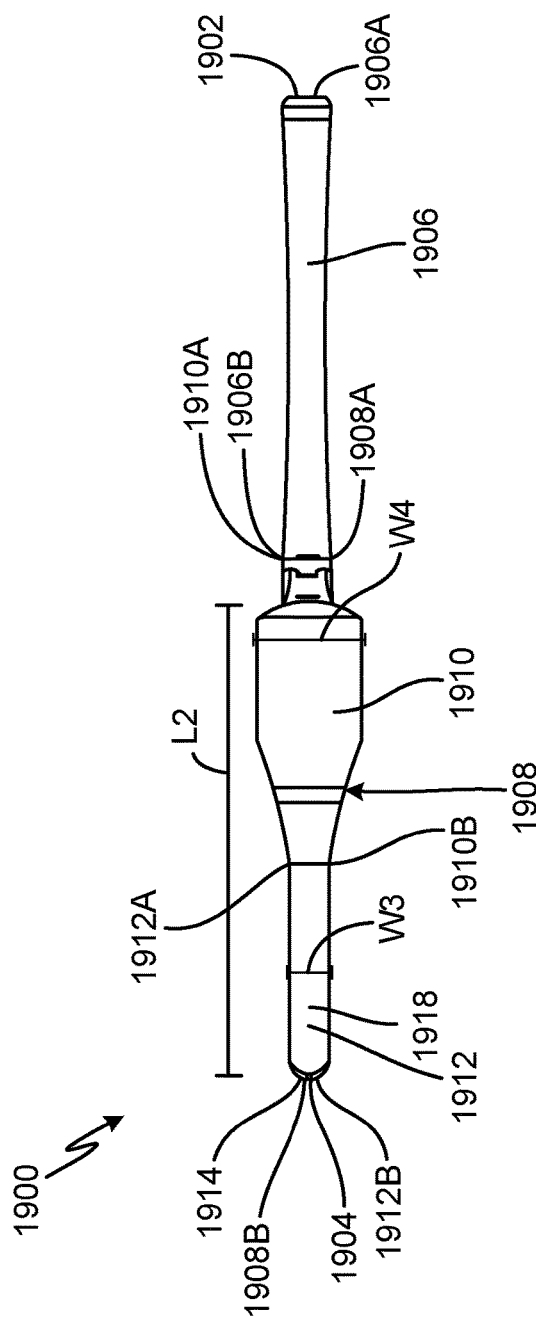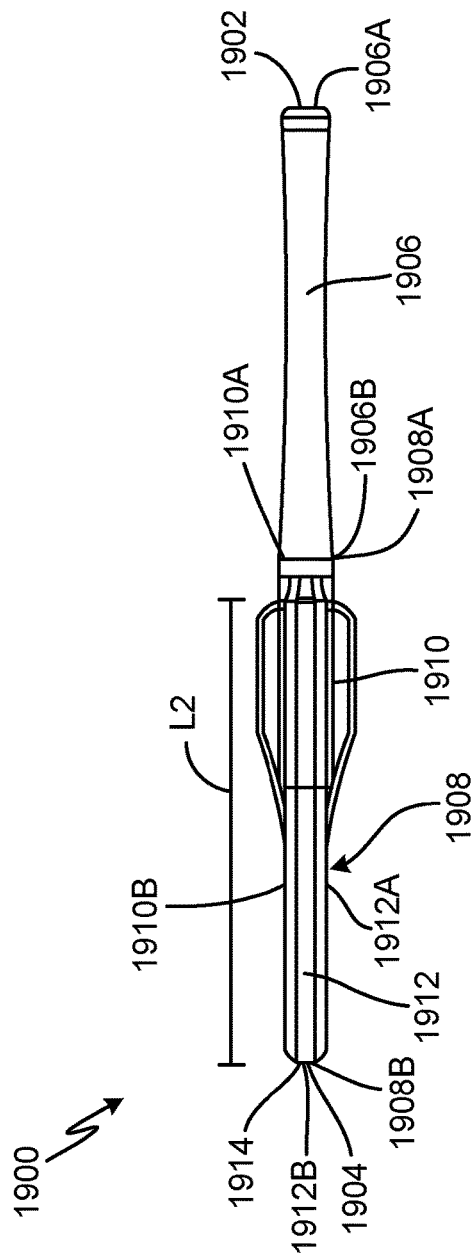
Fig. 48C
Fig. 48D

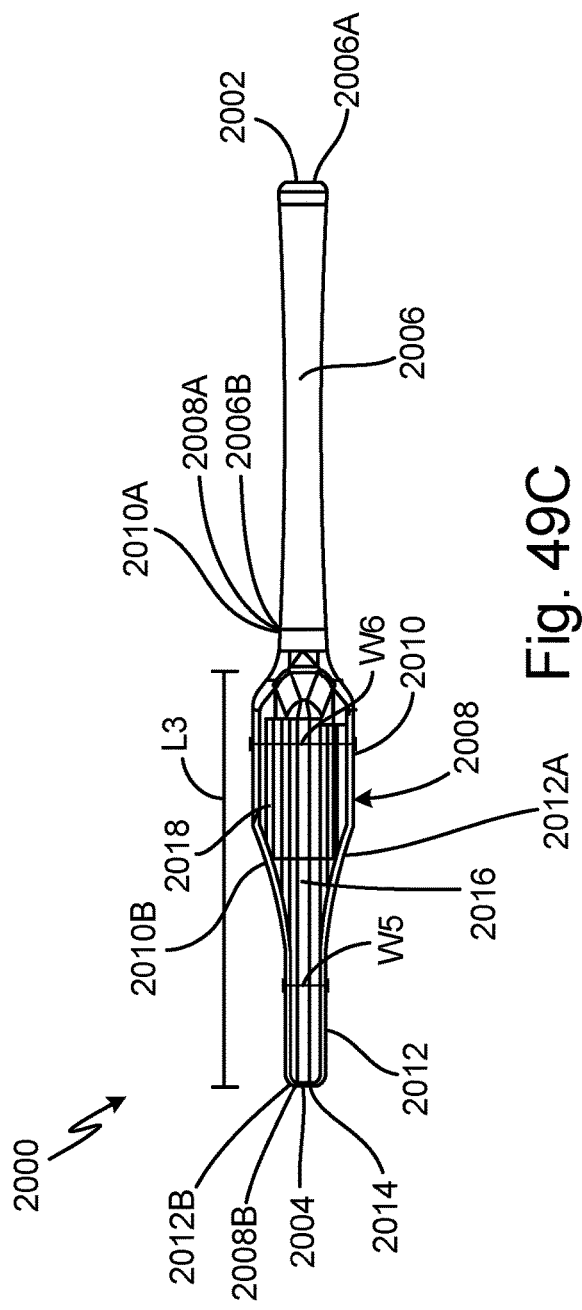
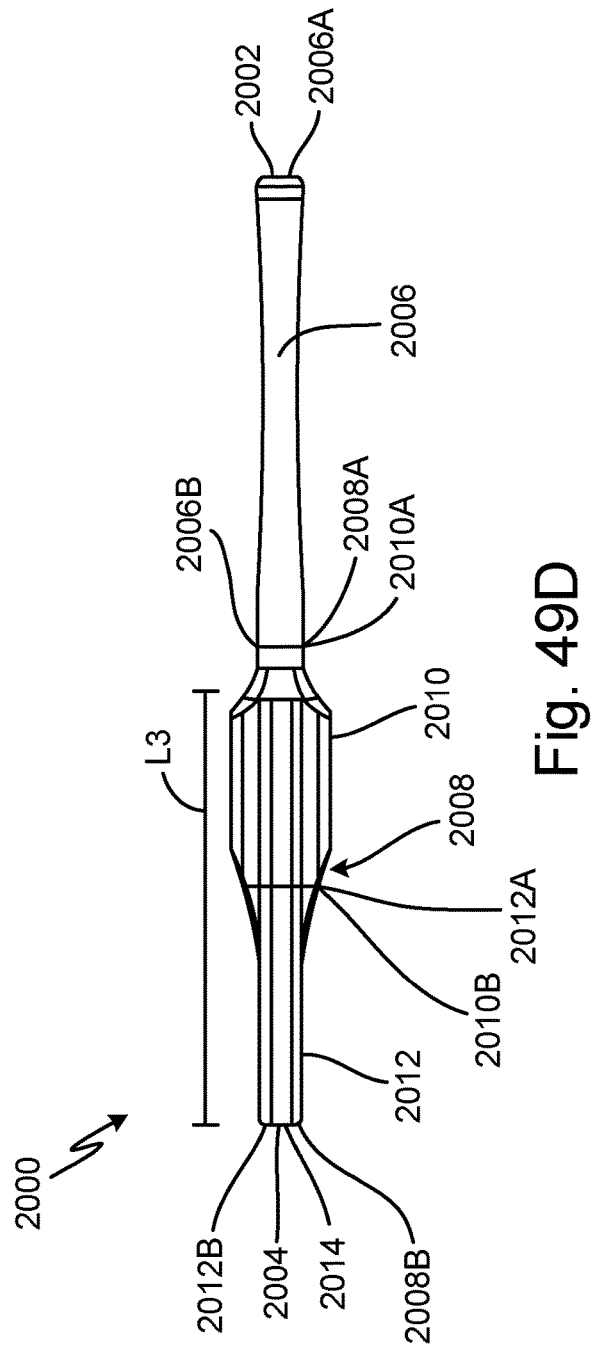
Fig. 49C
Fig. 49D

RESILIENT BODY COMPONENT CONTACT FOR A SUBCUTANEOUS DEVICE

CROSS-REFERENCE TO RELATED APPLICATION(S)

This application is a continuation of U.S. application Ser. No. 17/139,740 filed on Dec. 31, 2020 (incorporated by reference herein in its entirety), now U.S. Pat. No. 11,660,444 which in turn is:

(1) a continuation of U.S. application Ser. No. 17/105,447, filed on Nov. 25, 2020, now U.S. Pat. No. 11,433,233 entitled ELECTRODE CONTACT FOR A SUBCUTANEOUS DEVICE (incorporated by reference herein in its entirety);

(2) a continuation-in-part of U.S. application Ser. No. 16/355,236, filed on Mar. 15, 2019, now U.S. Pat. No. 10,894,155 entitled SUBCUTANEOUS DEVICE FOR MONITORING AND/OR PROVIDING THERAPIES, which in turn is a divisional of U.S. application Ser. No. 16/051,451, filed on Jul. 31, 2018, now U.S. Pat. No. 10,471,251 entitled SUBCUTANEOUS DEVICE FOR MONITORING AND/OR PROVIDING THERAPIES (both incorporated by reference herein in their entireties); and (3) related to U.S. application Ser. No. 17/105,457, entitled SURGICAL INSTRUMENT FOR A SUBCUTANEOUS DEVICE, filed on Nov. 25, 2020, to U.S. application Ser. No. 17/105,461, entitled SURGICAL INSTRUMENT FOR A SUBCUTANEOUS DEVICE, filed on Nov. 25, 2020, and to U.S. application Ser. No. 17/020,356, filed on Sep. 14, 2020, now U.S. Pat. No. 10,987,060 entitled CLIP DESIGN FOR A SUBCUTANEOUS DEVICE (all incorporated by reference herein in their entireties).

BACKGROUND

The present invention relates to implantable medical devices, and in particular, to a subcutaneous device.

Implantable medical devices include medical devices that are implanted in the body. Examples of implantable medical devices can include cardiac monitors, pacemakers, and implantable cardioverter-defibrillators, amongst many others. These implantable medical devices can receive signals from the body and use those signals for diagnostic purposes. These implantable medical devices can also transmit electrical stimulation or deliver drugs to the body for therapeutic purposes. For instance, a pacemaker can sense a heart rate of a patient, determine whether the heart is beating too fast or too slow, and transmit electrical stimulation to the heart to speed up or slow down different chambers of the heart. An implantable cardioverter-defibrillator can sense a heart rate of a patient, detect a dysrhythmia, and transmit an electrical shock to the patient.

Traditionally, cardiac monitors, pacemakers, and implantable cardioverter-defibrillators include a housing containing electrical circuitry. A proximal end of a lead is connected to the housing and a distal end of the lead is positioned in or on the heart. The distal end of the lead contains electrodes that can receive and transmit signals. Implantable medical devices such as cardiac monitors, pacemakers, and implantable cardioverter-defibrillators typically require invasive surgeries to implant the medical device in the body.

SUMMARY

A subcutaneously implantable device includes a housing that is implantable into a body of a patient, a prong, and an electrode. The prong is attached to the housing at a proximal end of the prong, and has a contact portion at or adjacent to a distal end of the prong that is configured to contact an organ, a nerve, a first tissue and/or a second tissue of the patient. The prong is constructed to apply pressure to the organ, the nerve, the first tissue and/or the second tissue so as to maintain contact between the contact portion and the organ, the nerve, the first tissue and/or the second tissue without fixing the contact portion to the organ, the nerve, the first tissue and/or the second tissue. The electrode is provided at the contact portion of the prong, is configured to contact the organ, the nerve, the first tissue and/or the second tissue, and is electrically coupled or couplable with circuitry that is configured to provide monitoring, therapeutic, and/or diagnostic capabilities with respect to the organ, the nerve, the first tissue and/or the second tissue.

A subcutaneously implantable device includes a clip that is configured to be anchored to a muscle, a bone, and/or a first tissue of a patient, a prong, and an electrode. The prong has a proximal end secured adjacent to the clip, and has a contact portion at or adjacent to a distal end of the prong that is configured to contact an organ, a nerve, the first tissue, and/or a second tissue. The prong is constructed to apply pressure to the organ, the nerve, the first tissue and/or the second tissue so as to maintain contact between the contact portion and the organ, the nerve, the first tissue and/or the second tissue without fixing the contact portion to the organ, the nerve, the first tissue and/or the second tissue. The electrode is provided at the contact portion of the prong, is configured to contact the organ, the nerve, the first tissue, and/or the second tissue, and is configured for electrical communication with circuitry for providing monitoring, therapeutic, and/or diagnostic capabilities with respect to the organ, the nerve, the first tissue, and/or the second tissue.

BRIEF DESCRIPTION OF THE DRAWINGS

Subcutaneous Device 100

FIG. 6C is a bottom view of the first embodiment of the subcutaneous device.

FIG. 6D is a back view of the first embodiment of the subcutaneous device.

FIG. 6E is a front view of the first embodiment of the subcutaneous device.

Surgical Instrument 200

Figure 10A:
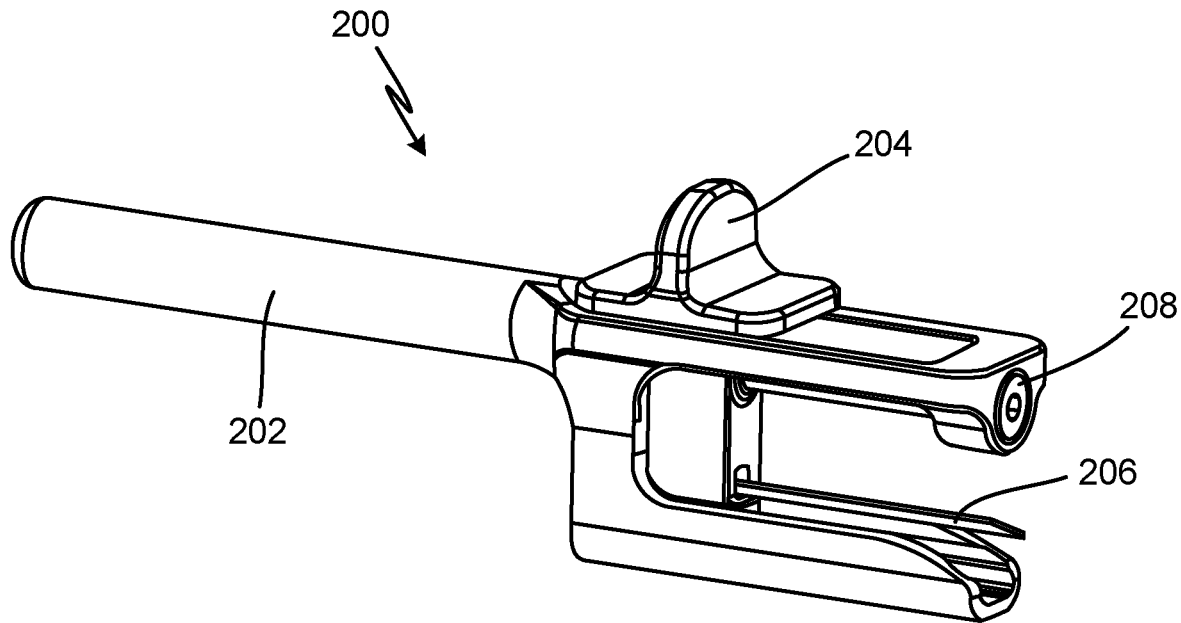

FIG. 10A is a perspective view of a surgical instrument in a first position.

Figure 10B:
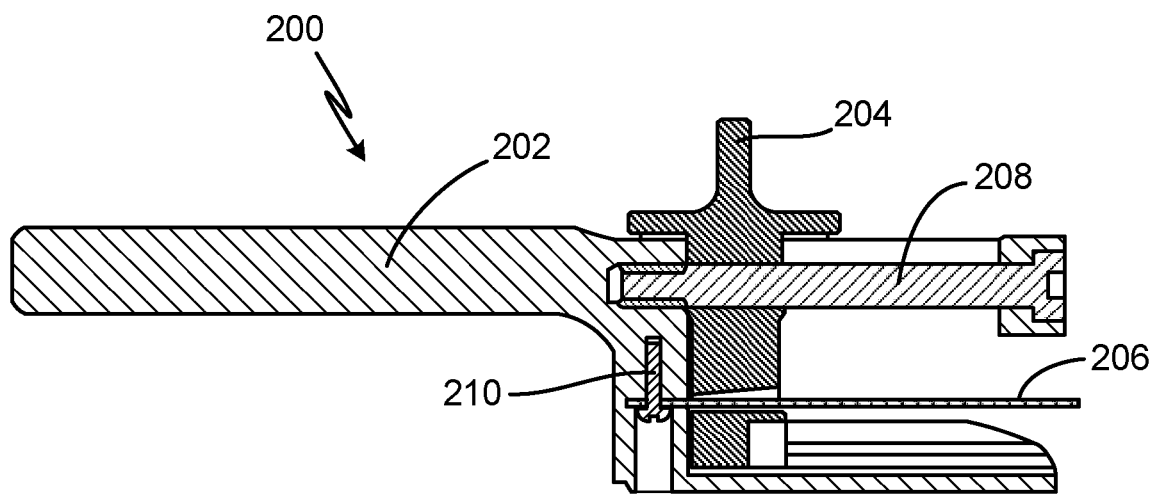

FIG. 10B is a cross-sectional view of the surgical instrument in the first position.

Figure 11A:
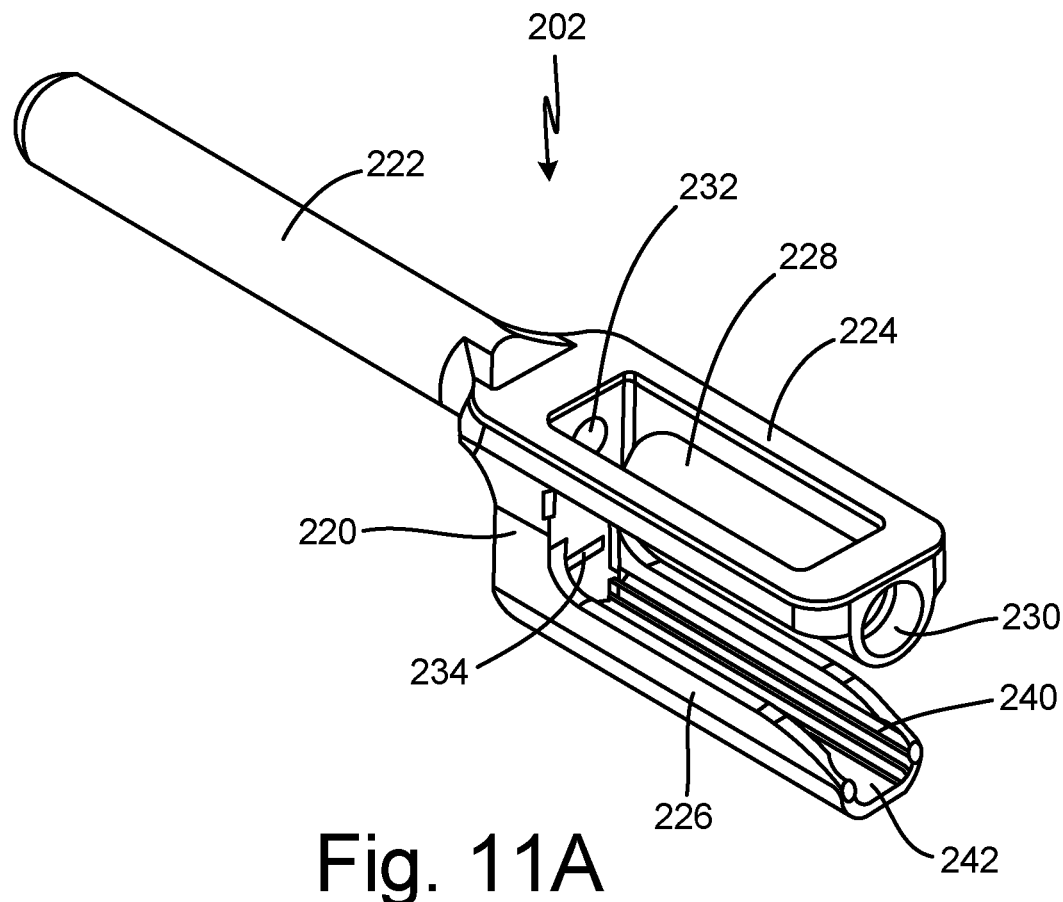

FIG. 11A is a perspective view of a body of the surgical instrument.

Figure 11B:
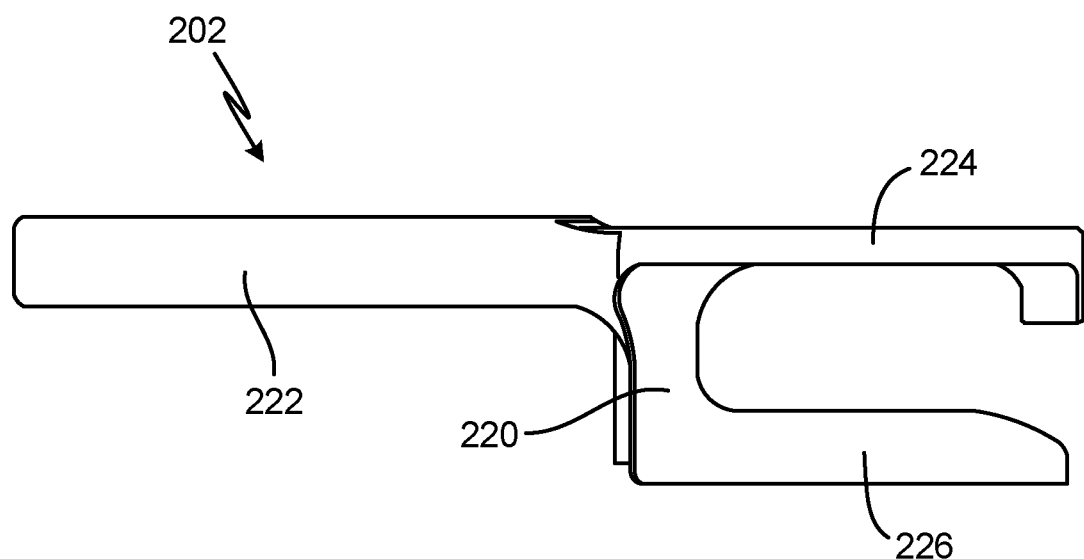

FIG. 11B is a side view of the body of the surgical instrument.

Figure 11C:
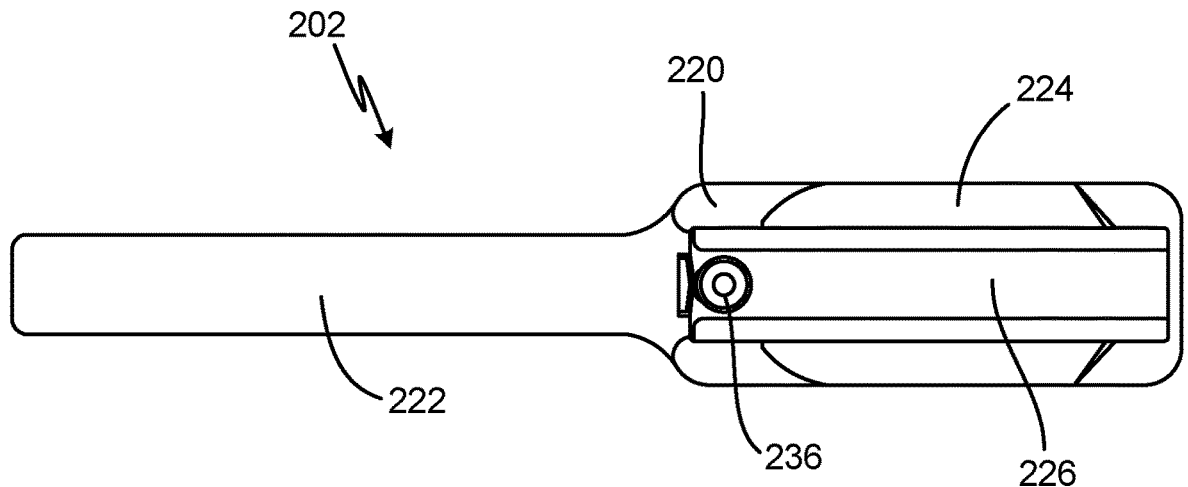

FIG. 11C is a bottom view of the body of the surgical instrument.

Figure 11D:
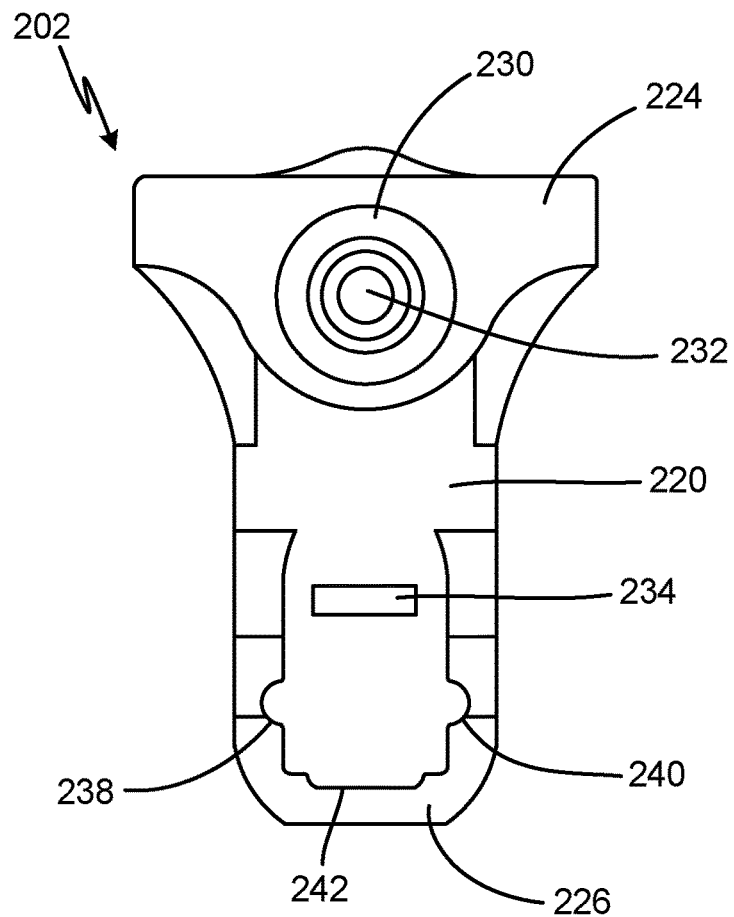

FIG. 11D is a front view of the body of the surgical instrument.

Figure 12A:
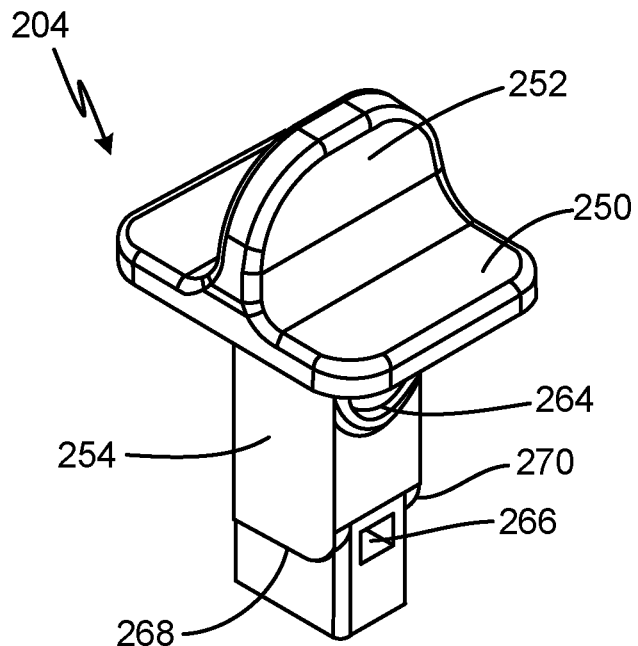

FIG. 12A is a perspective view of a slider of the surgical instrument.

Figure 12B:
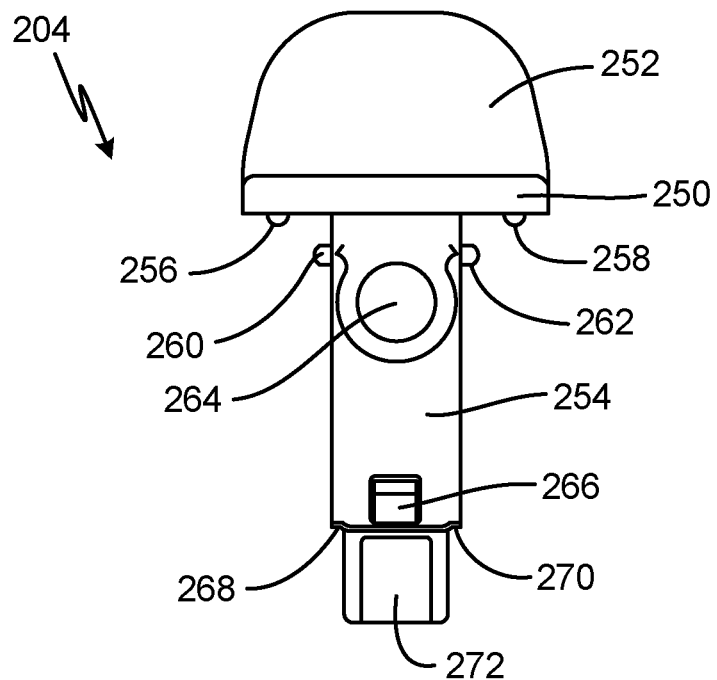

FIG. 12B is a front view of the slider of the surgical instrument.

Figure 12C:
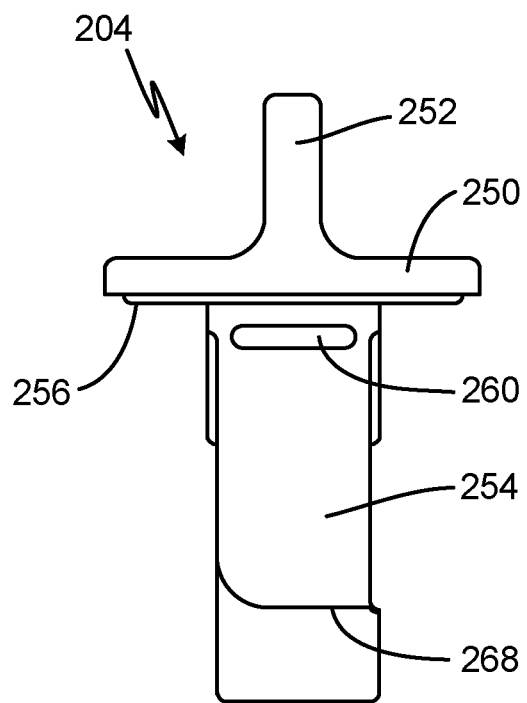

FIG. 12C is a side view of the slider of the surgical instrument.

Figure 12D:
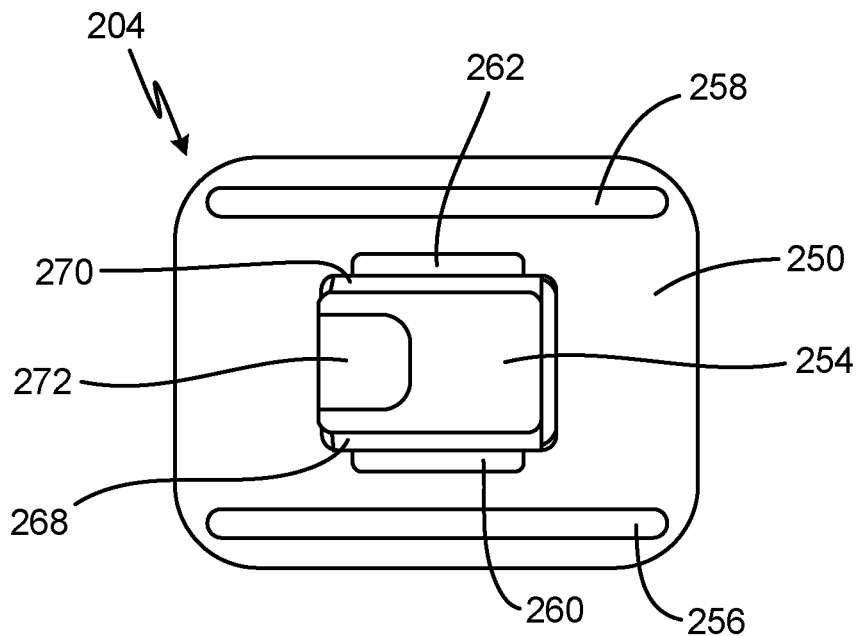

FIG. 12D is a bottom view of the slider of the surgical instrument.

Figure 13A:
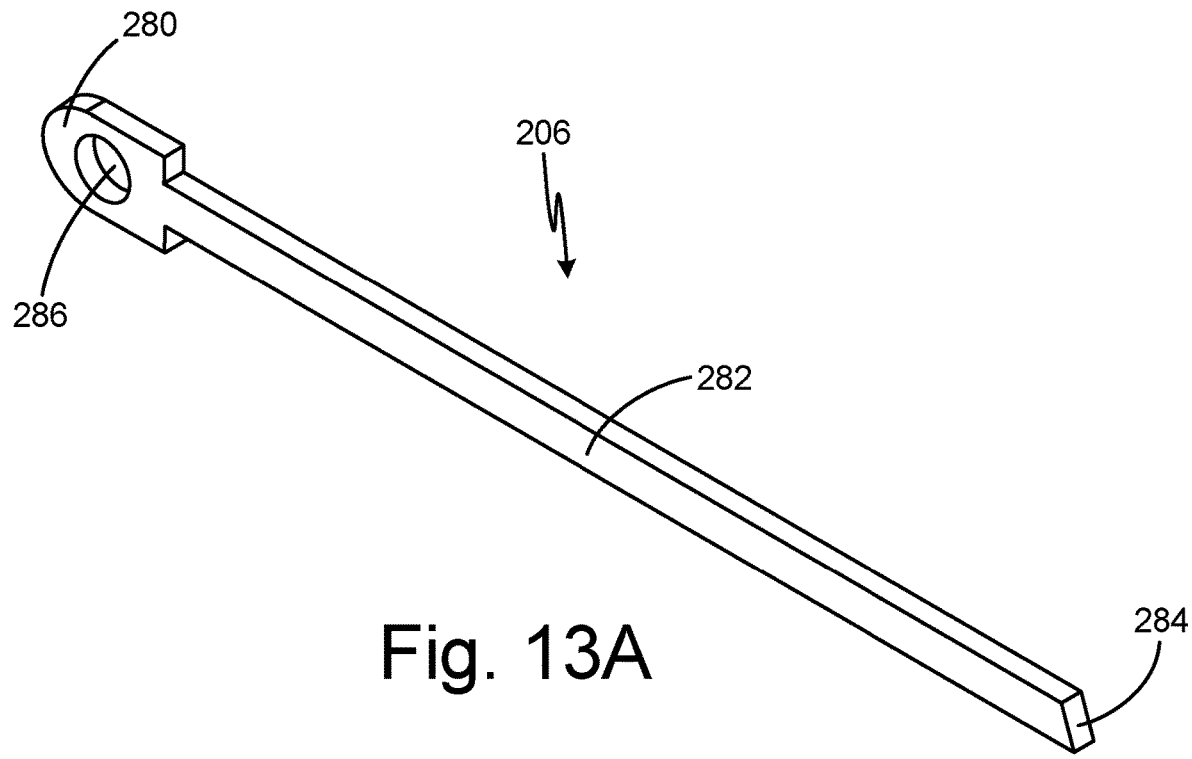

FIG. 13A is a perspective view of a blade of the surgical instrument.

Figure 13B:
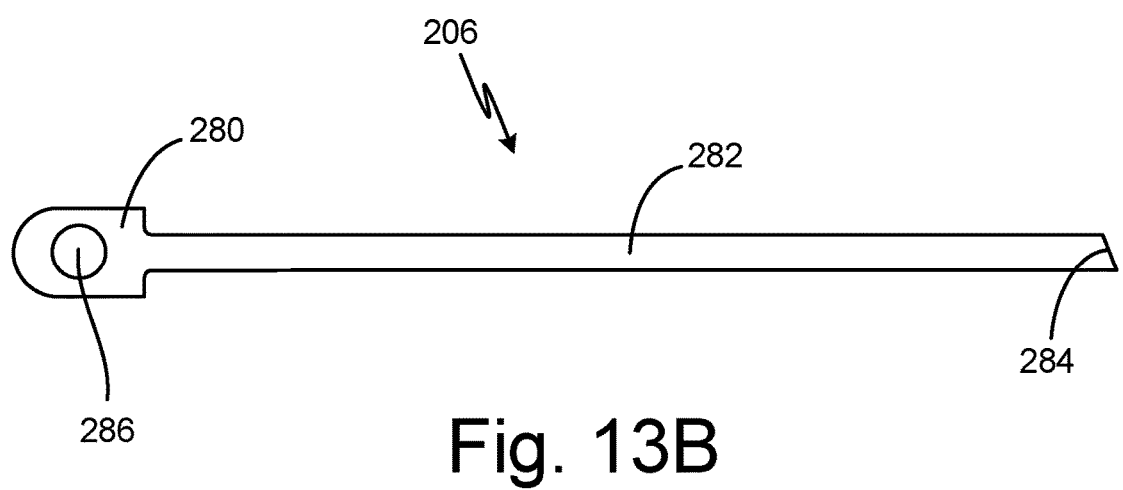

FIG. 13B is a side view of the blade of the surgical instrument.

Figure 14A:
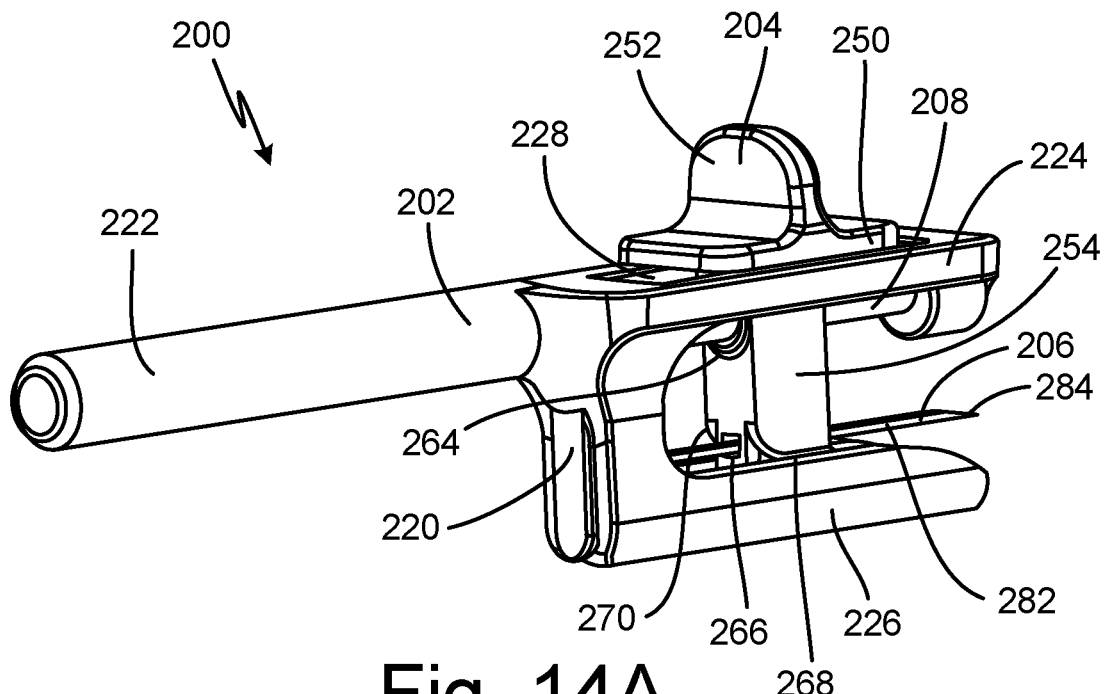

FIG. 14A is a perspective view of the surgical instrument in a second position.

Figure 14B:
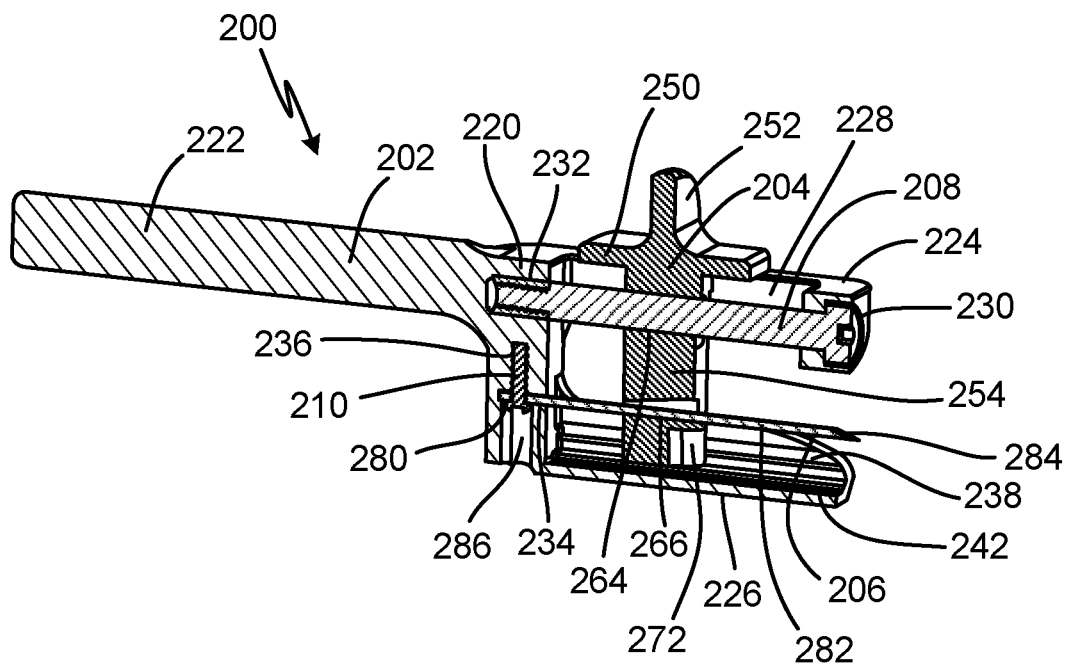

FIG. 14B is a cross-sectional view of the surgical instrument in a second position.

Method 300

Figure 15:
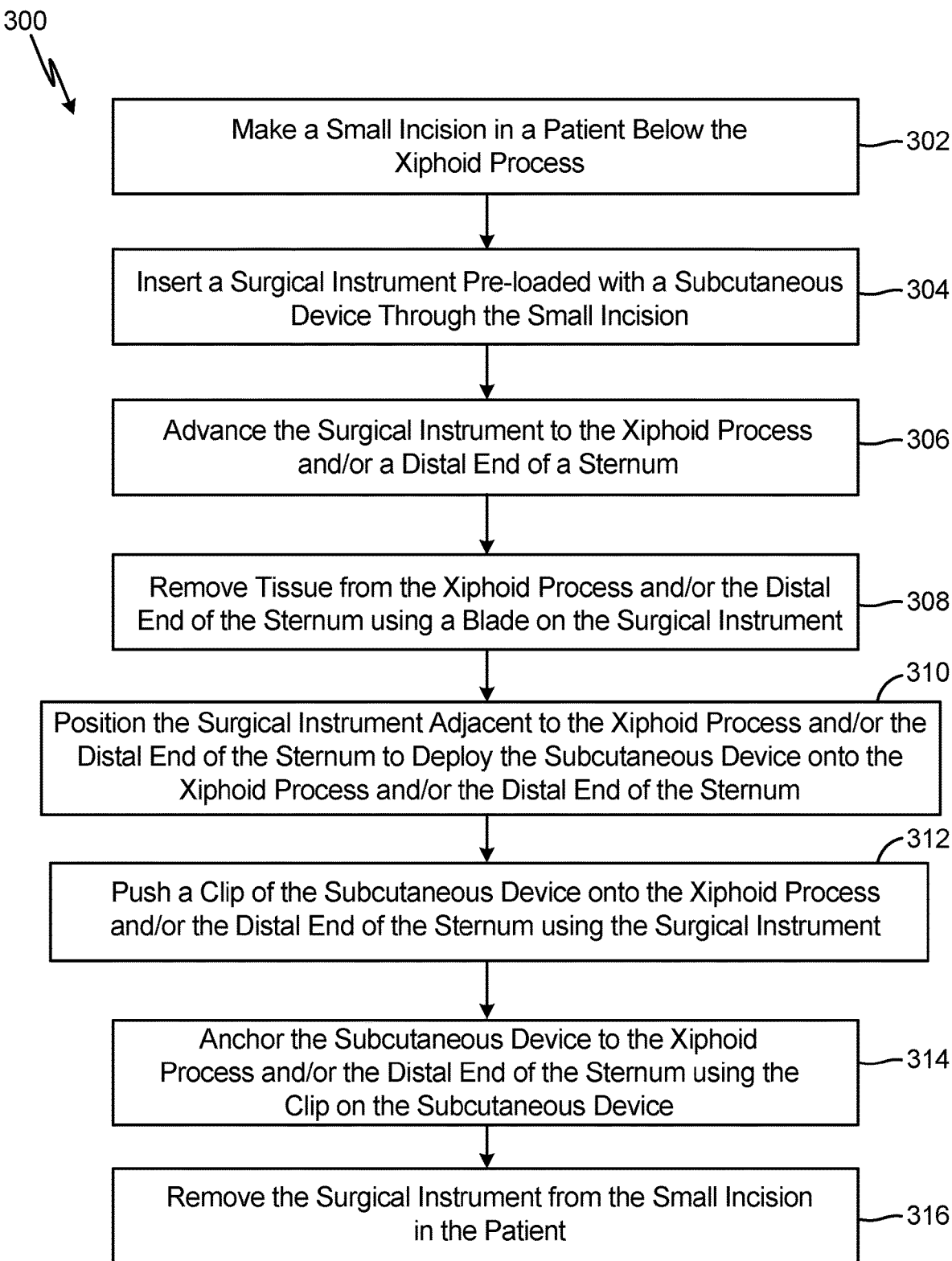

FIG. 15 is a flow chart showing the method for implanting the first embodiment of the subcutaneous device using the surgical instrument.

Figure 16A:
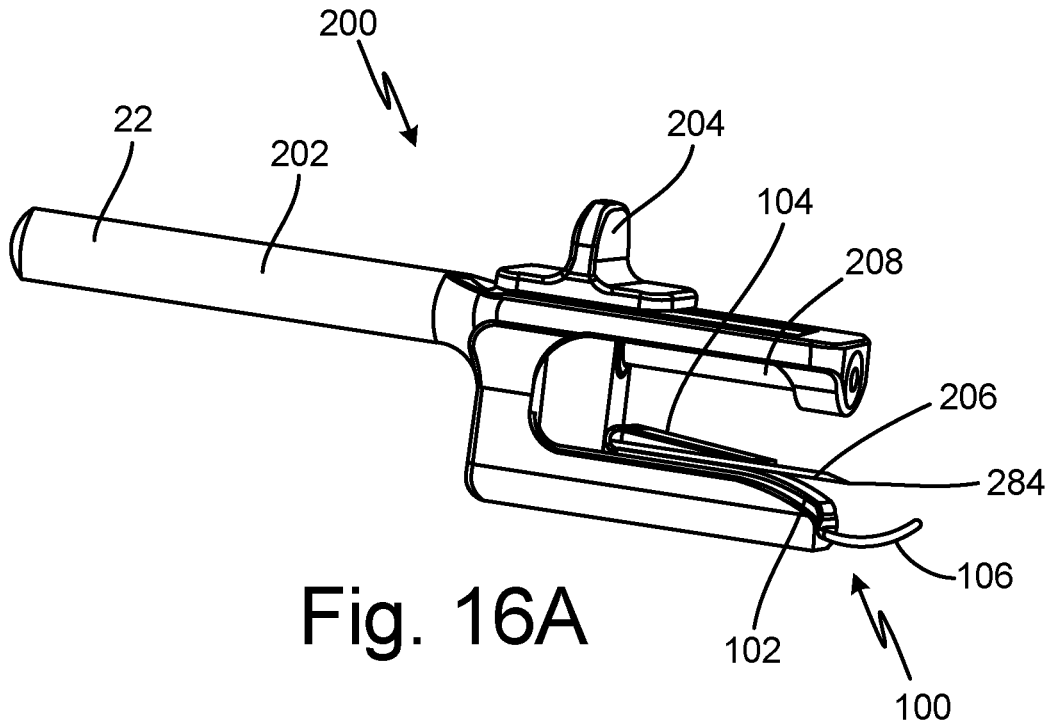

FIG. 16A is a perspective view of the first embodiment of the subcutaneous device in a first position in the surgical instrument.

Figure 16B:
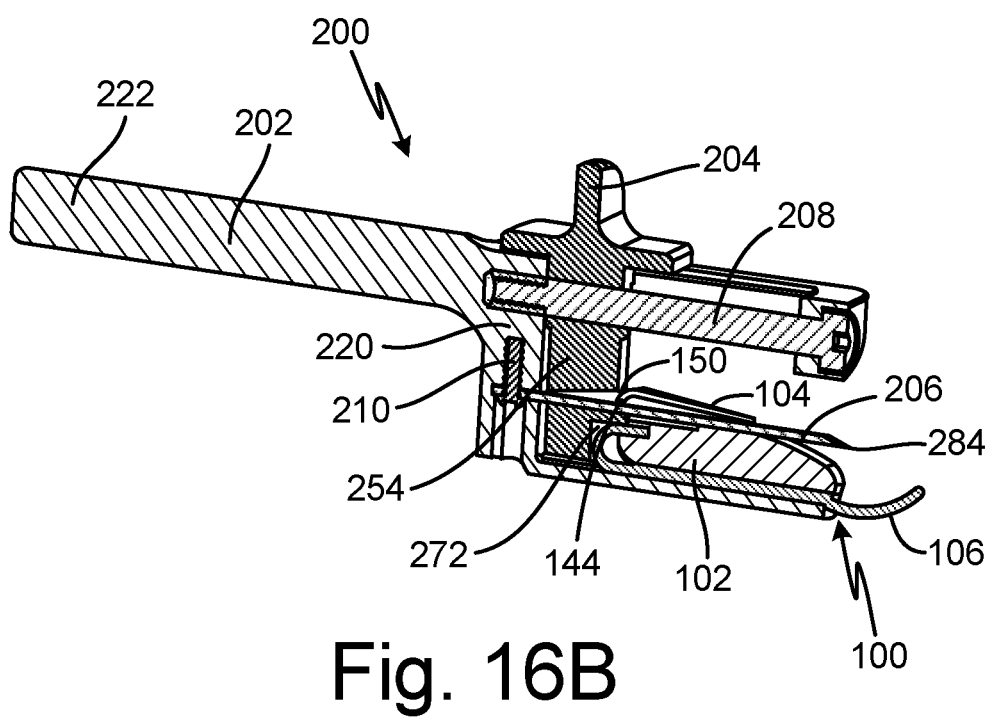

FIG. 16B is a cross-sectional view of the first embodiment of the subcutaneous device in the first position in the surgical instrument.

Figure 17A:
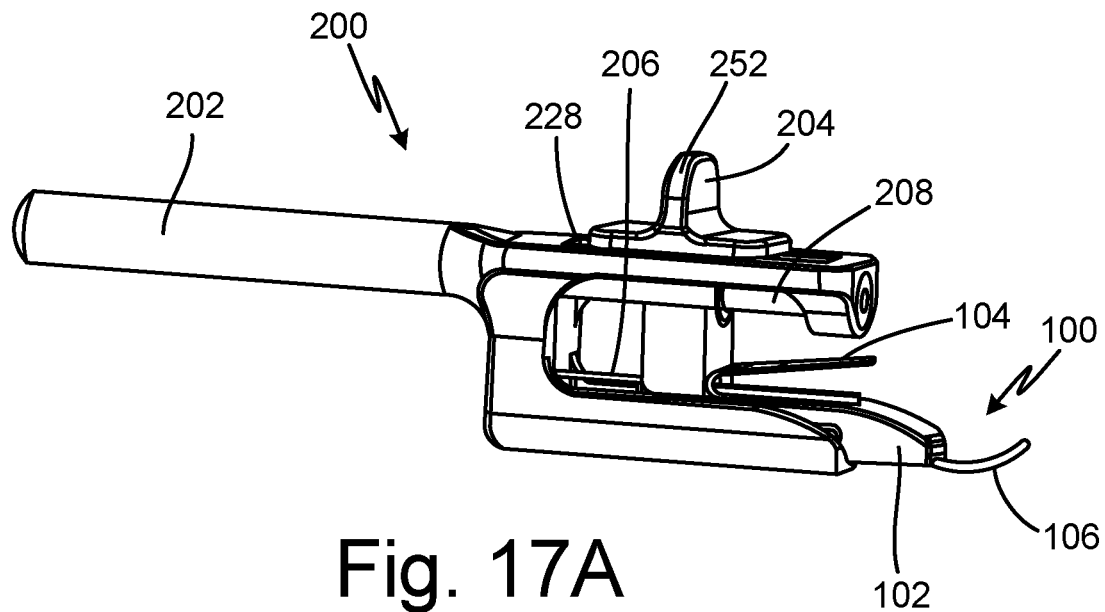

FIG. 17A is a perspective view of the first embodiment of the subcutaneous device in a second position in the surgical instrument as the subcutaneous device is being implanted.

Figure 17B:
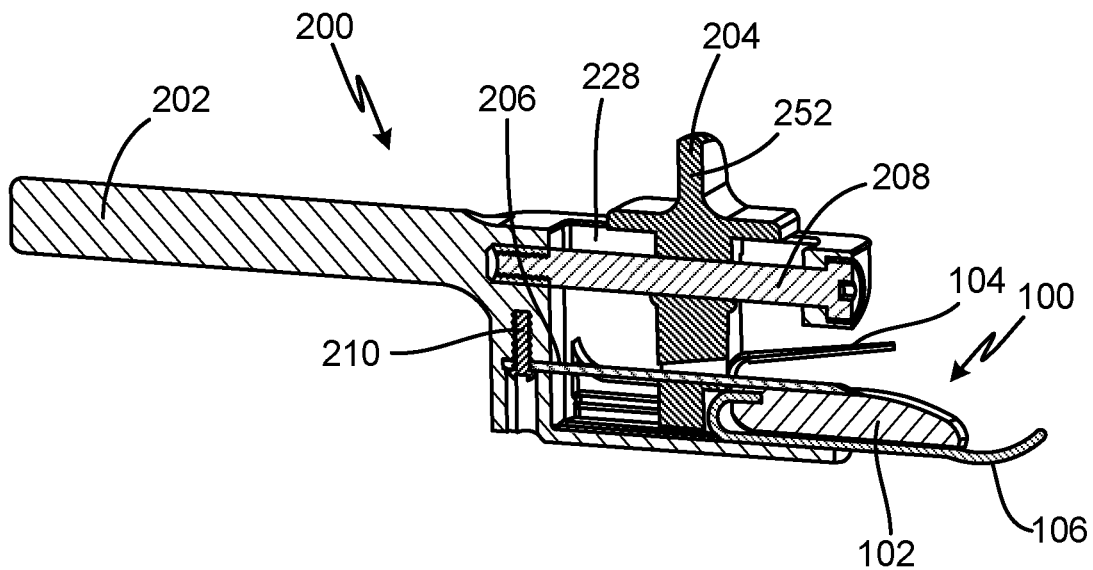

FIG. 17B is a cross-sectional view of the first embodiment of the subcutaneous device in the second position in the surgical instrument as the subcutaneous device is being implanted.

Figure 17C:
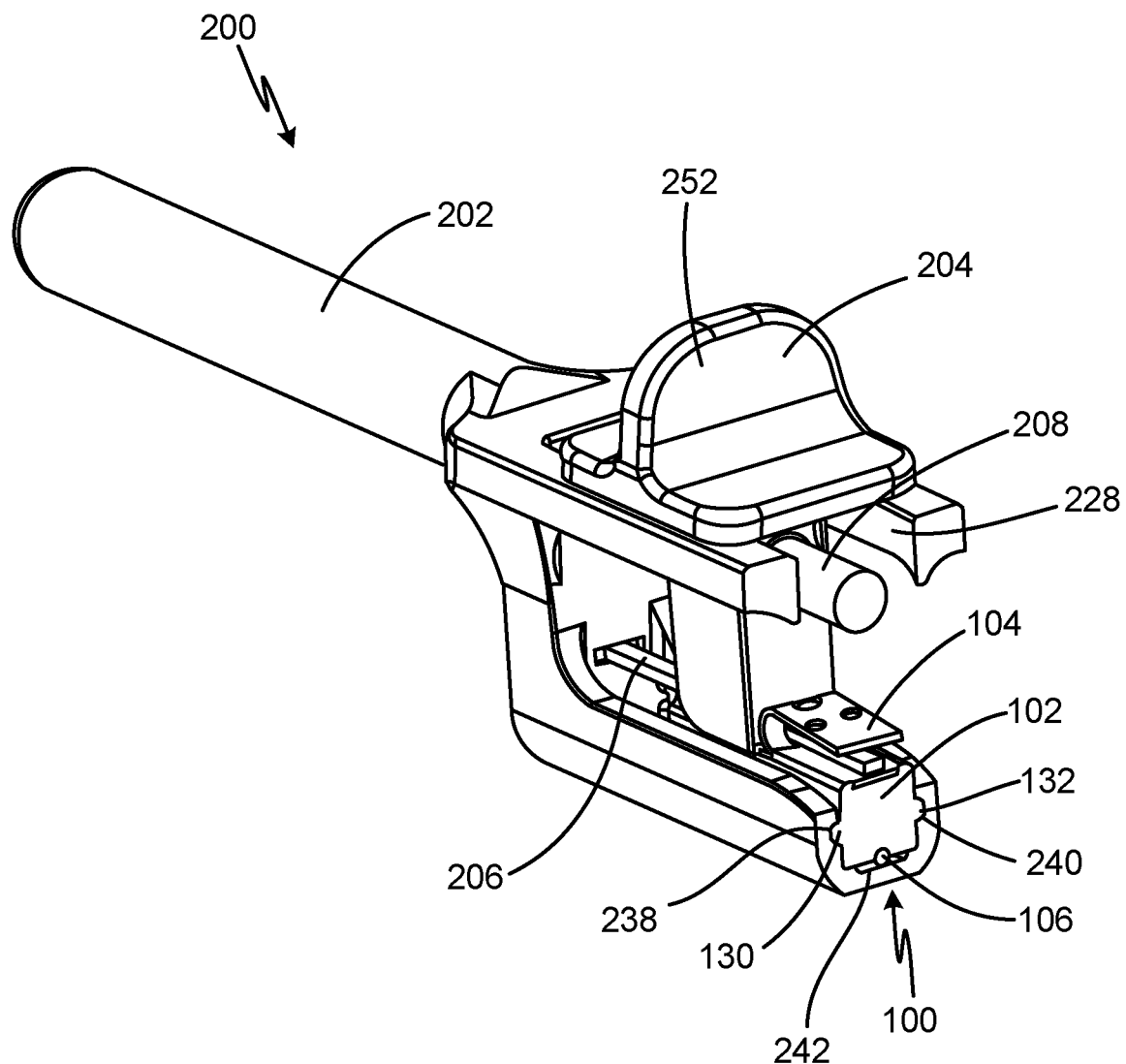

FIG. 17C is a cross-sectional view of the first embodiment of the subcutaneous device in the second position in the surgical instrument as the subcutaneous device is being implanted.

Figure 18A:
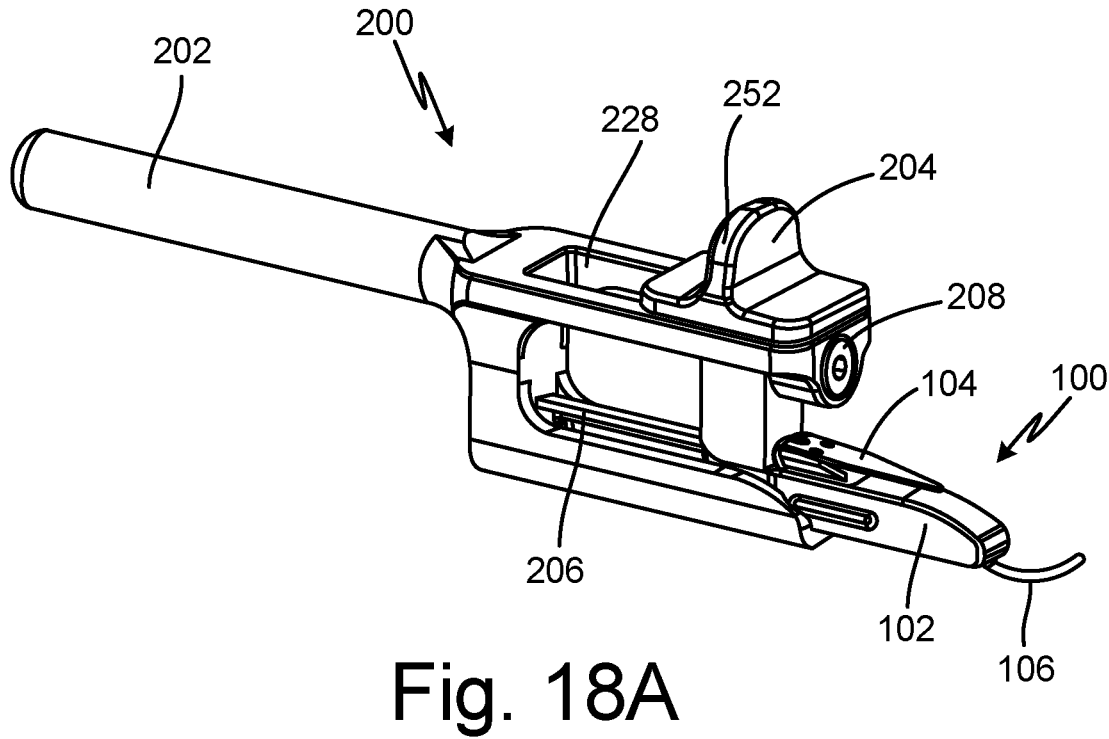

FIG. 18A is a perspective view of the first embodiment of the subcutaneous device in a third position in the surgical instrument as the subcutaneous device is being implanted.

Figure 18B:
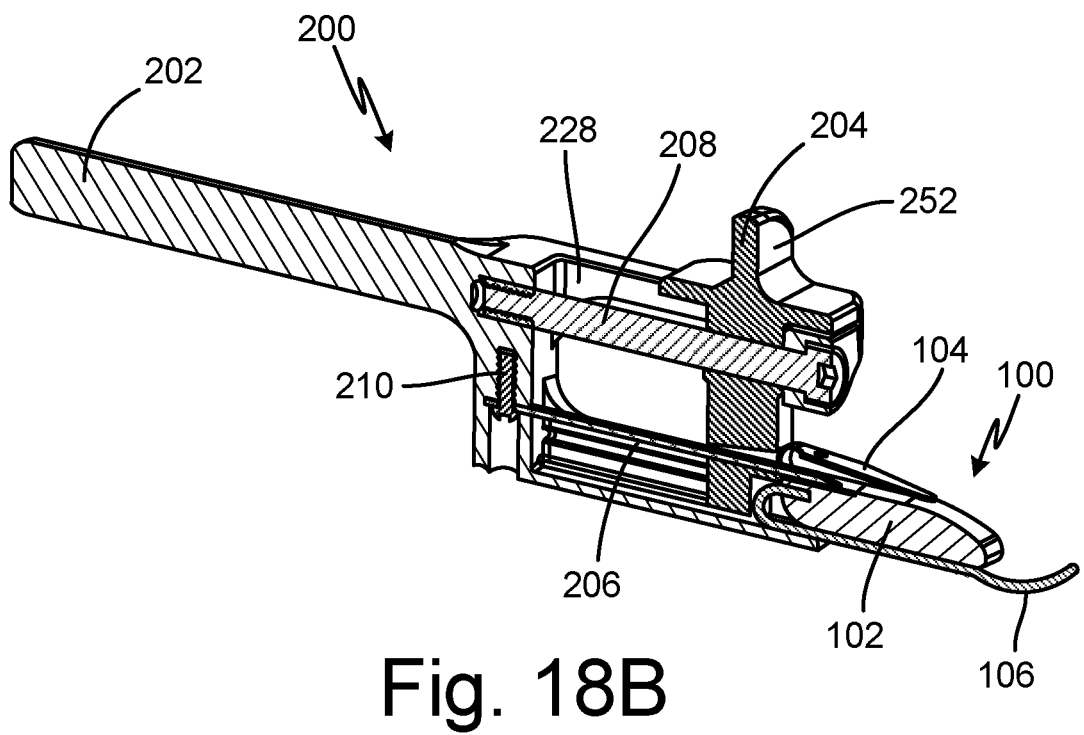

FIG. 18B is a cross-sectional view of the first embodiment of the subcutaneous device in the third position in the surgical instrument as the subcutaneous device is being implanted.

Figure 19:
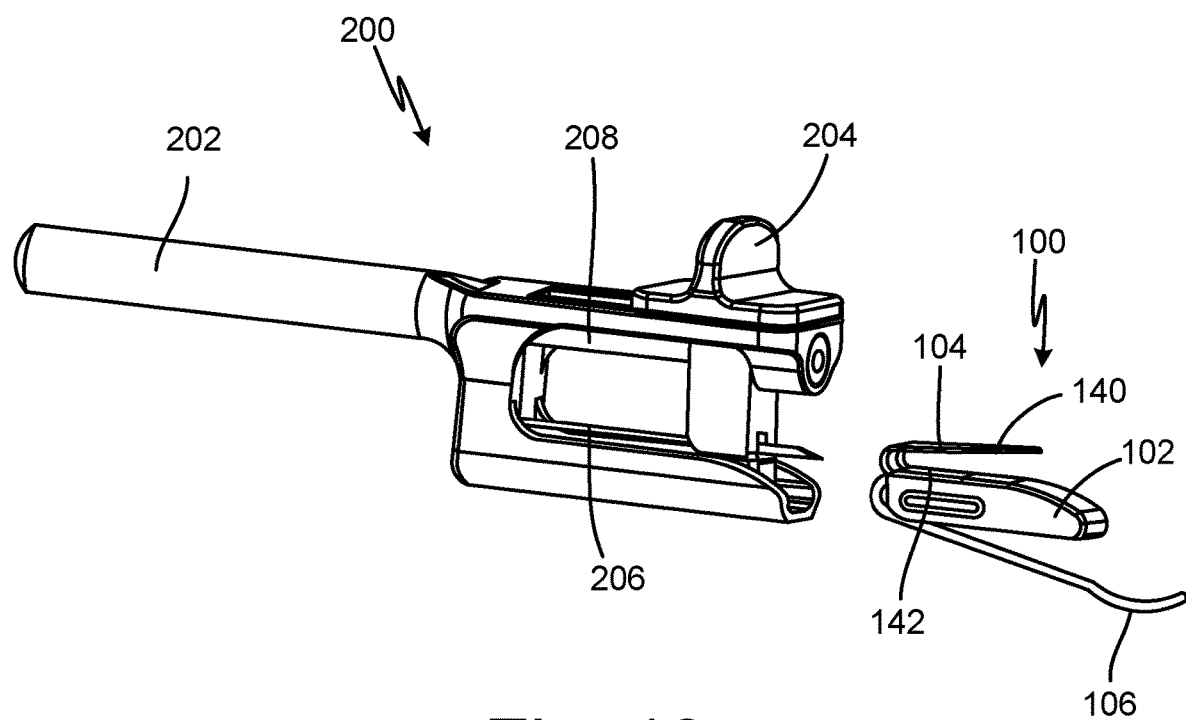

FIG. 19 is a perspective view of the first embodiment of the subcutaneous device after it has been deployed from the surgical instrument.

Subcutaneous Device 400

Figure 20:
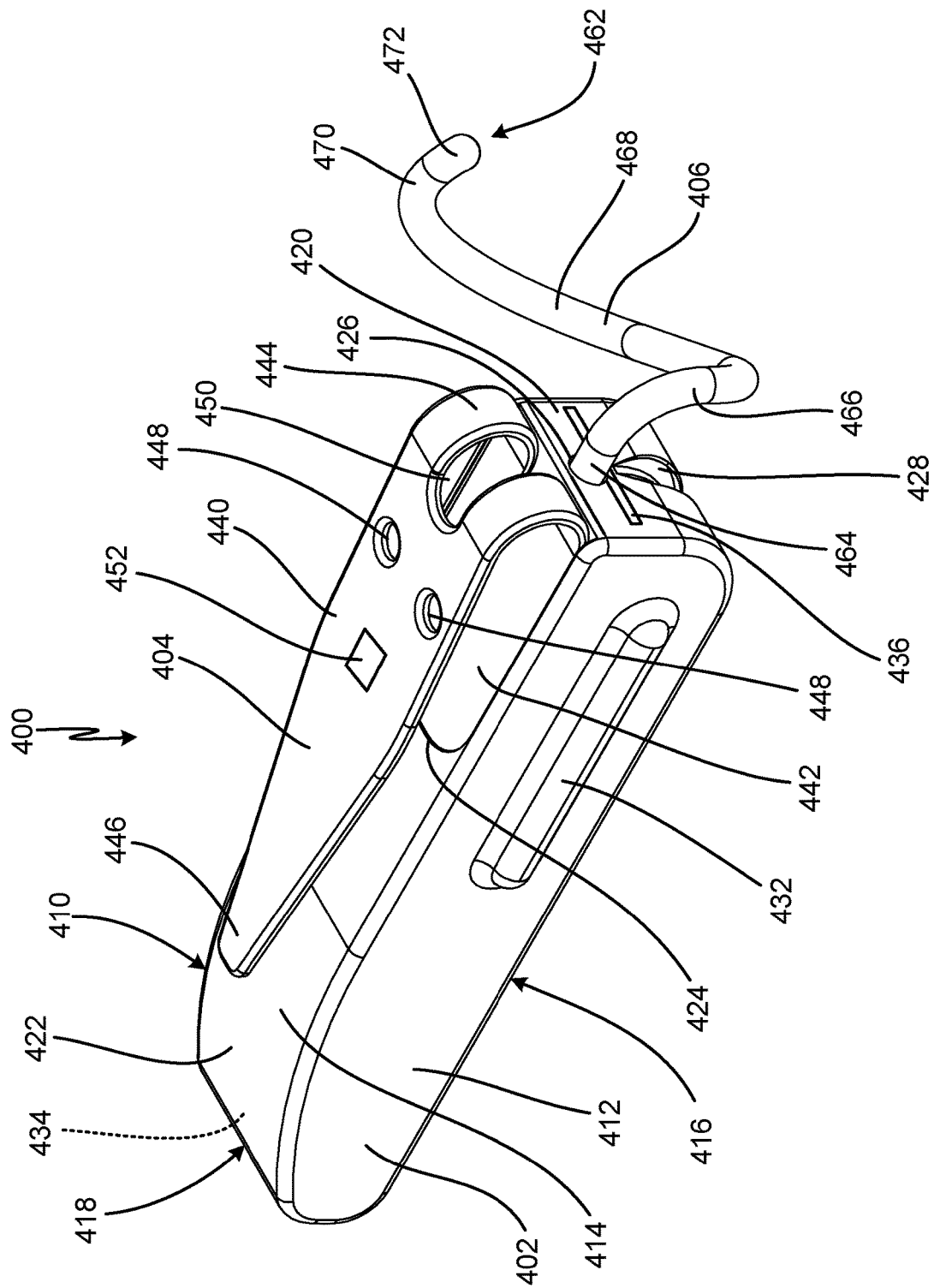

FIG. 20 is a perspective view of a second embodiment of a subcutaneous device.

Subcutaneous Device 500

Figure 21A:
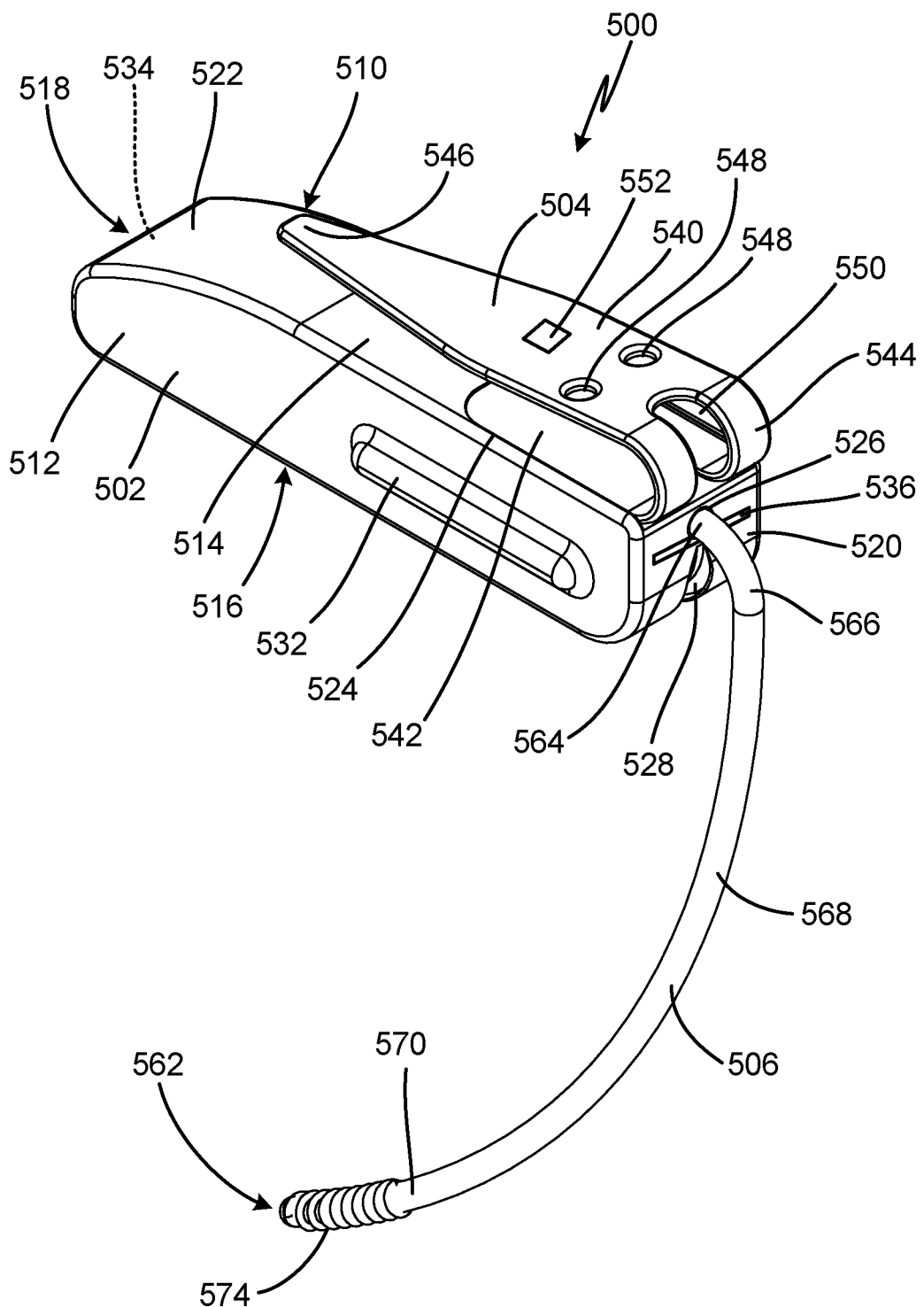

FIG. 21A is a perspective view of a third embodiment of a subcutaneous device.

Figure 21B:
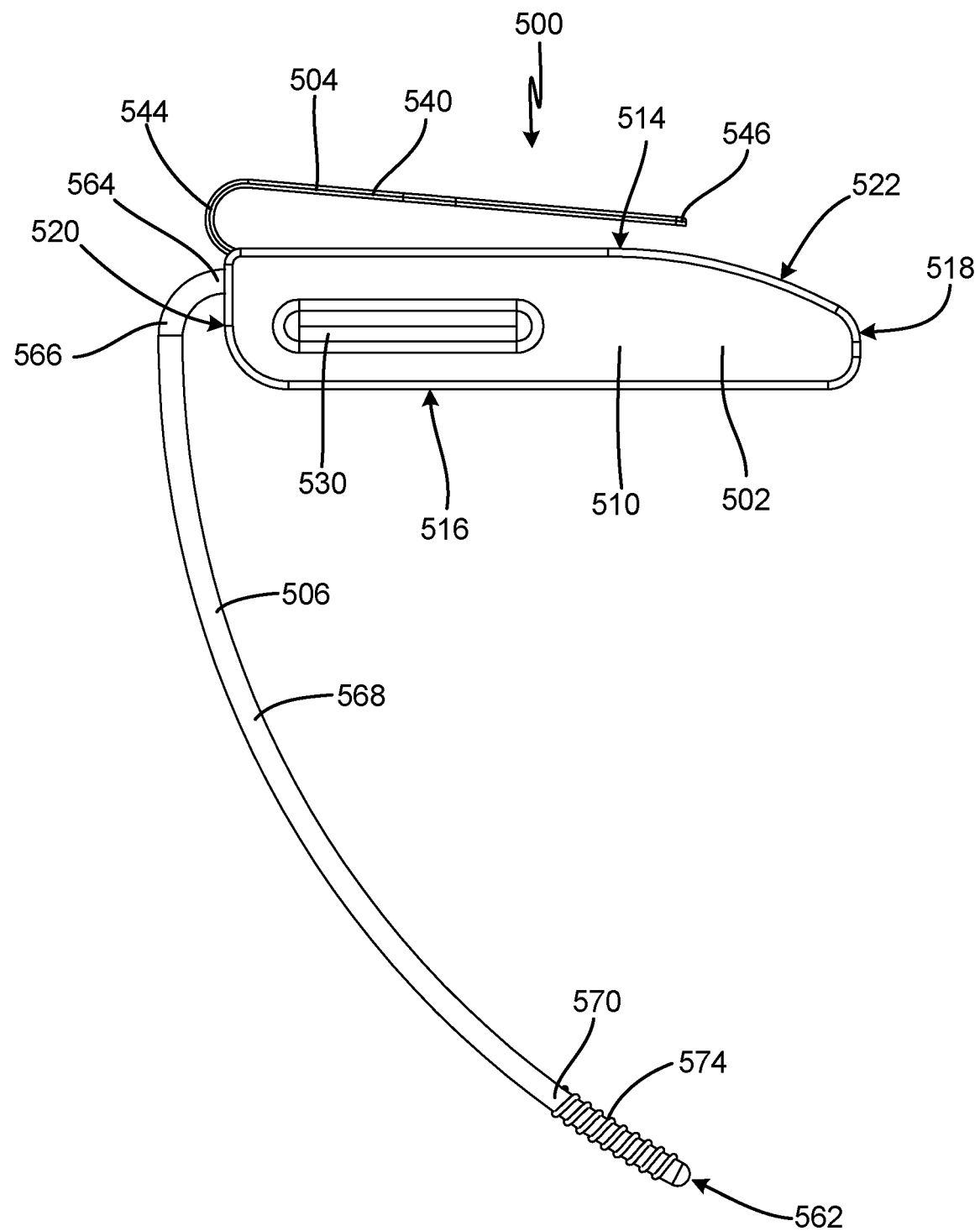

FIG. 21B is a side view of the third embodiment of the subcutaneous device.

Subcutaneous Device 600

Figure 22A:
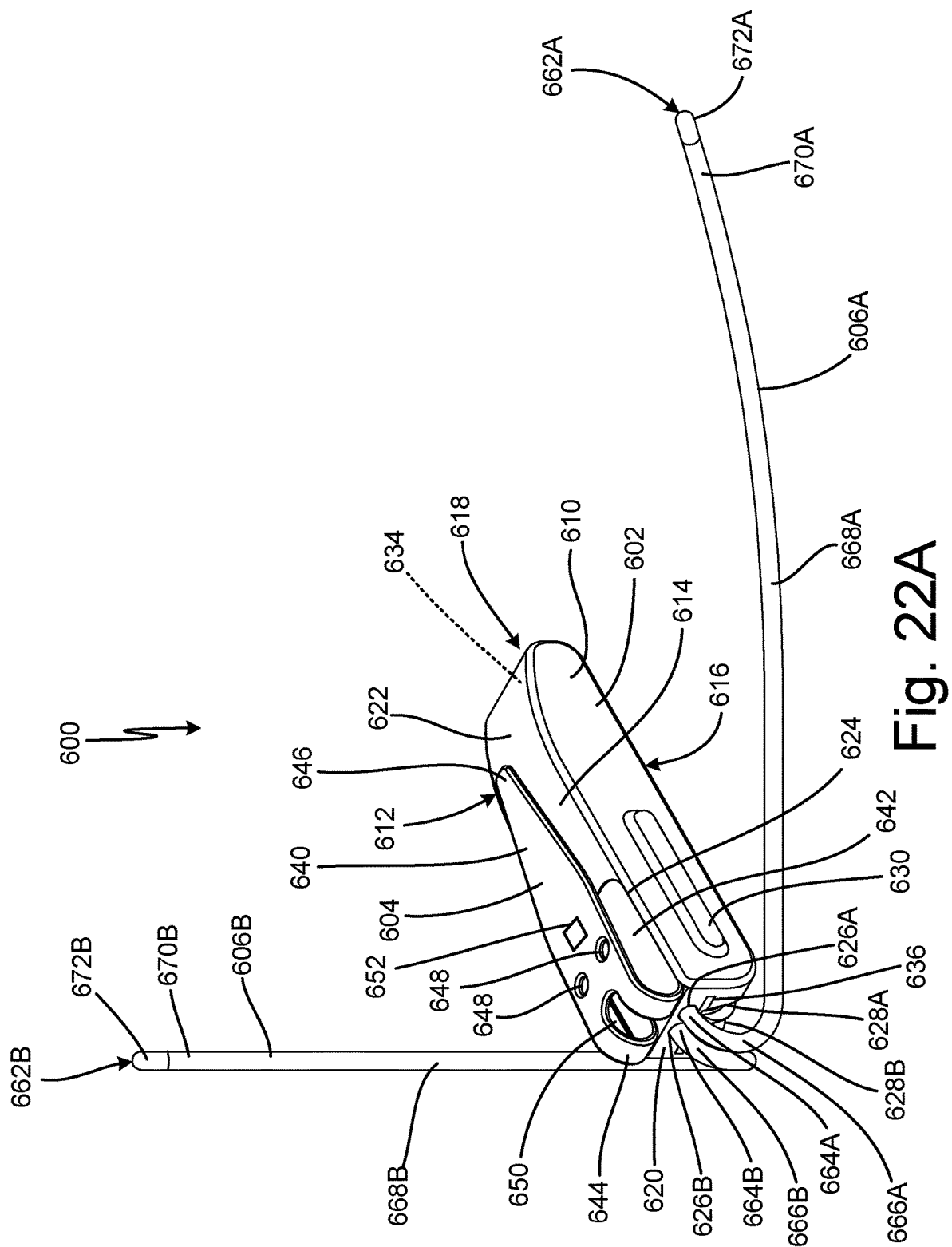

FIG. 22A is a perspective view of a fourth embodiment of a subcutaneous device.

Figure 22B:
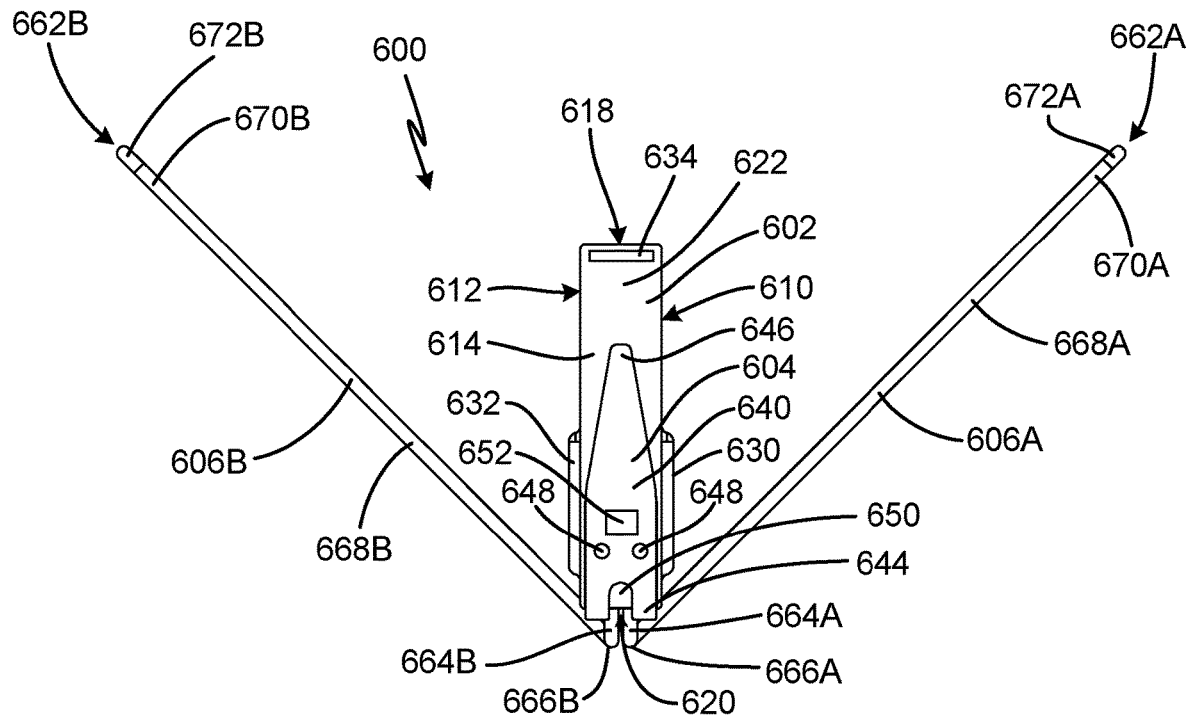

FIG. 22B is a top view of the fourth embodiment of the subcutaneous device.

Figure 22C:
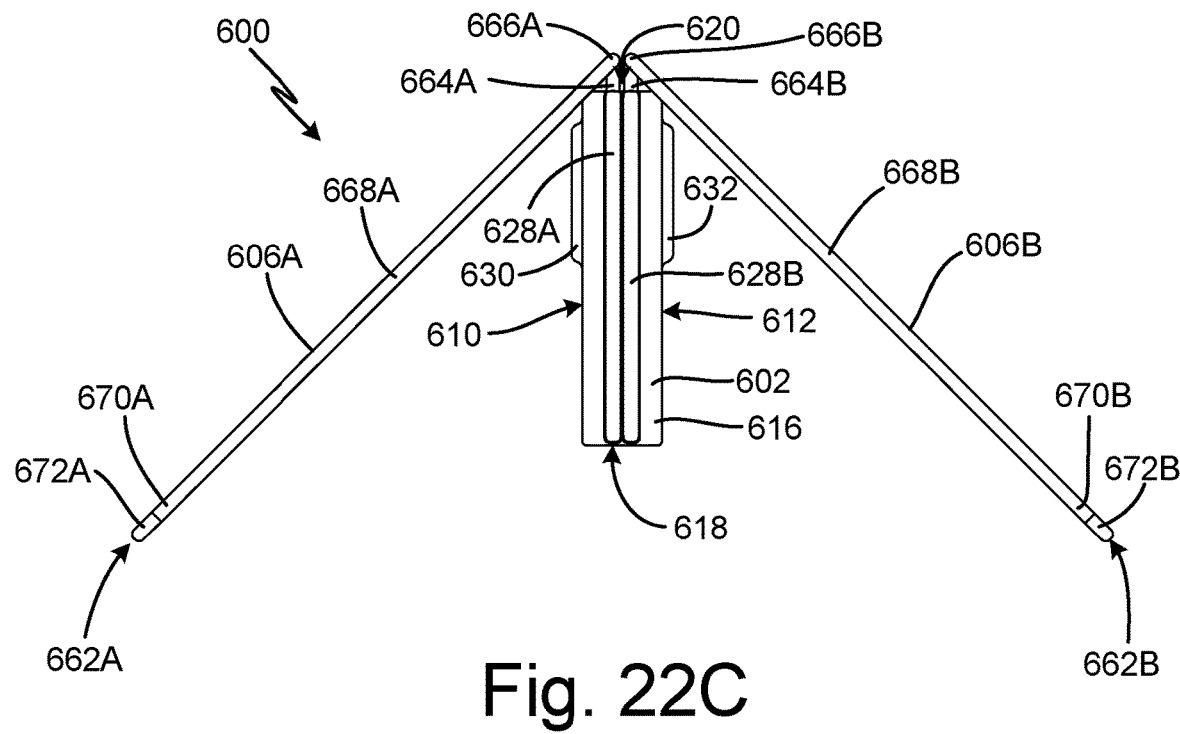

FIG. 22C is a bottom view of the fourth embodiment of the subcutaneous device.

Figure 22D:
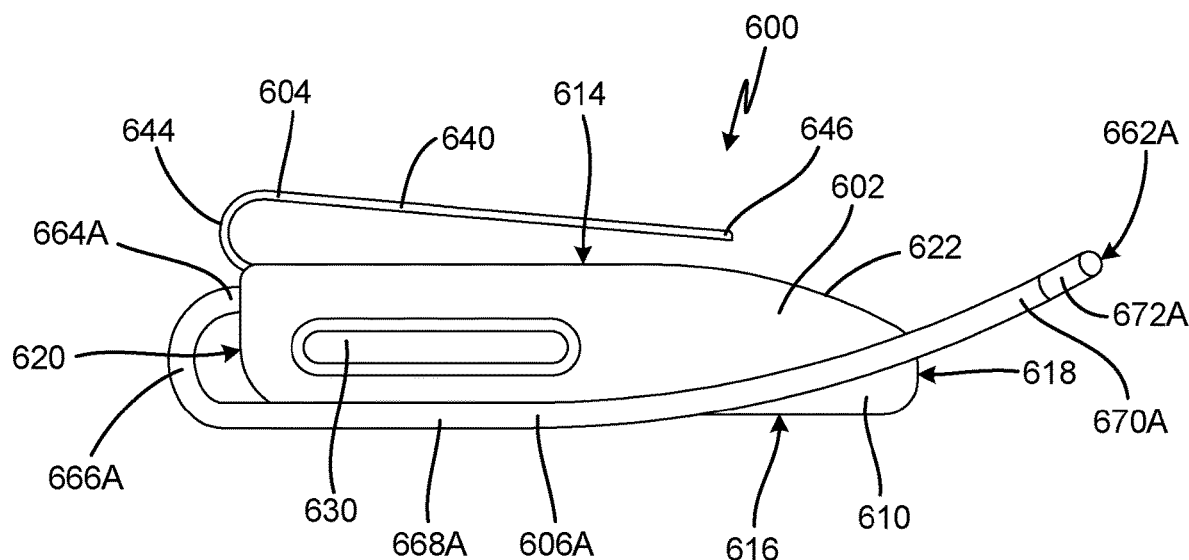

FIG. 22D is a side view of the fourth embodiment of the subcutaneous device.

Figure 22E:
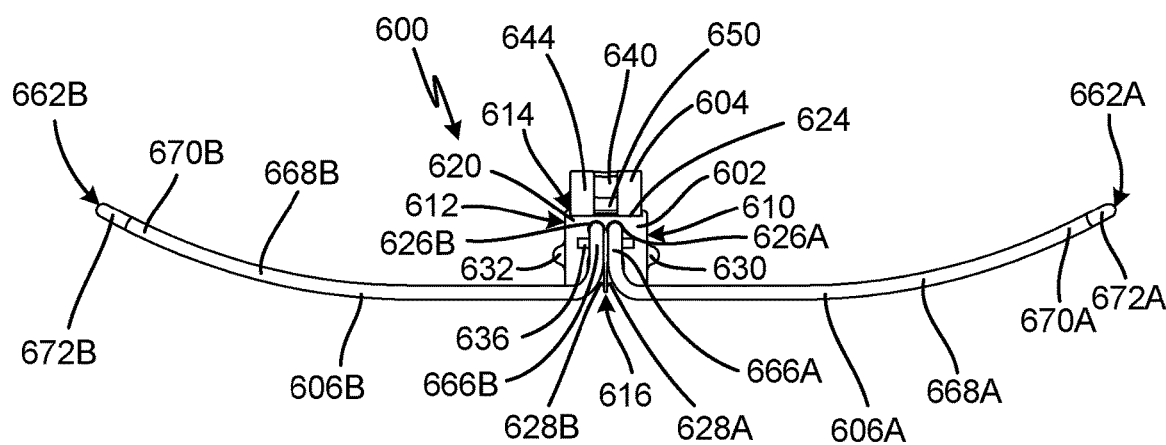

FIG. 22E is a back view of the fourth embodiment of the subcutaneous device.

Figure 23A:
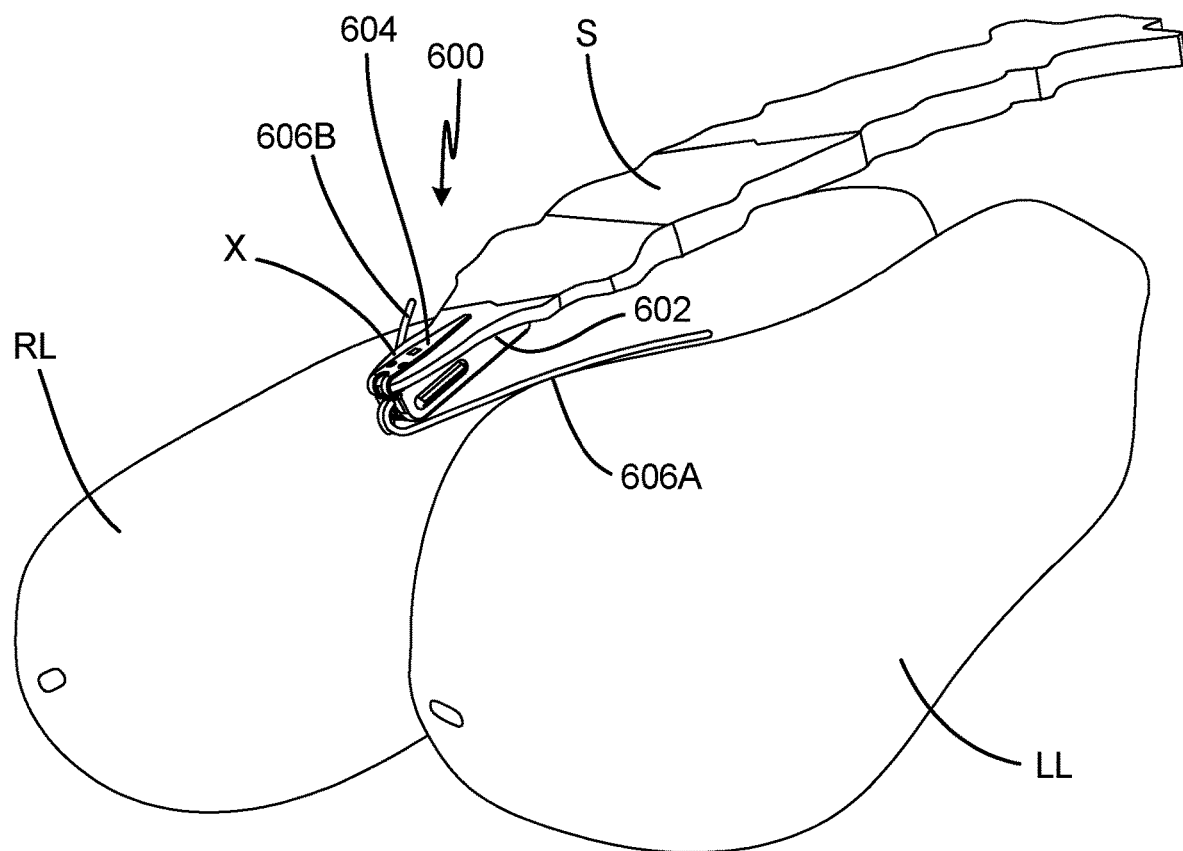

FIG. 23A is a perspective view of the fourth embodiment of the subcutaneous device positioned on a xiphoid process and a sternum and showing a positioning of prongs on lungs.

Figure 23B:
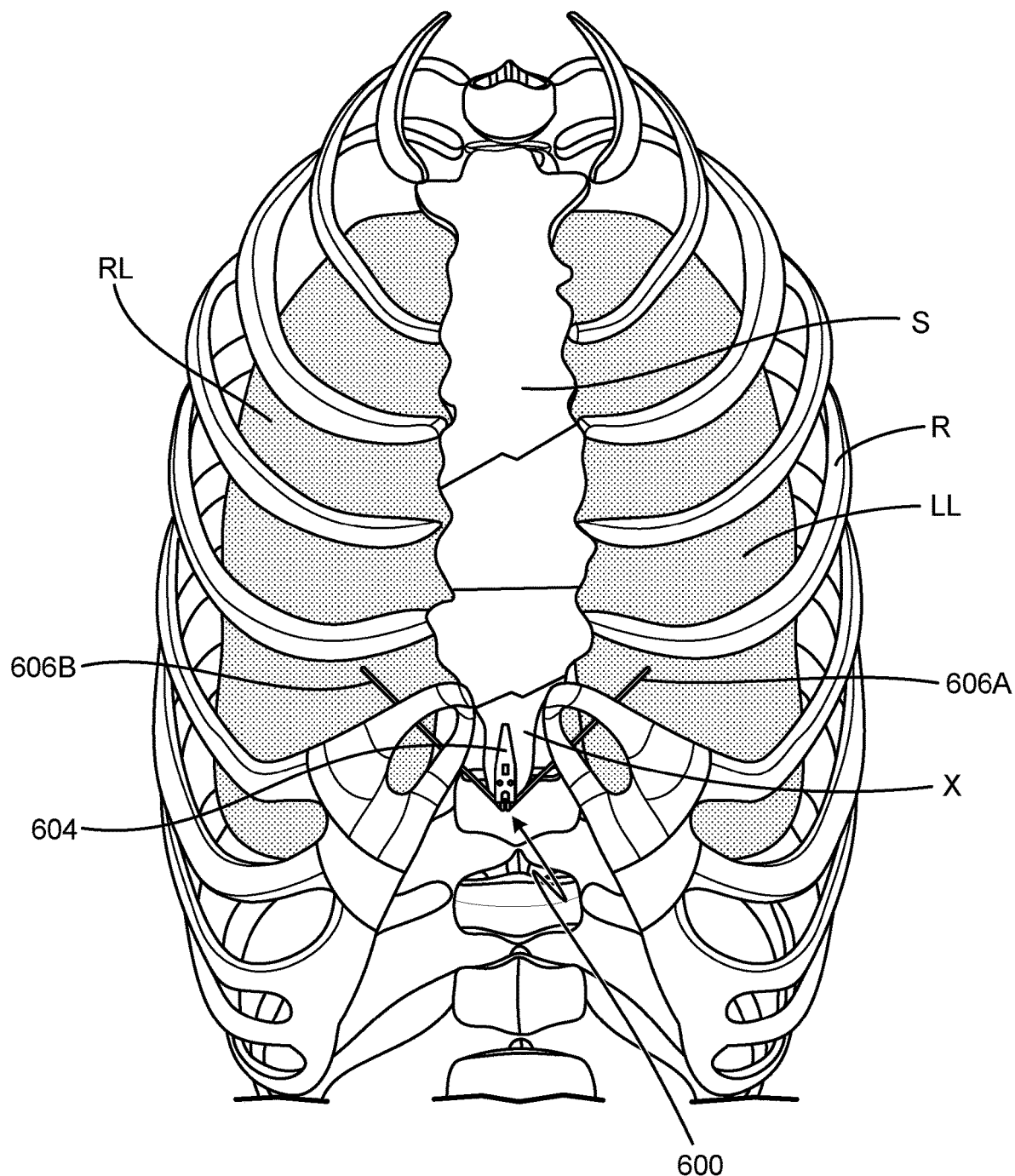

FIG. 23B is a front view of the fourth embodiment of the subcutaneous device positioned on the xiphoid process and the sternum and showing a positioning of the prongs on the lungs.

Figure 23C:
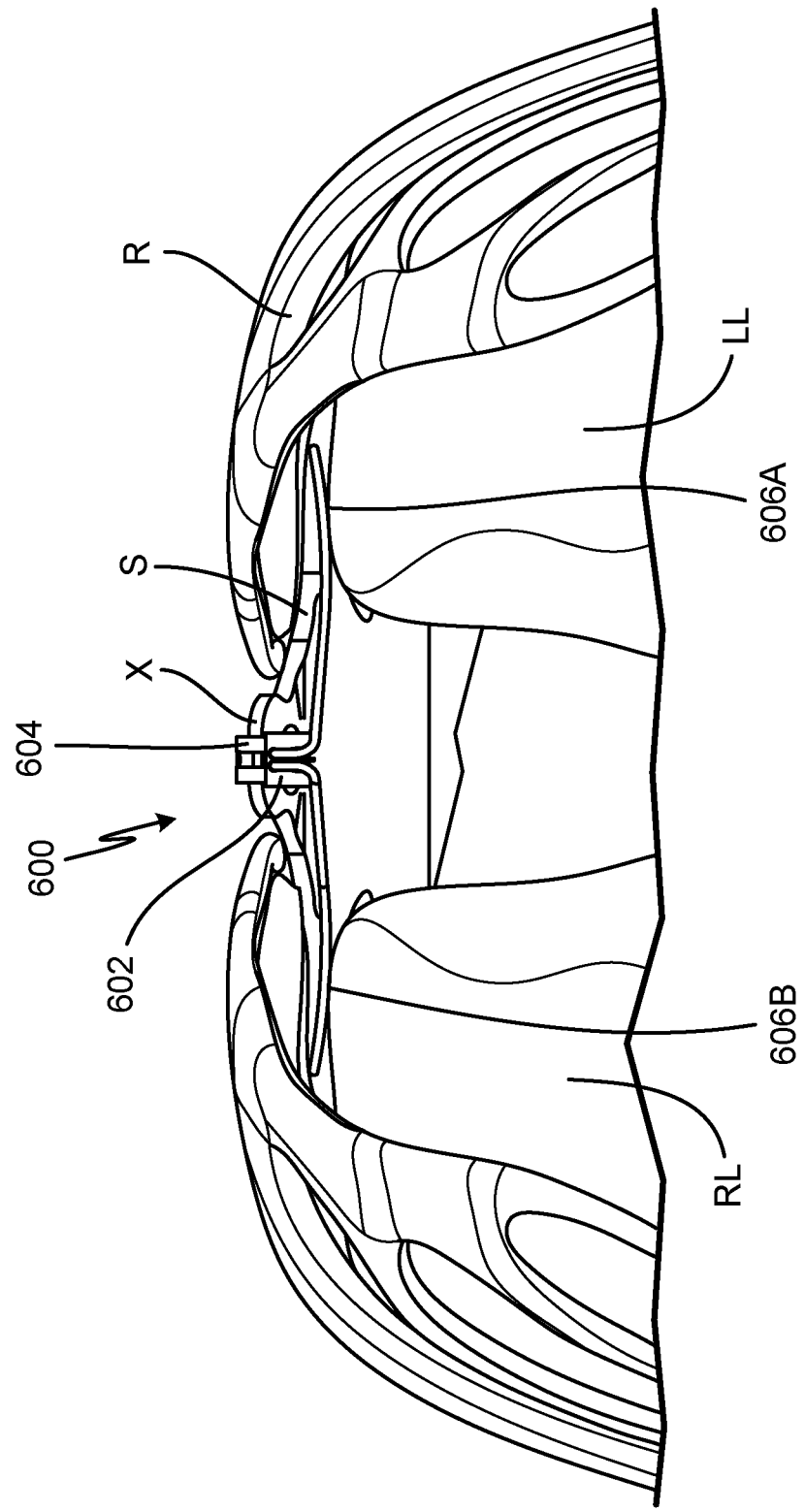

FIG. 23C is a side view of the fourth embodiment of the subcutaneous device positioned on the xiphoid process and the sternum and showing a positioning of the prongs on the lungs.

Subcutaneous Device 700

Figure 24A:
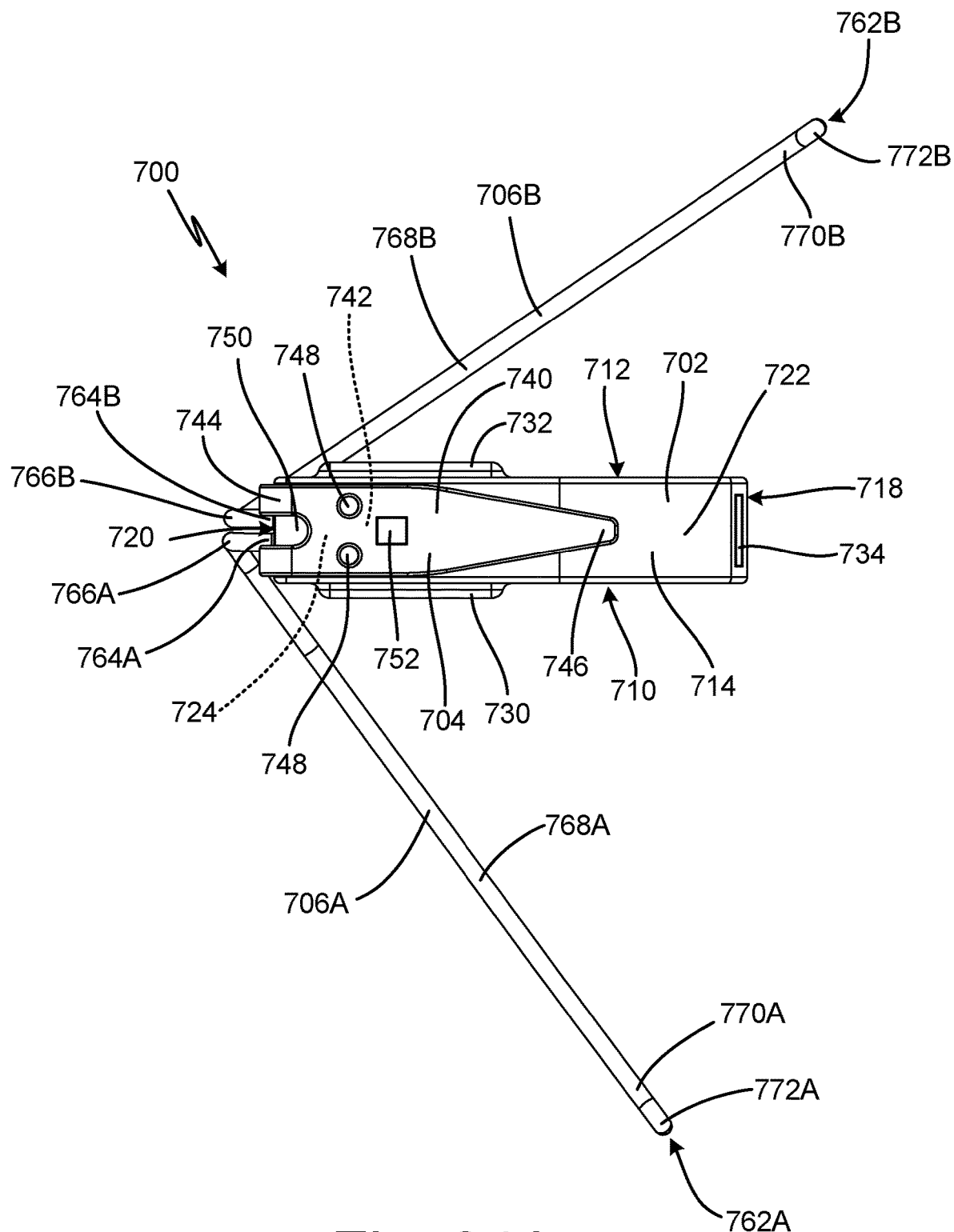

FIG. 24A is a top view of a fifth embodiment of a subcutaneous device.

Figure 24B:
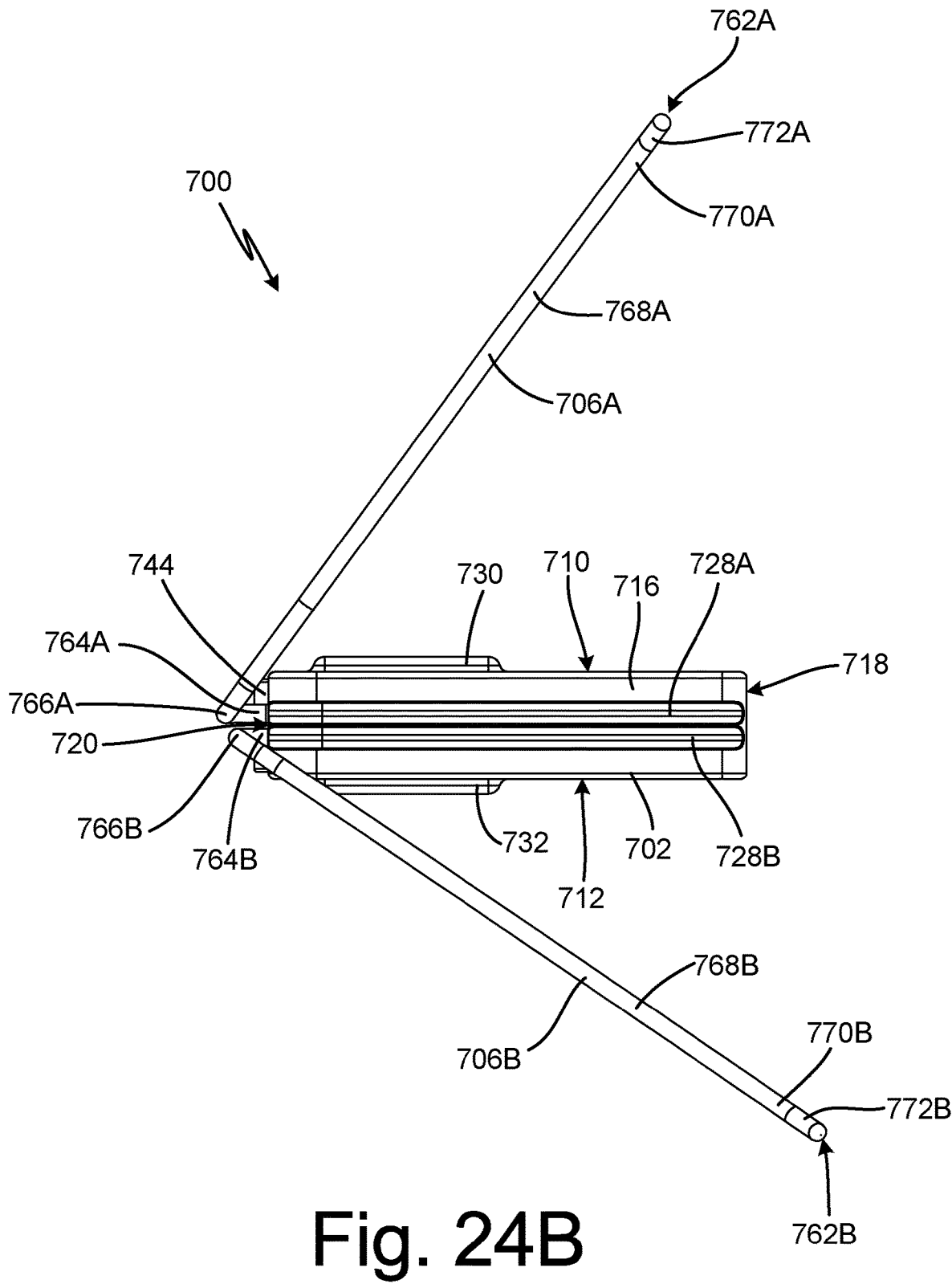

FIG. 24B is a bottom view of the fifth embodiment of the subcutaneous device.

Figure 24C:
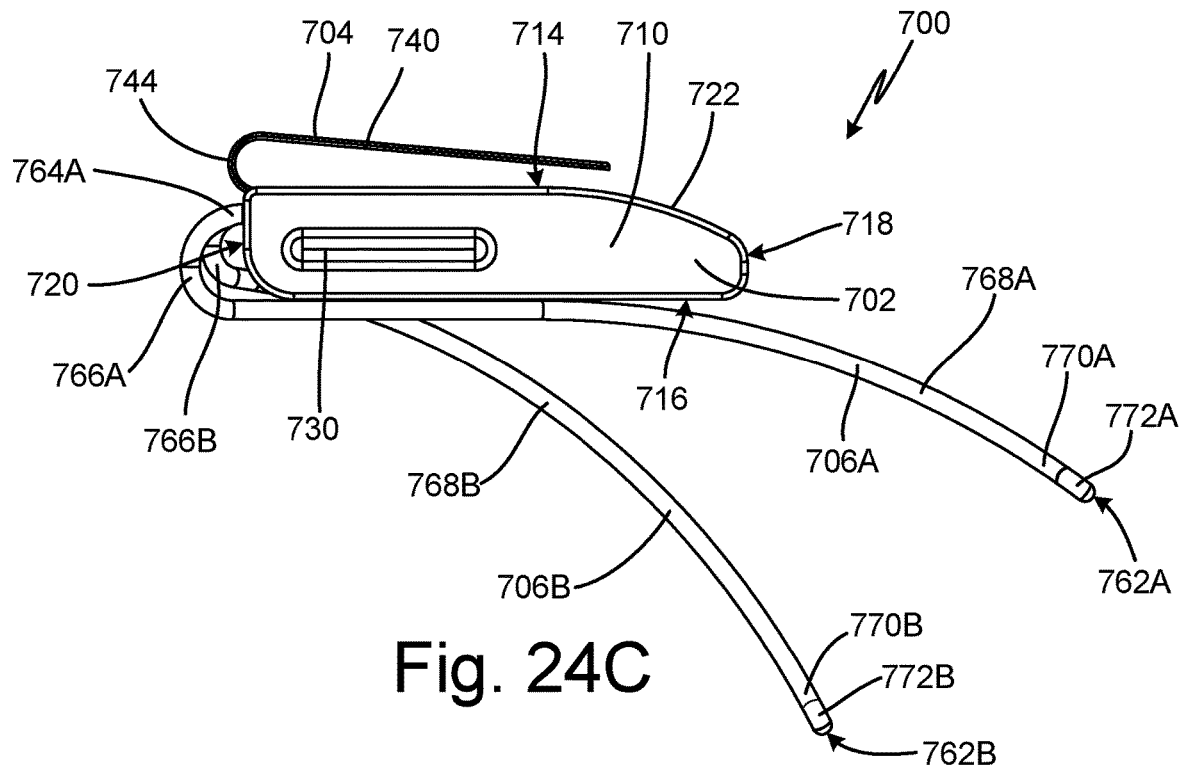

FIG. 24C is a side view of the fifth embodiment of the subcutaneous device.

Figure 24D:
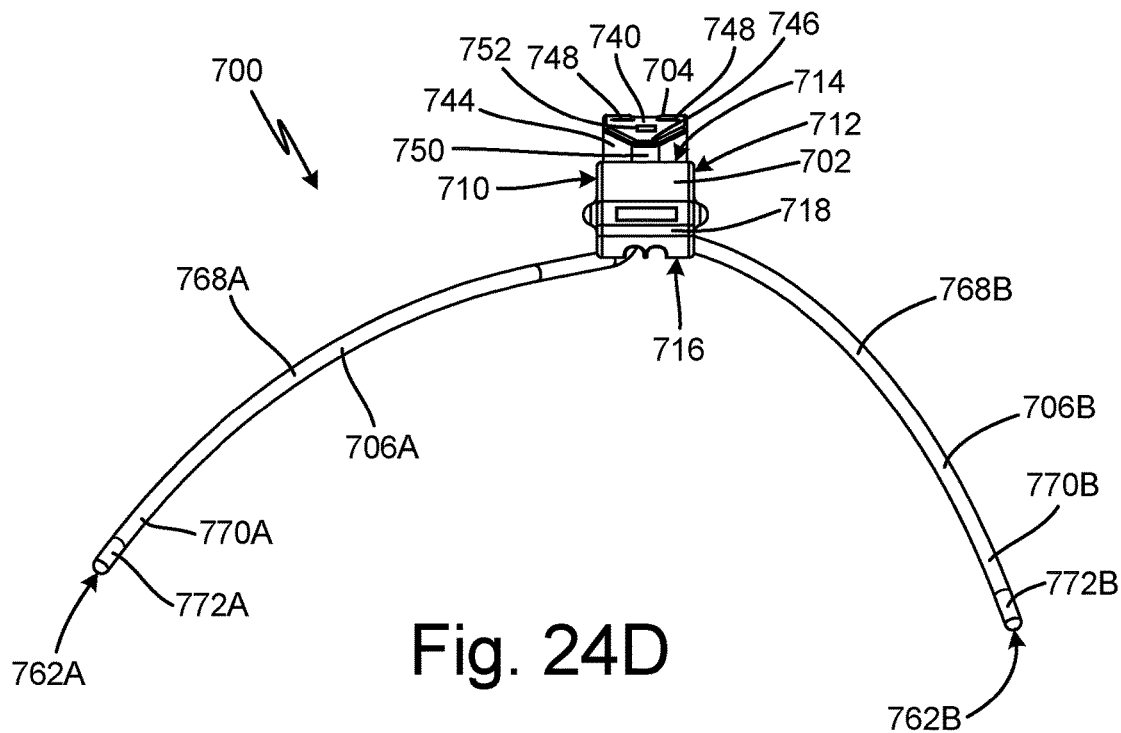

FIG. 24D is a front view of the fifth embodiment of the subcutaneous device.

Figure 25A:
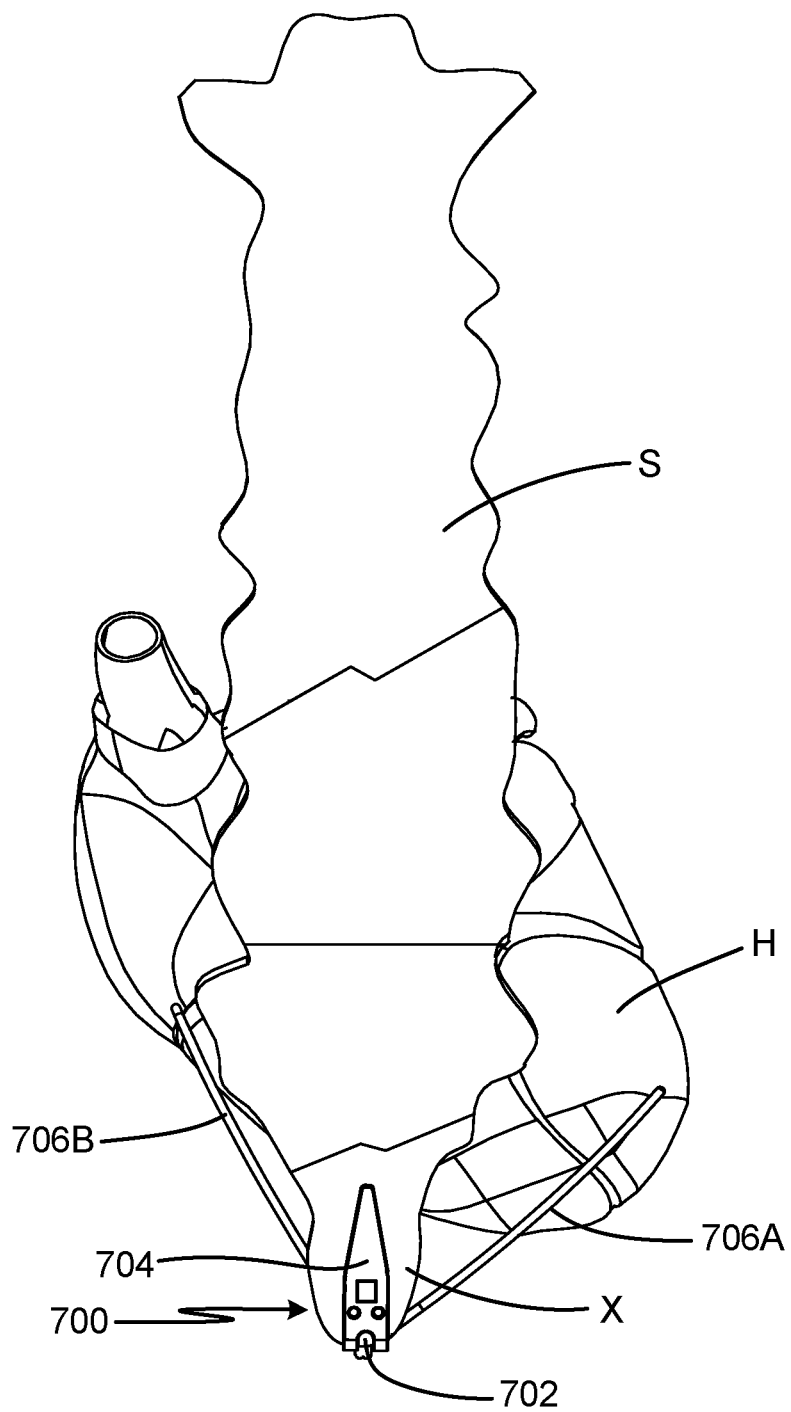

FIG. 25A is a front view of the fifth embodiment of the subcutaneous device positioned on a xiphoid process and a sternum and showing a positioning of prongs around a heart.

Figure 25B:
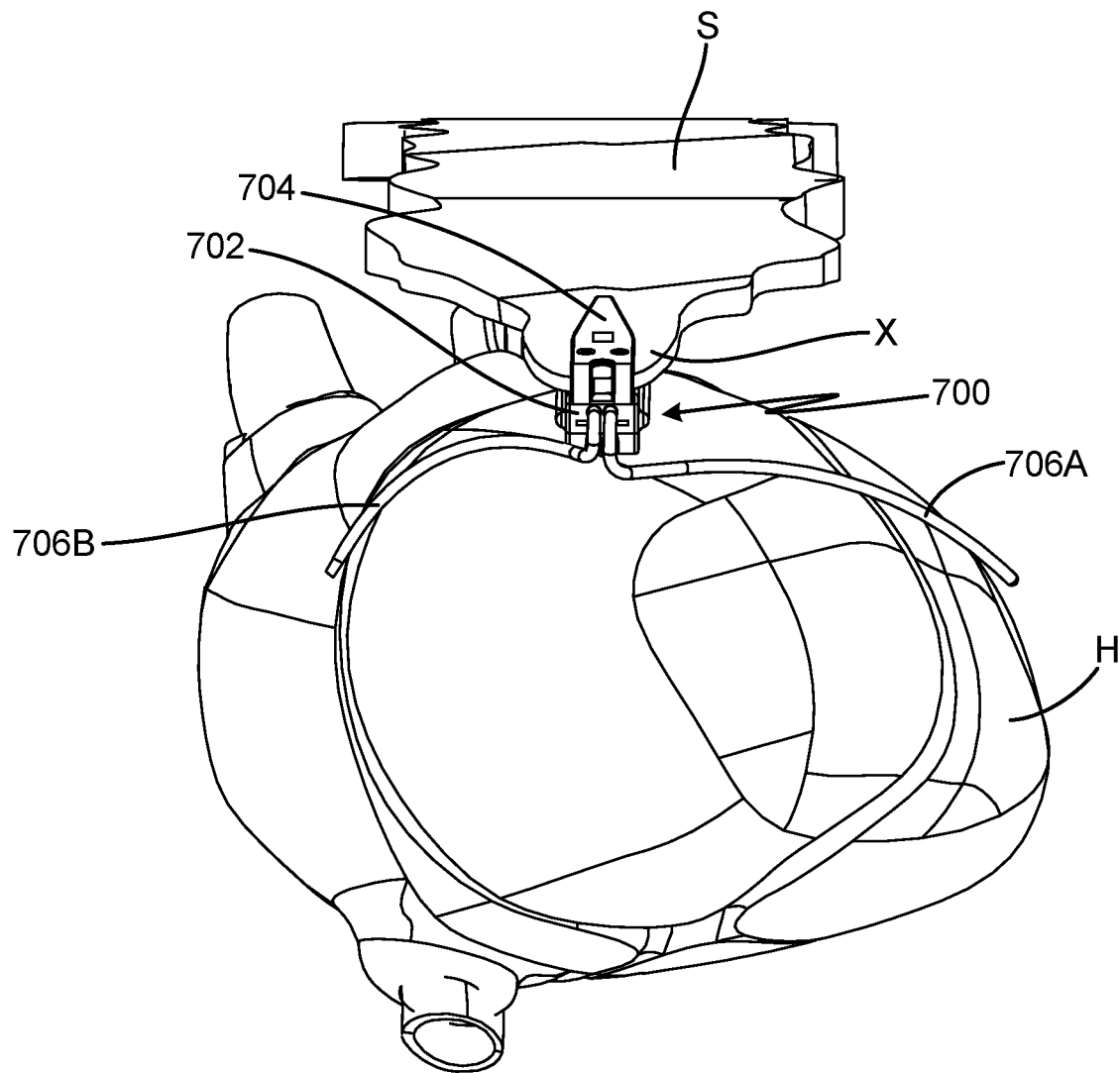

FIG. 25B is a perspective view of the fifth embodiment of the subcutaneous device positioned on the xiphoid process and the sternum and showing a positioning of the prongs around the heart.

Subcutaneous Device 800

Figure 26:
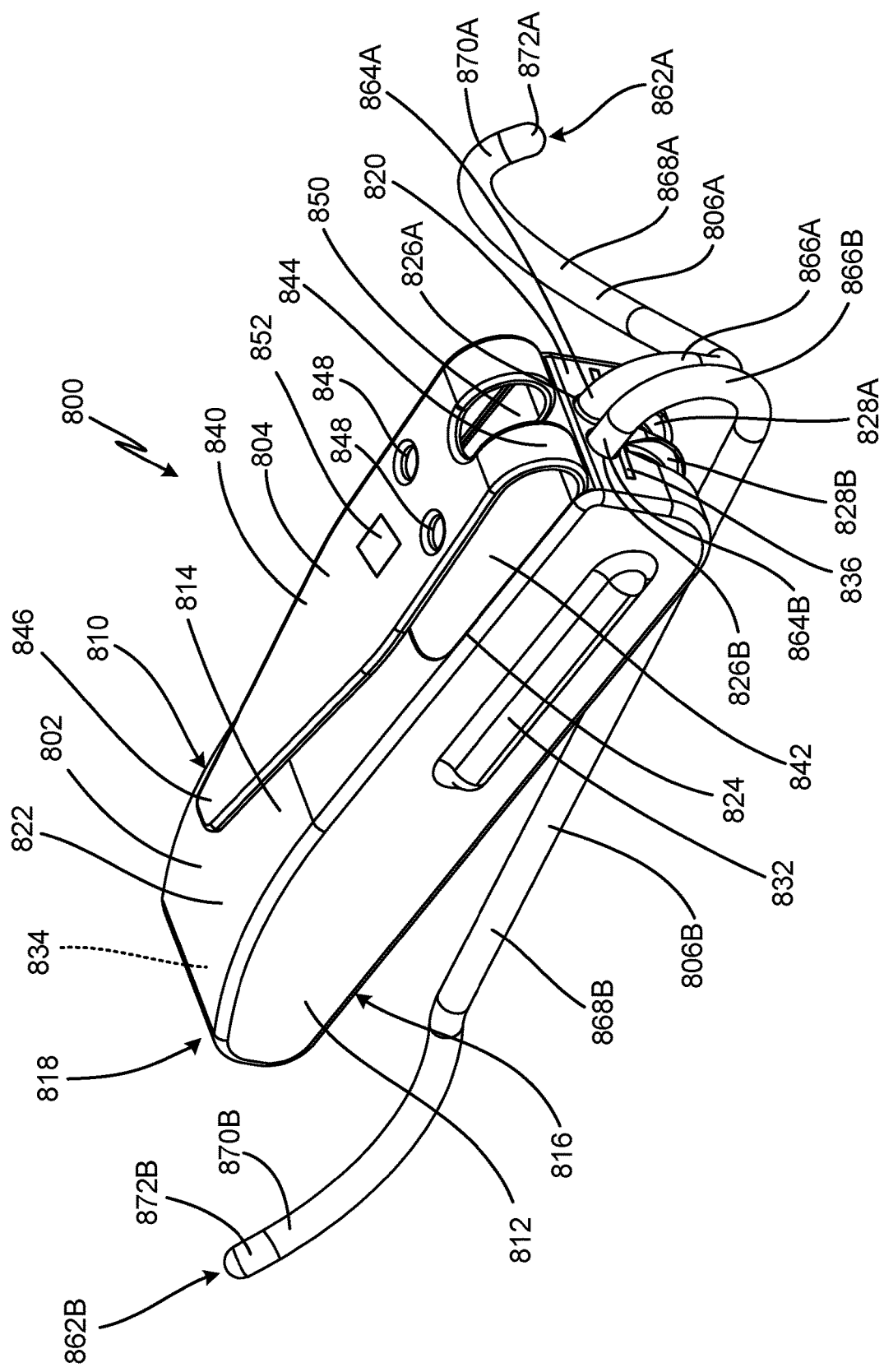

FIG. 26 is a perspective view of a sixth embodiment of a subcutaneous device.

Subcutaneous Device 900

Figure 27:
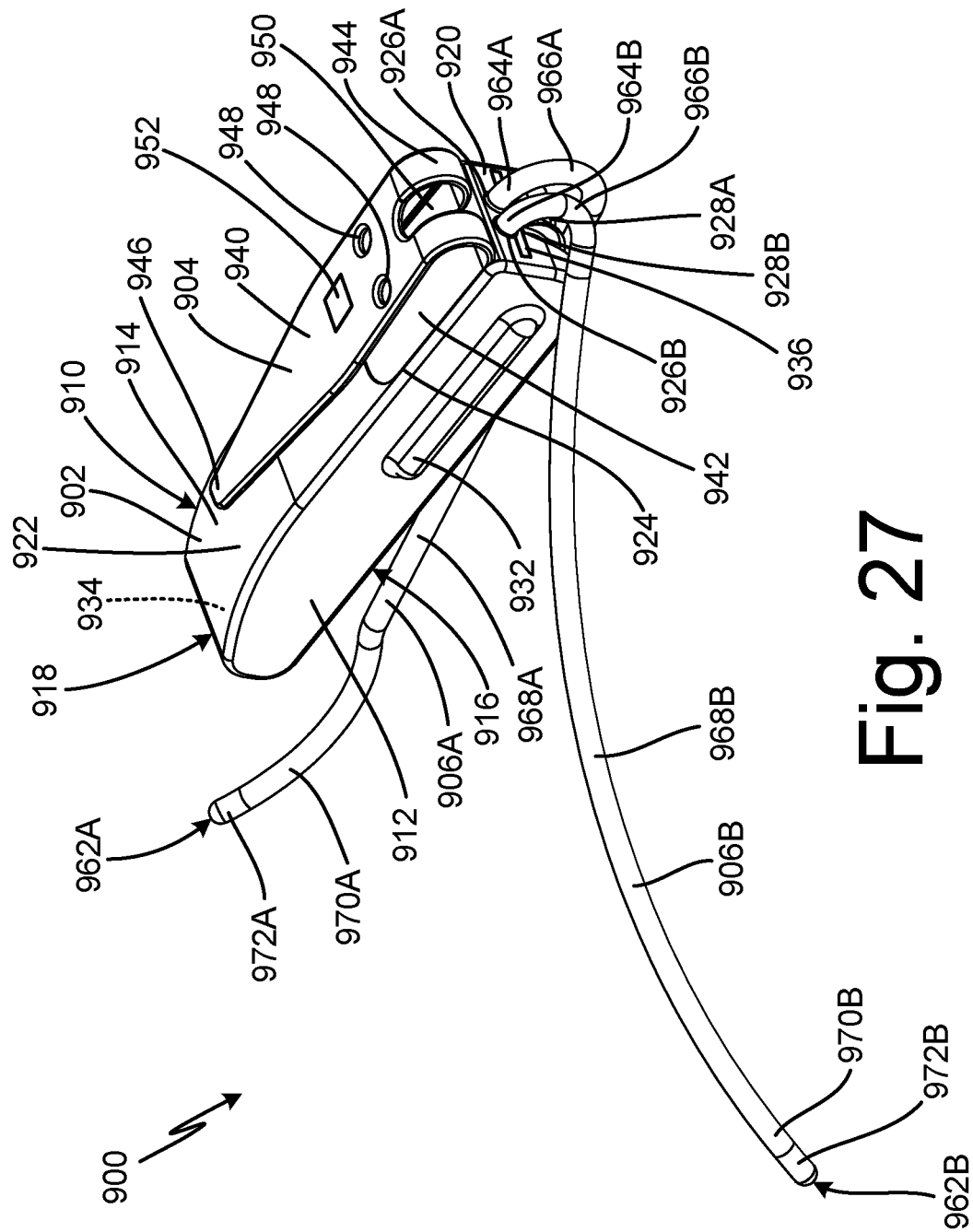

FIG. 27 is a perspective view of a seventh embodiment of a subcutaneous device.

Figure 28:
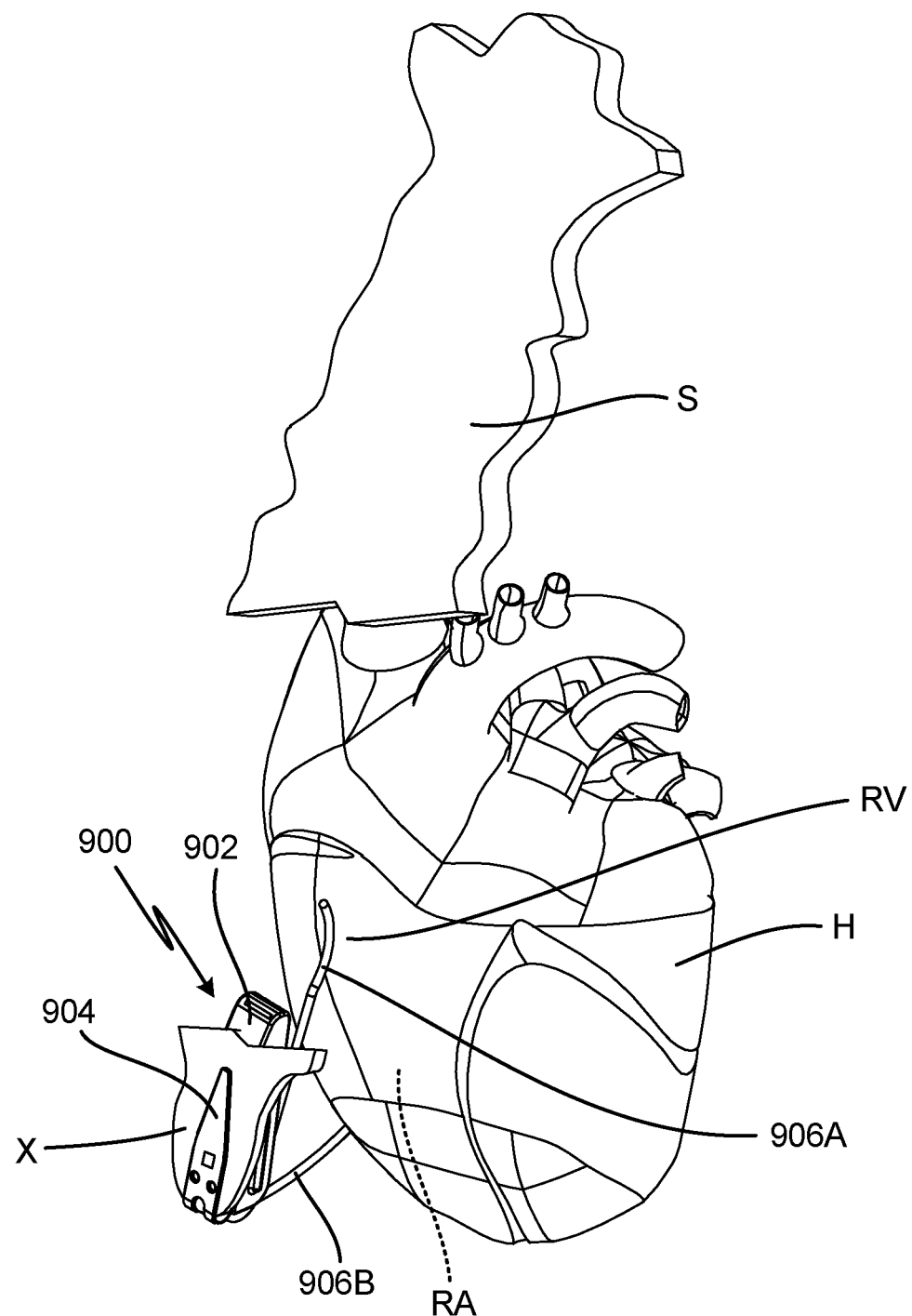

FIG. 28 is a cut-away perspective view of the seventh embodiment of the subcutaneous device positioned on a xiphoid process and a sternum and showing a positioning of prongs on a heart.

Subcutaneous Device 1000

Figure 29:
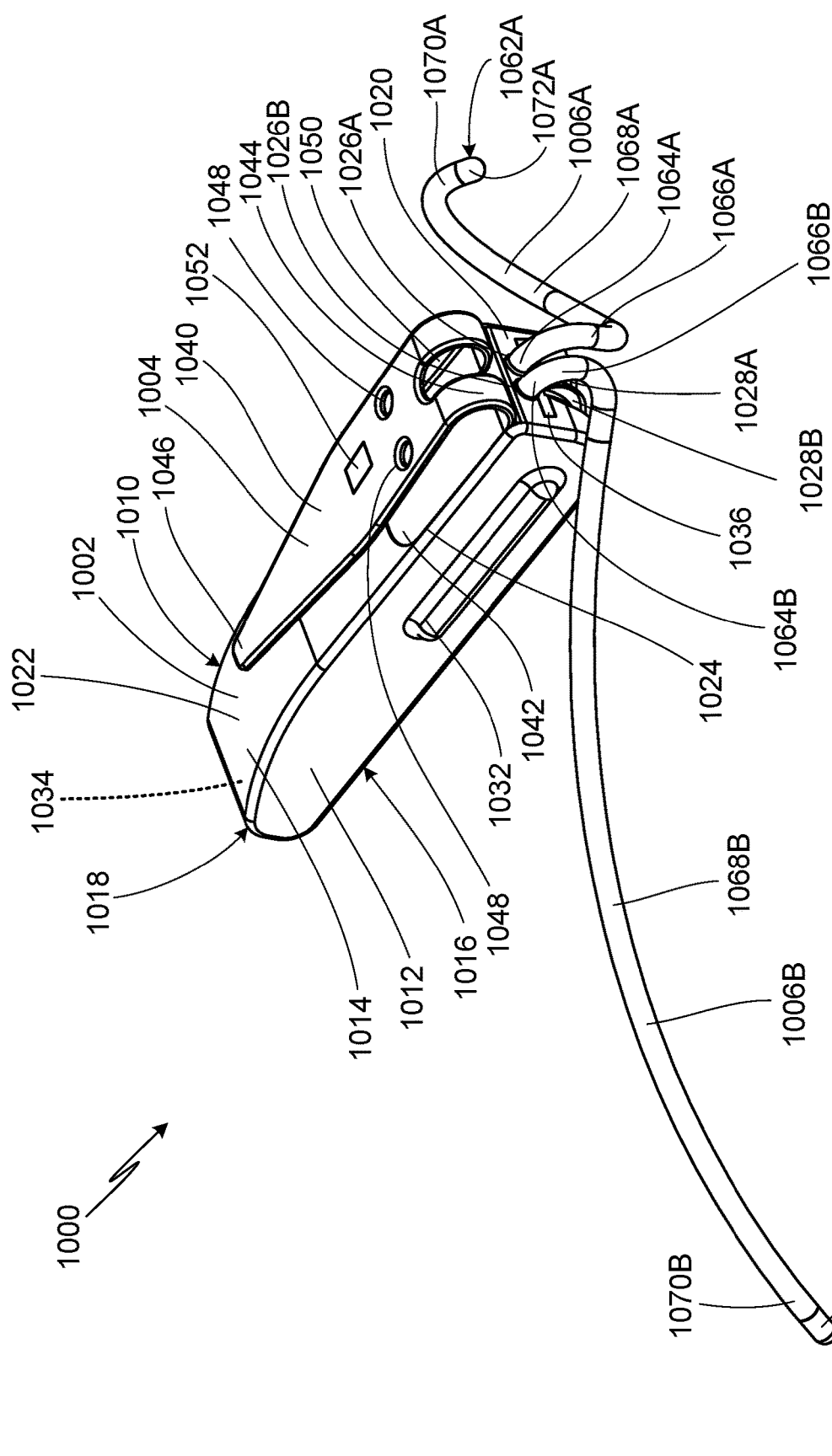

FIG. 29 is a perspective view of an eighth embodiment of a subcutaneous device.

Subcutaneous Device 1100

Figure 30:
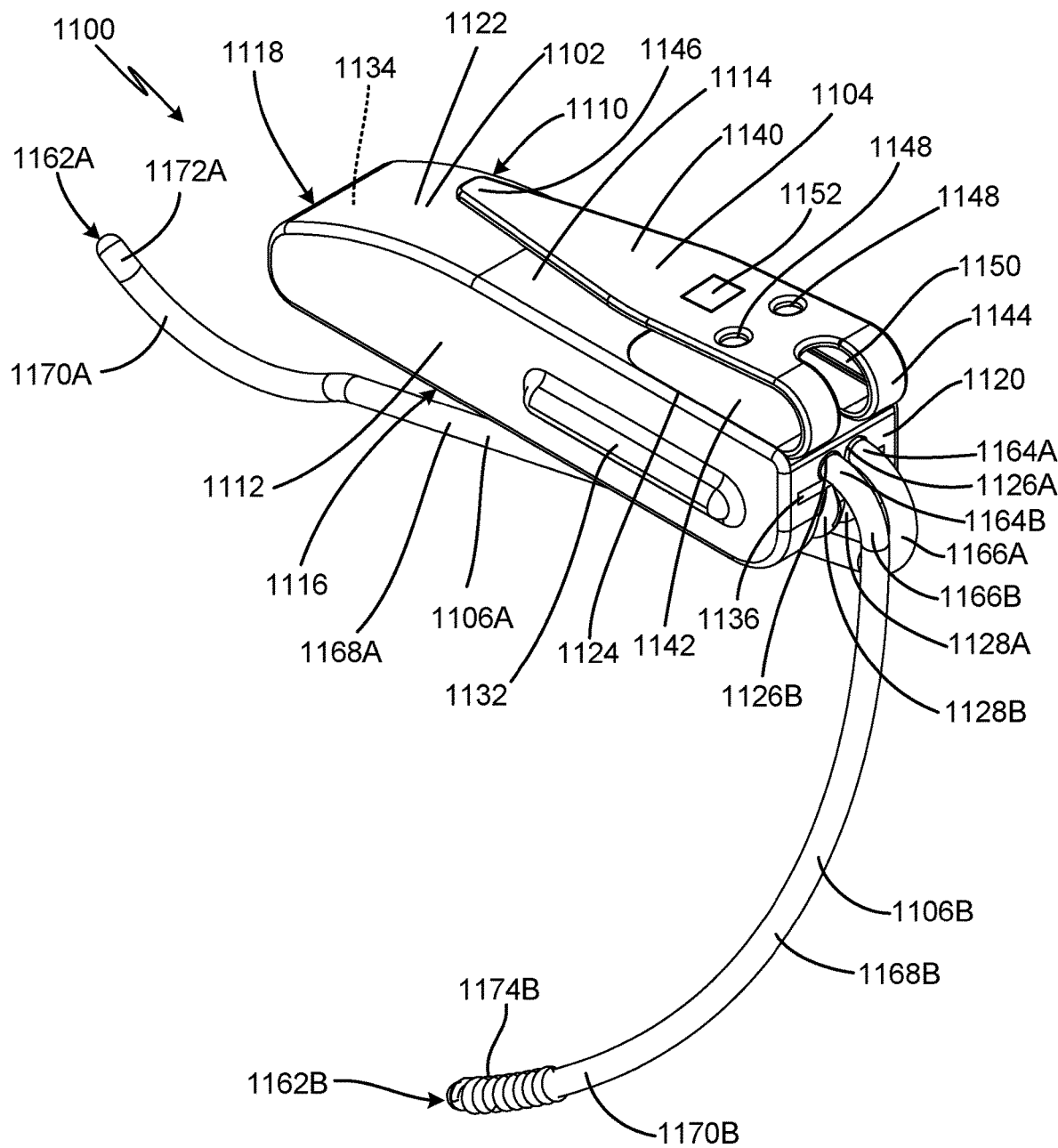

FIG. 30 is a perspective view of a ninth embodiment of a subcutaneous device.

Subcutaneous Device 1200

Figure 31A:
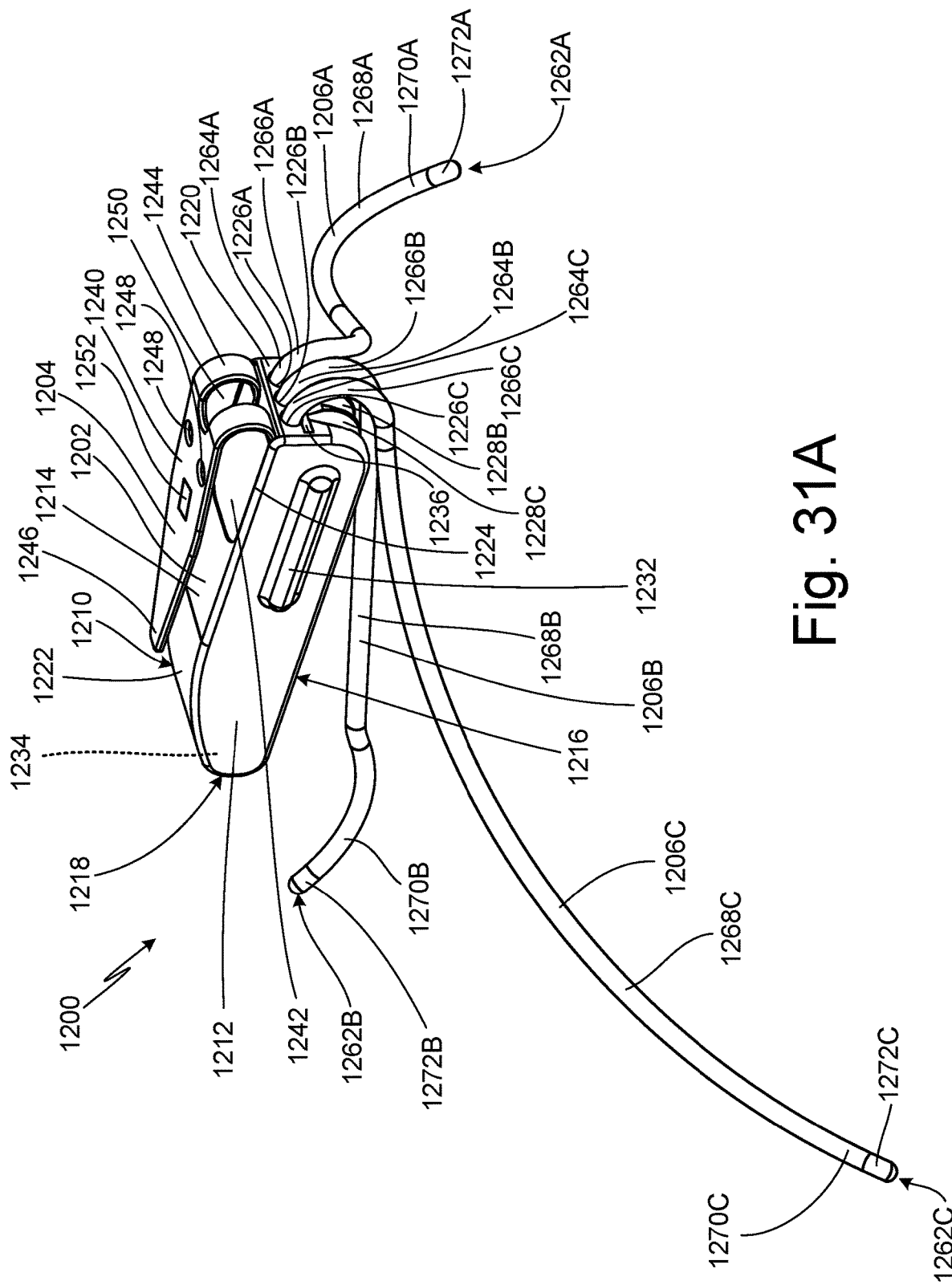

FIG. 31A is a perspective view of a tenth embodiment of a subcutaneous device.

Figure 31B:
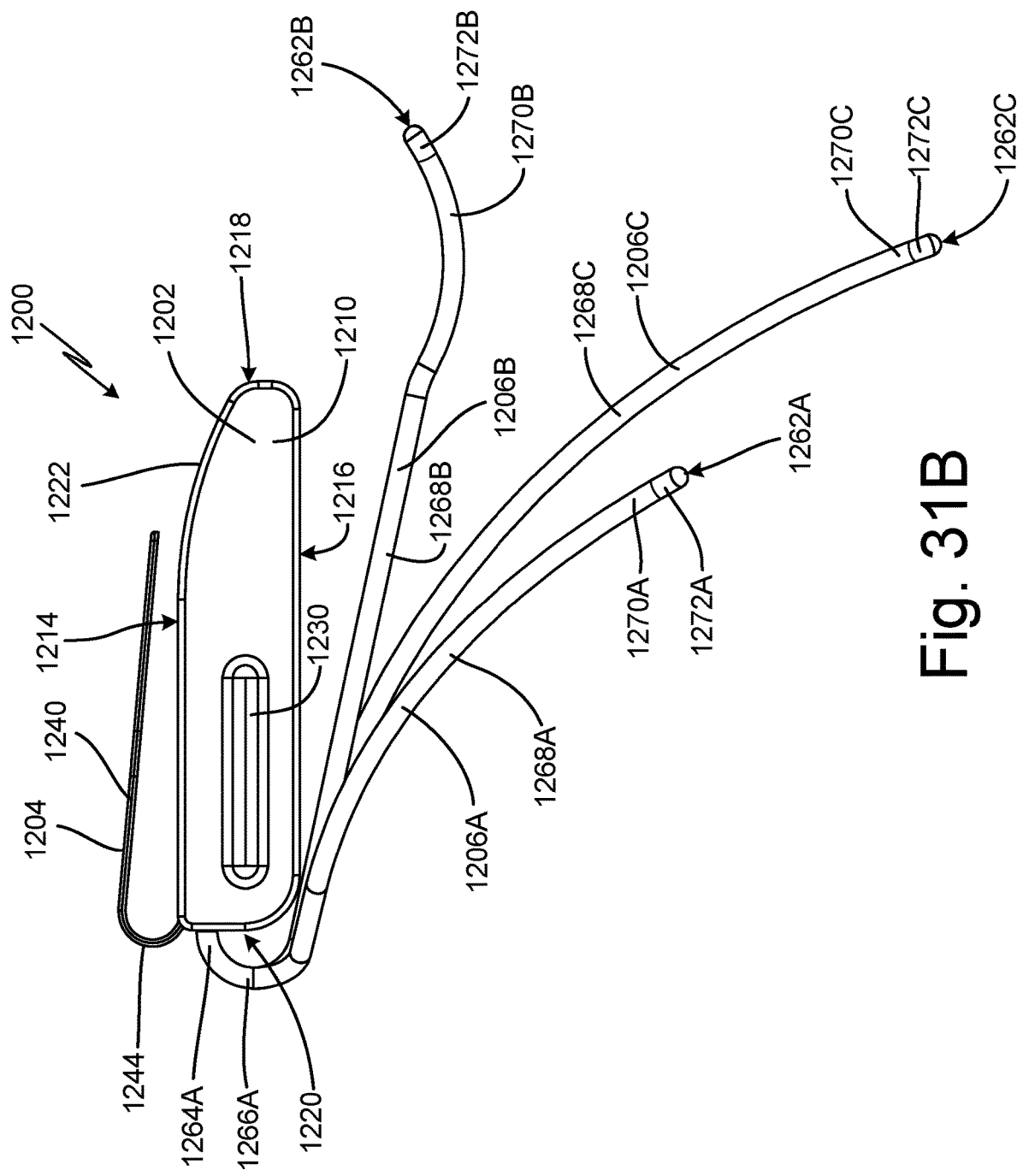

FIG. 31B is a side view of the tenth embodiment of the subcutaneous device.

Figure 31C:
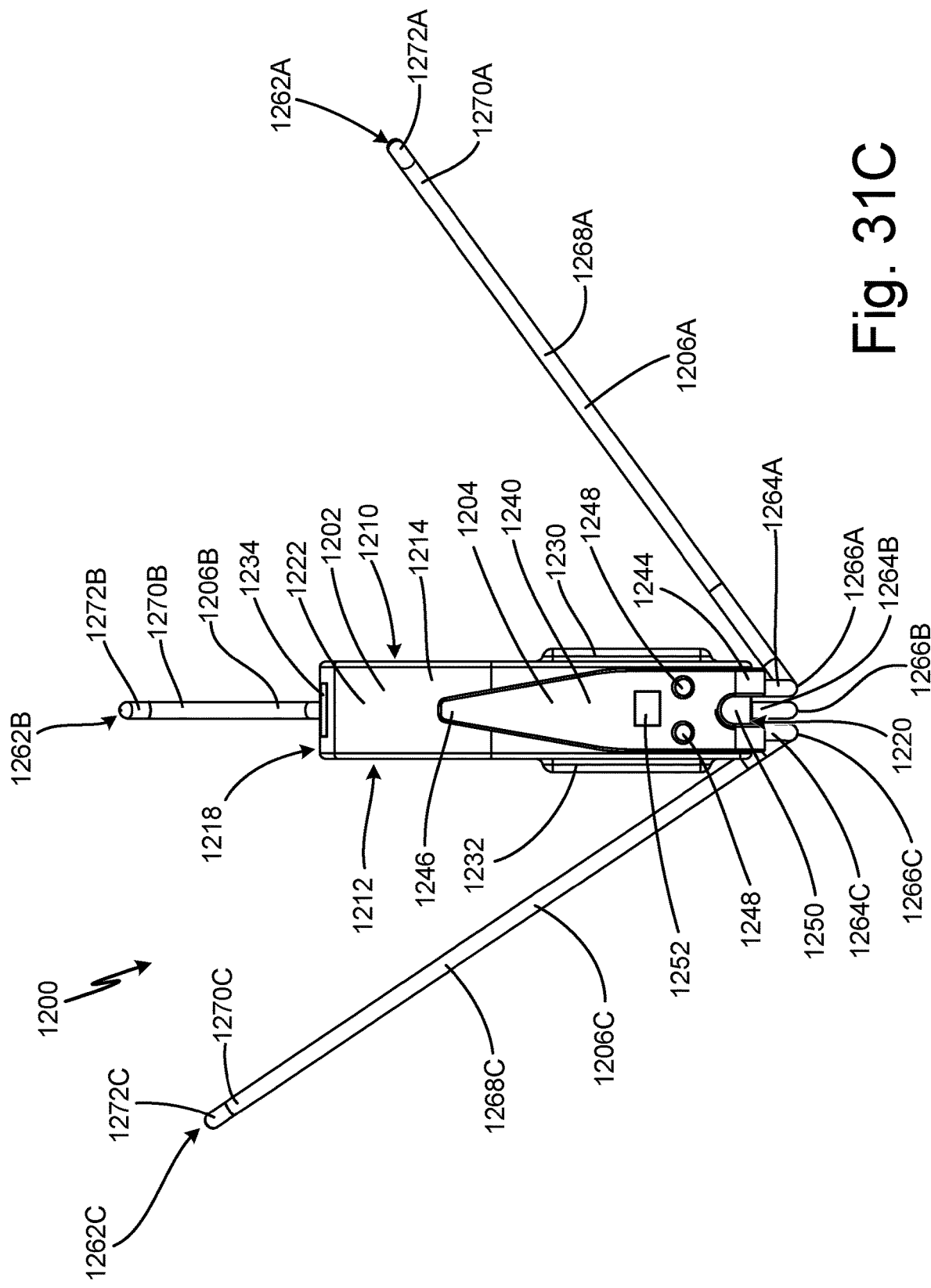

FIG. 31C is a top view of the tenth embodiment of the subcutaneous device.

Figure 31D:
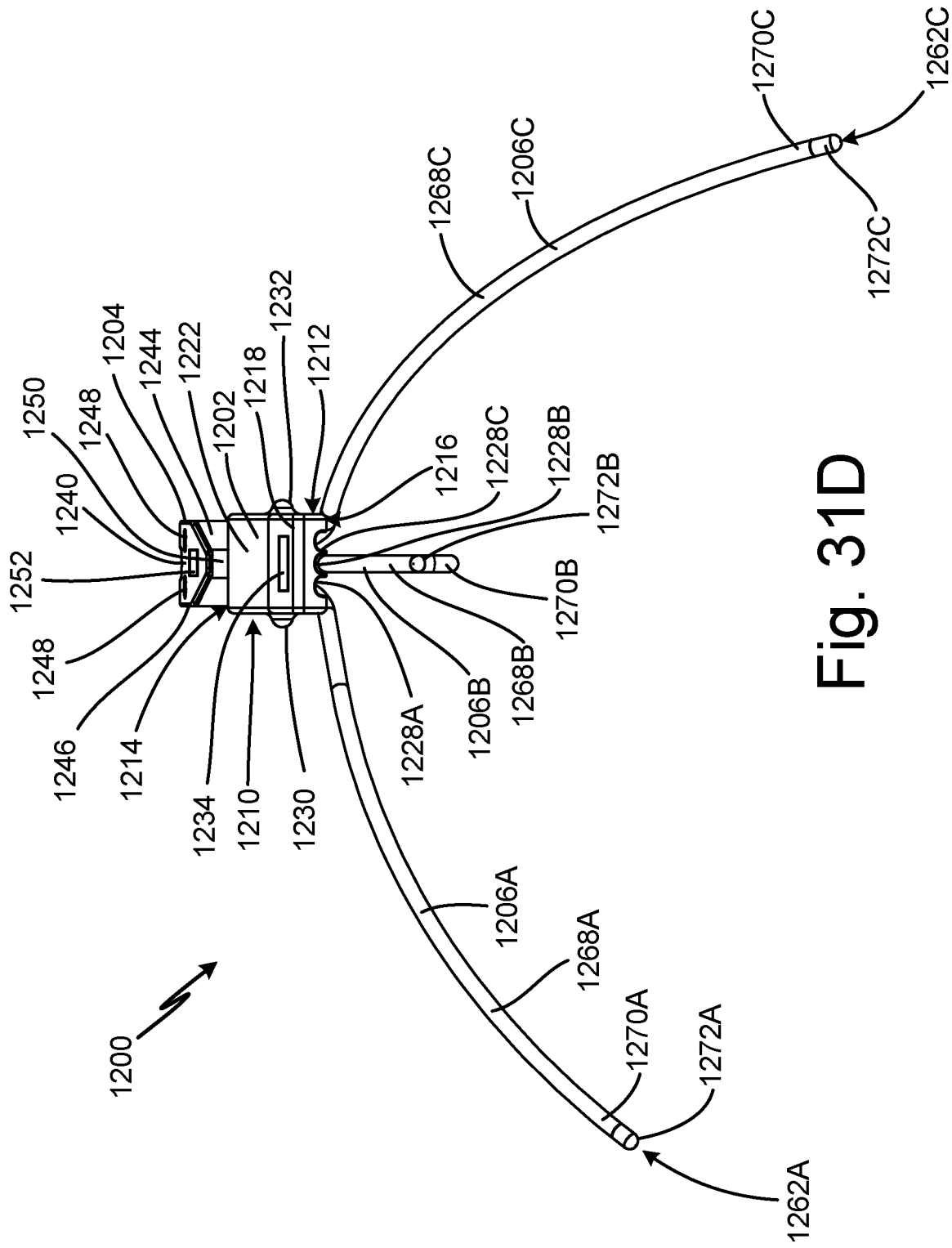

FIG. 31D is a front view of the tenth embodiment of the subcutaneous device.

Figure 31E:
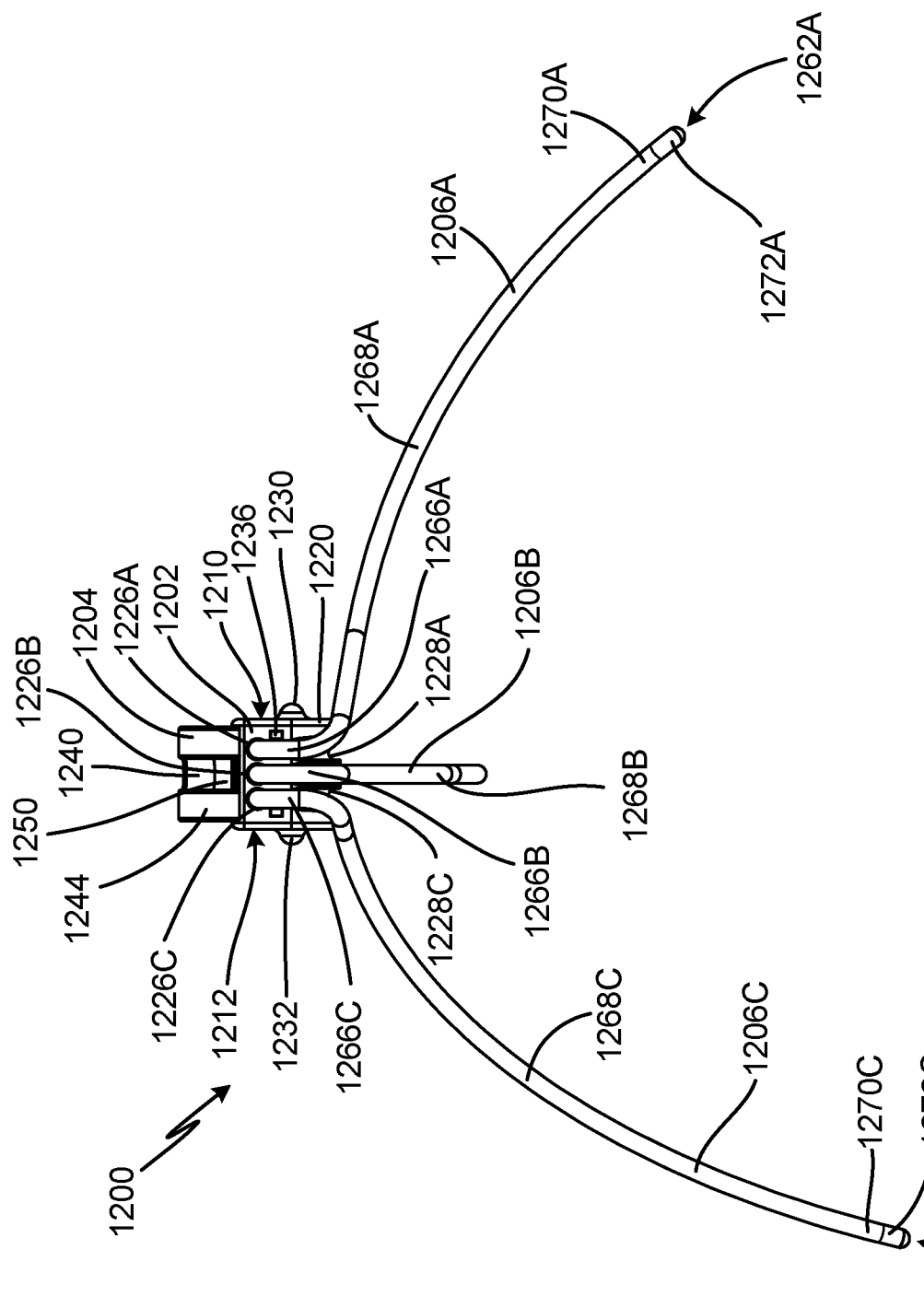

FIG. 31E is a back view of the tenth embodiment of the subcutaneous device.

Figure 32A:
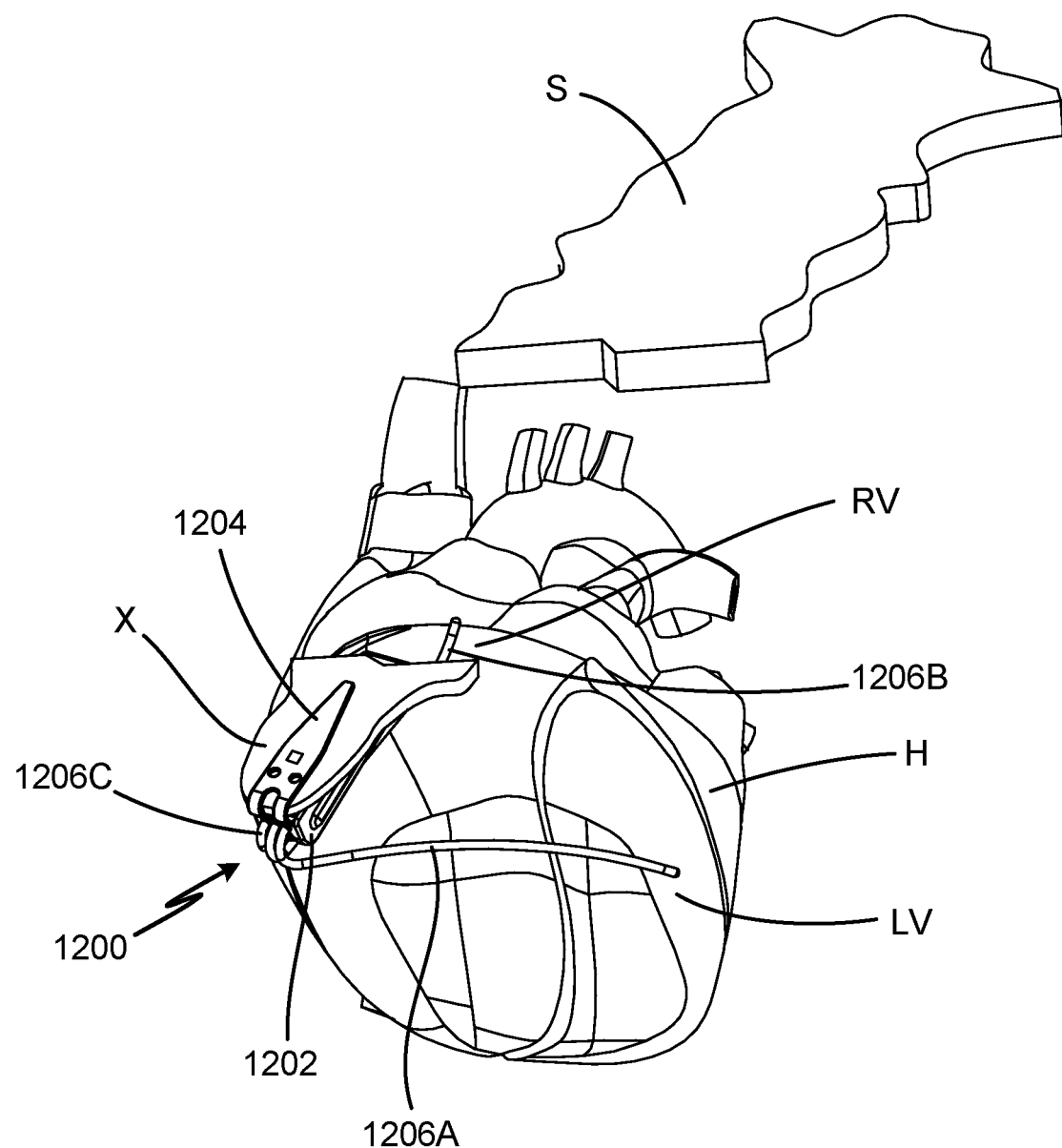

FIG. 32A is a cut-away perspective view of the tenth embodiment of the subcutaneous device positioned on a xiphoid process and a sternum and showing a positioning of prongs on a heart.

Figure 32B:
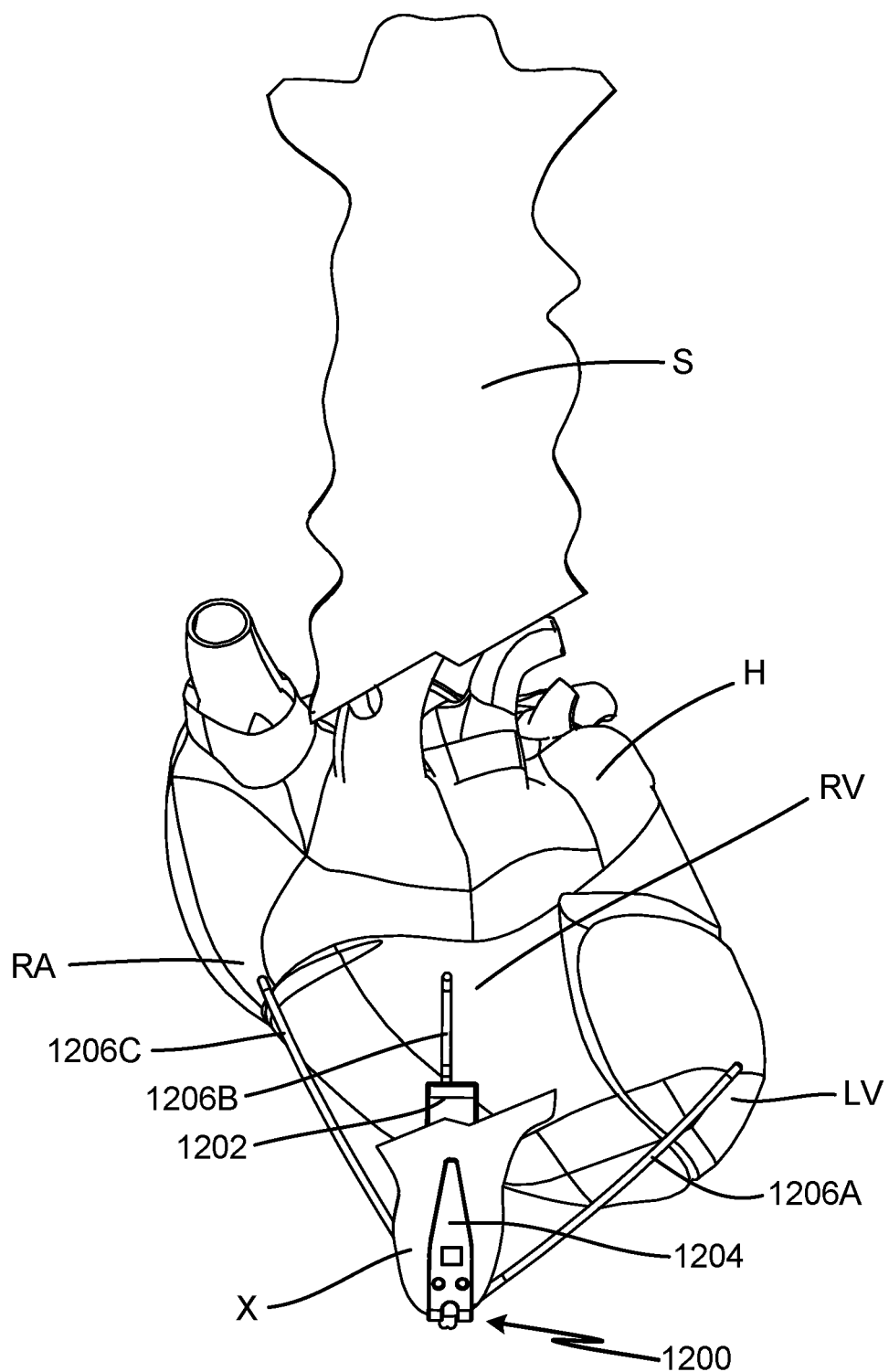

FIG. 32B is a cut-away front view of the tenth embodiment of the subcutaneous device positioned on the xiphoid process and the sternum and showing a positioning of the prongs on the heart.

Figure 32C:
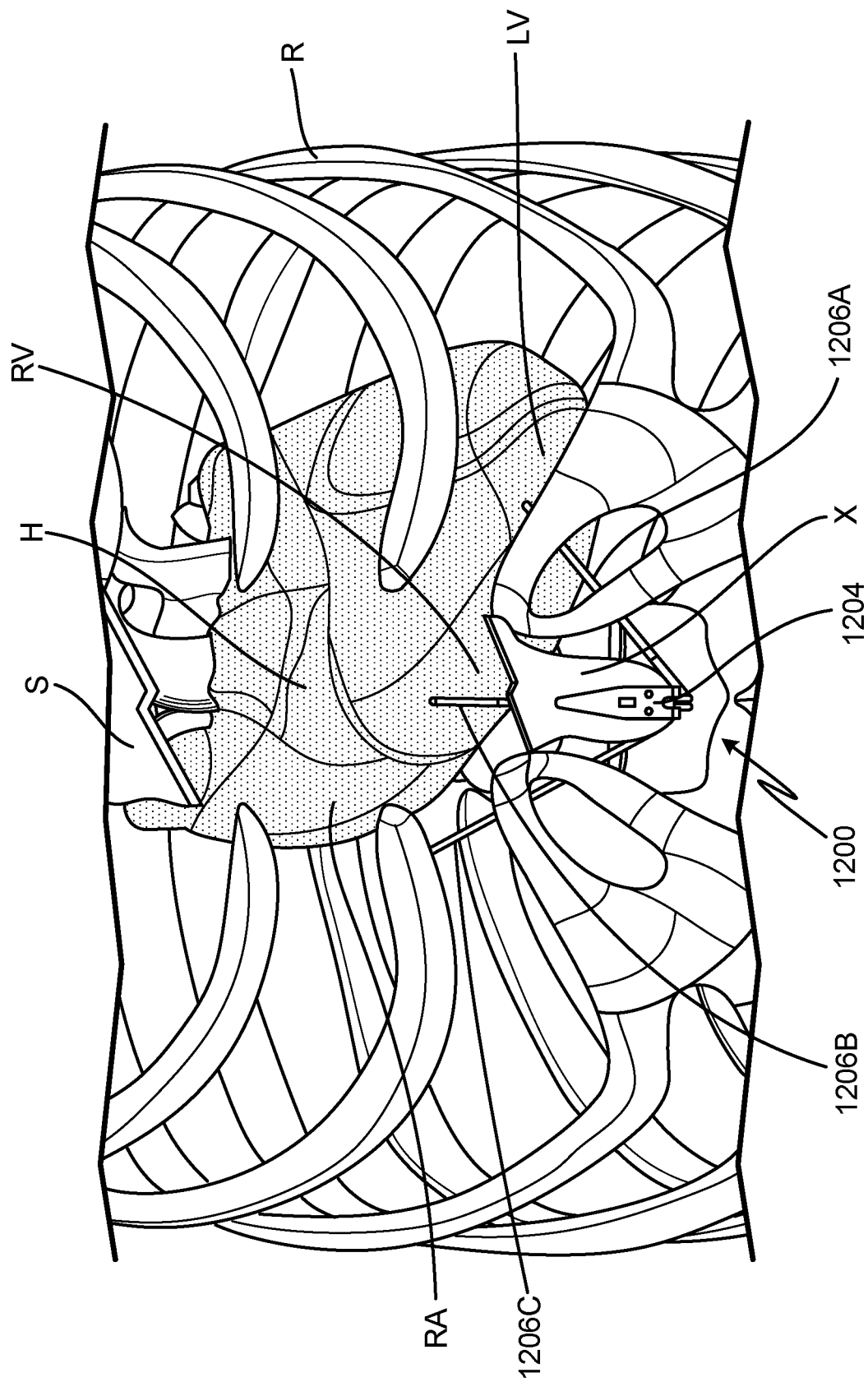

FIG. 32C is a cut-away front view of the tenth embodiment of the subcutaneous device positioned on the xiphoid process and the sternum and showing a positioning of the prongs on the heart.

Subcutaneous Device 1300

Figure 33:
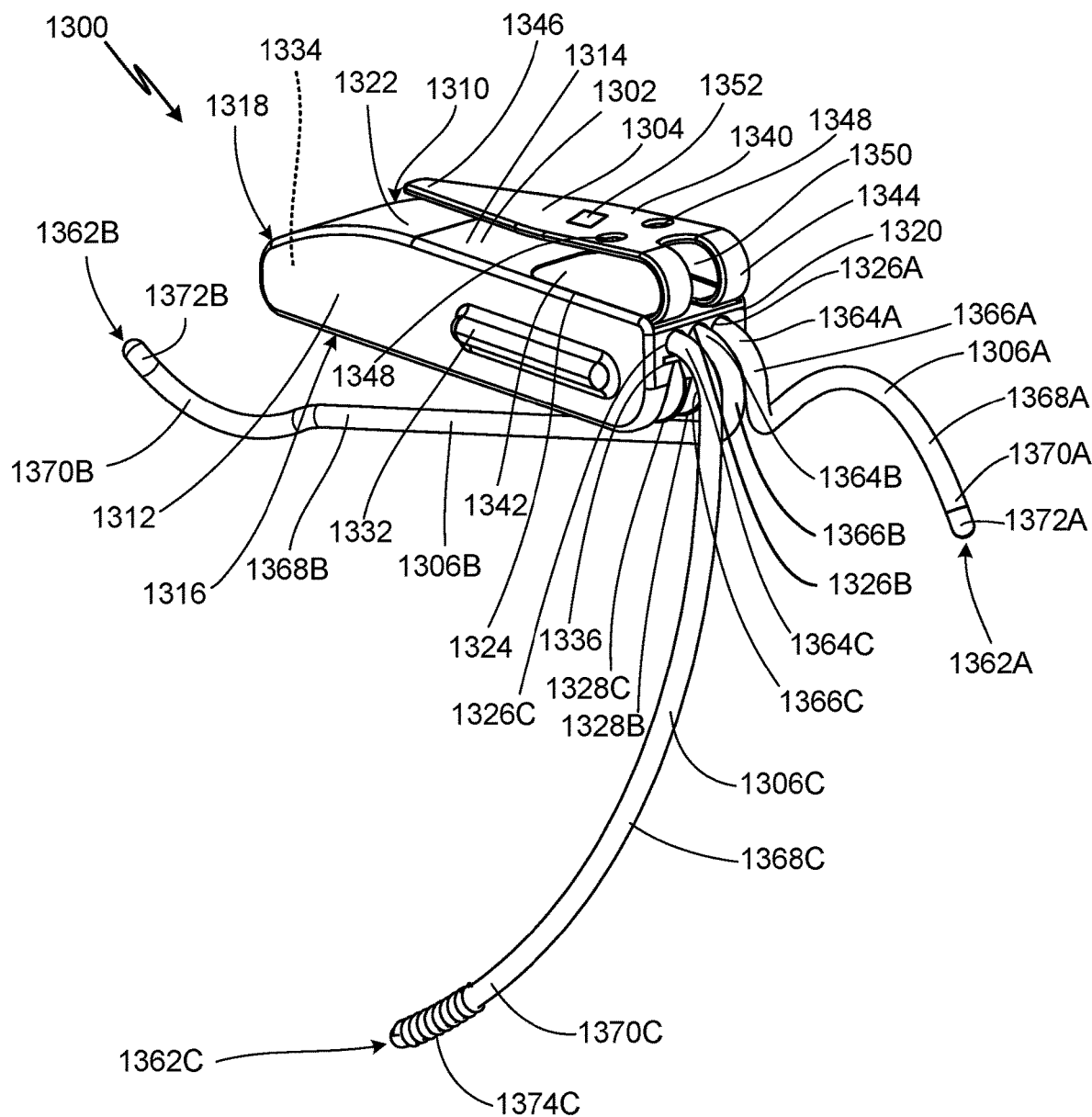

FIG. 33 is a perspective view of an eleventh embodiment of a subcutaneous device.

Subcutaneous Device 1400

Figure 34A:
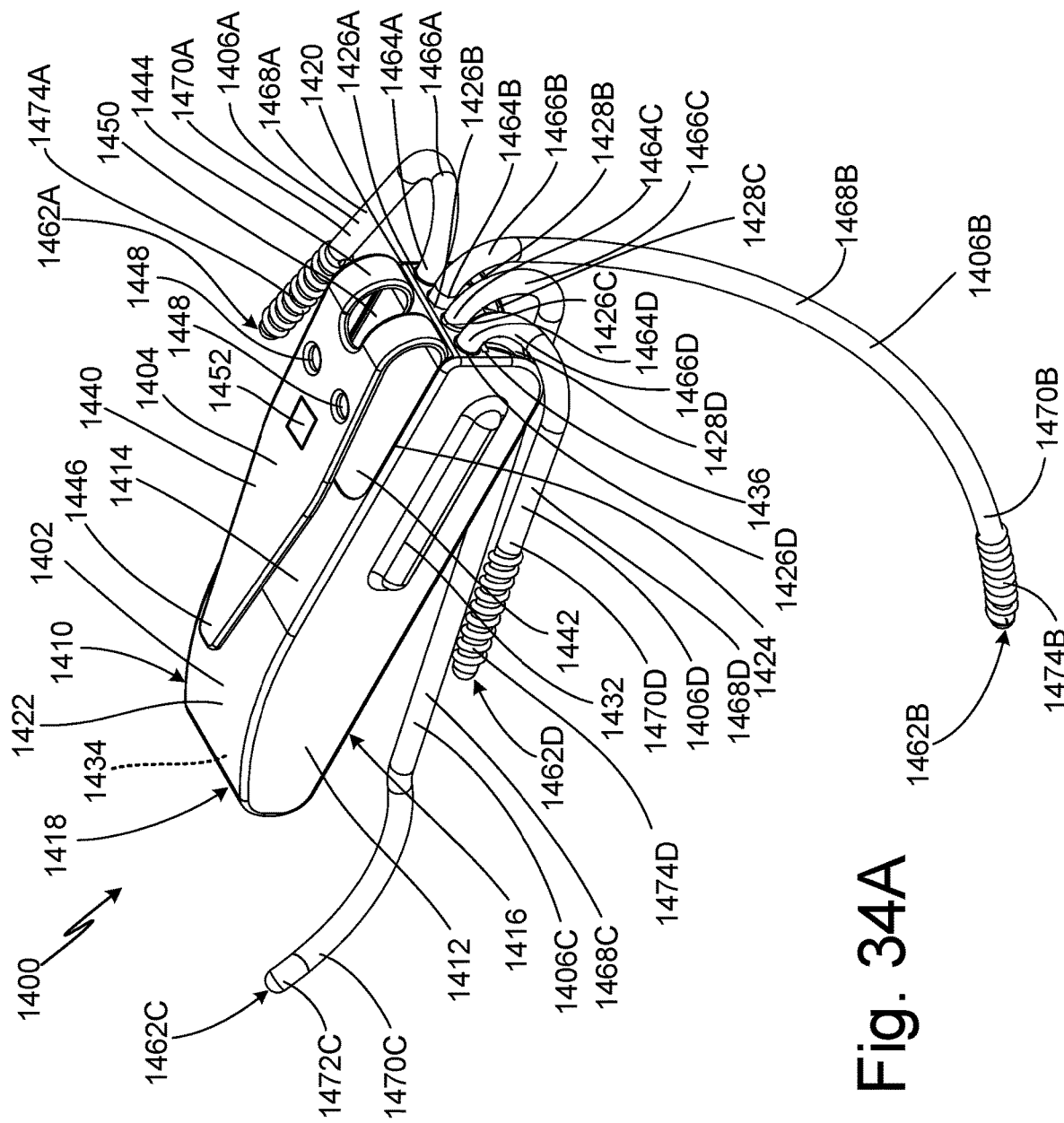

FIG. 34A is a perspective view of a twelfth embodiment of a subcutaneous device.

Figure 34B:
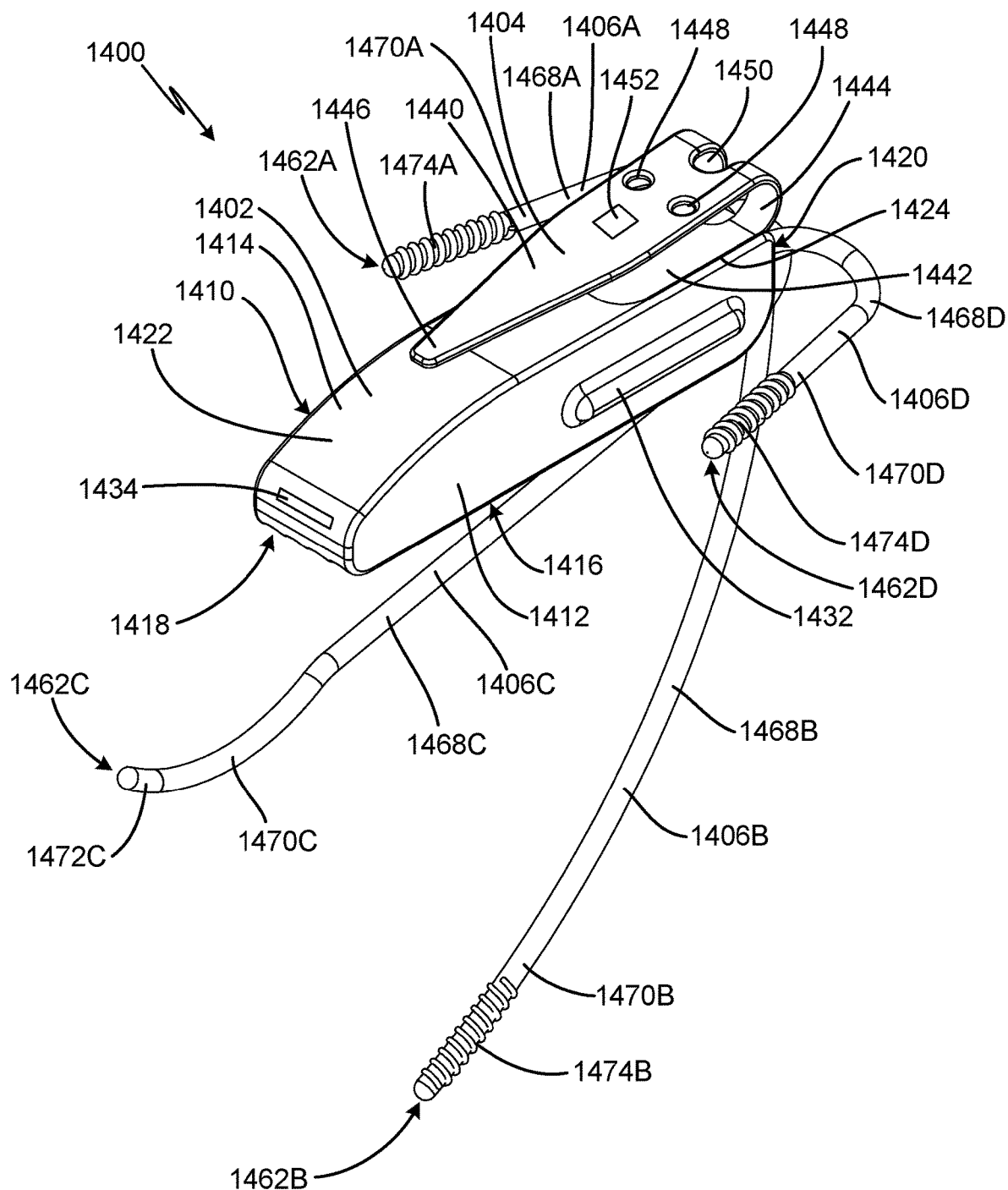

FIG. 34B is a perspective view of the twelfth embodiment of the subcutaneous device.

Figure 34C:
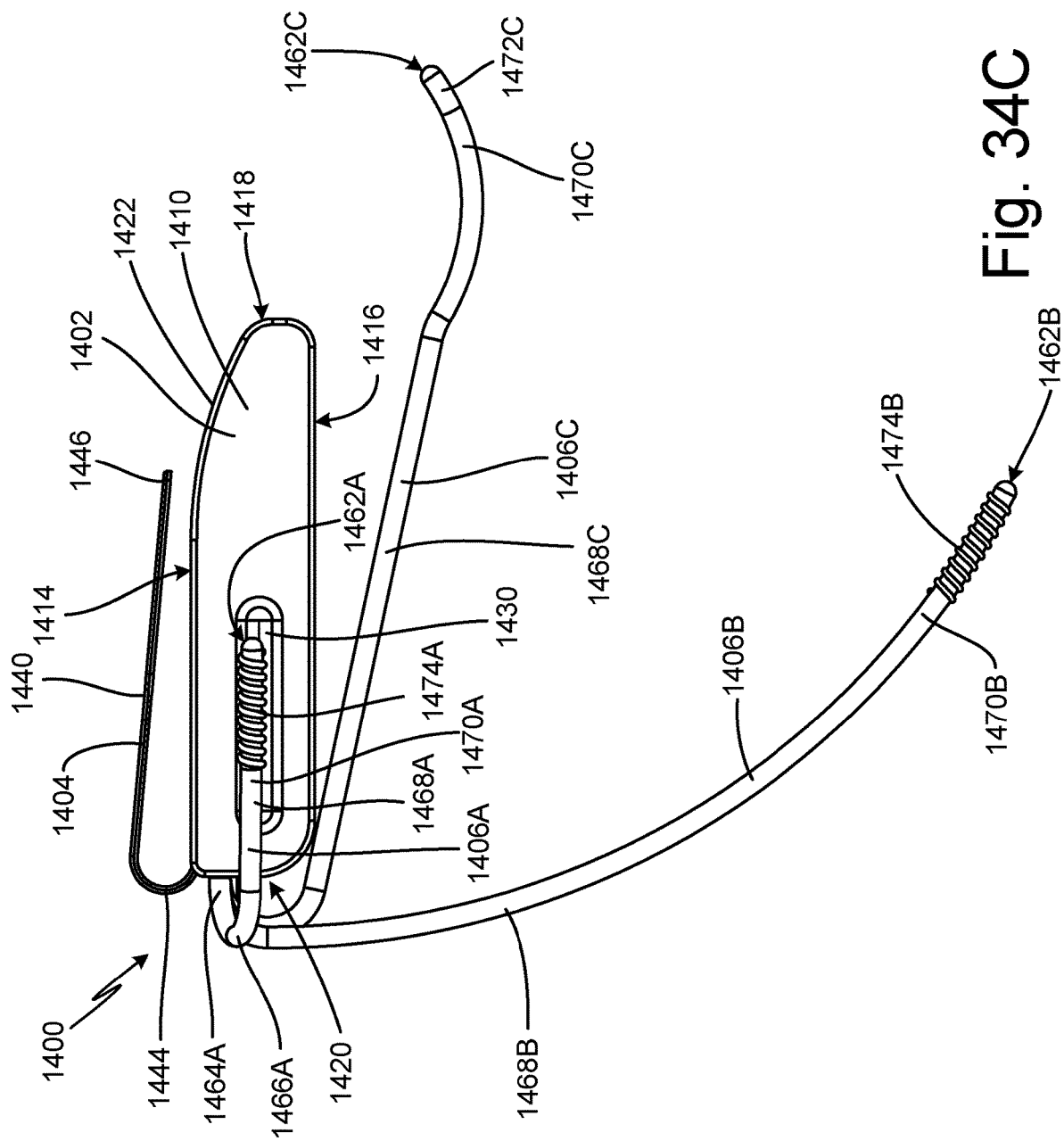

FIG. 34C is a side view of the twelfth embodiment of the subcutaneous device.

Subcutaneous Device 1500

Figure 35A:
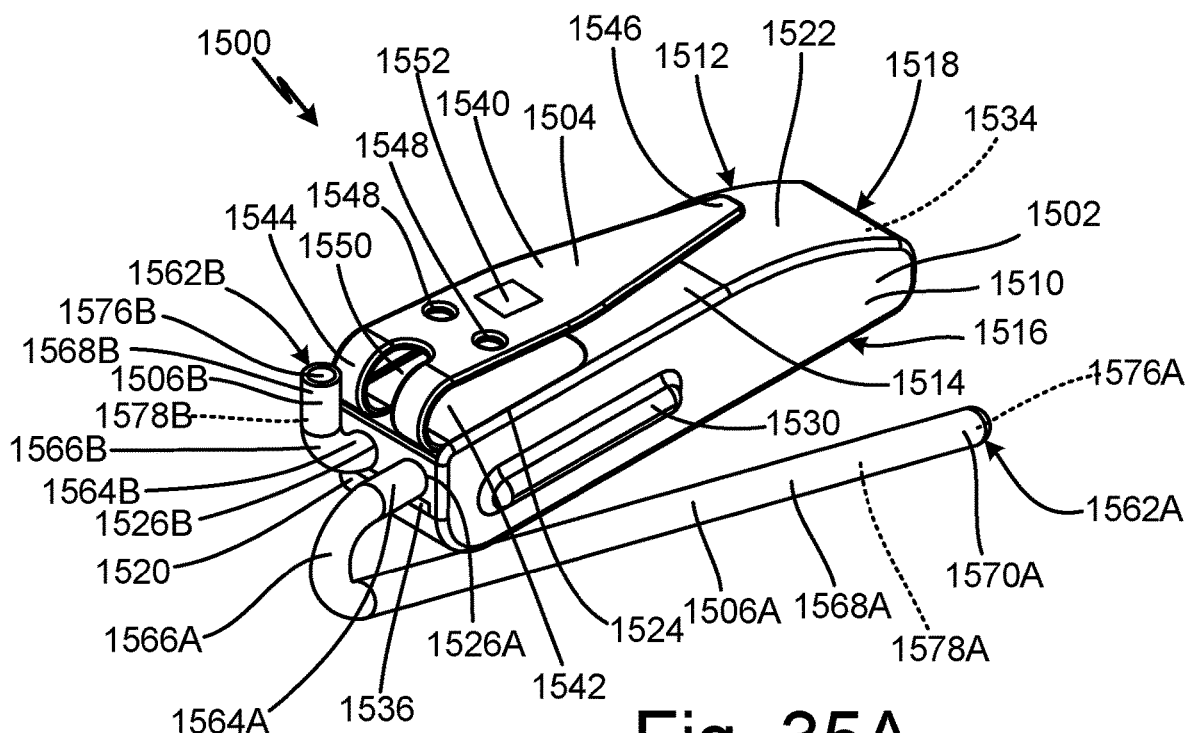

FIG. 35A is a perspective view of a thirteenth embodiment of a subcutaneous device.

Figure 35B:
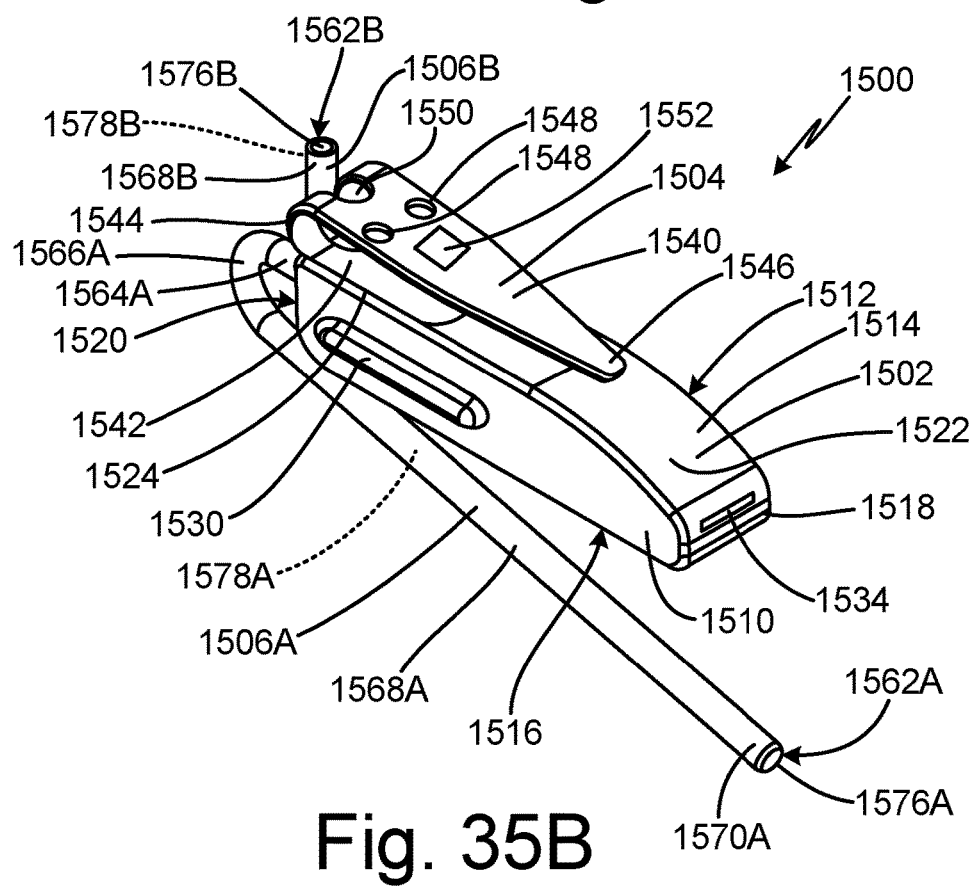

FIG. 35B is a perspective view of the thirteenth embodiment of the subcutaneous device.

Figure 35C:
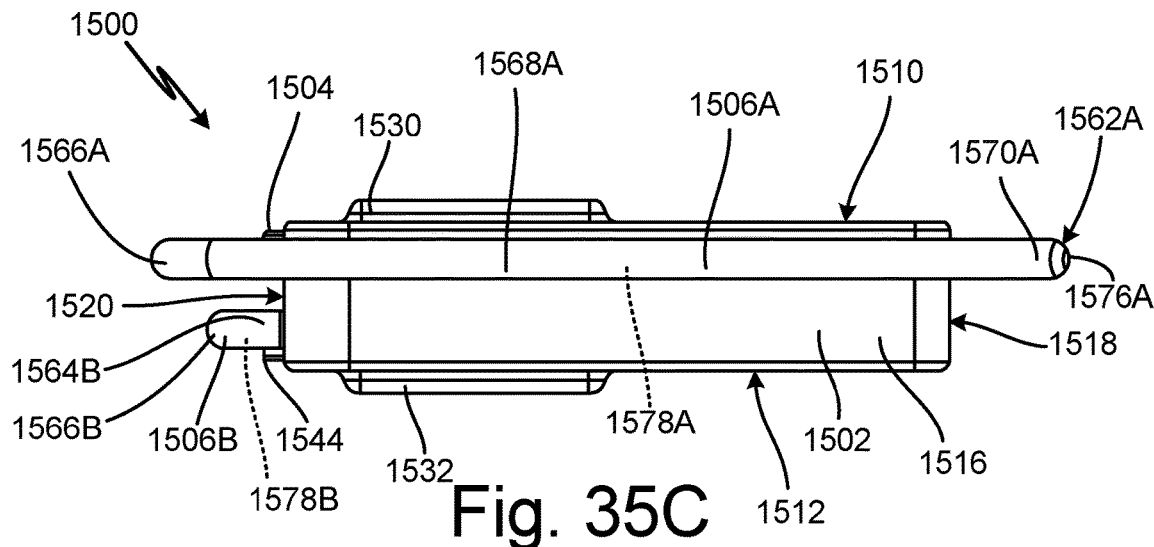

FIG. 35C is a bottom view of the thirteenth embodiment of the subcutaneous device.

Figure 35D:
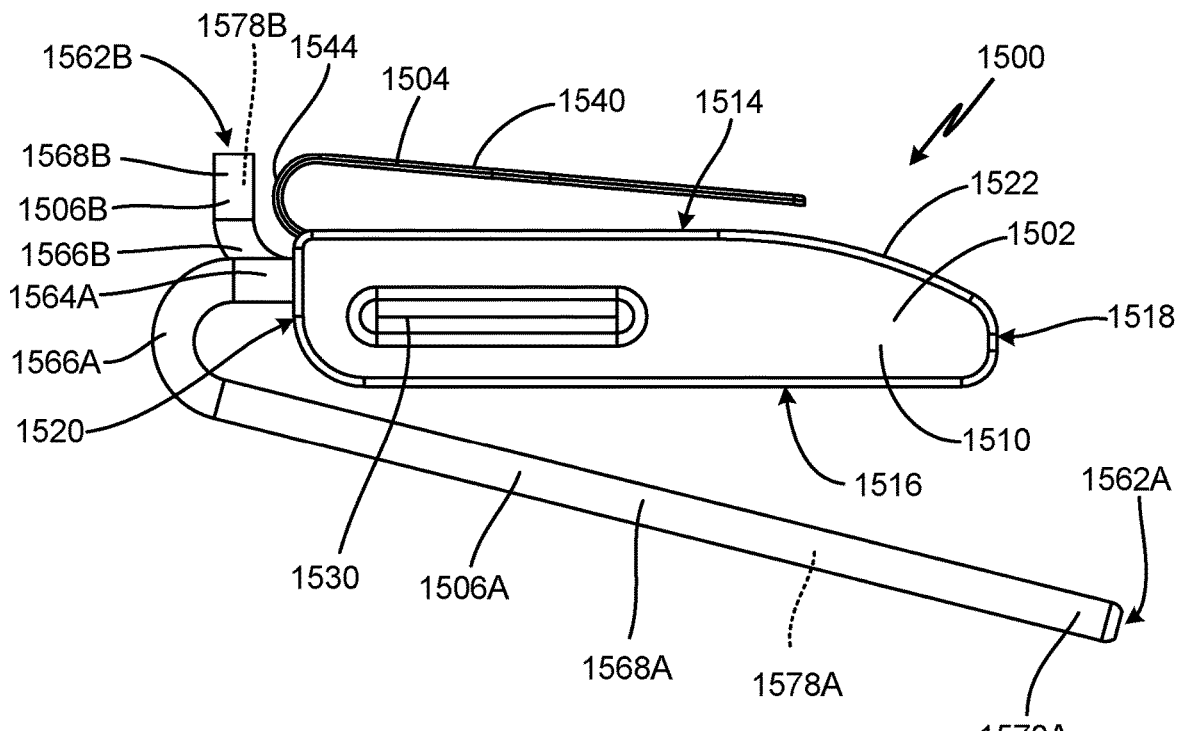

FIG. 35D is a side view of the thirteenth embodiment of the subcutaneous device.

Figures 35E, 35F:
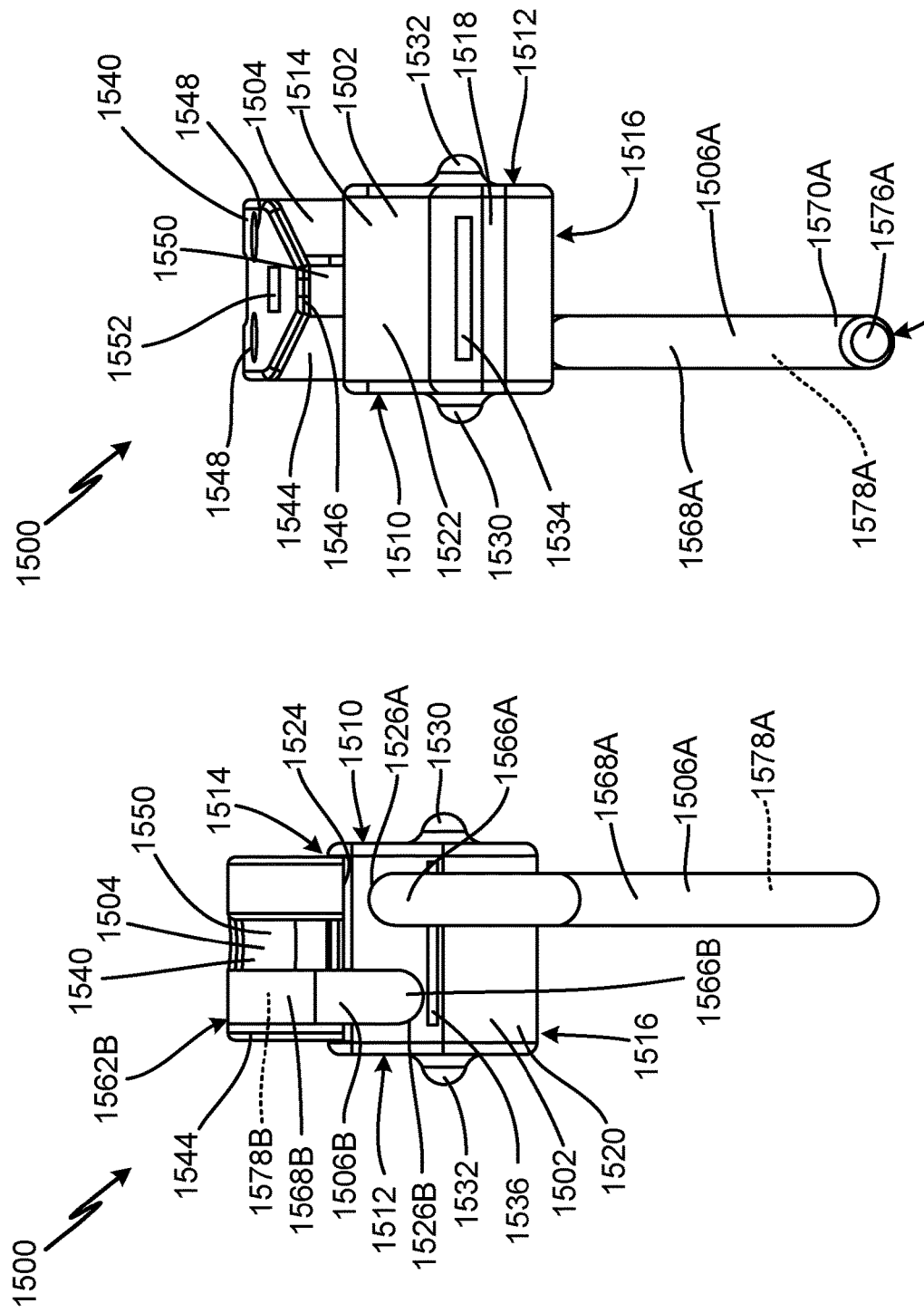

FIG. 35E is a back view of the thirteenth embodiment of the subcutaneous device.

FIG. 35F is a front view of the thirteenth embodiment of the subcutaneous device.

Figure 36A:
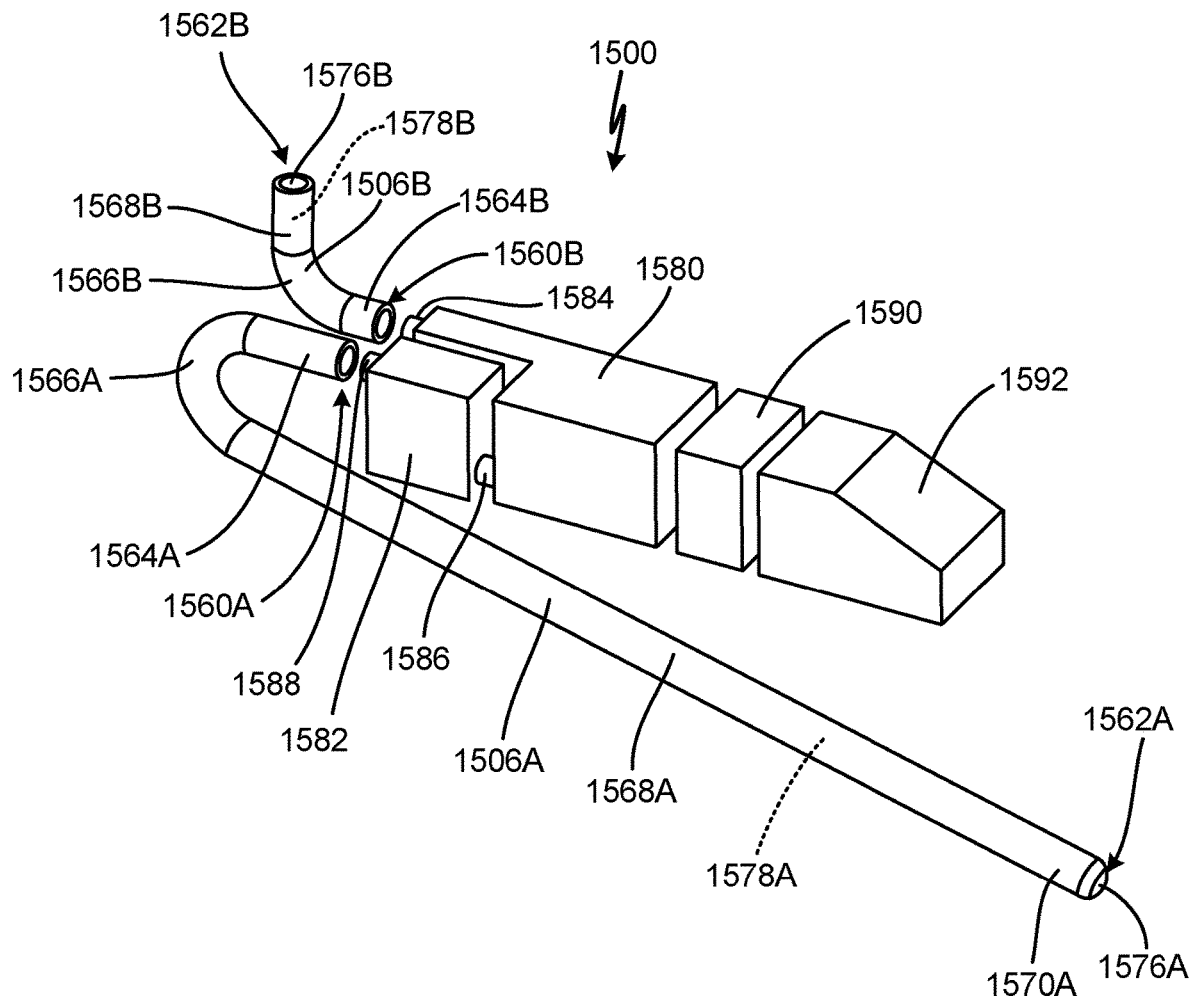

FIG. 36A is a schematic diagram of the thirteenth embodiment of the subcutaneous device.

Figure 36B:
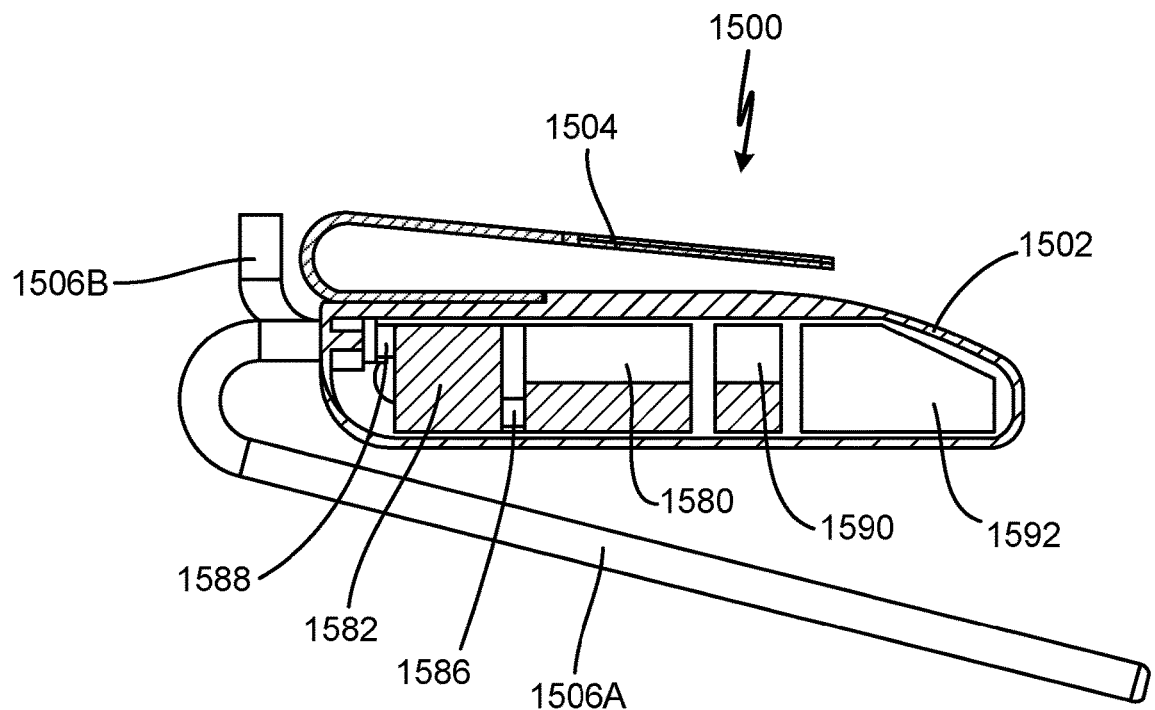

FIG. 36B is a sectional diagram illustrating portions of the thirteenth embodiment of the subcutaneous device from the side.

Figure 36C:
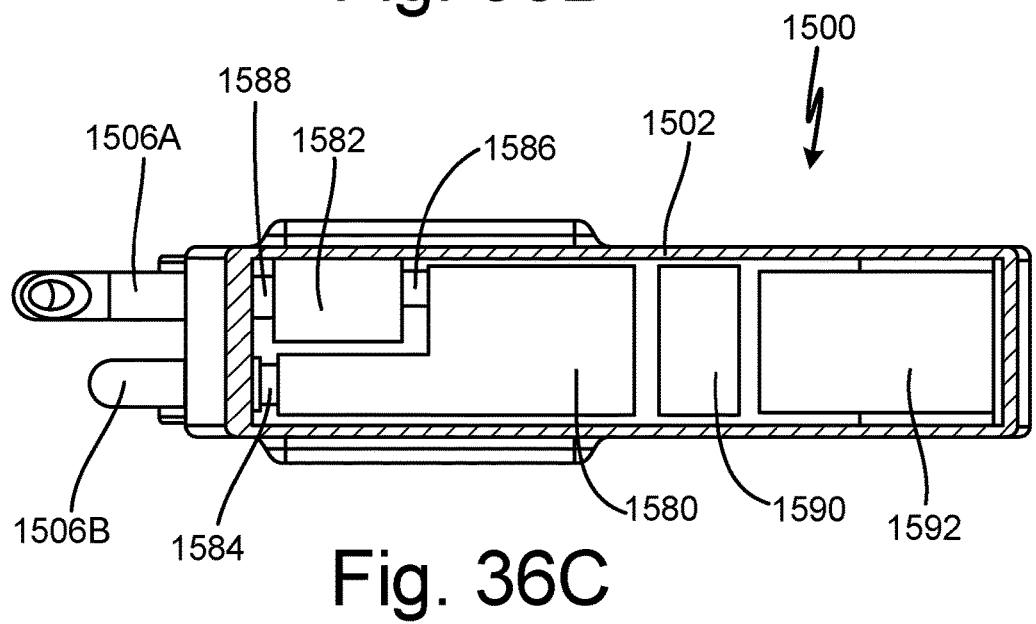

FIG. 36C is a sectional diagram illustrating portions of the thirteenth embodiment of the subcutaneous device from the bottom.

Figure 37:
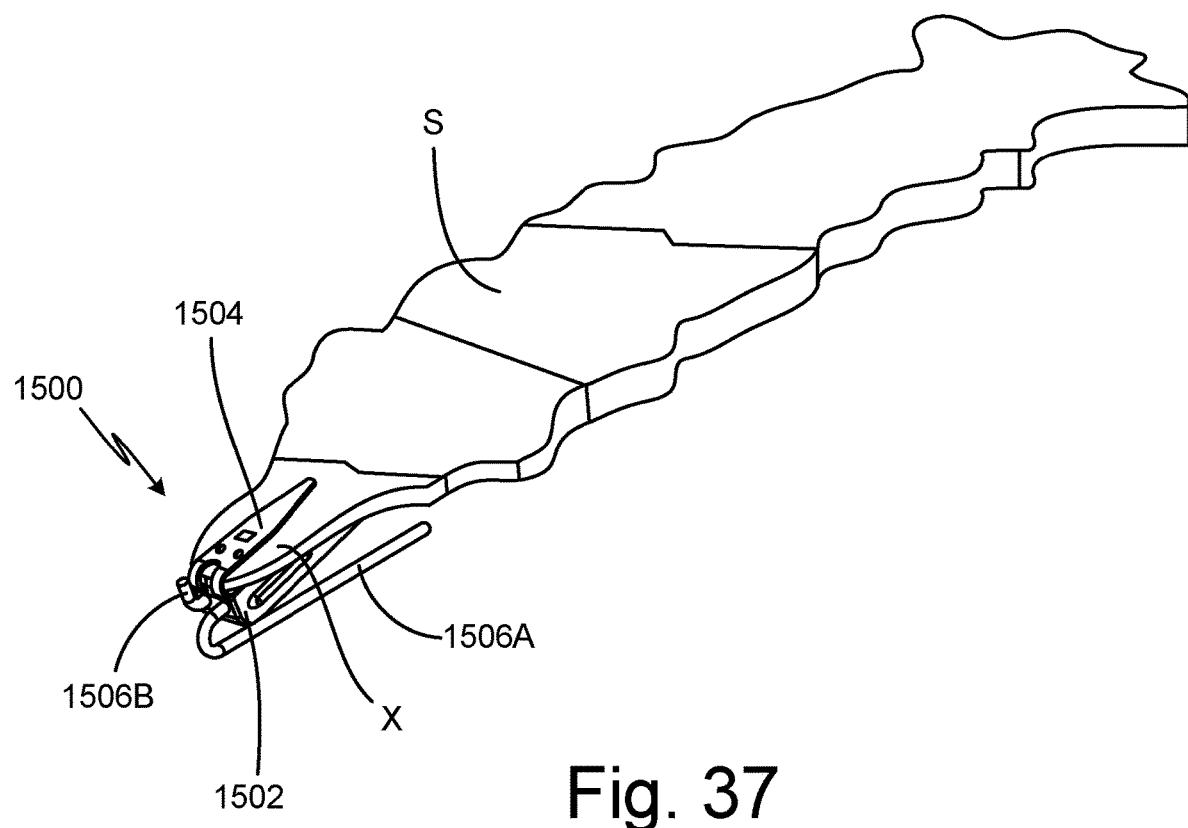

FIG. 37 is a perspective view of the thirteenth embodiment of the subcutaneous device positioned on a xiphoid process and a sternum.

Subcutaneous Device 1600

Figure 38:
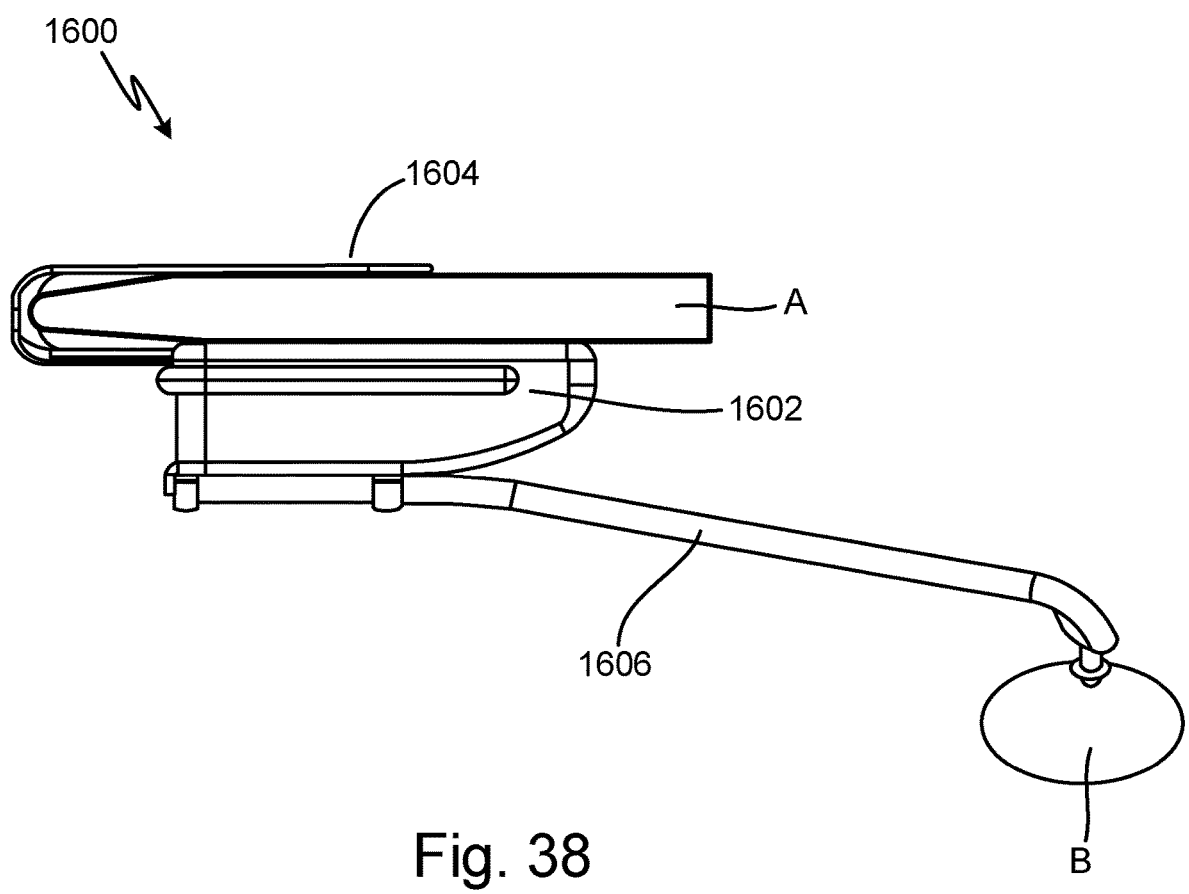

FIG. 38 is a side view of a seventeenth embodiment of a subcutaneous device anchored to a structural body component.

Figure 39A:
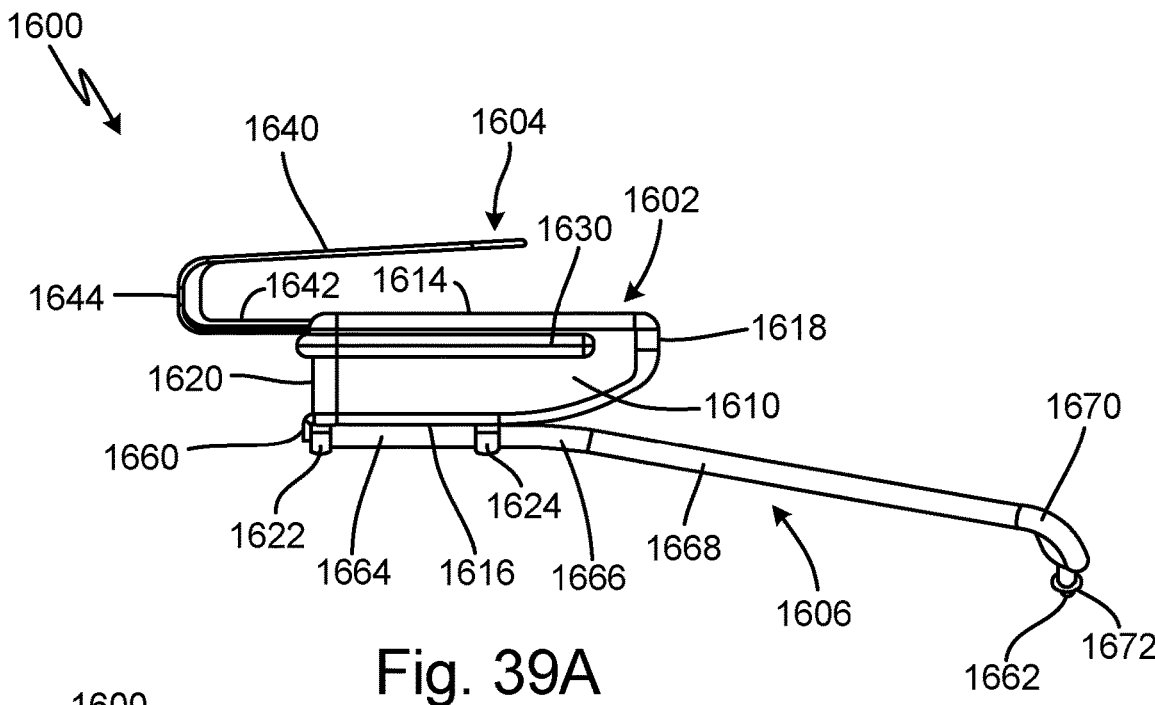

FIG. 39A is a side view of the seventeenth embodiment of the subcutaneous device.

Figure 39B:
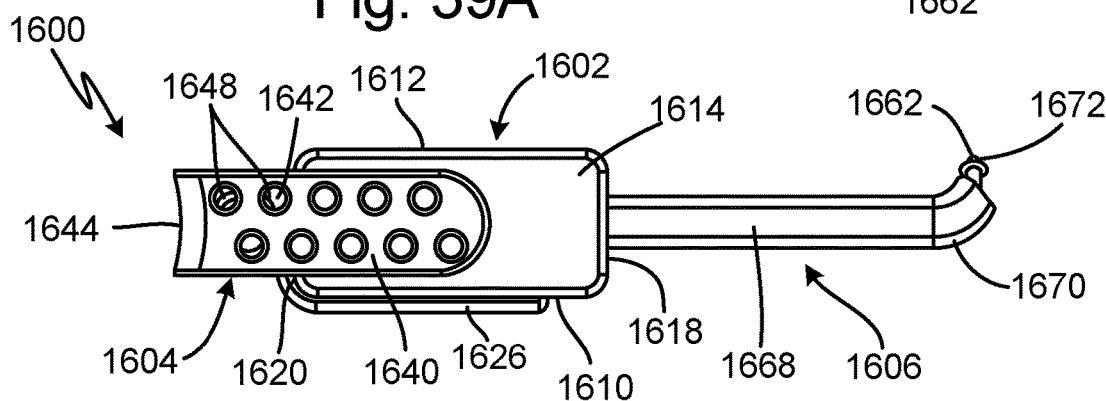

FIG. 39B is a top view of the seventeenth embodiment of the subcutaneous device.

Figure 39C:
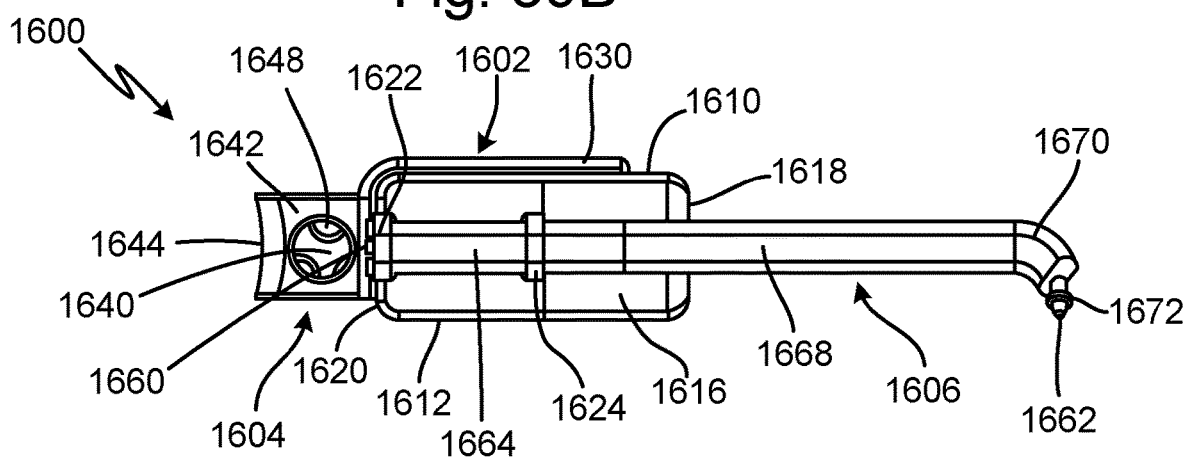

FIG. 39C is a bottom view of the seventeenth embodiment of the subcutaneous device.

Figure 39D:
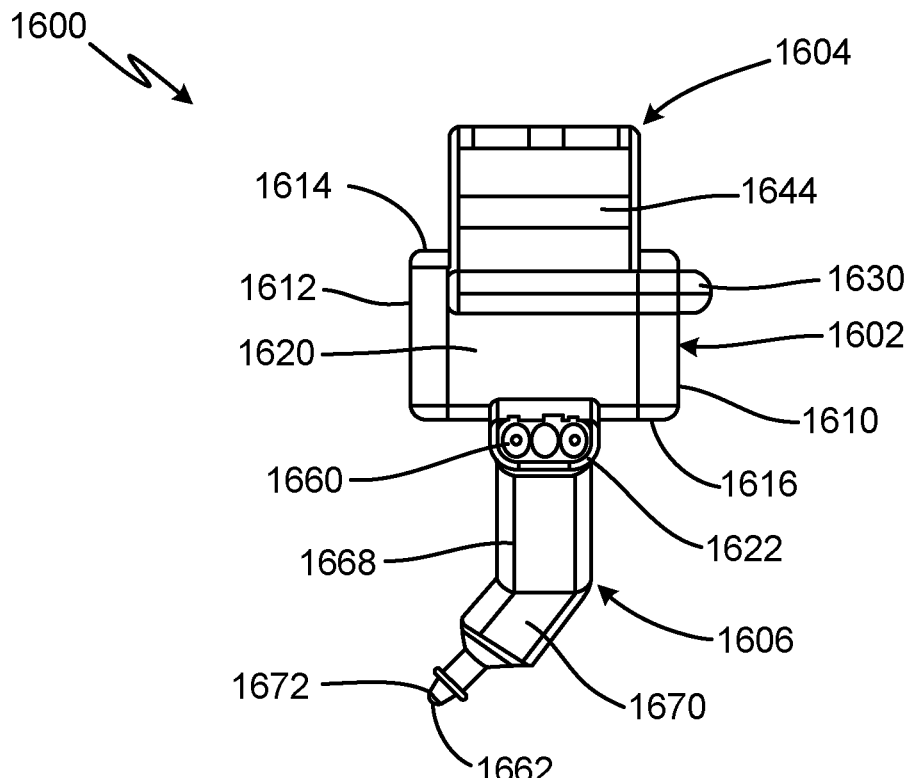

FIG. 39D is a back view of the seventeenth embodiment of the subcutaneous device.

Figure 39E:
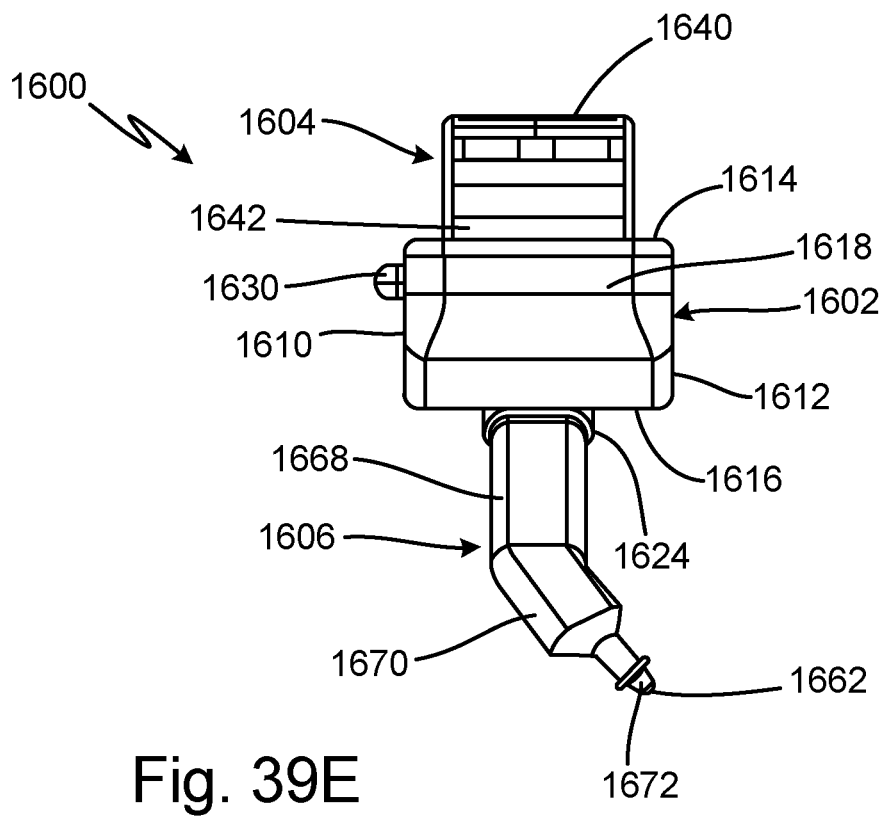

FIG. 39E is a front view of the seventeenth embodiment of the subcutaneous device.

Figure 40A:
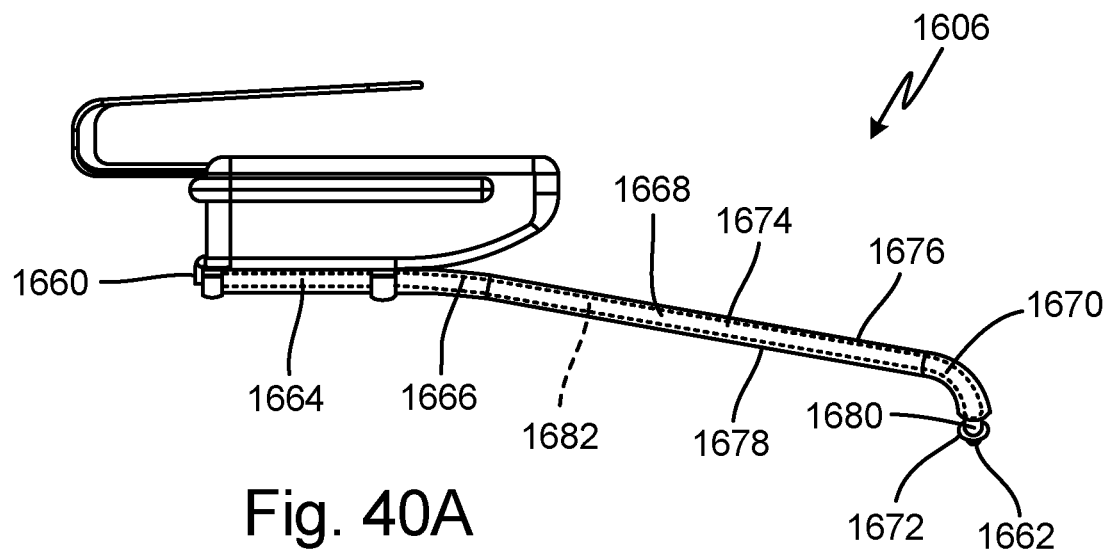

FIG. 40A is a side view of the seventeenth embodiment of the subcutaneous device showing the prong.

Figure 40B:
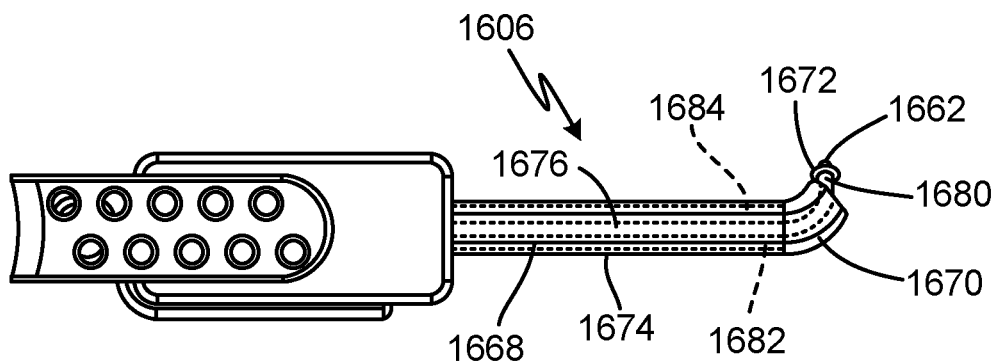

FIG. 40B is a top view of the seventeenth embodiment of the subcutaneous device showing the prong.

Figure 40C:
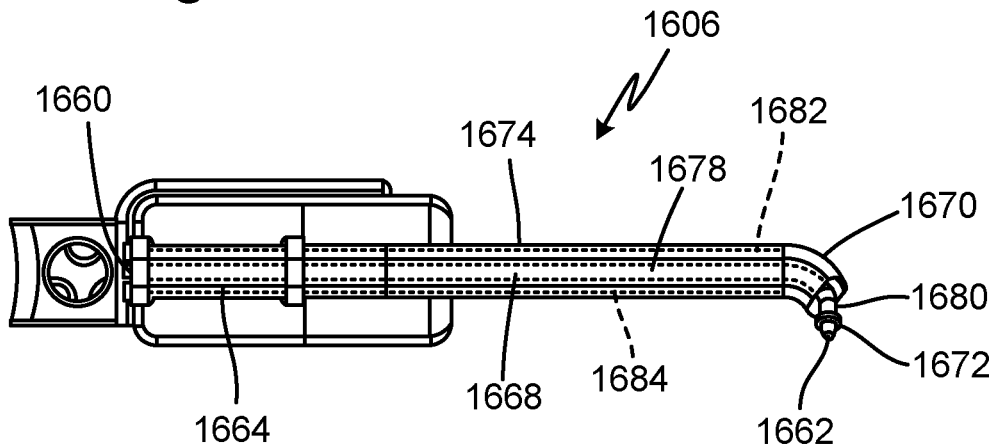

FIG. 40C is a bottom view of the seventeenth embodiment of the subcutaneous device showing the prong.

Figure 40D:
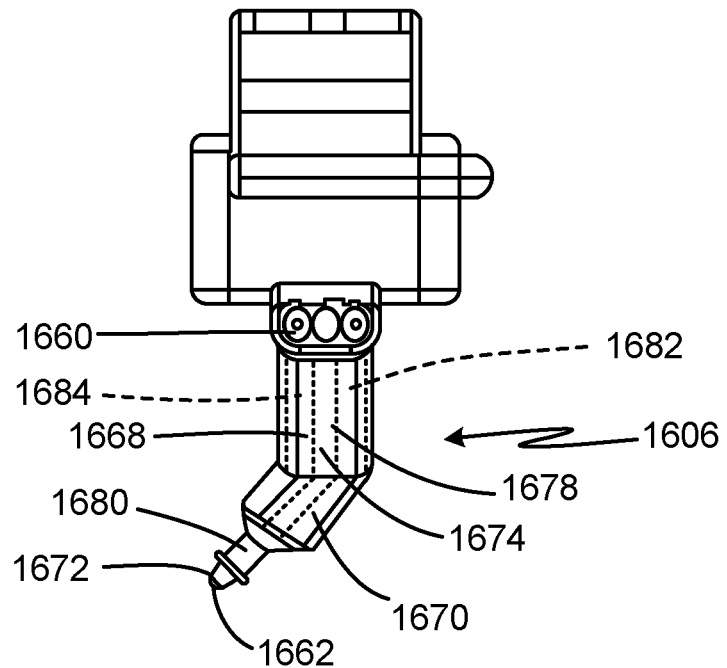

FIG. 40D is a back view of the seventeenth embodiment of the subcutaneous device showing the prong.

Figure 40E:
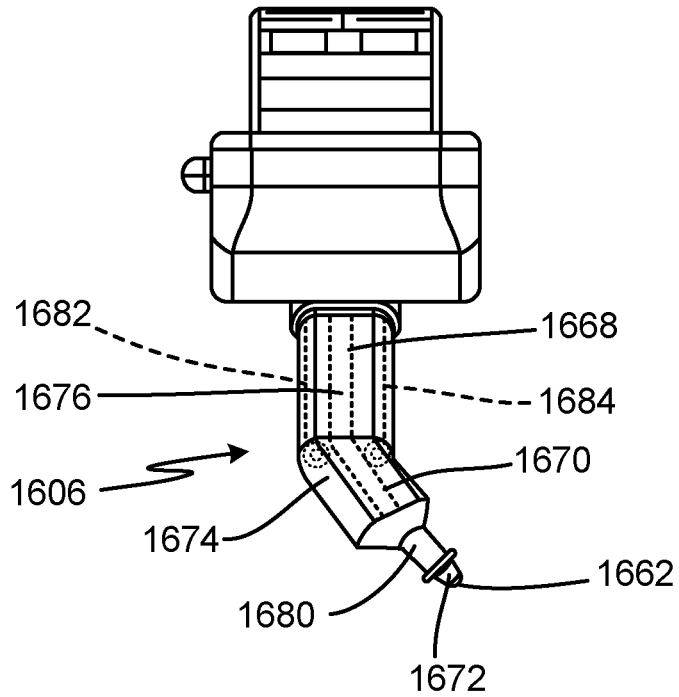

FIG. 40E is a front view of the seventeenth embodiment of the subcutaneous device showing the prong.

Figure 41A:
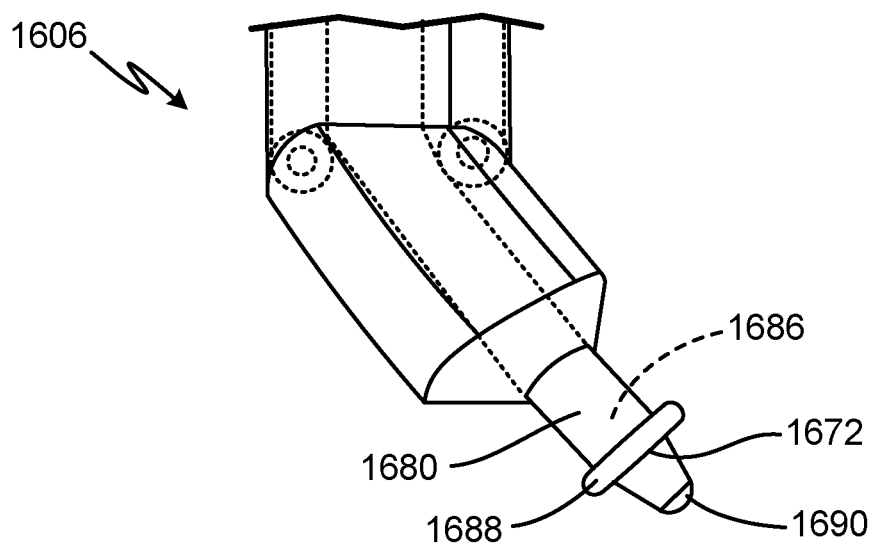

FIG. 41A is a partial perspective view of the prong showing the electrode.

Figure 41B:
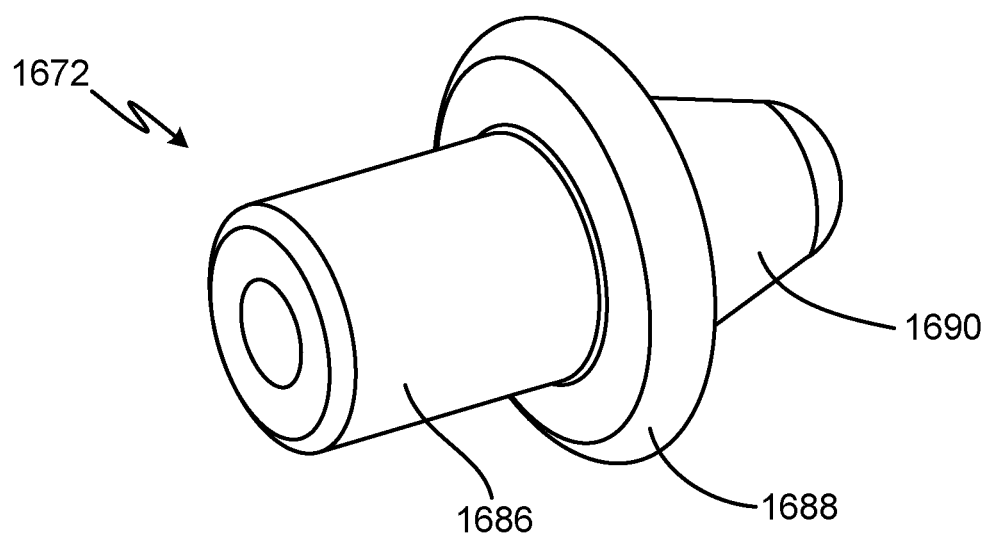

FIG. 41B is a perspective view of the electrode.

Figure 42A:
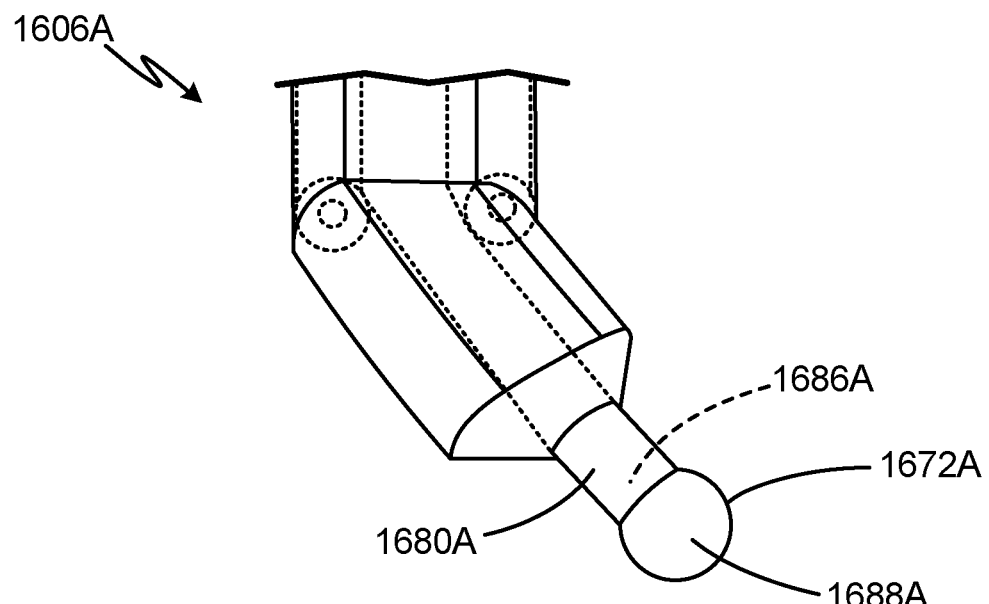

FIG. 42A is a partial perspective view of the prong showing a second embodiment of the electrode.

Figure 42B:
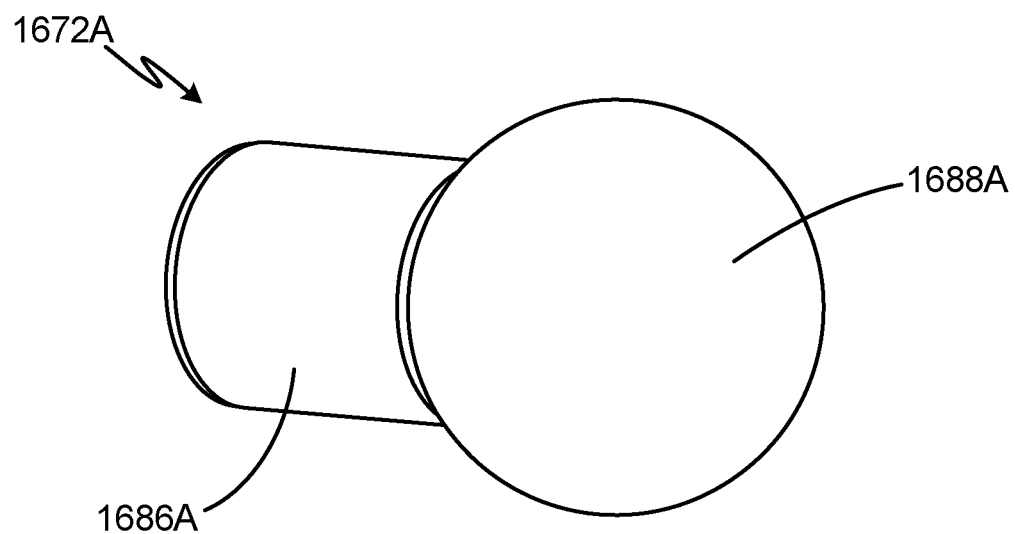

FIG. 42B is a perspective view of the second embodiment of the electrode.

Figure 43A:
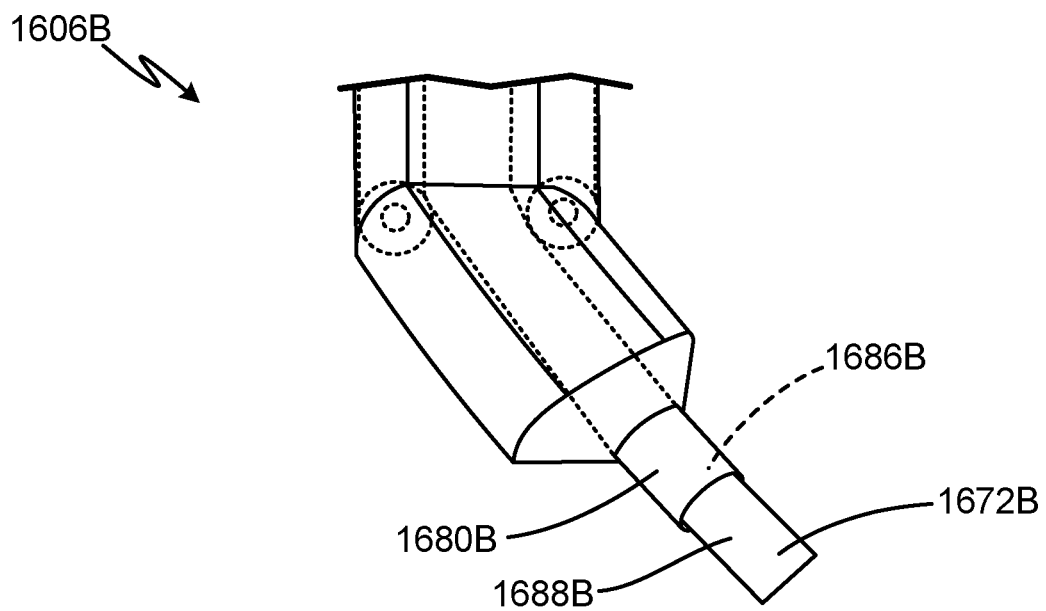

FIG. 43A is a partial perspective view of the prong showing a third embodiment of the electrode.

Figure 43B:
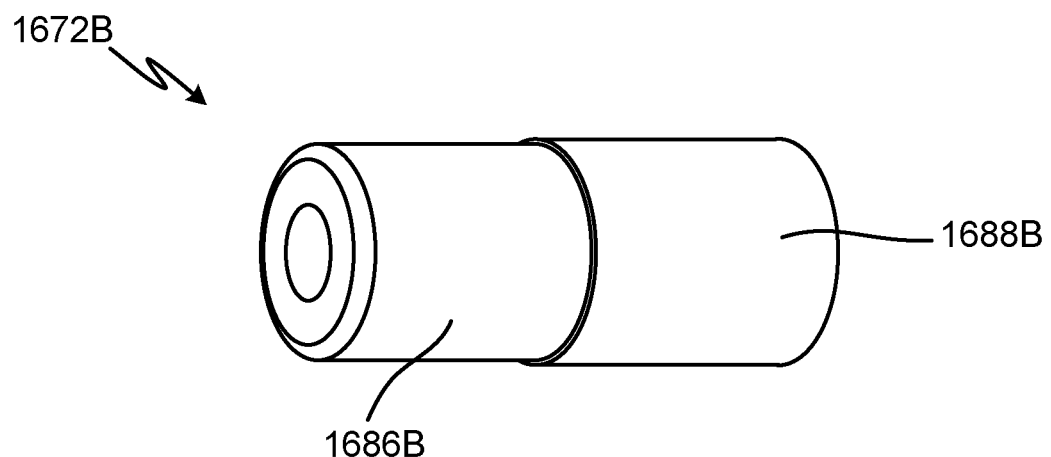

FIG. 43B is a perspective view of the third embodiment of the electrode.

Figure 44A:
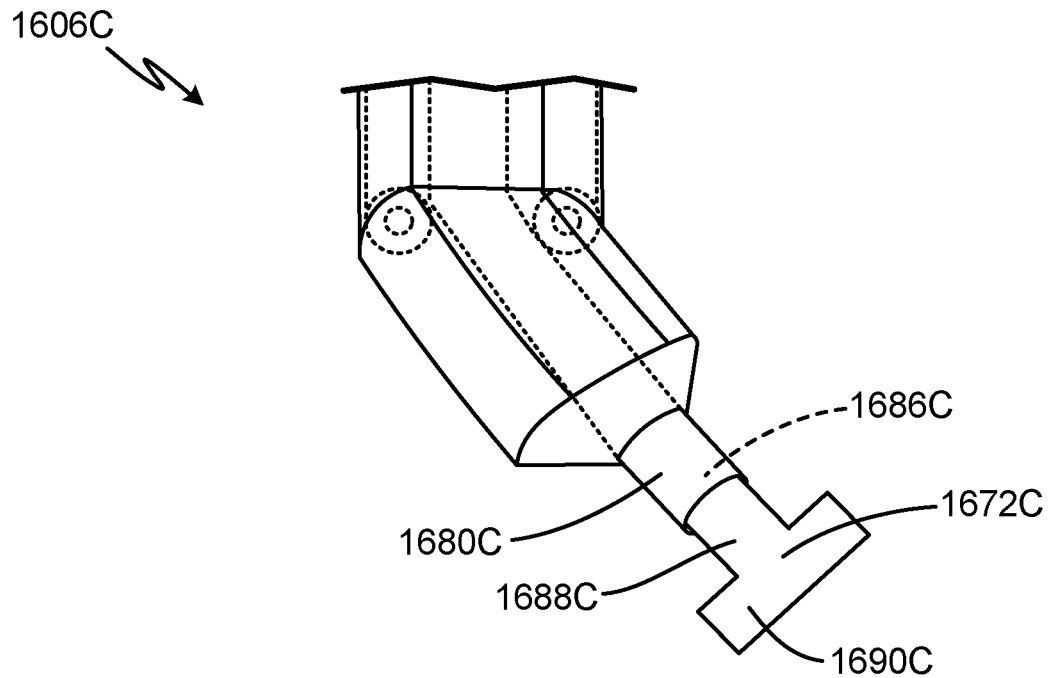

FIG. 44A is a partial perspective view of the prong showing a fourth embodiment of the electrode.

Figure 44B:
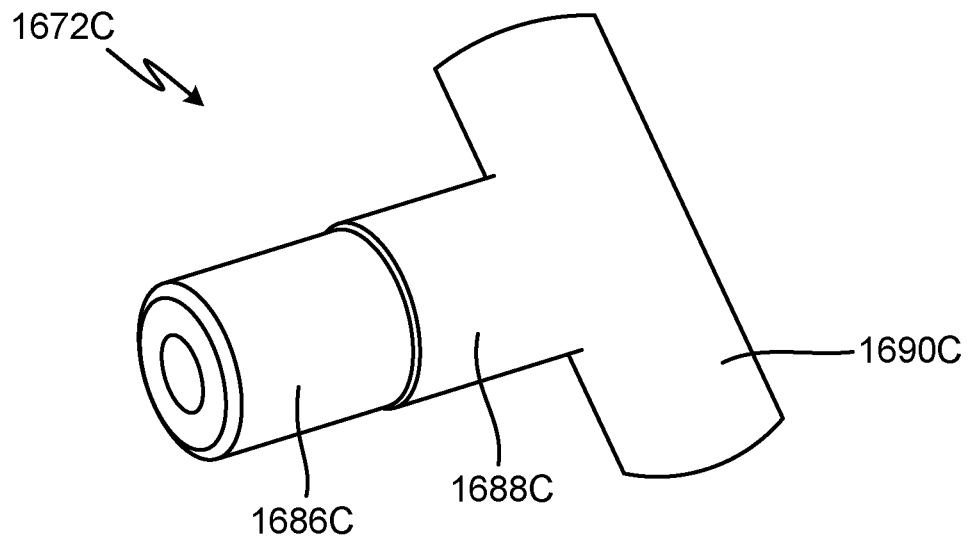

FIG. 44B is a perspective view of the fourth embodiment of the electrode.

Figure 45:
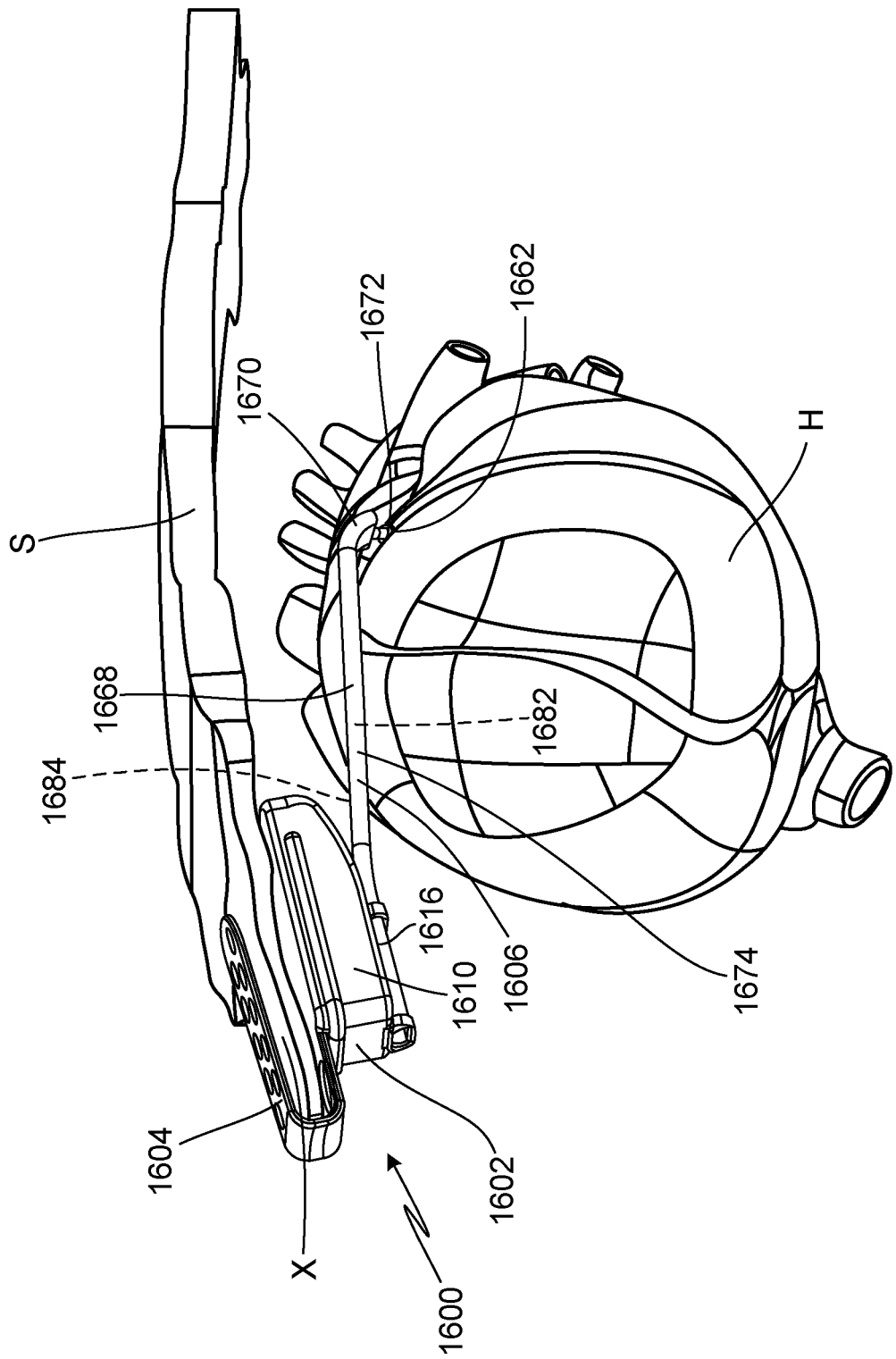

FIG. 45 is a perspective view of the seventeenth embodiment of the subcutaneous device positioned on the xiphoid process and/or the sternum and showing a positioning of a prong on the heart.

Surgical Instrument 1700

Figure 46A:
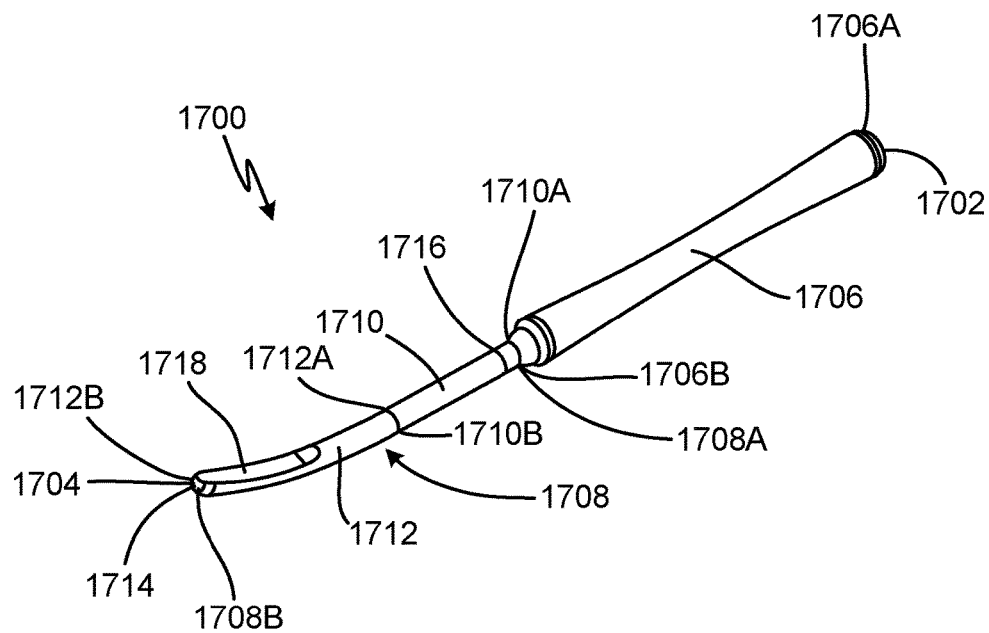

FIG. 46A is a perspective view of a first surgical instrument.

Figure 46B:
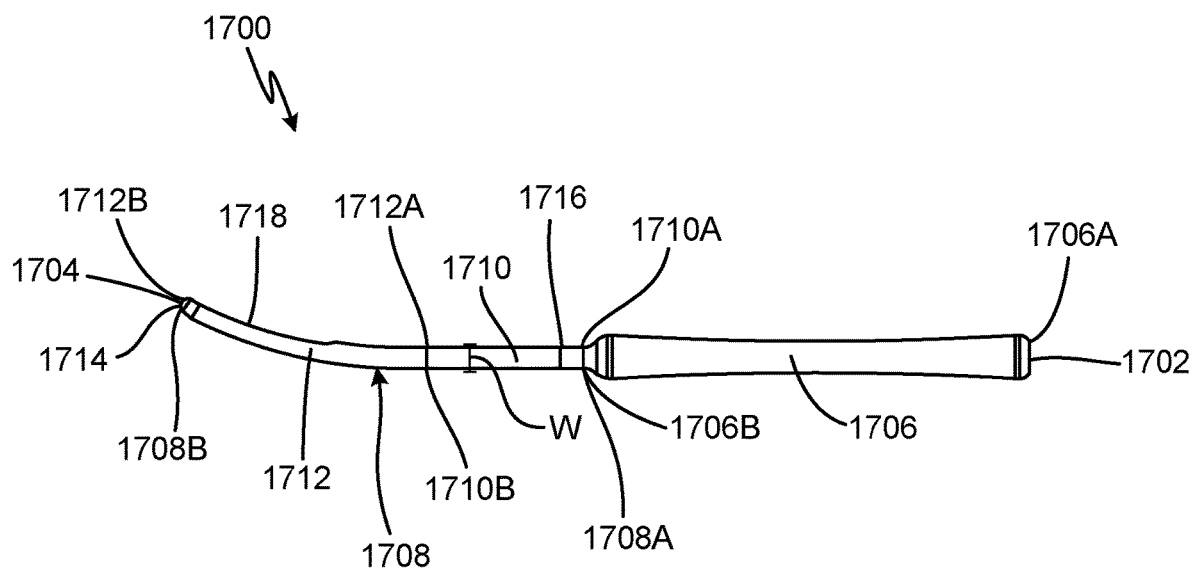

FIG. 46B is a side view of the first surgical instrument.

Figure 46C:
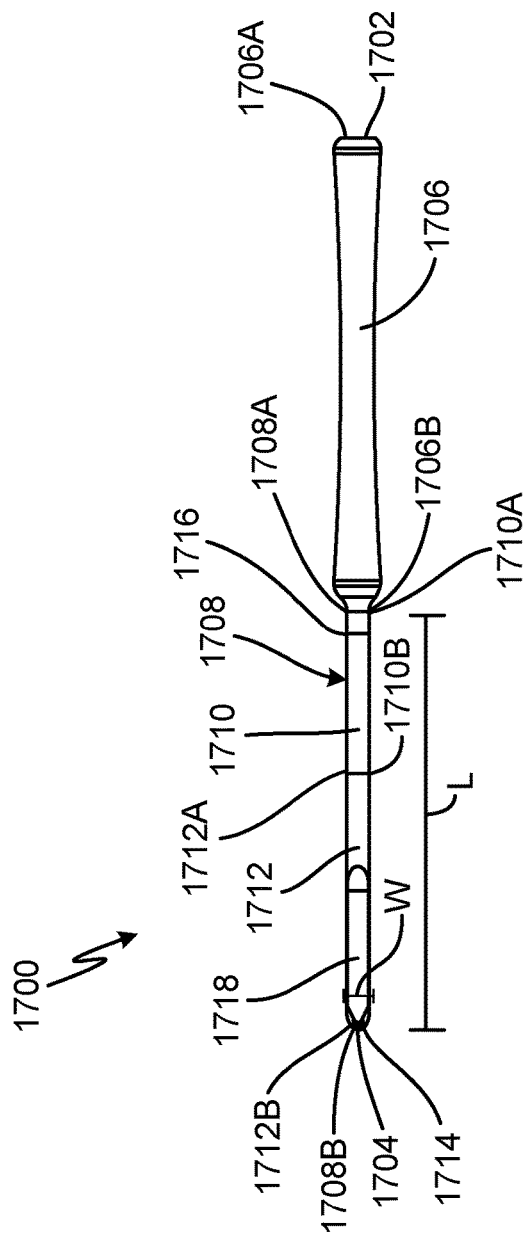

FIG. 46C is a top view of the first surgical instrument.

Figure 46D:
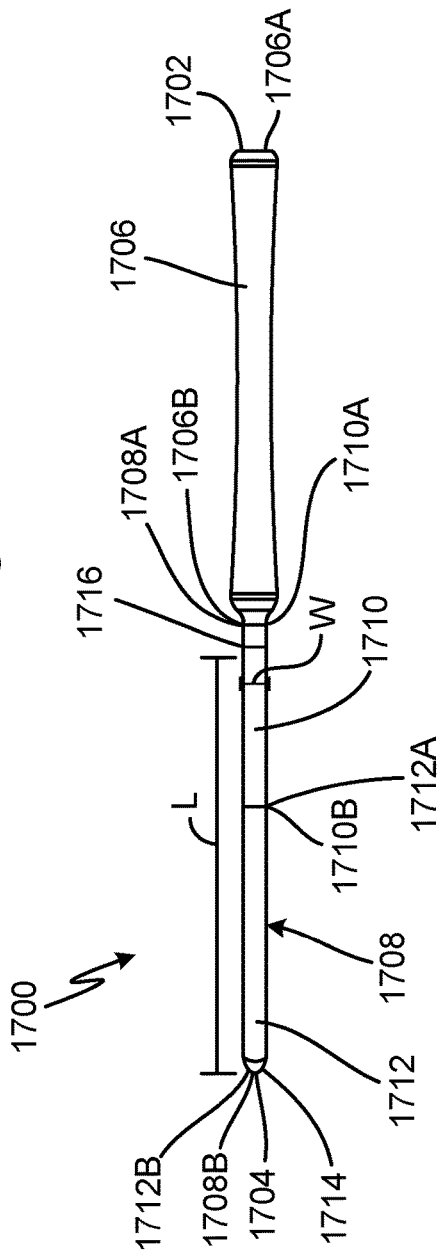

FIG. 46D is a bottom view of the first surgical instrument.

Figure 46E:
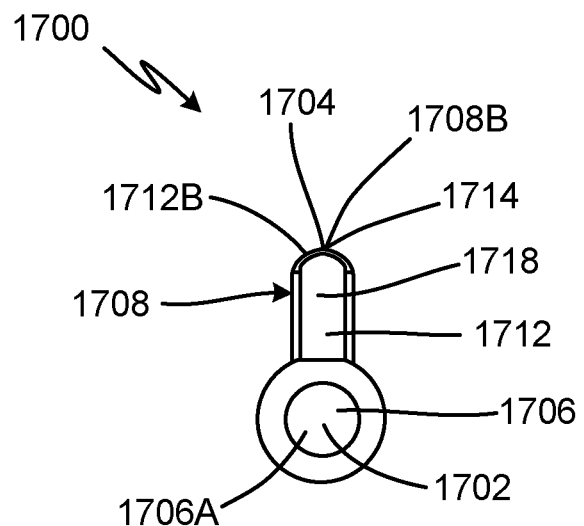

FIG. 46E is a back view of the first surgical instrument.

Figure 46F:
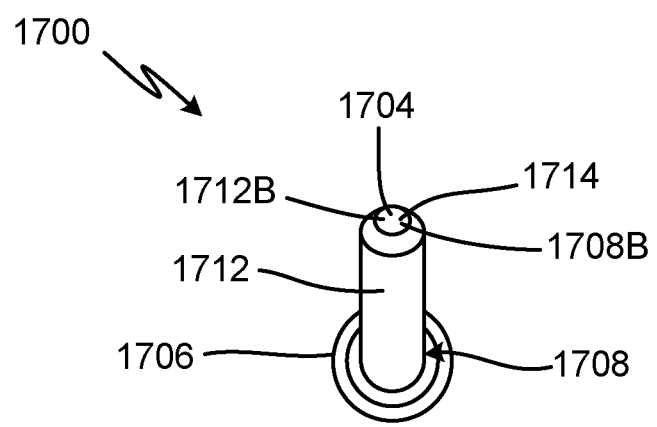

FIG. 46F is a front view of the first surgical instrument.

Surgical Instrument 1800

FIG. 47A is a perspective view of a second surgical instrument.

FIG. 47B is a side view of the second surgical instrument.

FIG. 47C is a top view of the second surgical instrument.

FIG. 47D is a bottom view of the second surgical instrument.

Figure 47E:
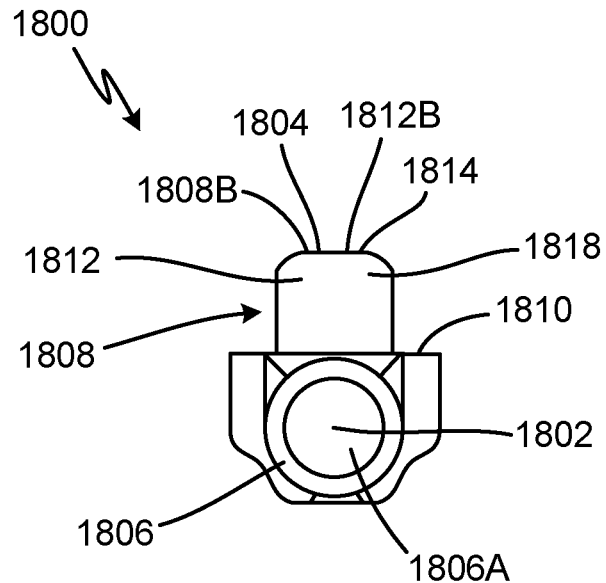

FIG. 47E is a back view of the second surgical instrument.

Figure 47F:
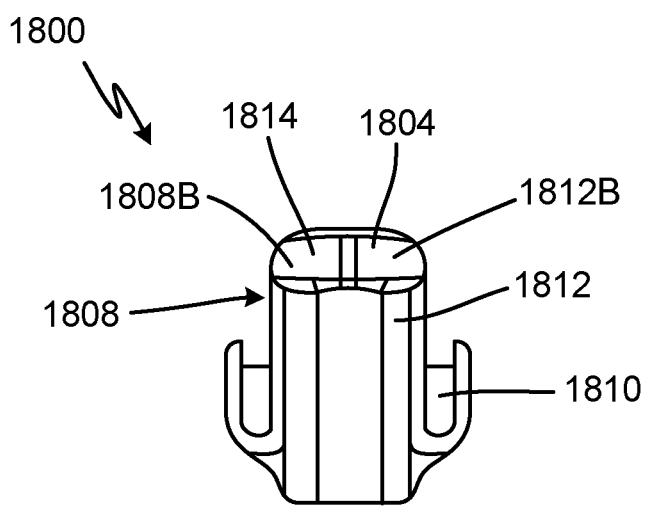

FIG. 47F is a front view of the second surgical instrument.

Surgical Instrument 1900

FIG. 48A is a perspective view of a third surgical instrument.

FIG. 48B is a side view of the third surgical instrument.

FIG. 48C is a top view of the third surgical instrument.

FIG. 48D is a bottom view of the third surgical instrument.

Figure 48E:
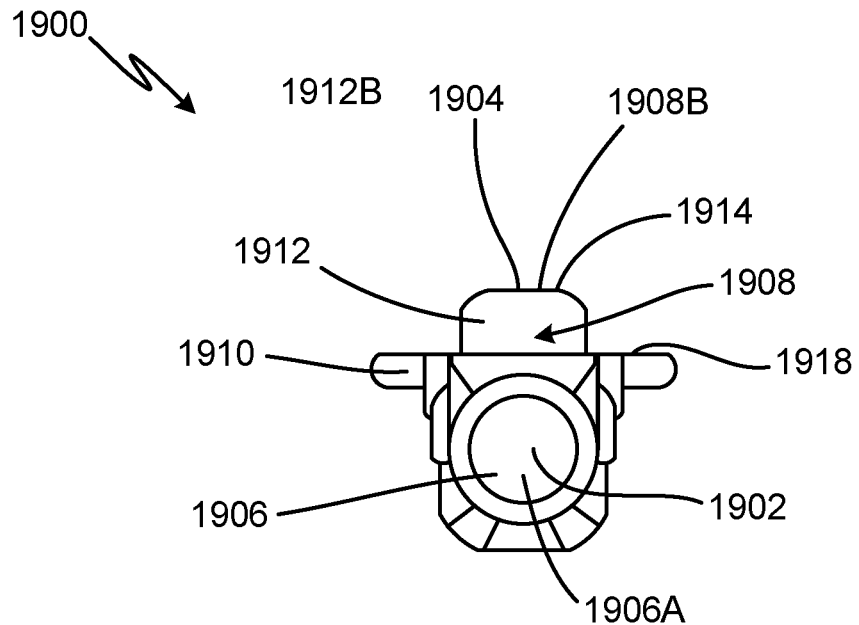

FIG. 48E is a back view of the third surgical instrument.

Figure 48F:
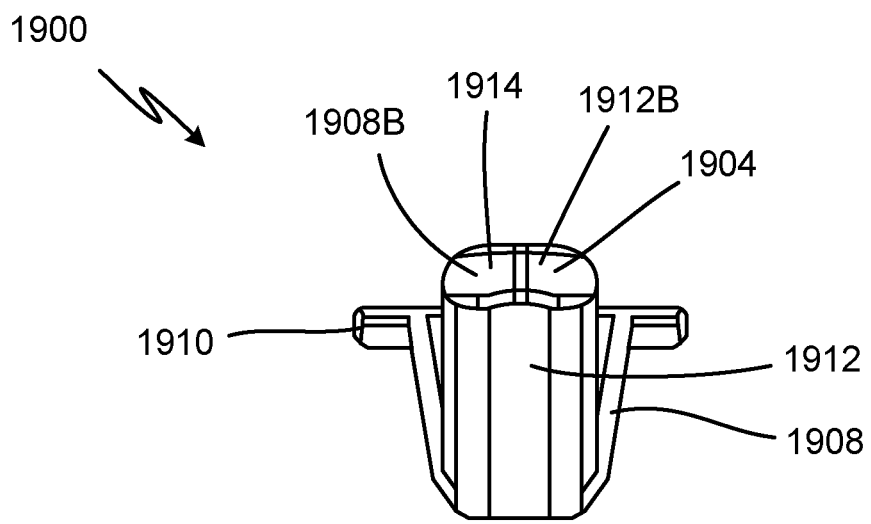

FIG. 48F is a front view of the third surgical instrument.

Surgical Instrument 2000

Figure 49A:
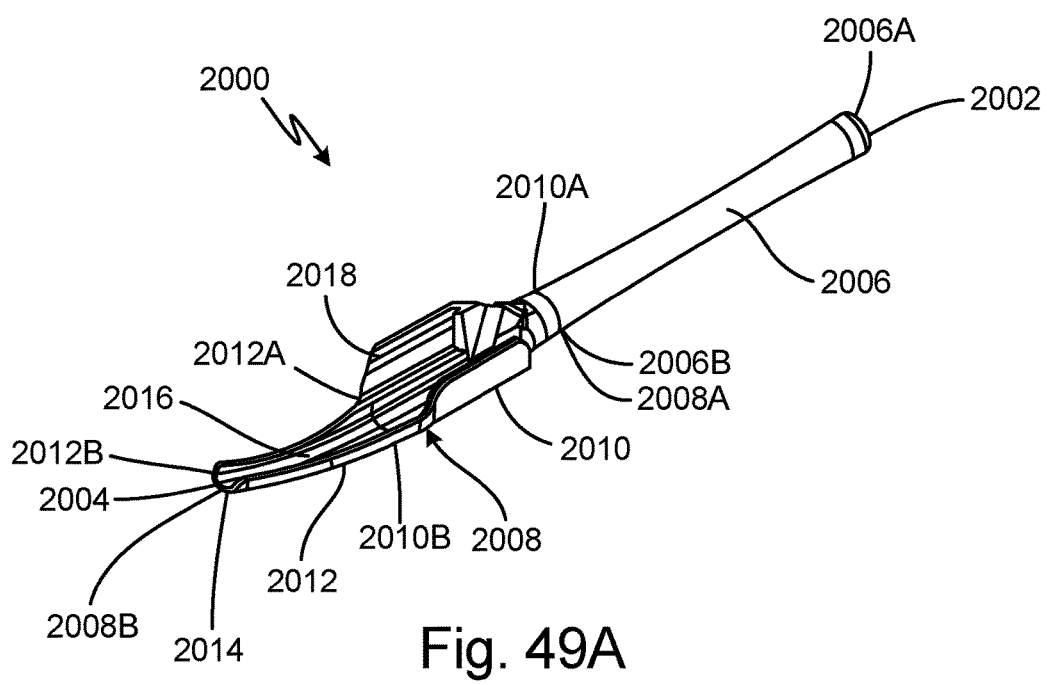

FIG. 49A is a perspective view of a fourth surgical instrument.

Figure 49B:
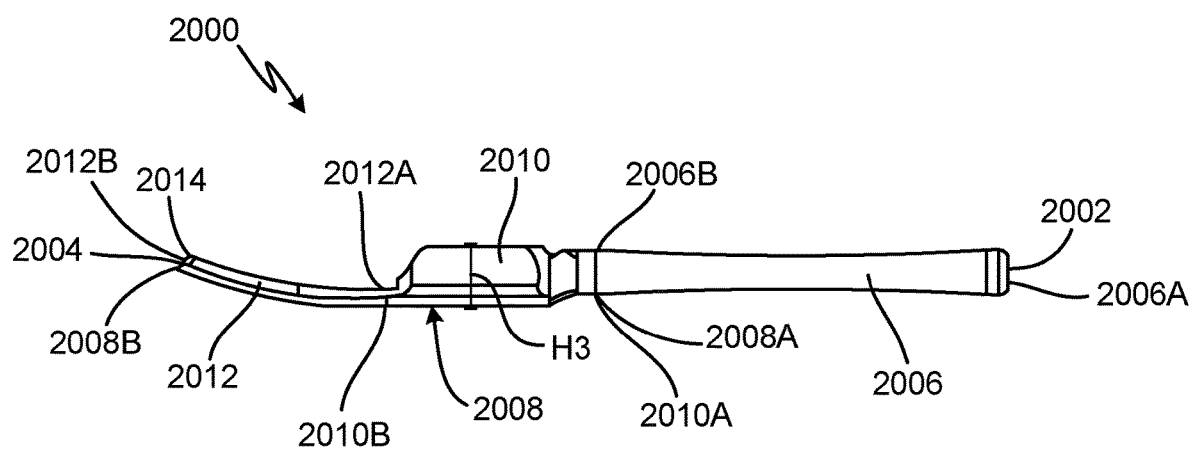

FIG. 49B is a side view of the fourth surgical instrument.

FIG. 49C is a top view of the fourth surgical instrument.

FIG. 49D is a bottom view of the fourth surgical instrument.

Figure 49E:
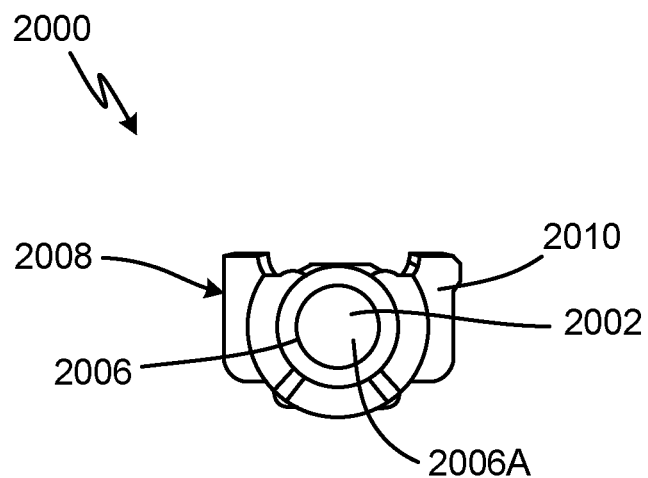

FIG. 49E is a back view of the fourth surgical instrument.

Figure 49F:
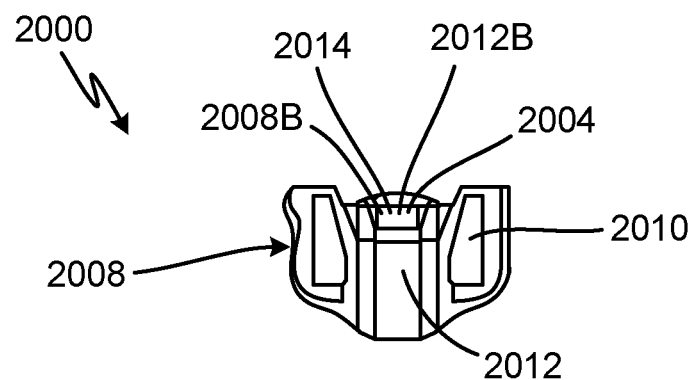

FIG. 49F is a front view of the fourth surgical instrument.

Figure 50:
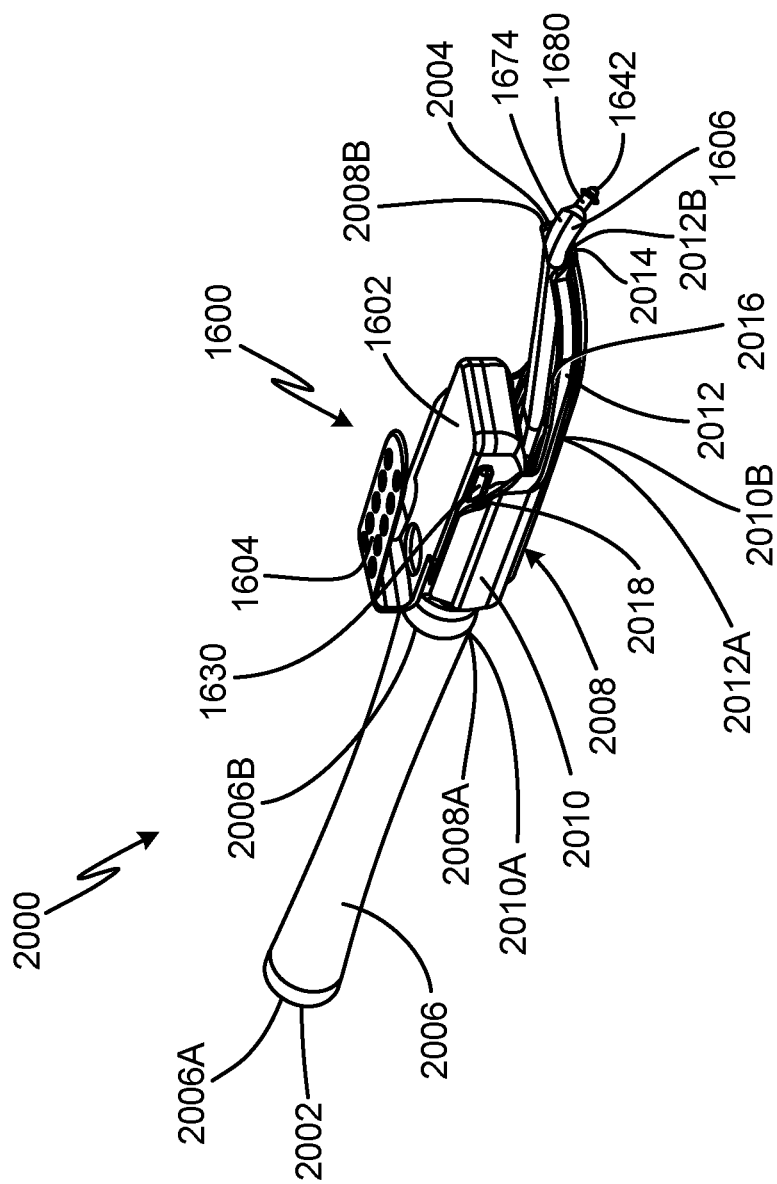

FIG. 50 is a perspective view of the seventeenth embodiment of the subcutaneous device positioned in the fourth surgical instrument.

Method 2100

Figure 51:
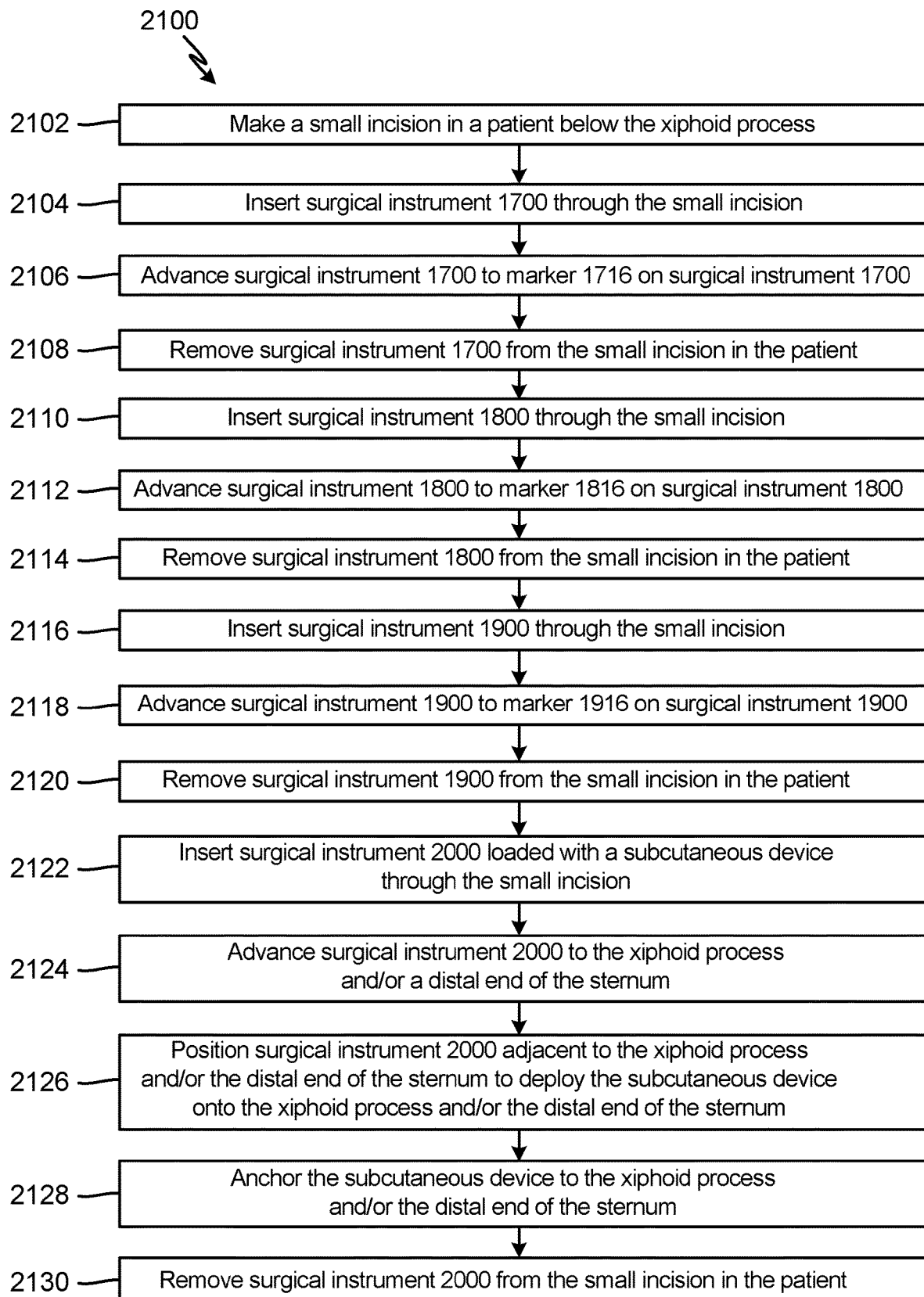

FIG. 51 is a flow chart showing a method for implanting the seventeenth embodiment of the subcutaneous device using the first surgical instrument, the second surgical instrument, the third surgical instrument, and the fourth surgical instrument.

Subcutaneous Device 2200

Figure 52:
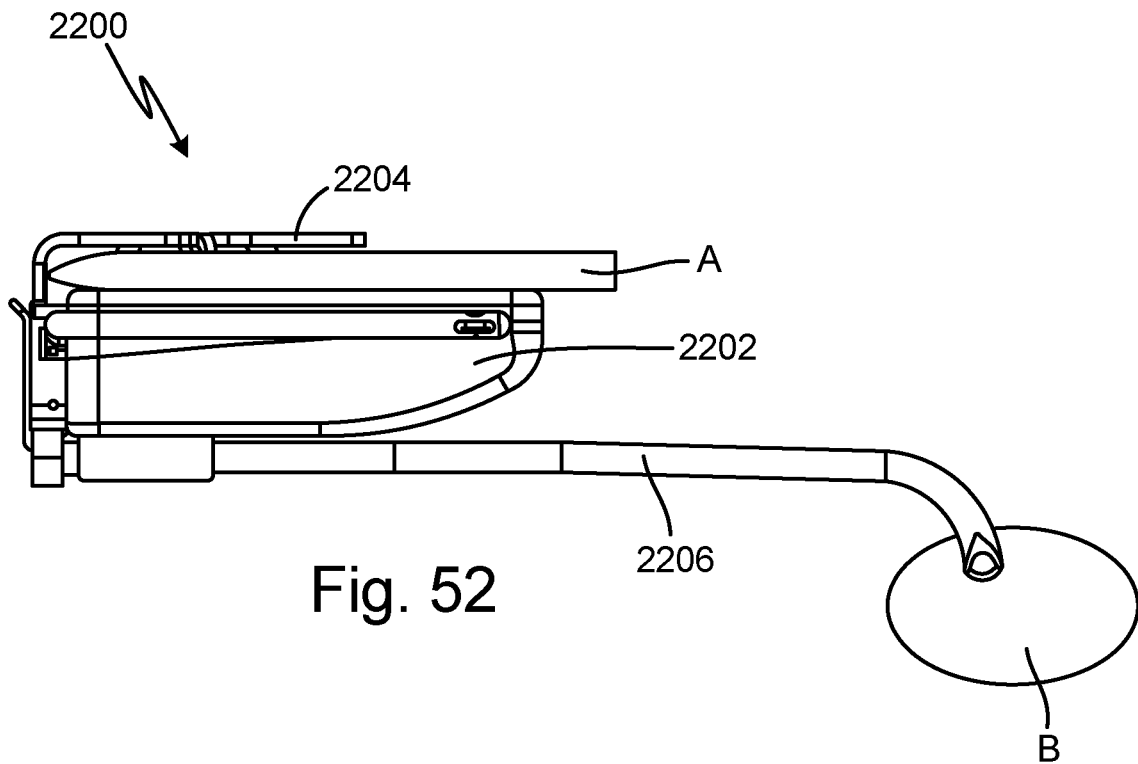

FIG. 52 is a side view of an eighteenth embodiment of a subcutaneous device anchored to a structural body component.

Figure 53A:
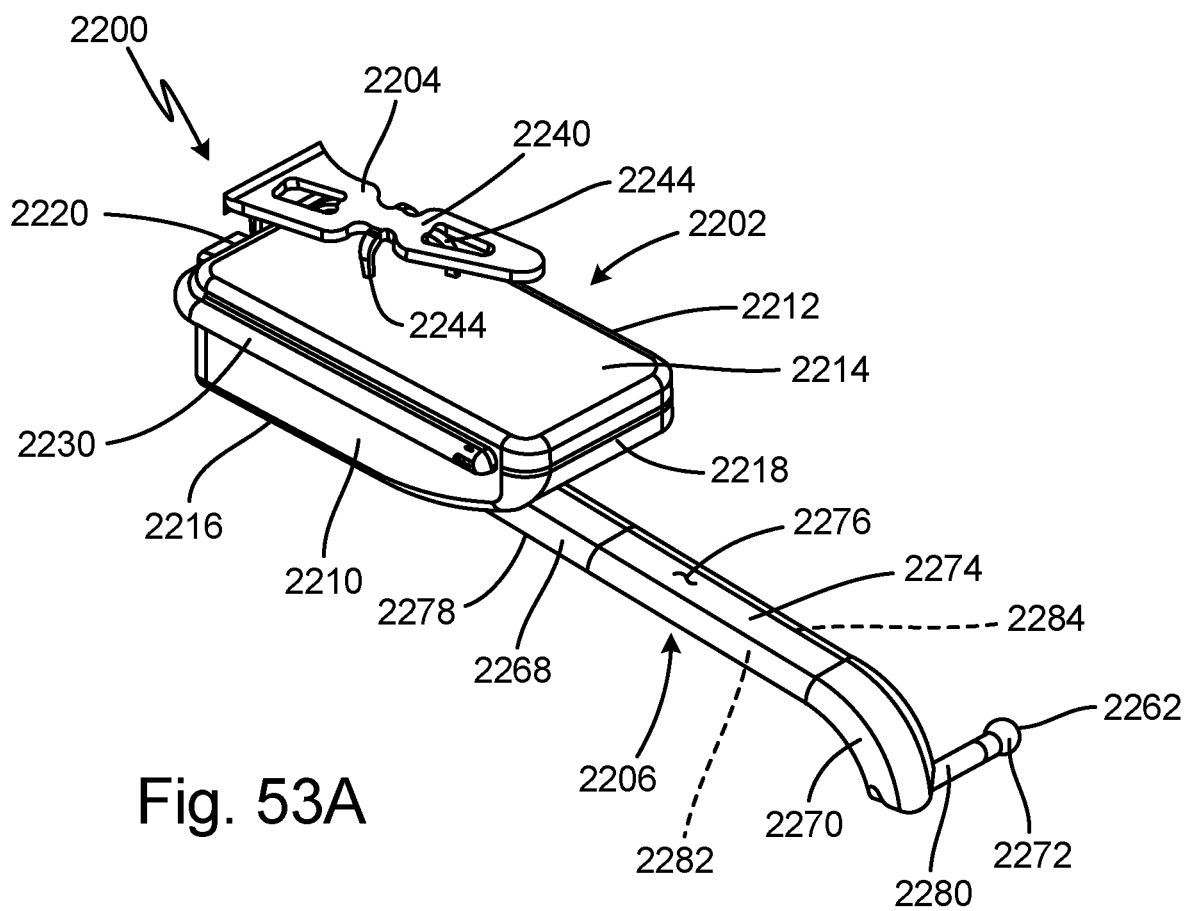

FIG. 53A is a top perspective view of the eighteenth embodiment of the subcutaneous device.

Figure 53B:
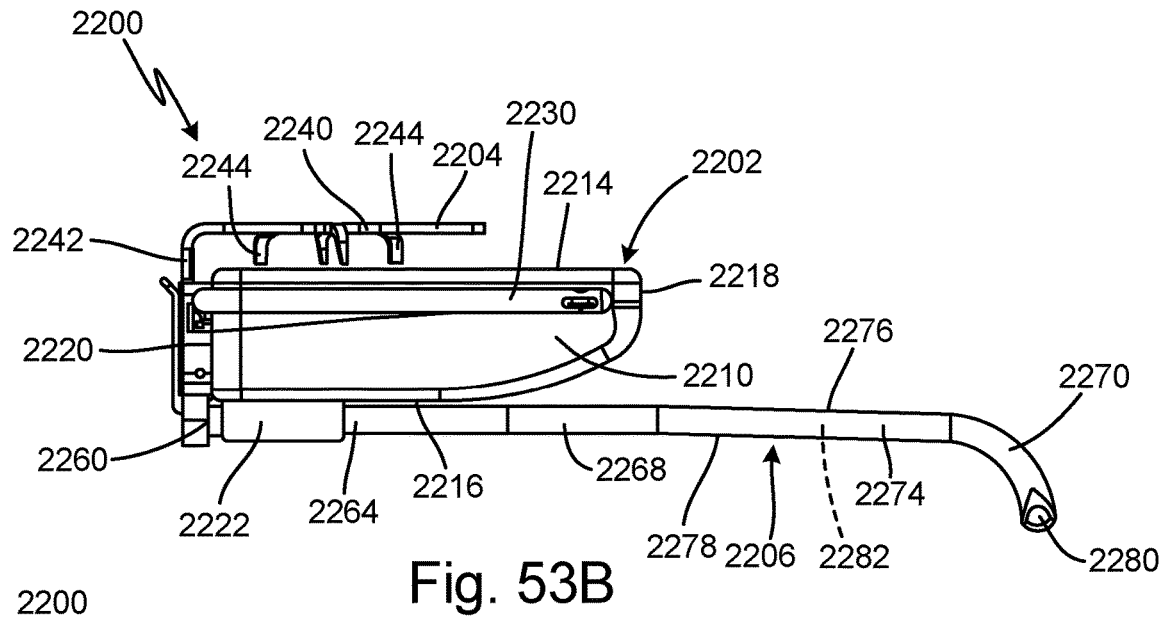

FIG. 53B is a side view of the eighteenth embodiment of the subcutaneous device.

Figure 53C:
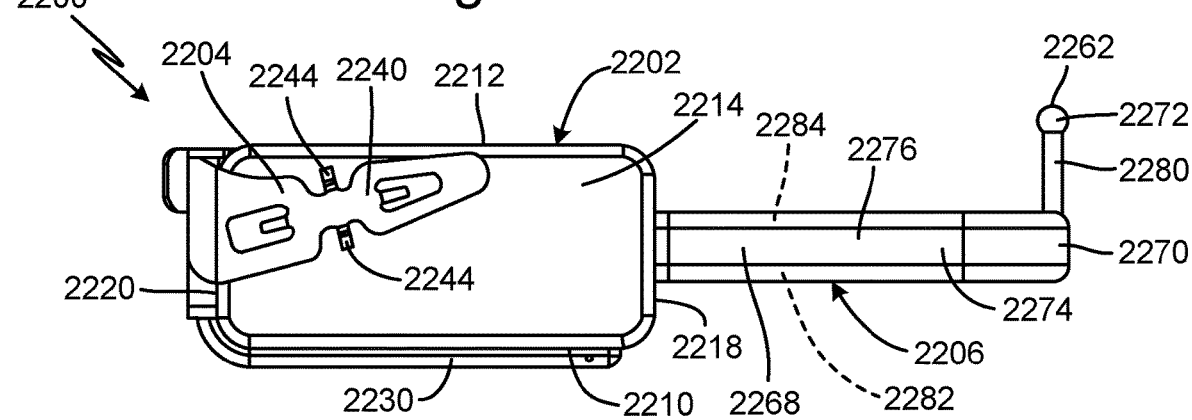

FIG. 53C is a top view of the eighteenth embodiment of the subcutaneous device.

Figure 53D:
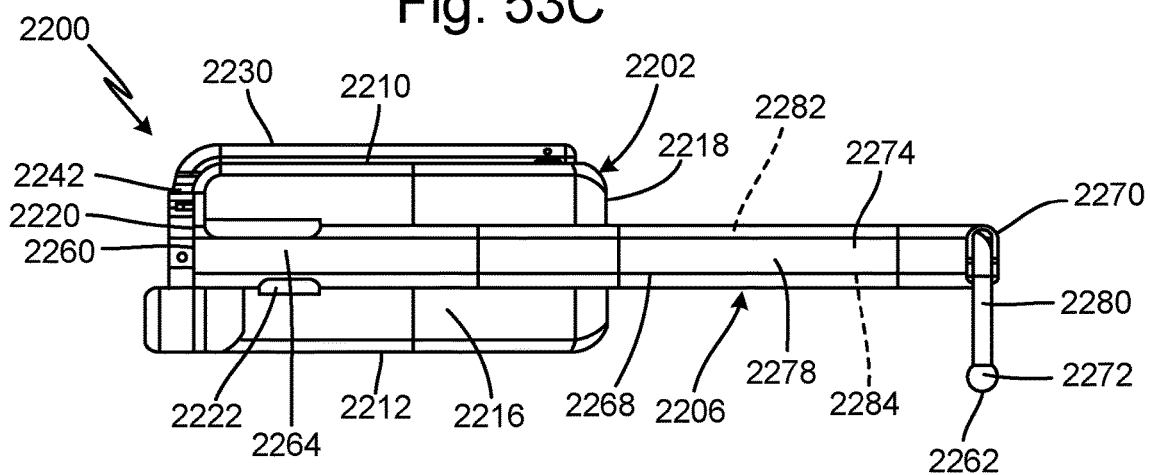

FIG. 53D is a bottom view of the eighteenth embodiment of the subcutaneous device.

Figure 53E:
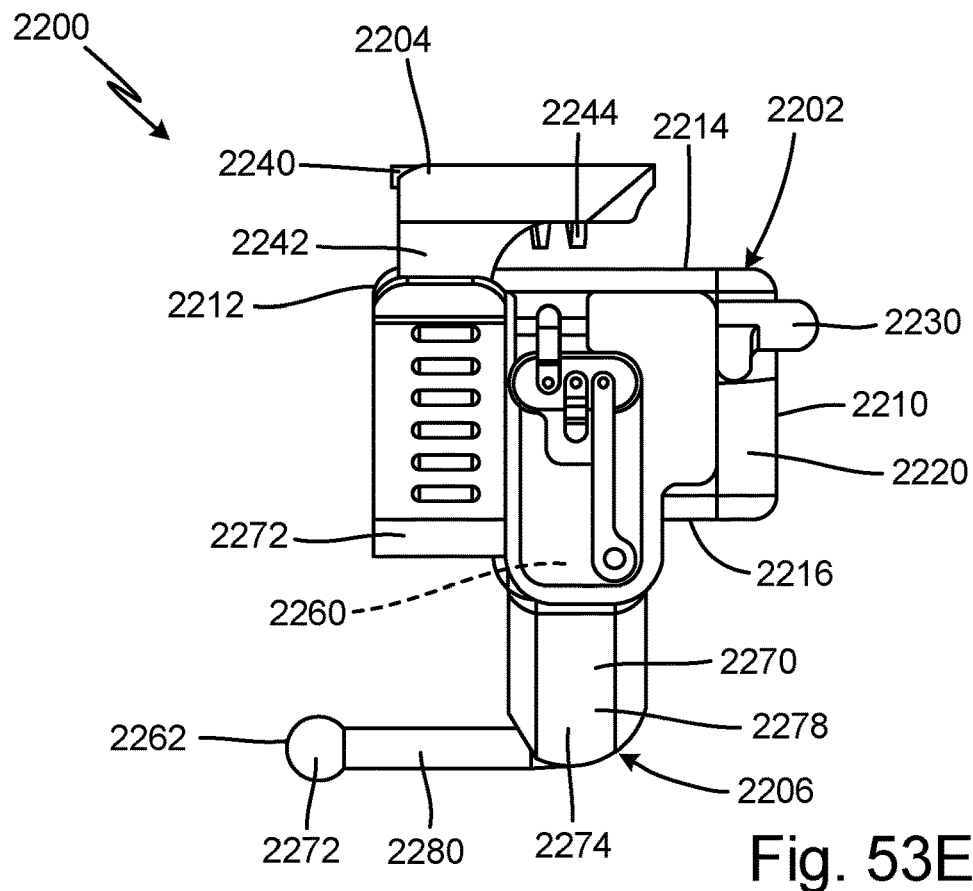

FIG. 53E is a back view of the eighteenth embodiment of the subcutaneous device.

Figure 53F:
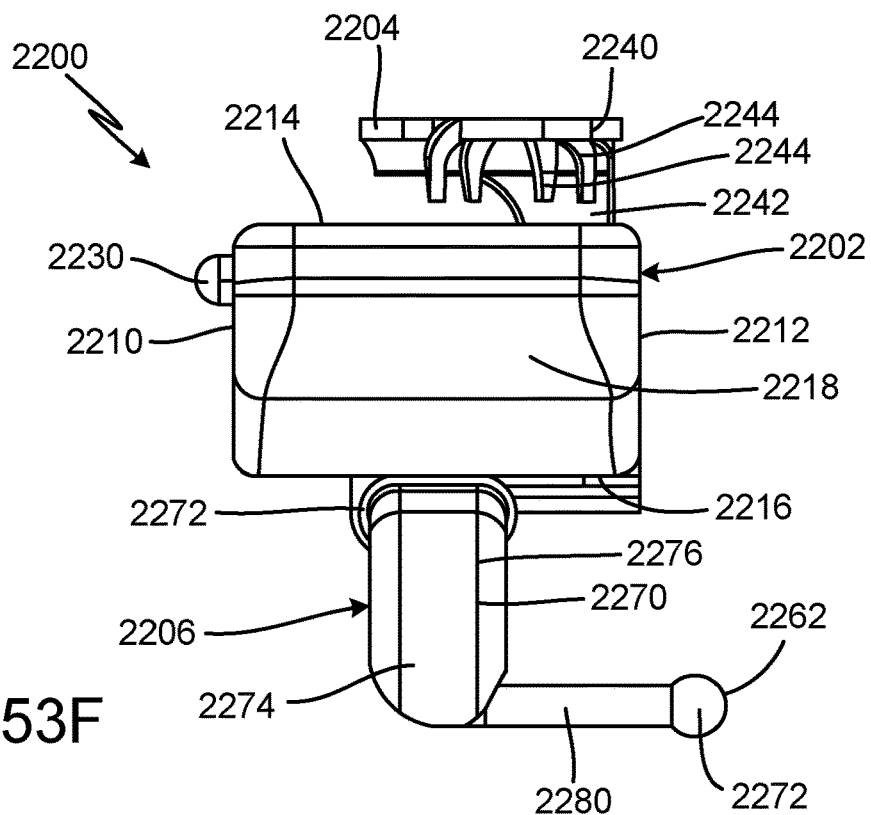

FIG. 53F is a front view of the eighteenth embodiment of the subcutaneous device.

Figure 54:
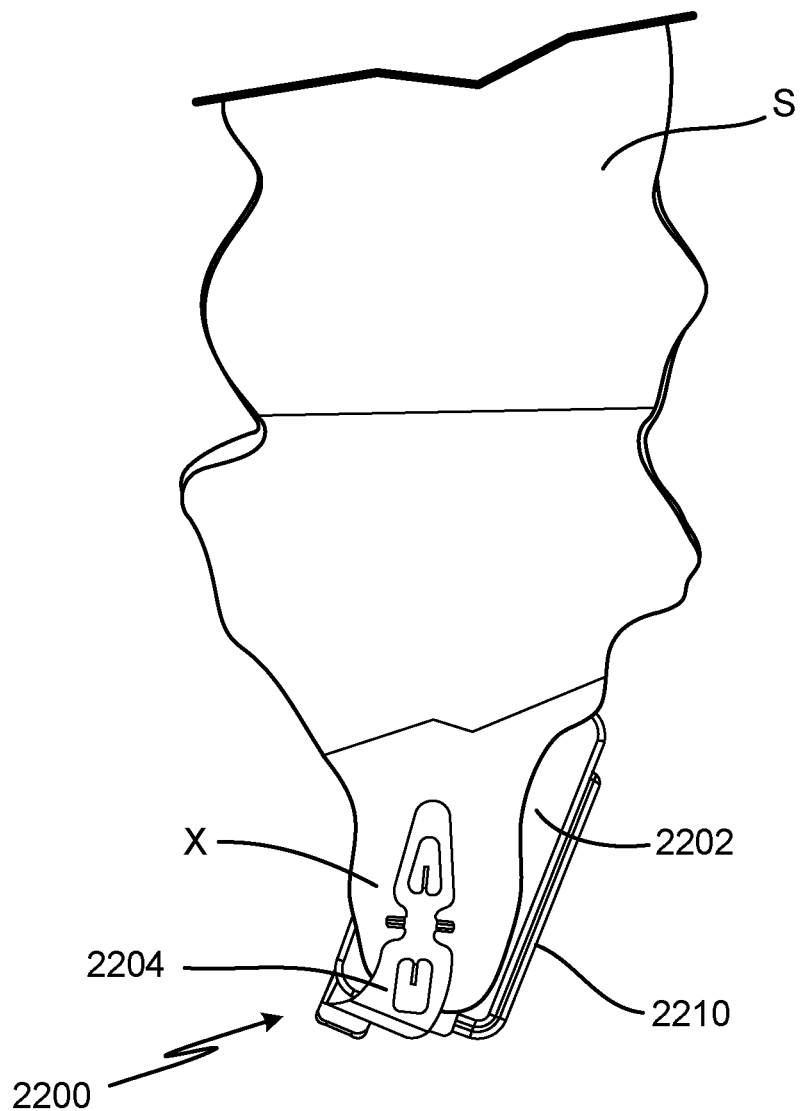

FIG. 54 is a top view of the eighteenth embodiment of the subcutaneous device positioned on the xiphoid process and/or the sternum.

Figure 55A:
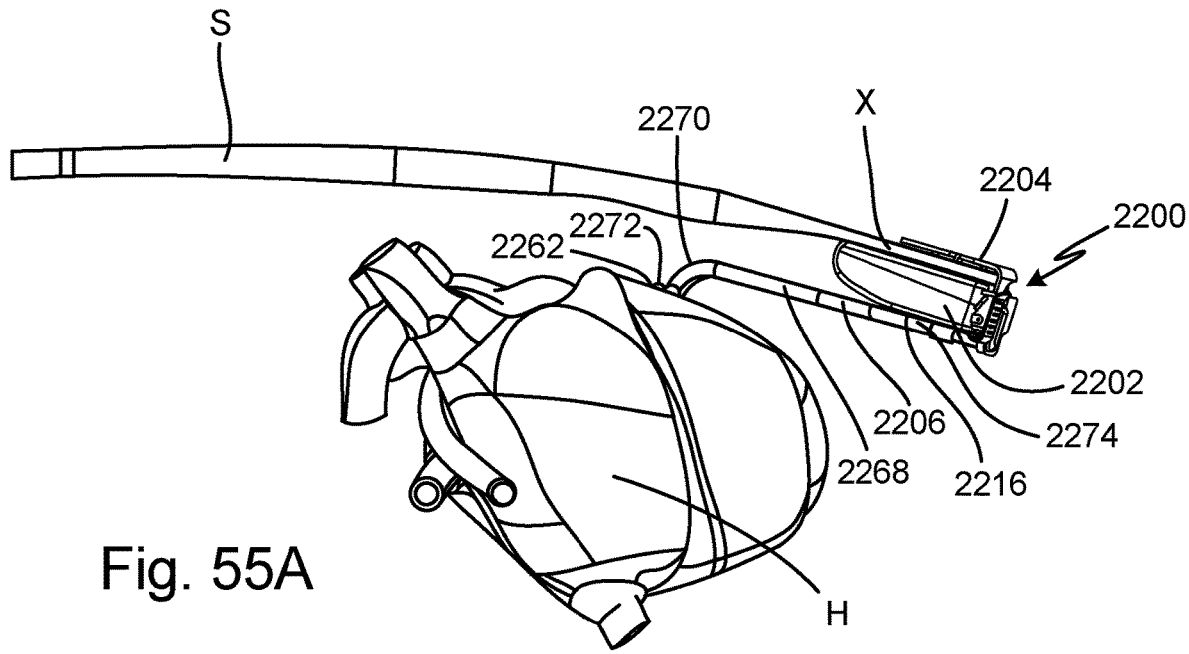

FIG. 55A is a perspective side view of the eighteenth embodiment of the subcutaneous device positioned on the xiphoid process and/or the sternum and showing a positioning of a prong on the heart.

Figure 55B:
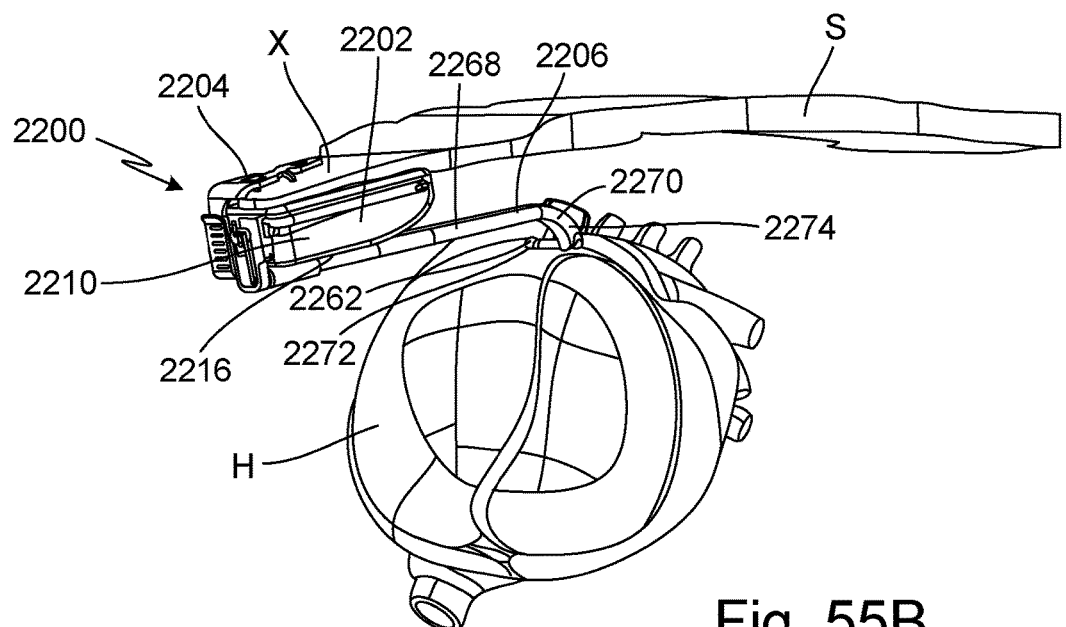

FIG. 55B is a perspective side view of the eighteenth embodiment of the subcutaneous device positioned on the xiphoid process and/or the sternum and showing a positioning of a prong on the heart.

Subcutaneous Device 2300

Figure 56:
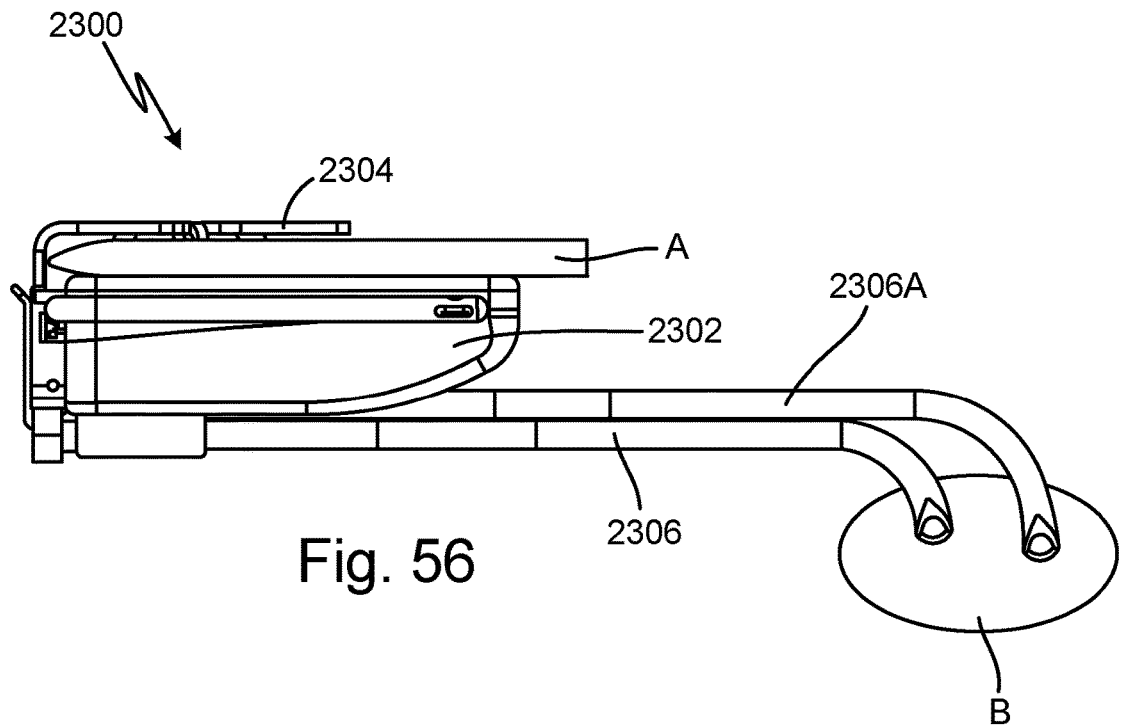

FIG. 56 is a side view of a nineteenth embodiment of a subcutaneous device anchored to a structural body component.

Figure 57A:
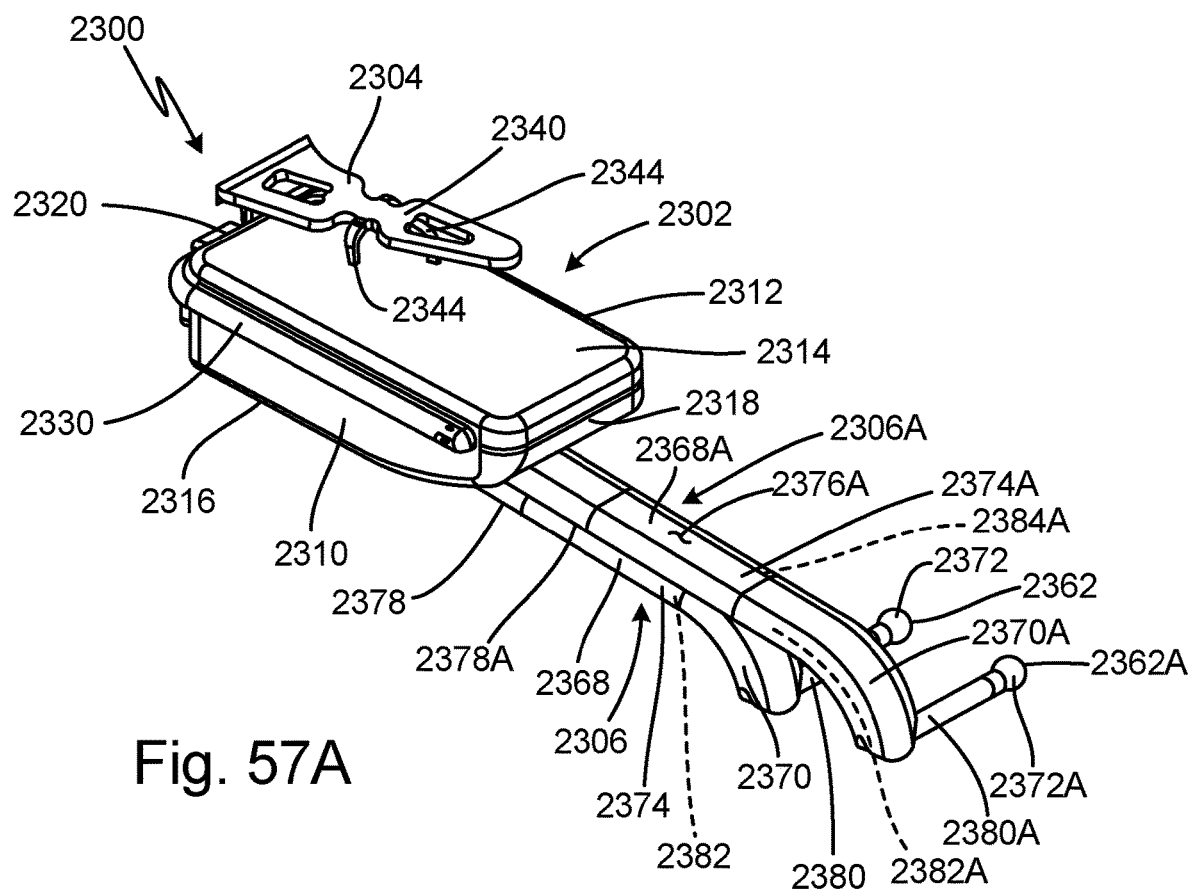

FIG. 57A is a perspective view of the nineteenth embodiment of the subcutaneous device.

Figure 57B:
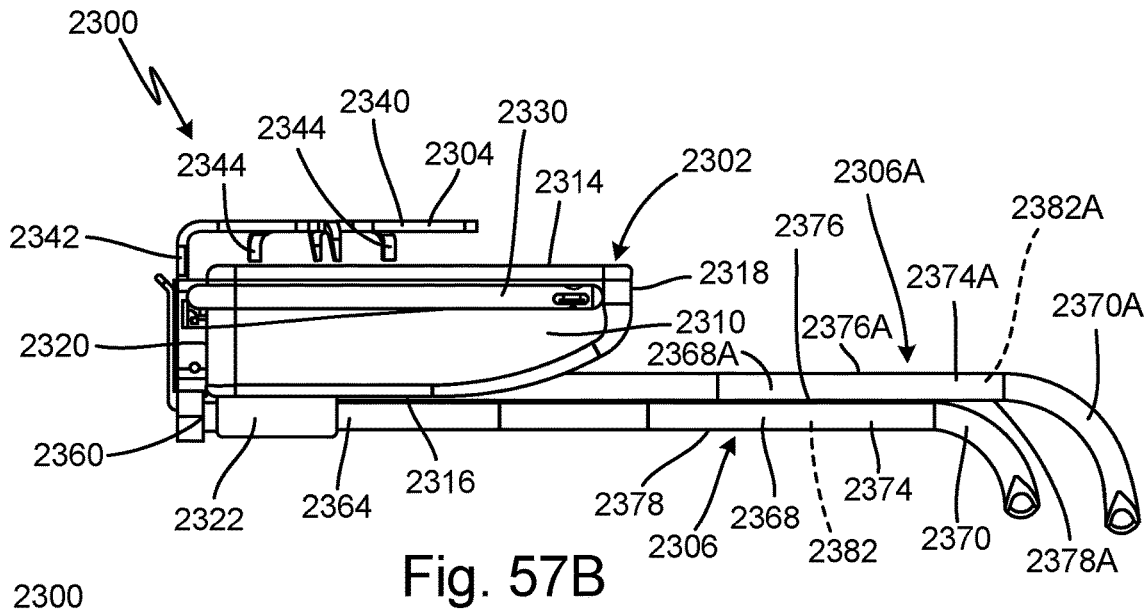

FIG. 57B is a side view of the nineteenth embodiment of the subcutaneous device.

Figure 57C:
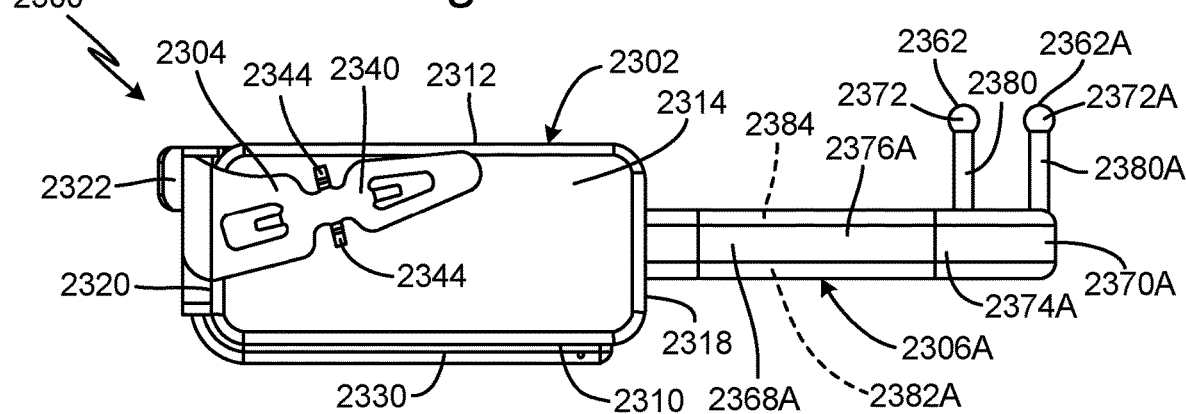

FIG. 57C is a top view of the nineteenth embodiment of the subcutaneous device.

Figure 57D:
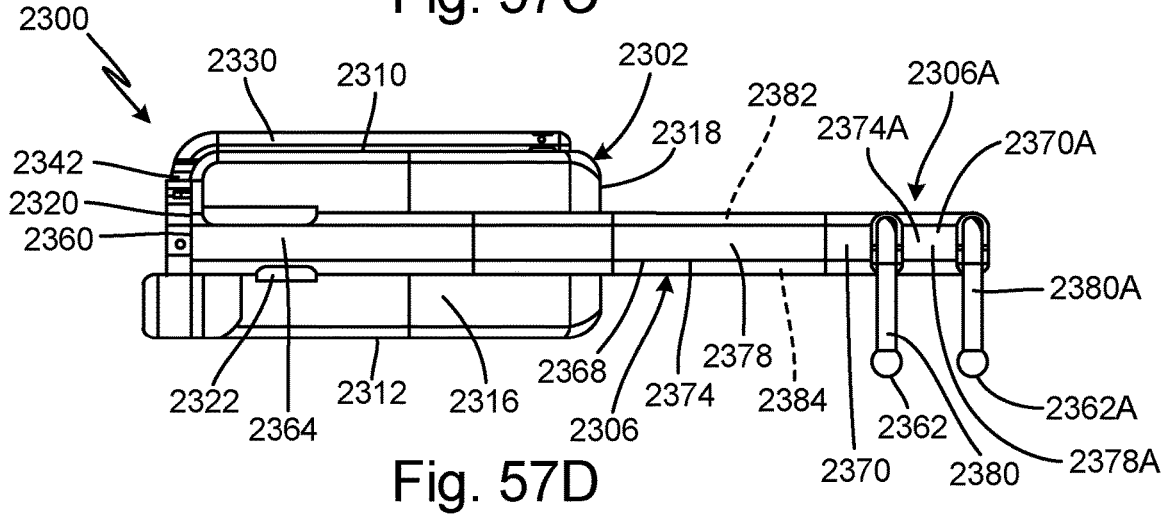

FIG. 57D is a bottom view of the nineteenth embodiment of the subcutaneous device.

Figure 57E:
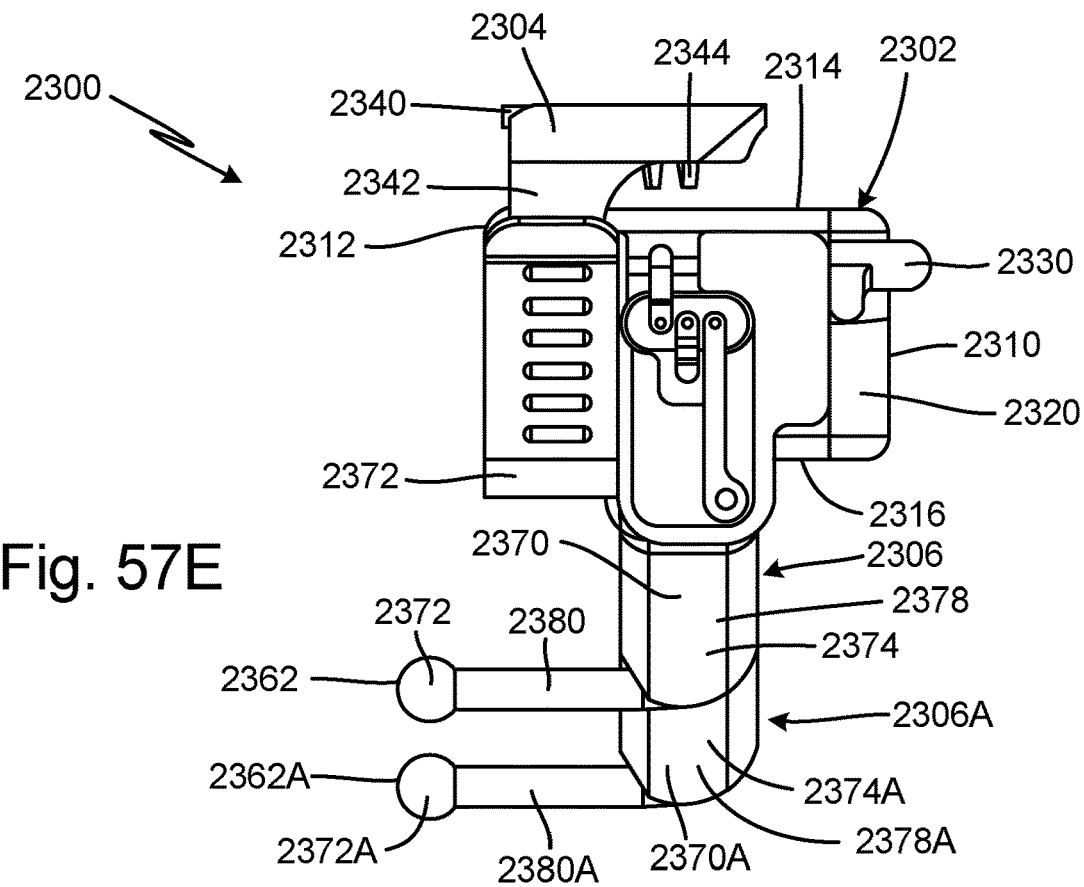

FIG. 57E is a back view of the nineteenth embodiment of the subcutaneous device.

Figure 57F:
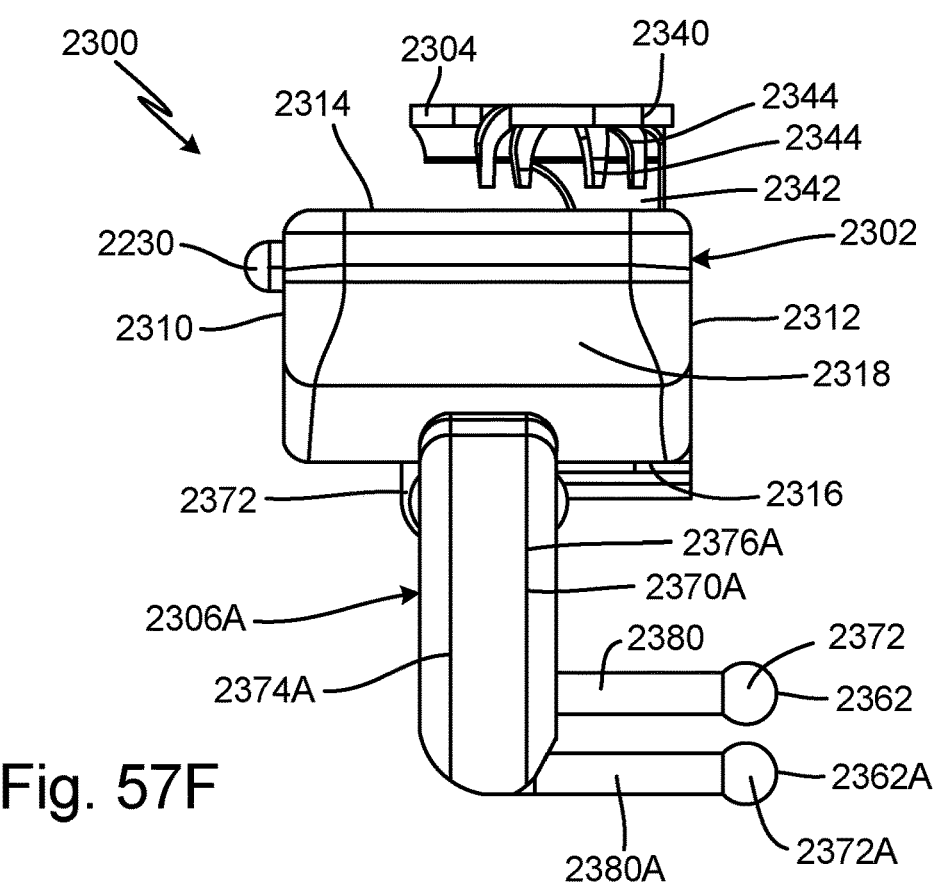

FIG. 57F is a front view of the nineteenth embodiment of the subcutaneous device.

Figure 57G:
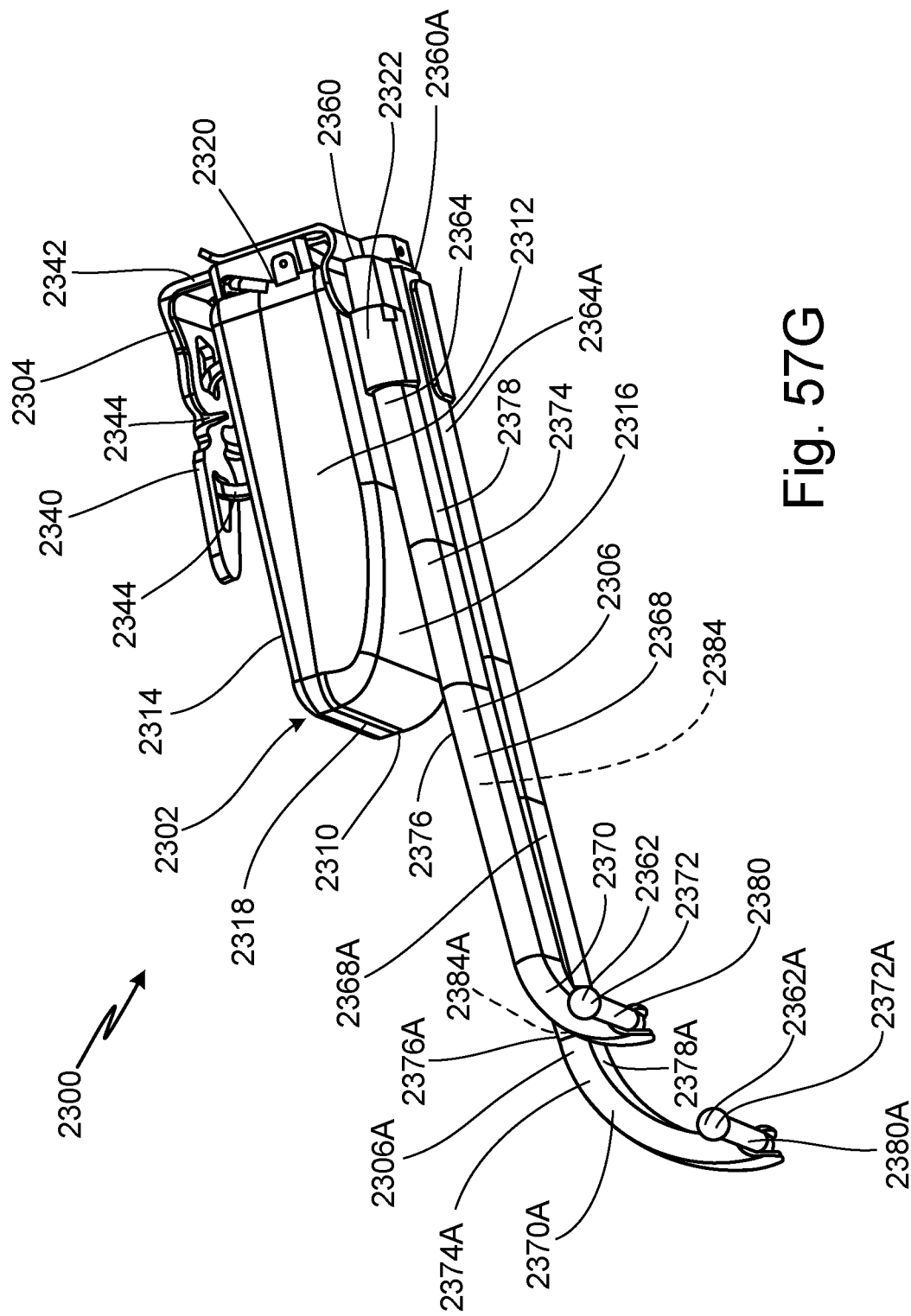

FIG. 57G is a perspective view of the nineteenth embodiment of the subcutaneous device showing prongs positioned side-by-side.

Figure 58:
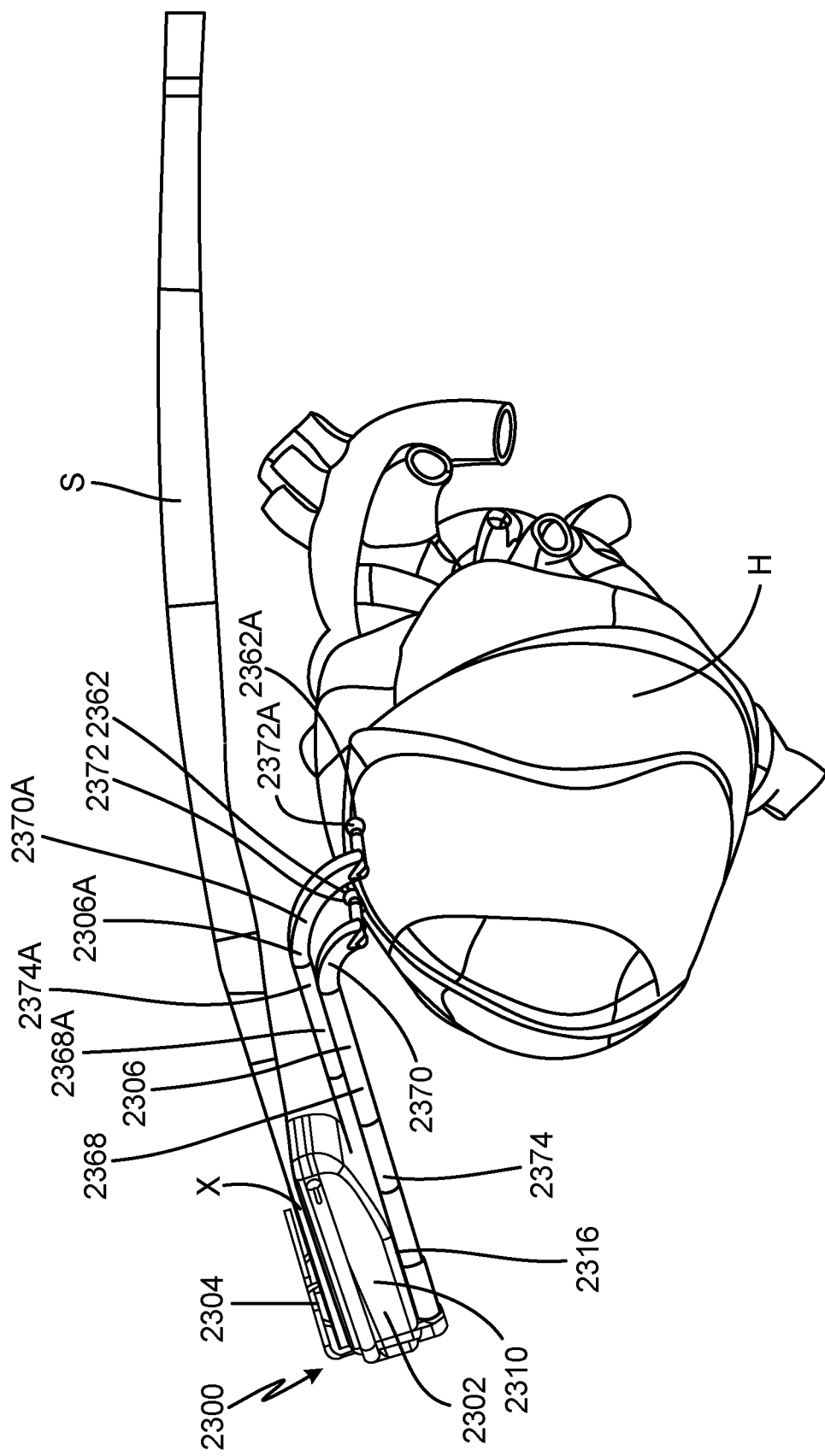

FIG. 58 is a perspective view of the nineteenth embodiment of the subcutaneous device positioned on the xiphoid process and/or the sternum and showing a positioning of prongs on the heart.

Subcutaneous Device 2400

Figure 59:
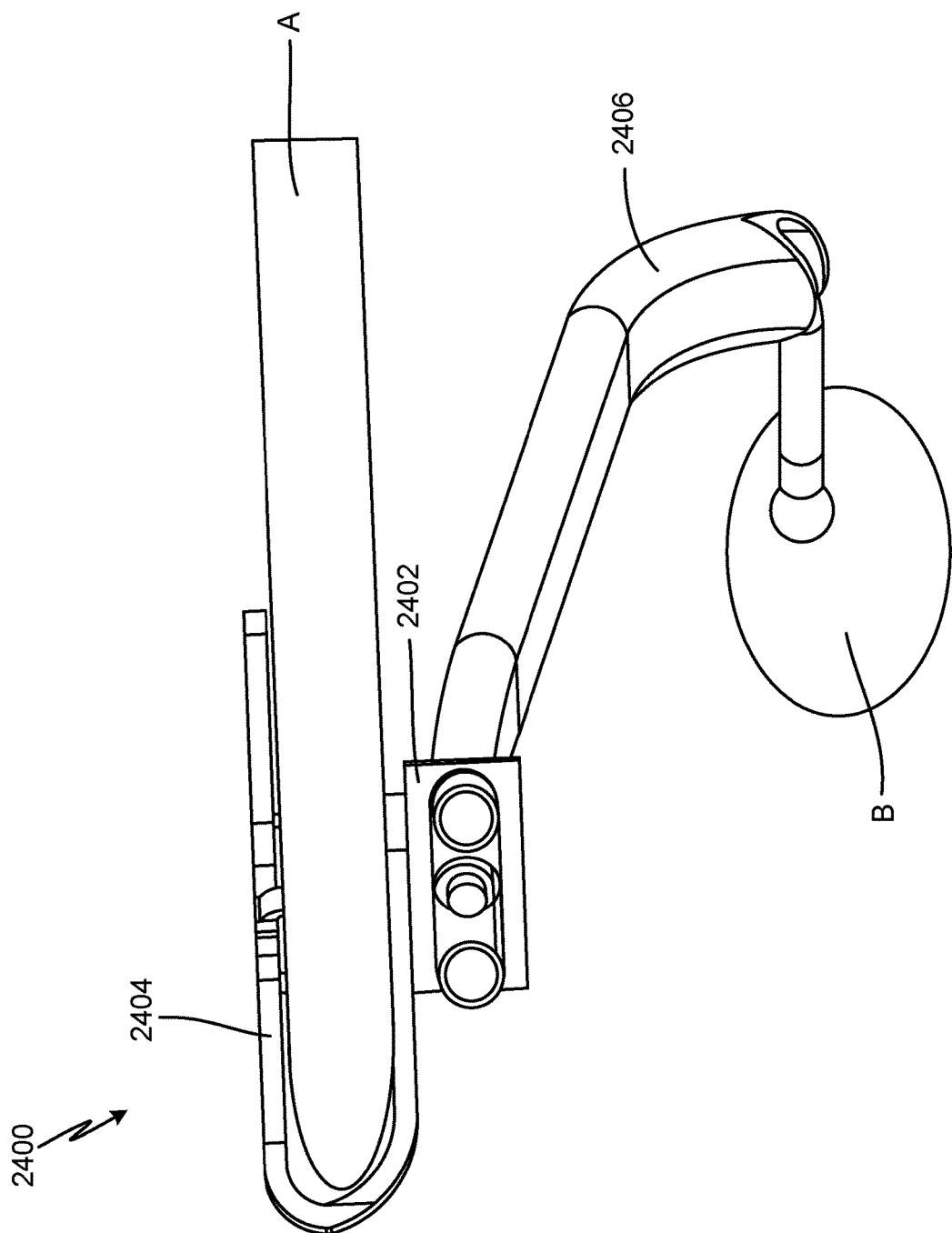

FIG. 59 is a side view of a twentieth embodiment of a subcutaneous device anchored to a structural body component.

Figure 60A:
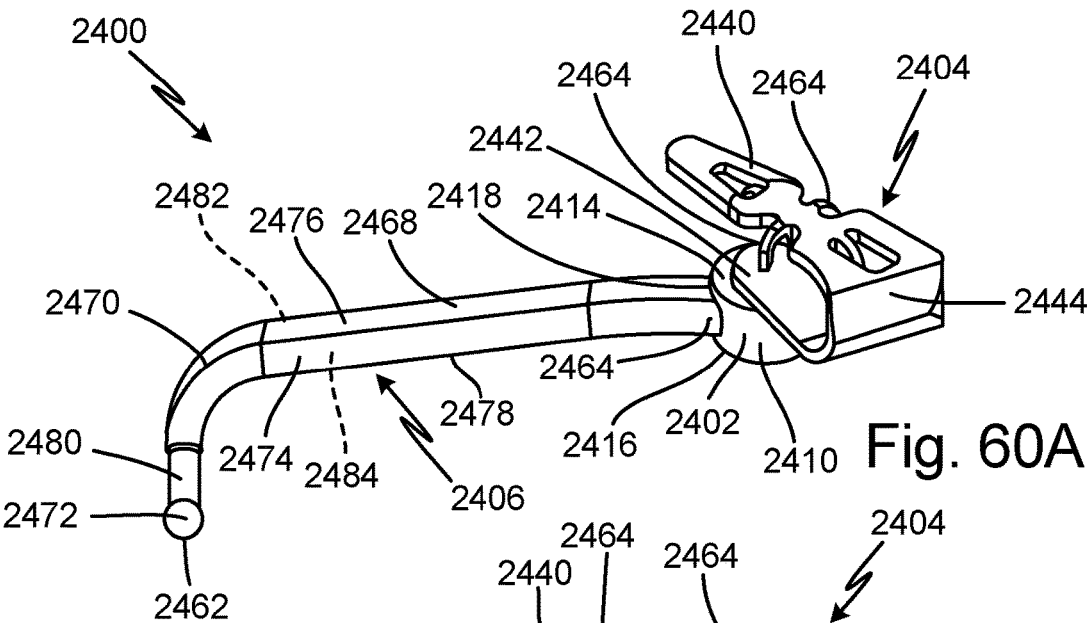

FIG. 60A is a top perspective view of the twentieth embodiment of the subcutaneous device.

Figure 60B:
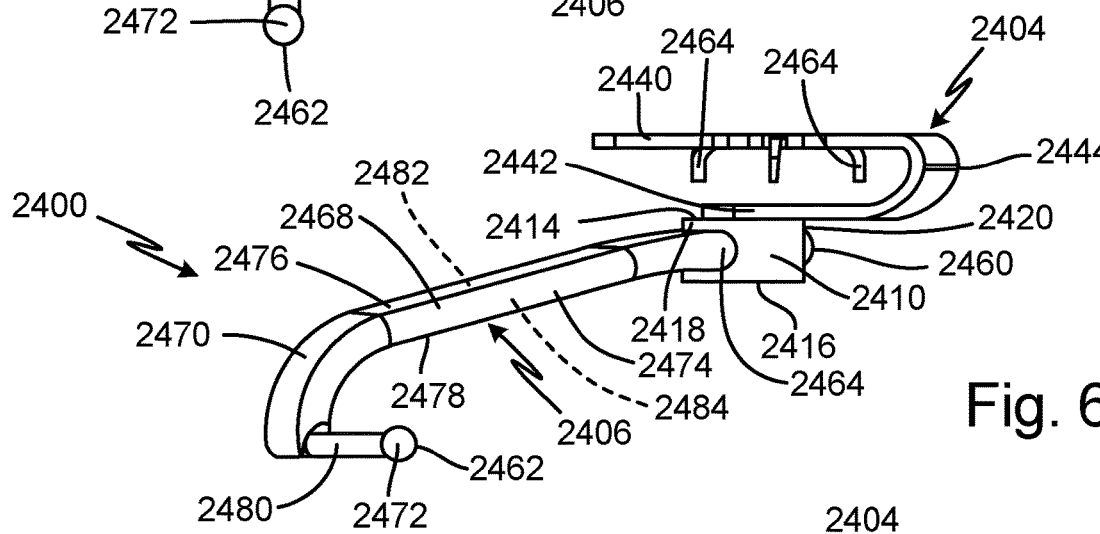

FIG. 60B is a side view of the twentieth embodiment of the subcutaneous device.

Figure 60C:
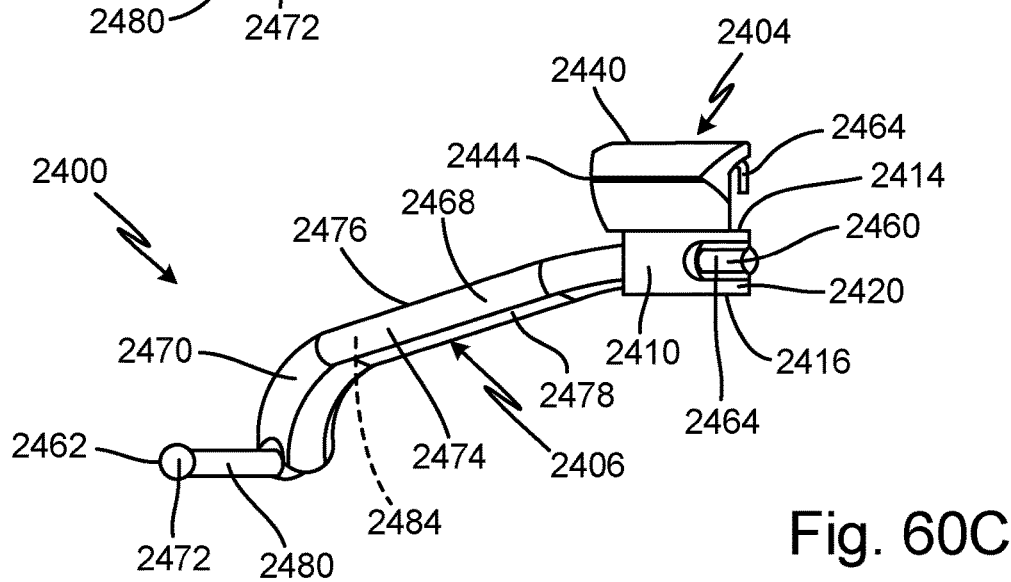

FIG. 60C is a side view of the twentieth embodiment of the subcutaneous device.

Figure 60D:
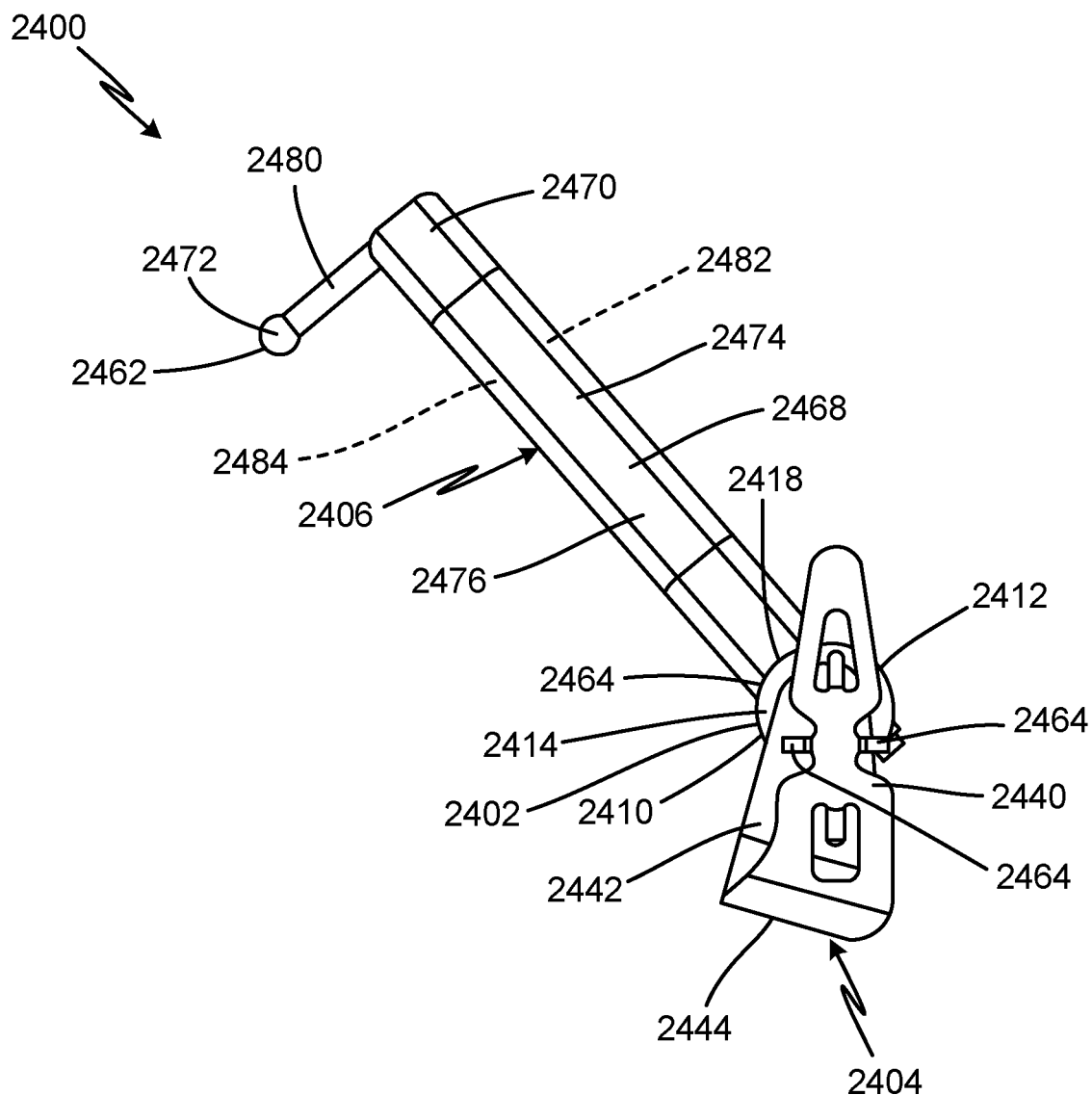

FIG. 60D is a top view of the twentieth embodiment of the subcutaneous device.

Figure 61A:
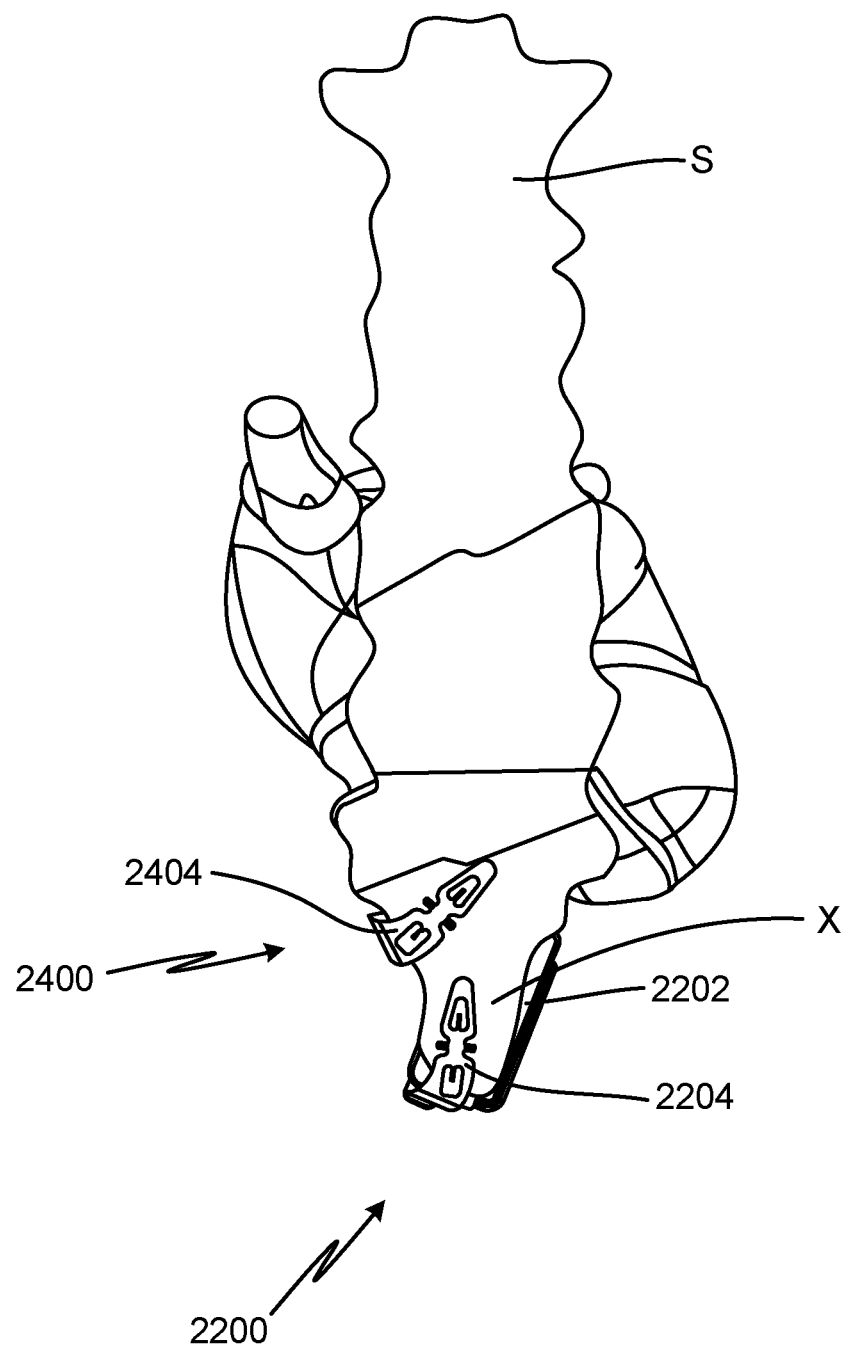

FIG. 61A is a top view of the twentieth embodiment of the subcutaneous device positioned on the xiphoid process and/or the sternum.

Figure 61B:
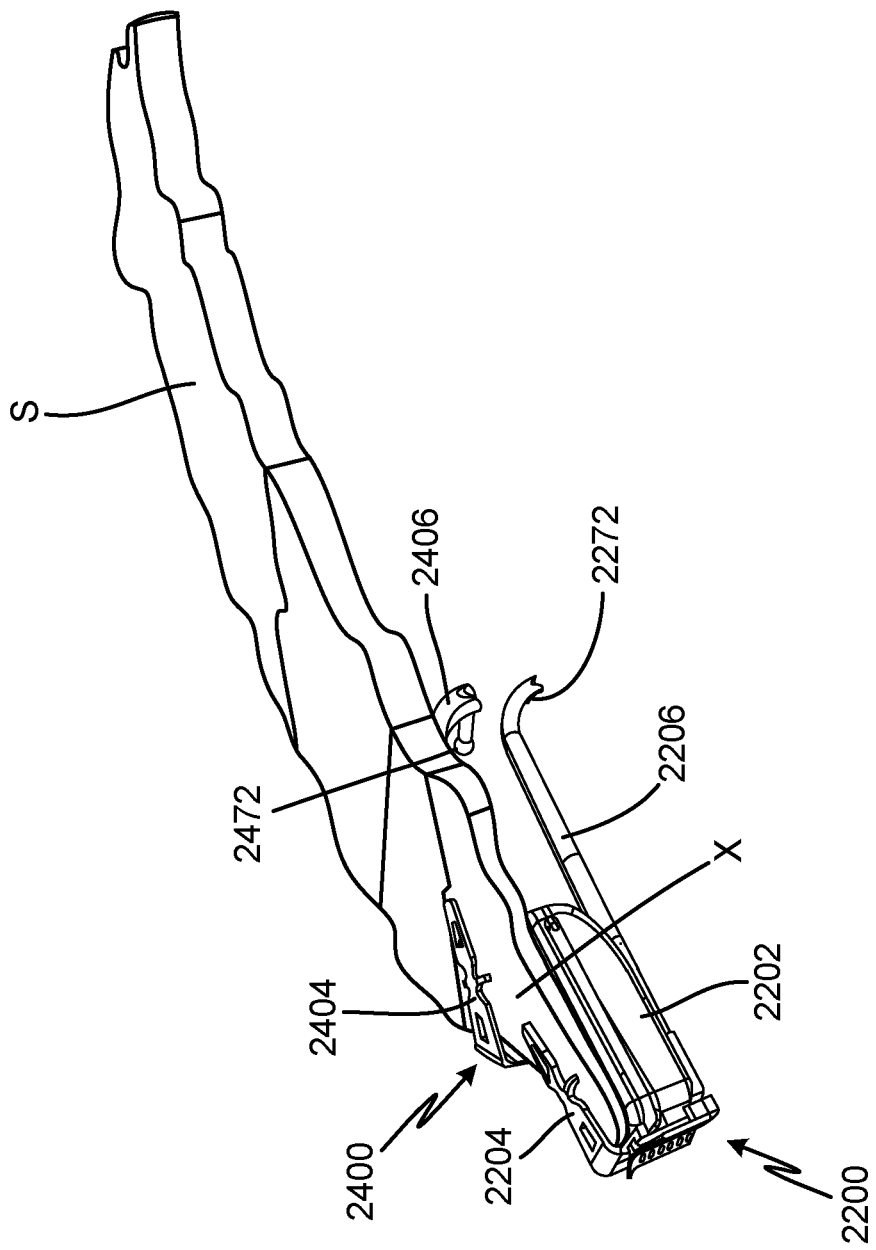

FIG. 61B is a perspective side view of the twentieth embodiment of the subcutaneous device positioned on the xiphoid process and/or the sternum.

Figure 62A:
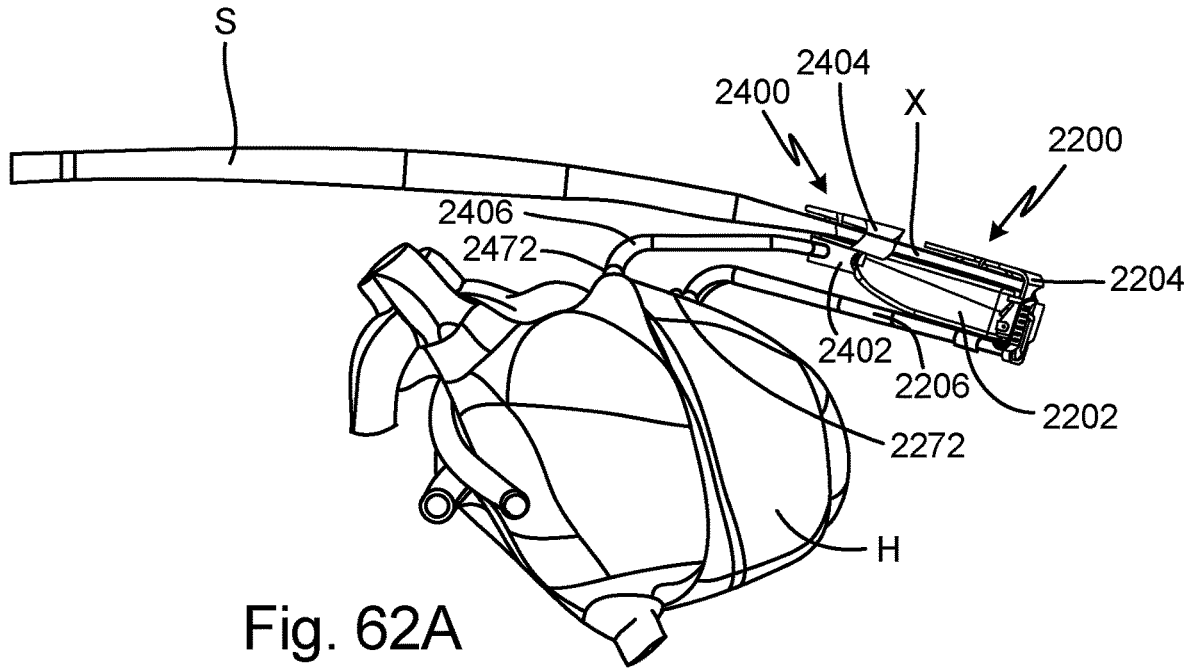

FIG. 62A is a perspective side view of the twentieth embodiment of the subcutaneous device positioned on the xiphoid process and/or the sternum and showing a positioning of prongs on the heart.

Figure 62B:
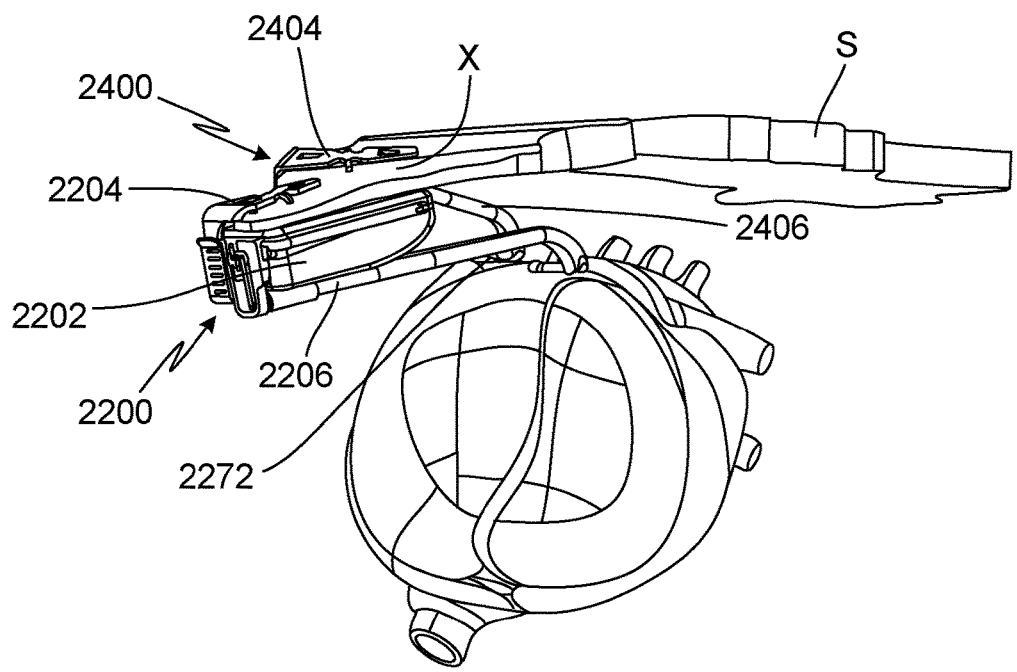

FIG. 62B is a perspective side view of the twentieth embodiment of the subcutaneous device positioned on the xiphoid process and/or the sternum and showing a positioning of prongs on the heart.

Figure 62C:
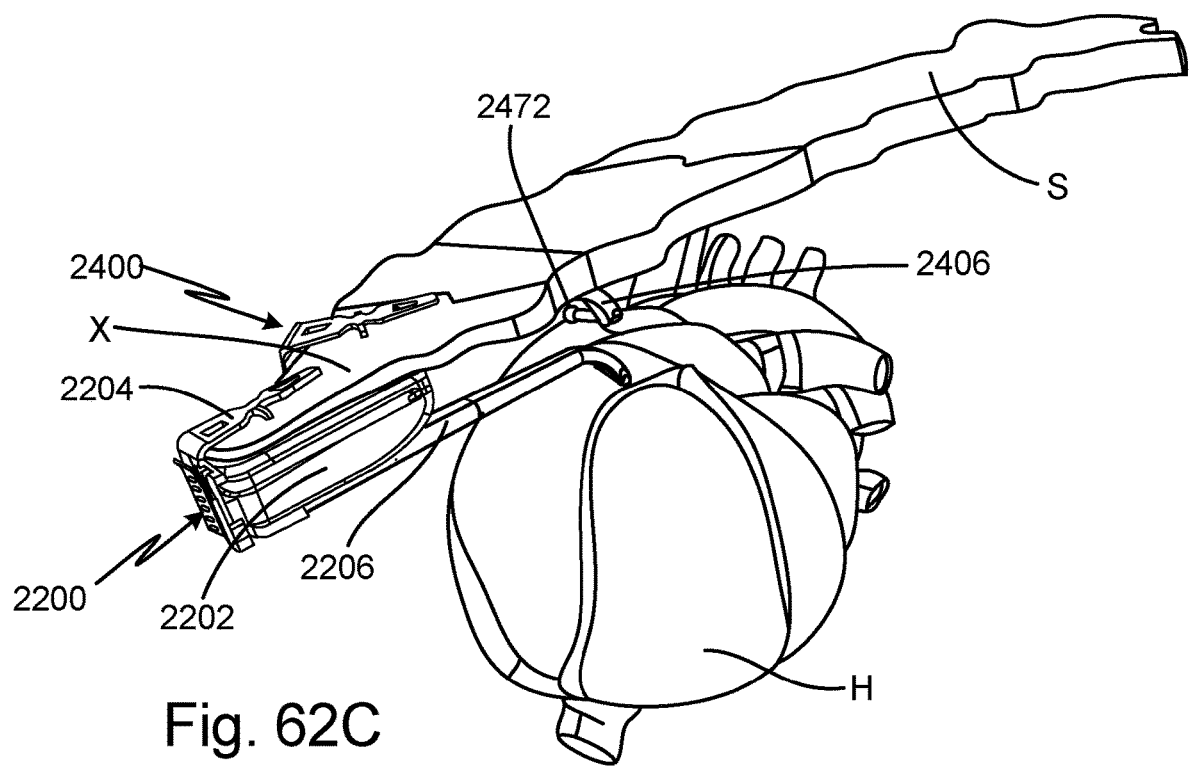

FIG. 62C is a perspective side view of the twentieth embodiment of the subcutaneous device positioned on the xiphoid process and/or the sternum and showing a positioning of prongs on the heart.

Figure 62D:
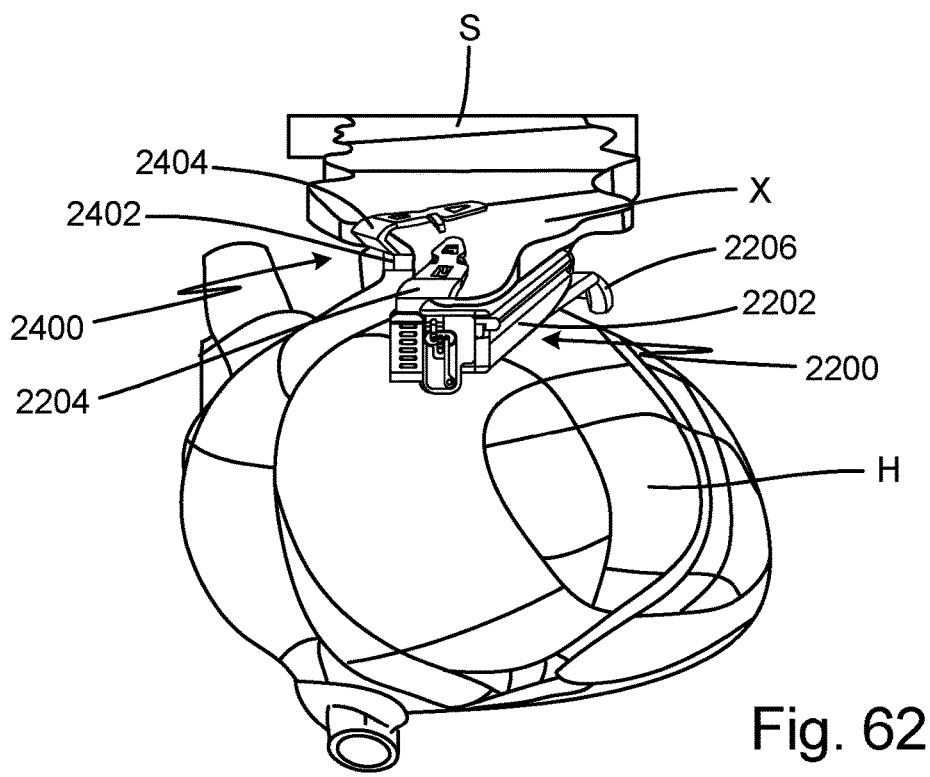

FIG. 62D is a perspective end view of the twentieth embodiment of the subcutaneous device positioned on the xiphoid process and/or the sternum and showing a positioning of prongs on the heart.

Figure 62E:
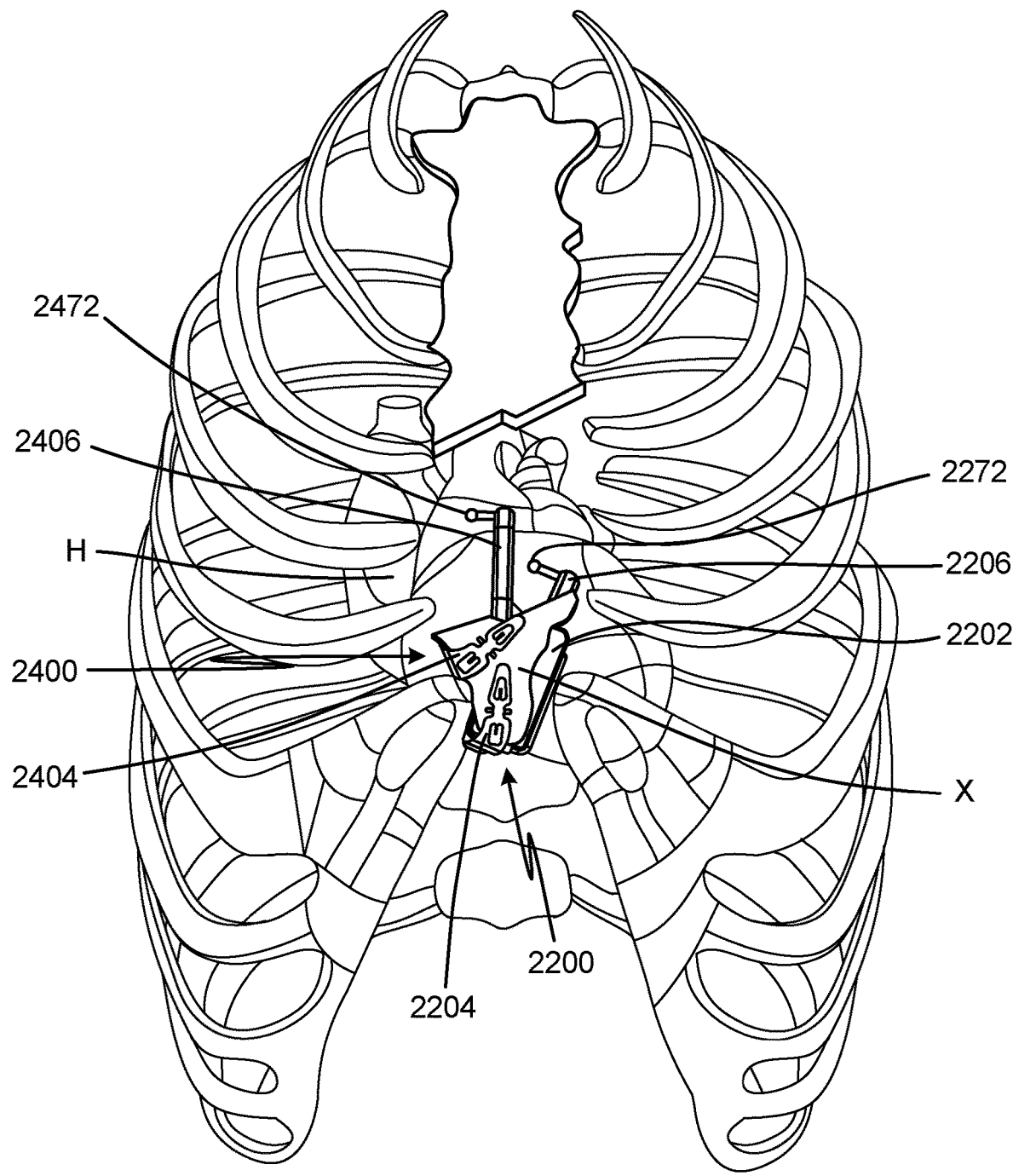

FIG. 62E is a front cut away view of the twentieth embodiment of the subcutaneous device positioned on the xiphoid process and the sternum and showing a positioning of prongs on the heart.

Figure 63:
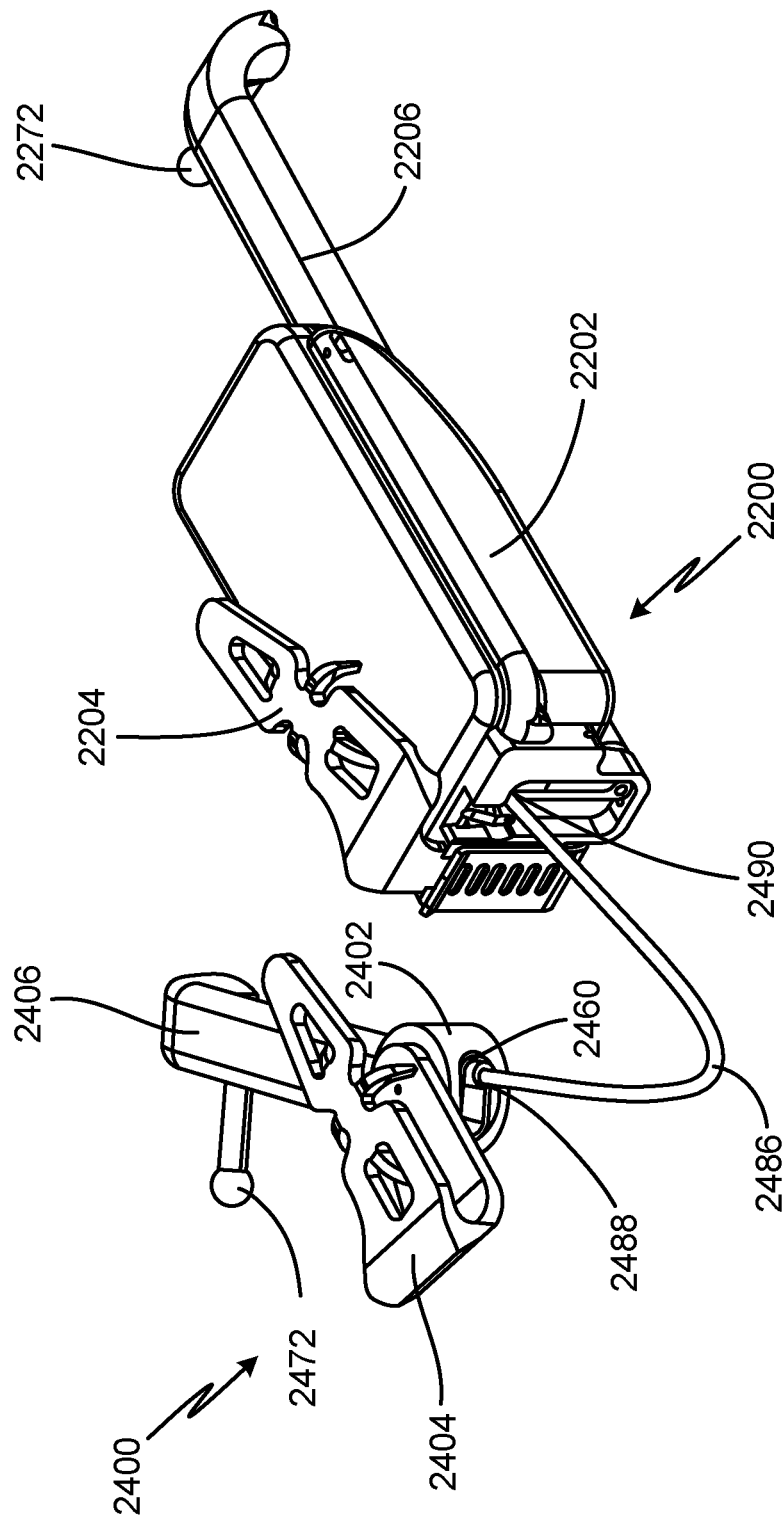

FIG. 63 is a perspective view of the twentieth embodiment of the subcutaneous device connected to the eighteenth embodiment of the subcutaneous device.

DETAILED DESCRIPTION

In general, the present disclosure relates to a subcutaneous device that can be injected into a patient for monitoring, diagnostic, and therapeutic purposes. The subcutaneous device includes a housing that contains the electrical circuitry of the subcutaneous device, a clip on a top side of the housing, and one or more prongs extending away from the housing. The clip is configured to attach and anchor the subcutaneous device onto a muscle, a bone, or tissue. The prong extends away from the housing and a distal end of the prong comes into contact with an organ, a nerve, or tissue remote from the subcutaneous device.

The subcutaneous device can be a monitoring device, a diagnostic device, a pacemaker, an implantable cardioverter-defibrillator, a general organ/nerve/tissue stimulator, and/or a drug delivery device. A monitoring device can monitor physiological parameters of a patient. A diagnostic device can measure physiological parameters of a patient for diagnostic purposes. A pacemaker and an implantable cardioverter-defibrillator can sense a patient's heart rate and provide a therapeutic electrical stimulation to the patient's heart if an abnormality is detected. A pacemaker will provide an electrical stimulation to the heart in response to an arrhythmia, such as bradycardia, tachycardia, atrial flutter, and atrial fibrillation. The electrical stimulation provided by a pacemaker will contract the heart muscles to regulate the heart rate of the patient. An implantable cardioverter-defibrillator will provide an electrical stimulation to the heart in response to ventricular fibrillation and ventricular tachycardia, both of which can lead to sudden cardiac death. An implantable cardioverter-defibrillator will provide cardioversion or defibrillation to the patient's heart. Cardioversion includes providing an electrical stimulation to the heart at a specific moment that is in synchrony with the cardiac cycle to restore the patient's heart rate. Cardioversion can be used to restore the patient's heart rate when ventricular tachycardia is detected. If ventricular fibrillation is detected, defibrillation is needed. Defibrillation includes providing a large electrical stimulation to the heart at an appropriate moment in the cardiac cycle to restore the patient's heart rate. An implantable cardioverter-defibrillator can also provide pacing to multiple chambers of a patient's heart. A general organ/nerve/tissue stimulator can provide electrical stimulation to an organ, nerve, or tissue of a patient for therapeutic purposes. A drug delivery device can provide targeted or systemic therapeutic drugs to an organ, nerve, or tissue of a patient.

The subcutaneous device described in this disclosure can, in some embodiments, be anchored to a patient's xiphoid process and/or a distal end of a patient's sternum. The xiphoid process is a process on the lower part of the sternum. At birth, the xiphoid process is a cartilaginous process. The xiphoid process ossifies over time, causing it to fuse to the sternum with a fibrous joint. The subcutaneous device can be anchored to the xiphoid process so that the housing of the subcutaneous device is positioned below the xiphoid process and sternum. In some patients, the xiphoid process is absent, small, narrow, or elongated. In such cases, the subcutaneous device can be attached directly to the distal end of the patient's sternum. When the subcutaneous device is anchored to the xiphoid process and/or sternum, the one or more prongs of the subcutaneous device extend into the anterior mediastinum.

Different embodiments of the subcutaneous device are described in detail below. The different embodiments of the subcutaneous device can include: a single prong cardiac monitoring device, a multi-prong cardiac monitoring device, a pulmonary monitoring device, a single chamber pacemaker, a dual chamber pacemaker, a triple chamber pacemaker, an atrial defibrillator, a single-vector ventricular defibrillator, a multi-vector ventricular defibrillator, and an implantable drug pump and/or drug delivery device. These embodiments are included as examples and are not intended to be limiting. The subcutaneous device can have any suitable design and can be used for any suitable purpose in other embodiments. The features of each embodiment may be combined and/or substituted with features of any other embodiment, unless explicitly disclosed otherwise. Further, many of the embodiments can be used for multiple purposes. For example, a defibrillator device can also be used for monitoring and pacing. A surgical instrument and a method for implanting the subcutaneous device into a body of a patient is also described.

Subcutaneous Device 100

Figure 1:
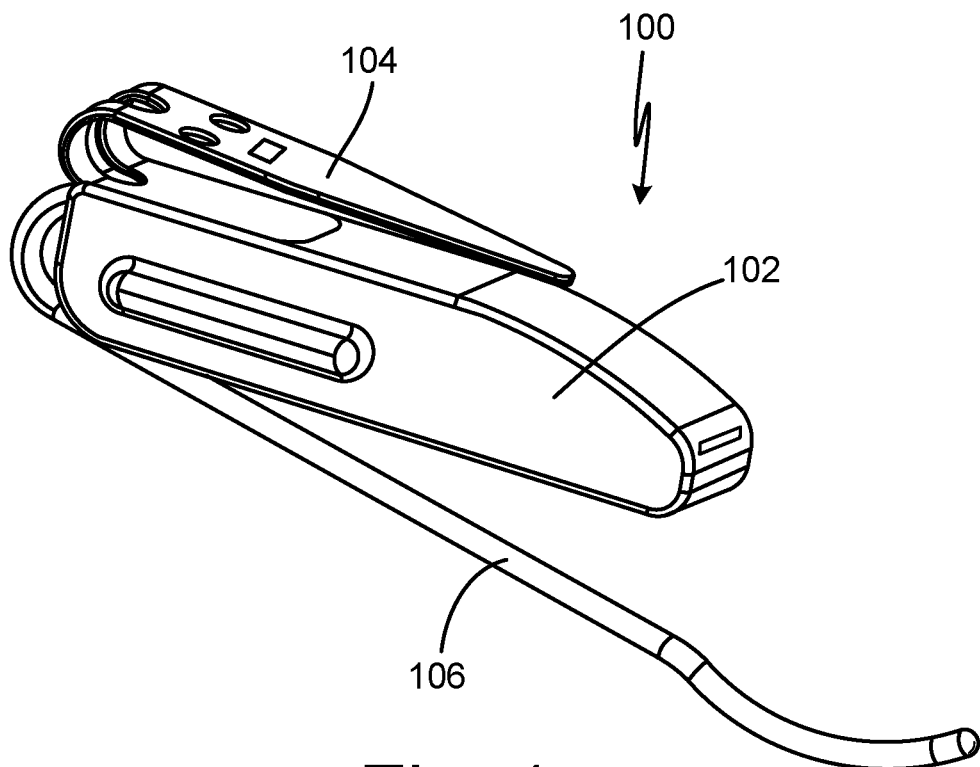
FIG. 1 is a perspective view of a first embodiment of a subcutaneous device.
Figure 2:
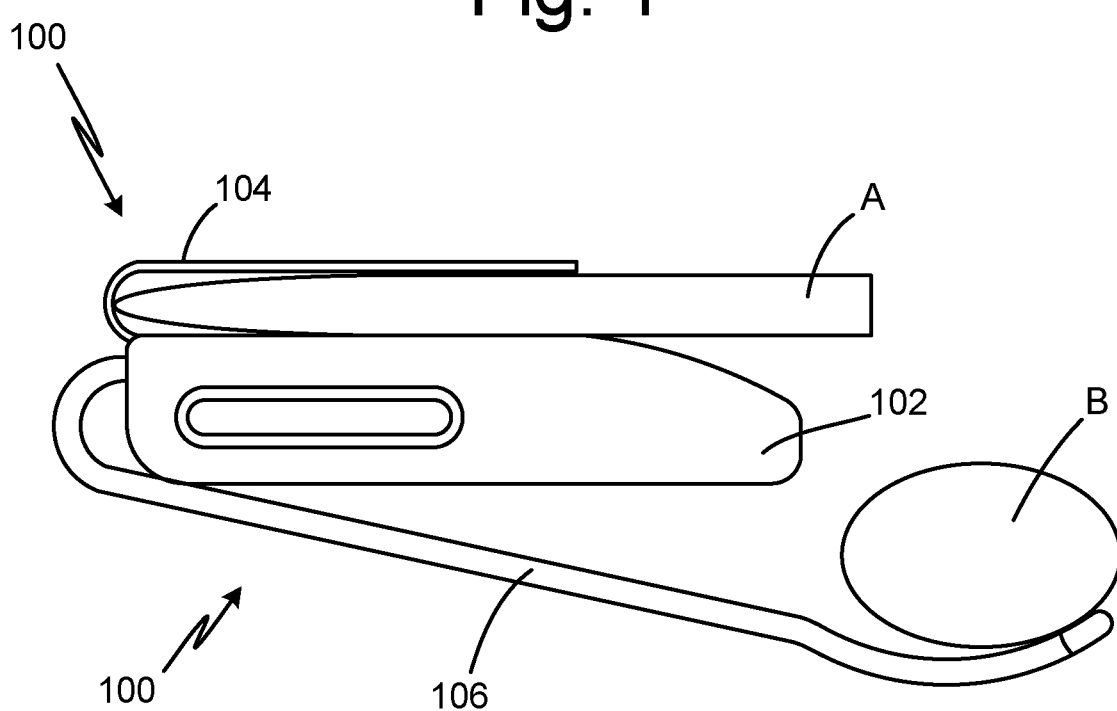
FIG. 2 is a side view of the first embodiment of the subcutaneous device anchored to a structural body component.

FIG. 1 is a perspective view of subcutaneous device 100. FIG. 2 is a side view of subcutaneous device 100 anchored to structural body component A. Subcutaneous device 100 includes housing 102, clip 104, and prong 106. FIG. 2 shows structural body component A and remote body component B.

Subcutaneous device 100 is a medical device that is anchored to structural body component A. Structural body component A may be a muscle, a bone, or a tissue of a patient. Subcutaneous device 100 can be a monitoring device, a diagnostic device, a therapeutic device, or any combination thereof. For example, subcutaneous device 100 can be a pacemaker device that is capable of monitoring a patient's heart rate, diagnosing an arrhythmia of the patient's heart, and providing therapeutic electrical stimulation to the patient's heart. Subcutaneous device 100 includes housing 102. Housing 102 can contain a power source, a controller, a memory, a transceiver, sensors, sensing circuitry, therapeutic circuitry, and/or any other component of the medical device. Housing 102 can also include one or more electrodes that are capable of sensing an electrical activity or physiological parameter of tissue surrounding housing 102 and/or provide therapeutic electrical stimulation to the tissue surrounding housing 102.

Clip 104 is attached to housing 102. Clip 104 is configured to anchor subcutaneous device 100 to structural body component A. Clip 104 will expand as it is advanced around structural body component A. Clip 104 can be a passive clip or an active clip. A passive clip only uses the stiffness of clamping components to attach to the bone, the muscle, or the tissue. This stiffness can be the result of design or active crimping during the implant procedure. An active clip may additionally use an active fixation method such as sutures, tines, pins, or screws to secure the clip to the bone, the muscle, or the tissue. In the embodiment shown in FIGS. 1-2, clip 104 has a spring bias that will put tension on structural body component A when it is expanded and fit onto structural body component A. The spring bias of clip 104 will anchor subcutaneous device 100 to structural body component A. Clip 104 can include one or more electrodes that are capable of sensing an electrical activity or physiological parameter of tissue surrounding clip 104 and/or provide therapeutic electrical stimulation to the tissue surrounding clip 104.

Prong 106 is connected to and extends away from housing 102 of subcutaneous device 100. Prong 106 is configured to contact remote body component B that is positioned away from structural body component A. Remote body component B may be an organ, a nerve, or tissue of the patient. For example, remote body component B can include a heart, a lung, or any other suitable organ in the body. Prong 106 includes one or more electrodes that are capable of sensing an electrical activity or physiological parameter of remote body component B and/or providing therapeutic electrical stimulation to remote body component B.

In one example, subcutaneous device 100 can be a pacemaker and the one or more electrodes on prong 106 of subcutaneous device 100 can sense the electrical activity of a heart. The sensed electrical activity can be transmitted to sensing circuitry and a controller in housing 102 of subcutaneous device 100. The controller can determine the heart rate of the patient and can detect whether an arrhythmia is present. If an arrhythmia is detected, the controller can send instructions to therapeutic circuitry to provide a therapeutic electrical stimulation to the heart. In this manner, subcutaneous device 100 functions as a monitoring device, a diagnostic device, and a therapeutic device.

Subcutaneous device 100 will be discussed in greater detail in relation to FIGS. 3A-9 below. Subcutaneous device 100 will be discussed as a pacemaker that can be used for monitoring, diagnostics, and therapeutics in the discussion of FIGS. 3A-9 below. Subcutaneous device 100 can also be used only for monitoring, diagnostics, or a combination of the two in alternate embodiments. Further, subcutaneous device 100 can be a unipolar pacemaker or a bipolar pacemaker.

Figure 3A:
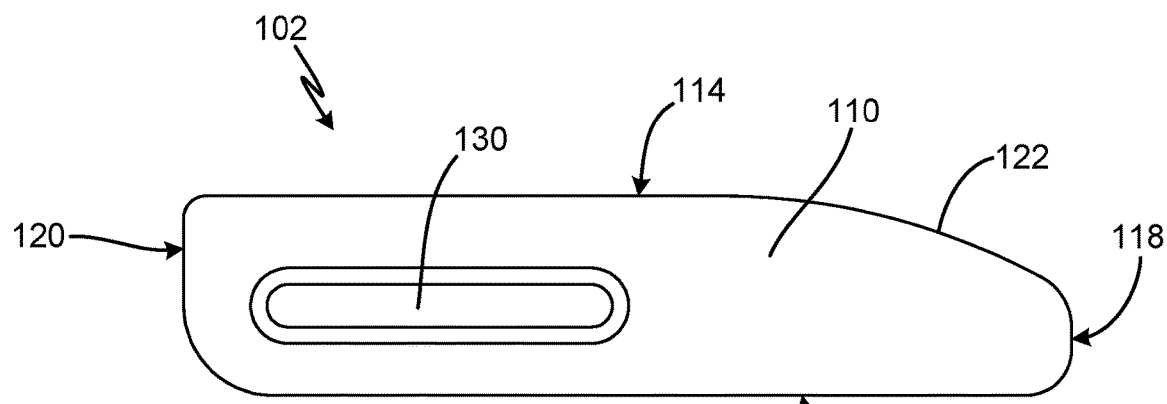
FIG. 3A is a side view of a housing of the first embodiment of the subcutaneous device.
Figure 3B:
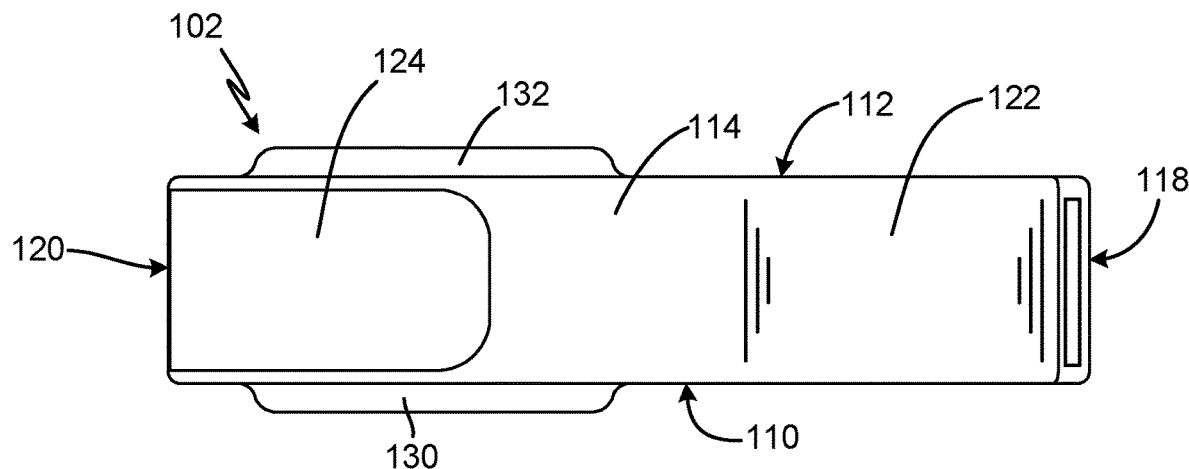
FIG. 3B is a top view of the housing of the first embodiment of the subcutaneous device.
Figure 3C:
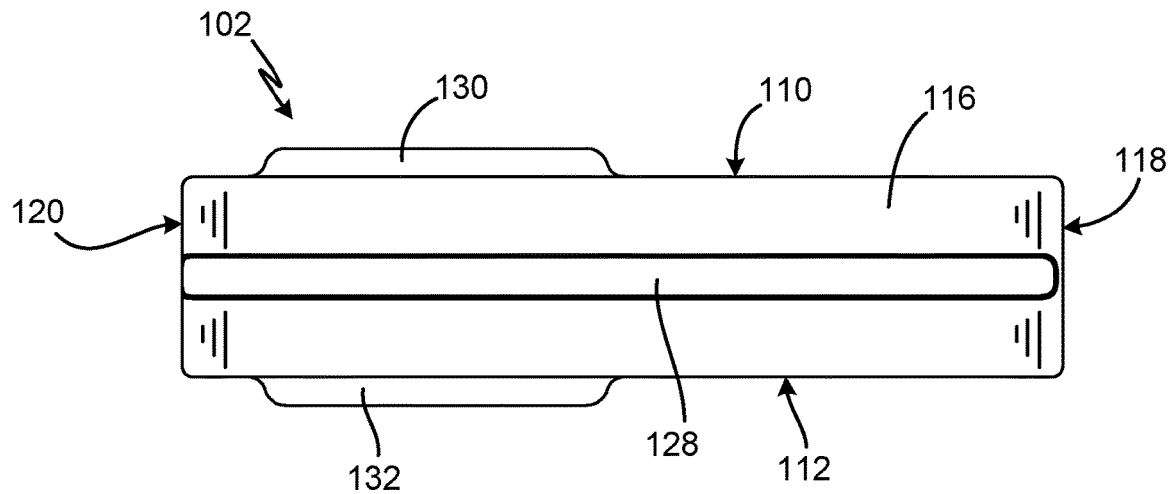
FIG. 3C is a bottom view of the housing of the first embodiment of the subcutaneous device.
Figure 3D:
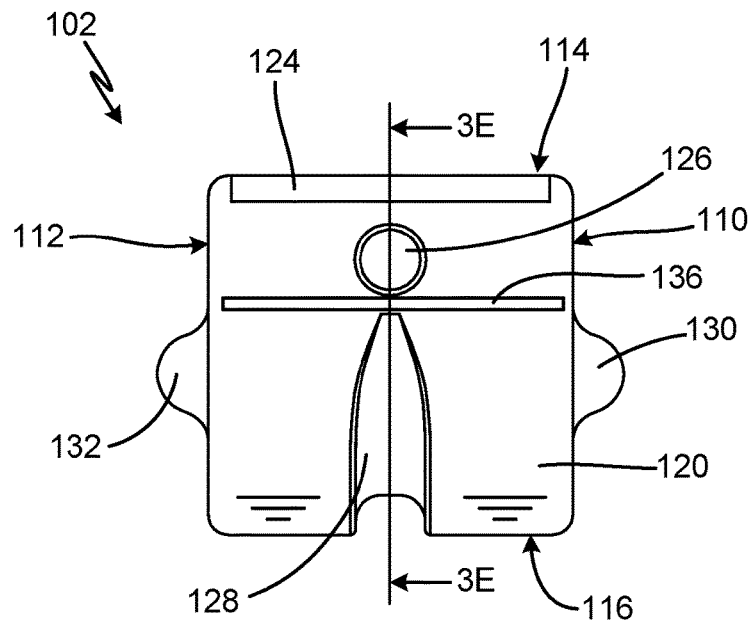
FIG. 3D is a back end view of the housing of the first embodiment of the subcutaneous device.
Figure 3E:
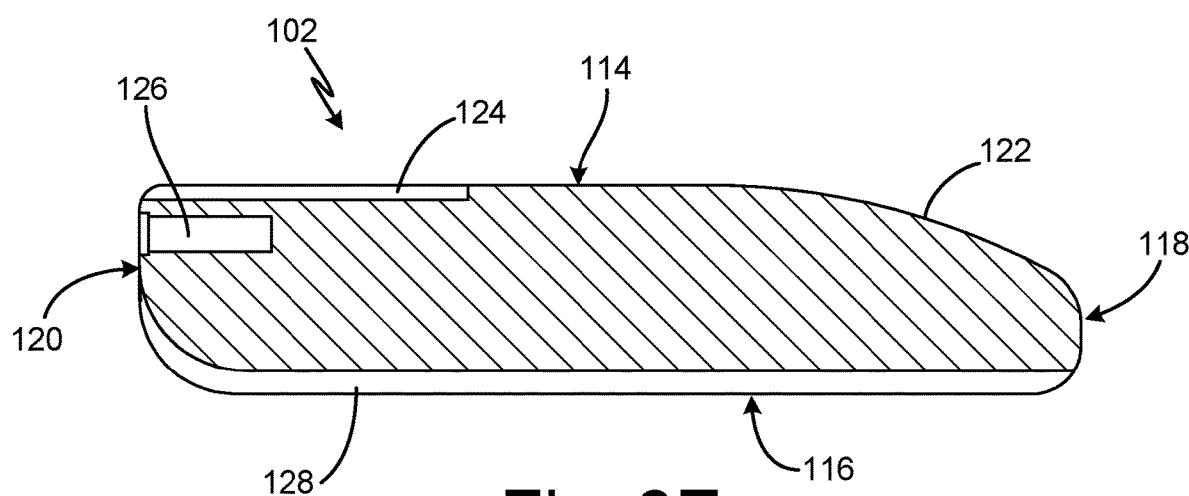
FIG. 3E is a cross-sectional view of the housing of the first embodiment of the subcutaneous device, taken along line 3E-3E of FIG. 3D.

FIG. 3A is a side view of housing 102 of subcutaneous device 100. FIG. 3B is a top view of housing 102 of subcutaneous device 100. FIG. 3C is a bottom view of housing 102 of subcutaneous device 100. FIG. 3D is a back end view of housing 102 of subcutaneous device 100. FIG. 3E is a cross-sectional view of housing 102 of subcutaneous device 100. Housing 102 includes first side 110, second side 112, top side 114, bottom side 116, front end 118, back end 120, curved surface 122, recess 124, port 126, channel 128, first guide 130, second guide 132, electrode 134, and electrode 136.

Housing 102 includes first side 110, second side 112, top side 114, bottom side 116, front end 118, and back end 120. First side 110 is opposite of second side 112; top side 114 is opposite of bottom side 116; and front end 118 is opposite of back end 120. Housing 102 is substantially rectangular-shaped in the embodiment shown. In alternate embodiments, housing 102 can be shaped as a cone, frustum, or cylinder. Housing 102 can be made out of stainless steel, titanium, nitinol, epoxy, silicone, polyurethane with metallic reinforcements, or any other material that is suitable for non-porous implants. Housing 102 can also include an exterior coating. Curved surface 122 is positioned on top side 114 of housing 102 adjacent front end 118 of housing 102. Curved surface 122 creates a tapered front end 118 of housing 102 of subcutaneous device 100. In an alternate embodiment, front end 118 of housing 102 can be wedge shaped. The tapered front end 118 of housing 102 helps front end 118 of housing 102 to push through tissue in a body of a patient to permit easier advancement of subcutaneous device 100 during the implantation or injection process.

Housing 102 includes recess 124 on top side 114. Recess 124 is a groove that extends into housing 102 on top side 114 of housing 102 adjacent back end 120 of housing 102. A portion of clip 104 of subcutaneous device 100 (shown in FIGS. 1-2) is positioned in recess 124 to attach clip 104 to housing 102. In an alternate embodiment, recess 124 may not be included on housing 102 and clip 104 can be welded to top side 114 of housing 102 or connected to a header. Housing 102 further includes port 126 on back end 120. Port 126 is a bore that extends into housing 102 on back end 120 of housing 102. A proximal end of prong 106 of subcutaneous device 100 (shown in FIGS. 1-2) is positioned in port 126 to attach prong 106 to housing 102. In an alternate embodiment, port 126 can be positioned in a header. Housing 102 also includes channel 128 on back end 120 and bottom side 116. Channel 128 is a groove that extends into housing 102 on back end 120 and bottom side 116 of housing 102. Channel 128 is configured to receive a portion of prong 106 of subcutaneous device 100 (shown in FIGS. 1-2) when subcutaneous device 100 is in a stowed position.

Housing 102 also includes first guide 130 on first side 110 and second guide 132 on second side 112. First guide 130 is a ridge that extends out from first side 110 of housing 102. Second guide 132 is a ridge that extends out from second side 112 of housing 102. First guide 130 and second guide 132 are configured to guide housing 102 of subcutaneous device 100 through a surgical instrument used to implant subcutaneous device 100 in a patient.

Housing 102 further includes electrode 134 on front end 118 of housing 102 and electrode 136 on back end 120 of housing 102. In the embodiment shown in FIGS. 3A-3E, there are two electrodes 134 and 136 positioned on housing 102. In alternate embodiments, any number of electrodes can be positioned on housing 102 or housing 102 can include no electrodes. Electrode 134 and electrode 136 are positioned to sense an electrical activity or physiological parameter of the tissue surrounding housing 102. Electrode 134 and electrode 136 can also provide therapeutic electrical stimulation to the tissue surrounding housing 102.

Figure 4A:
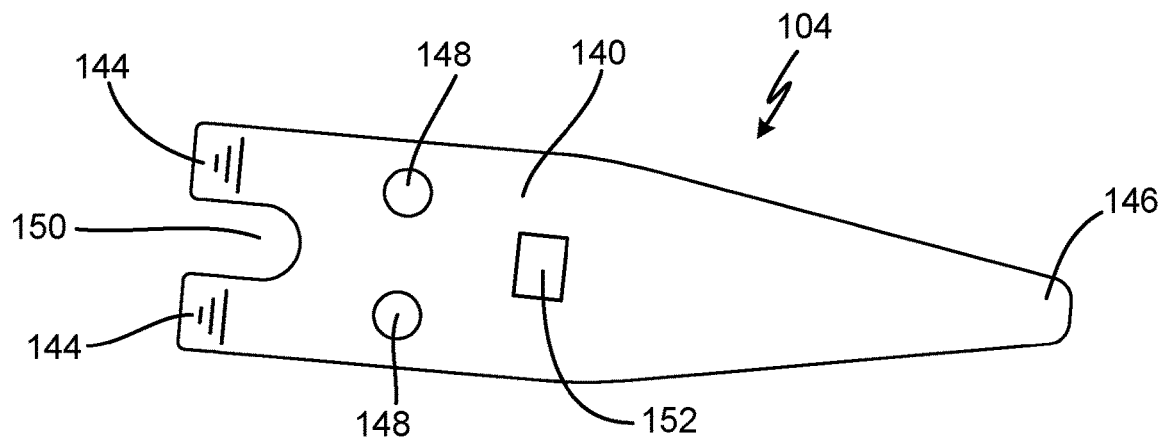
FIG. 4A is a top view of a clip of the first embodiment of the subcutaneous device.
Figure 4B:
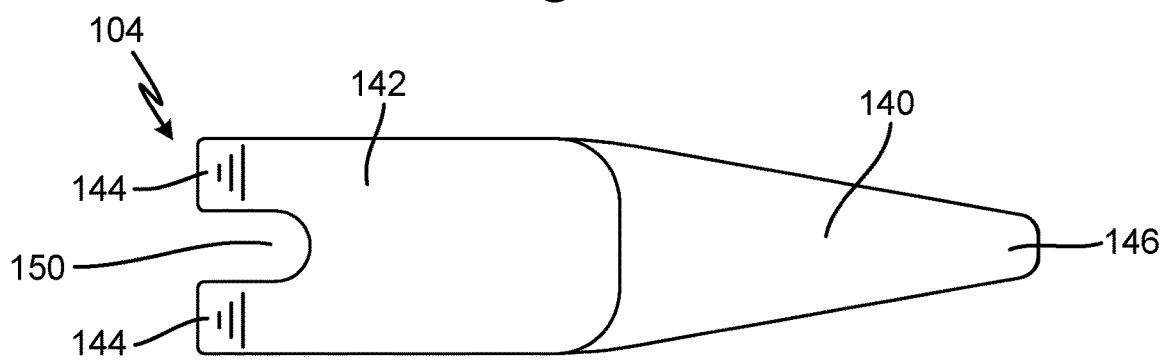
FIG. 4B is a bottom view of the clip of the first embodiment of the subcutaneous device.
Figure 4C:
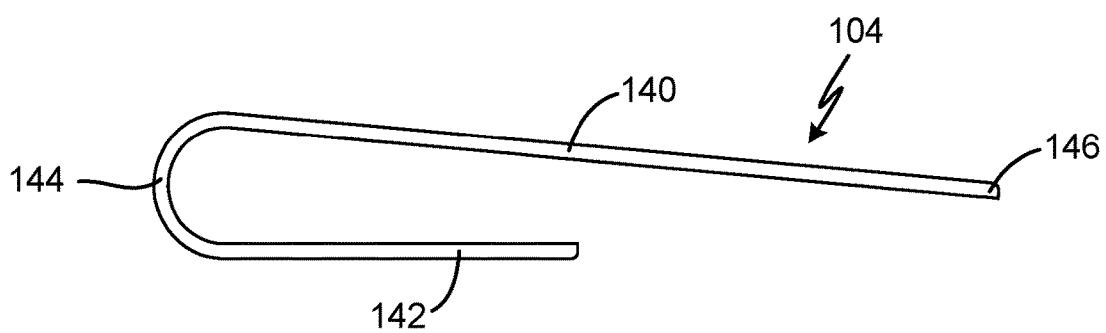
FIG. 4C is a side view of the clip of the first embodiment of the subcutaneous device.
Figure 4D:
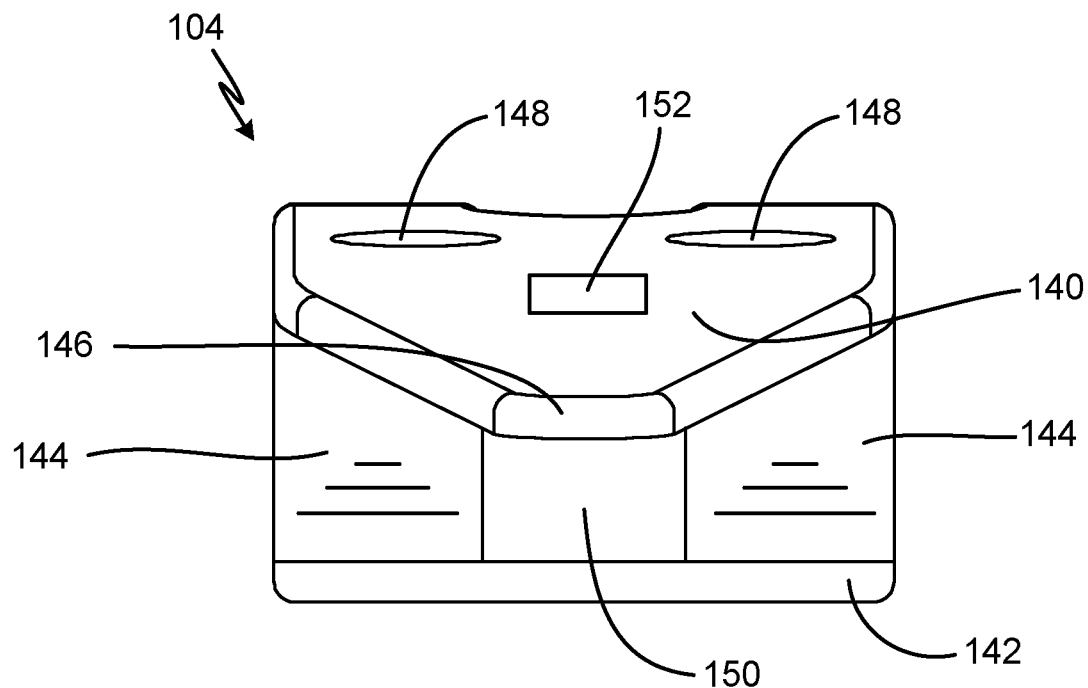
FIG. 4D is a front view of the clip of the first embodiment of the subcutaneous device.
Figure 4E:
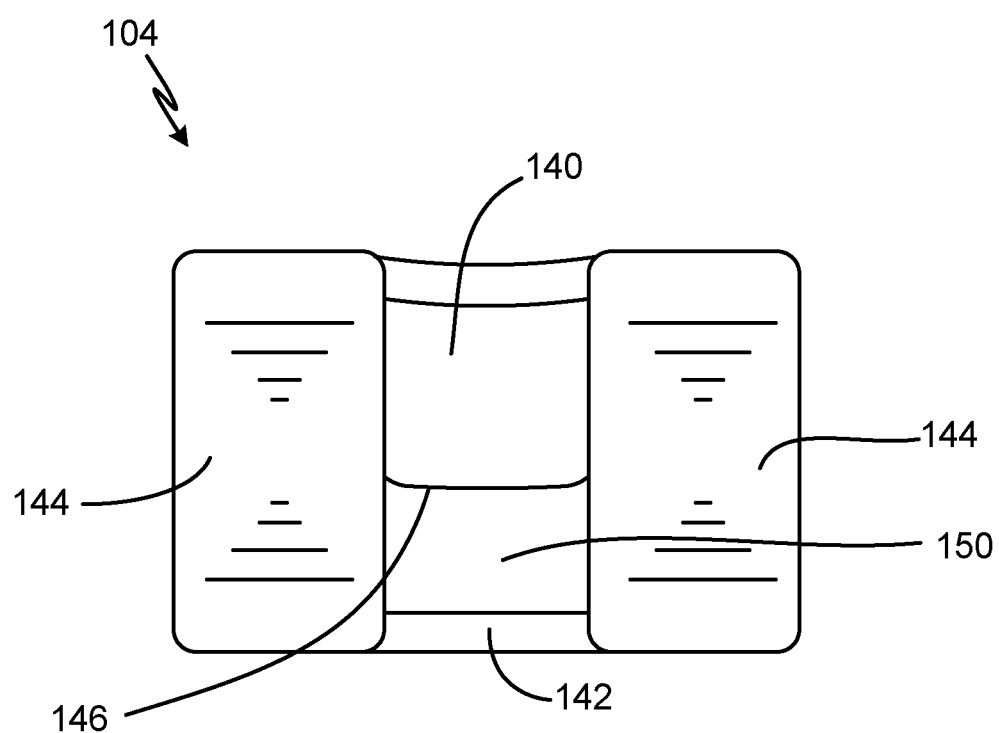
FIG. 4E is a back view of the clip of the first embodiment of the subcutaneous device.

FIG. 4A is a top view of clip 104 of subcutaneous device 100. FIG. 4B is a bottom view of clip 104 of subcutaneous device 100. FIG. 4C is a side view of clip 104 of subcutaneous device 100. FIG. 4D is a front view of clip 104 of subcutaneous device 100. FIG. 4E is a back view of clip 104 of subcutaneous device 100. Clip 104 includes top portion 140, bottom portion 142, spring portion 144, tip 146, openings 148, slot 150, and electrode 152.

Clip 104 includes top portion 140, bottom portion 142, and spring portion 144. Top portion 140 is a flat portion that forms a top of clip 104, and bottom portion 142 is a flat portion that forms a bottom of clip 104. Bottom portion 142 is configured to be attached to housing 102 of subcutaneous device 100 (shown in FIGS. 1-3E). Spring portion 144 is a curved portion positioned on a back end of clip 104 that extends between and connects top portion 140 to bottom portion 142. Clip 104 can be made out of stainless steel, titanium, nitinol, epoxy, silicone, polyurethane with metallic reinforcements, or any other material that is suitable for non-porous implants.

Top portion 140 of clip 104 includes tip 146 adjacent to a front end of clip 104. Top portion 140 tapers from a middle of top portion 140 to tip 146. The taper of tip 146 of top portion 140 of clip 104 helps clip 104 push through tissue when clip 104 is being anchored to a muscle, a bone, or a tissue of a patient. A surgeon does not have to cut a path through the tissue of the patient, as the taper of tip 146 of top portion 140 of clip 104 will create a path through the tissue.

Top portion 140 further includes openings 148. Openings 148 extend through top portion 140. There are two openings 148 in top portion 140 in the embodiment shown in FIGS. 3A-3E, but there could be any number of openings 148 in alternate embodiments. Openings 148 are configured to allow clip 104 to be sutured to a muscle, a bone, or a tissue in a patient to secure subcutaneous device 100 to the muscle, the bone, or the tissue. Further, openings 148 can receive additional fixation mechanisms, such as tines, pins, or screws, to secure subcutaneous device 100 to the muscle, the bone, or the tissue. These additional fixation mechanisms can be made from bioabsorbable materials. Clip 104 also includes slot 150. Slot 150 is an opening that extends through spring portion 144 of clip 104. Slot 150 is configured to receive a blade of a surgical instrument that is used to implant subcutaneous device 100 in a patient.

Spring portion 144 acts as a spring for clip 104 and is under tension. Top portion 140 acts as a tension arm and the forces from spring portion 144 translate to and push down on top portion 140. In its natural state, a spring bias of spring portion 144 forces tip 146 of top portion 140 towards bottom portion 142 of clip 104. Tip 146 of top portion 140 can be lifted up and clip 104 can be positioned on a muscle, a bone, or tissue of a patient. When clip 104 is positioned on a muscle, a bone, or tissue of a patient, the tension in spring portion 144 will force top portion 140 down onto the muscle, the bone, or the tissue. This tension will anchor clip 104 to the muscle, the bone, or the tissue. Additional fixation mechanisms, such as tines, pins, or screws can also be used to anchor clip 104 to the bone, the muscle, or the tissue.

Clip 104 also includes electrode 152 on top surface 140 of clip 104. In the embodiment shown in FIGS. 4A-4E, there is a single electrode 152 positioned on clip 104. In alternate embodiments, any number of electrodes can be positioned on clip 104 or clip 104 can include no electrodes. Electrode 152 is positioned on top surface 140 of clip 104 to sense an electrical activity or physiological parameter of the tissue surrounding clip 104. Electrode 152 can also provide therapeutic electrical stimulation to the tissue surrounding clip 104.

Figure 5A:
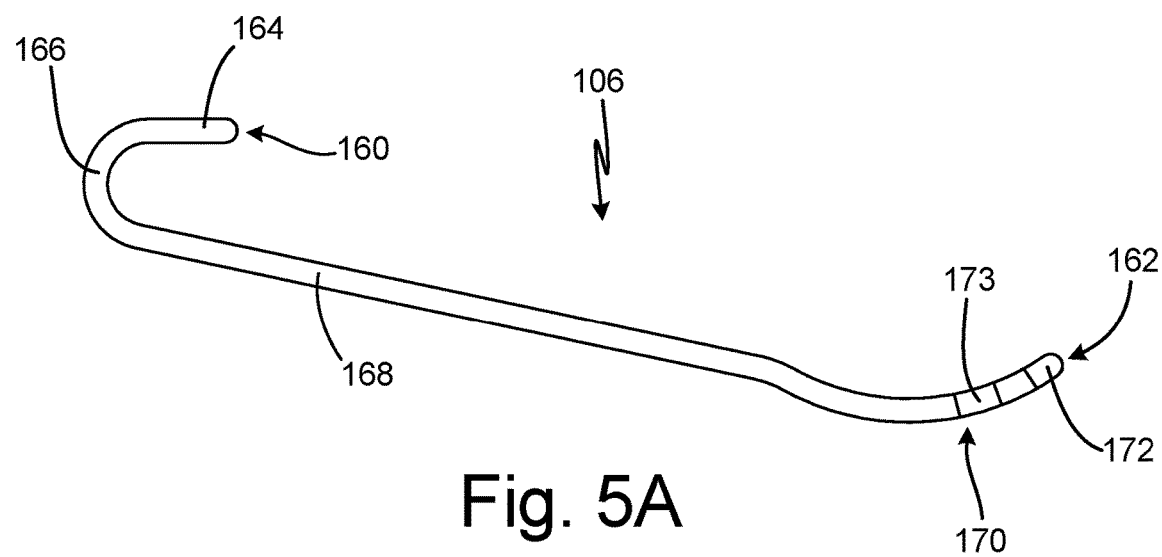
FIG. 5A is a side view of a prong of the first embodiment of the subcutaneous device.
Figure 5B:
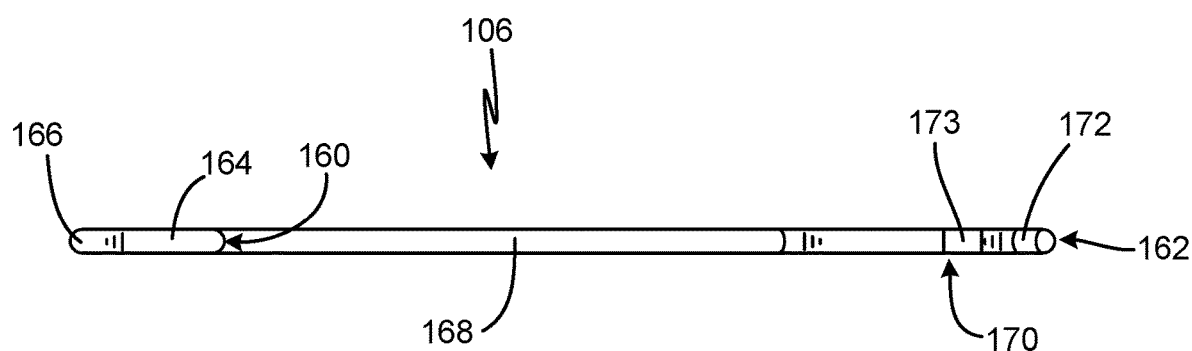
FIG. 5B is a top view of the prong of the first embodiment of the subcutaneous device.

FIG. 5A is a side view of prong 106 of subcutaneous device 100. FIG. 5B is a top view of prong 106 of subcutaneous device 100. Prong 106 includes proximal end 160, distal end 162, base portion 164, spring portion 166, arm portion 168, contact portion 170, and electrode 172.

Prong 106 includes proximal end 160 and distal end 162 that is opposite of proximal end 160. Proximal end 160 of prong 106 may have strain relief or additional material to support movement. Prong 106 includes base portion 164, spring portion 166, arm portion 168, and contact portion 170. A first end of base portion 164 is aligned with proximal end 160 of prong 106, and a second end of base portion 164 is connected to a first end of spring portion 166. Base portion 164 is a straight portion that positioned in port 126 of housing 102 (shown in FIGS. 3D-3E). The first end of spring portion 166 is connected to the second end of base portion 164, and a second end of spring portion 166 is connected to a first end of arm portion 168. The first end of arm portion 168 is connected to the second end of spring portion 166, and a second end of arm portion 168 is connected to a first end of contact portion 170. Arm portion 168 is a straight portion. The first end of contact portion 170 is connected to the second end of arm portion 168, and a second end of contact portion 170 is aligned with distal end 162 of prong 106. Contact portion 170 can be positioned to contact remote body component B (shown in FIG. 2). Spring portion 166 acts as a spring for prong 106 and is under tension. Arm portion 168 acts as a tension arm and the forces from spring portion 166 translate to and push down on arm portion 168. In its natural state, a spring bias of spring portion 166 forces distal end 162 of prong 106 away from bottom side 116 of housing 102.

Prong 106 further includes electrode 172. Electrode 172 is shown as being on distal end 162 in the embodiment shown in FIGS. 5A-5B. In alternate embodiments, electrode 172 can be positioned at any point on contact portion 170 and can have any shape and configuration. Further, prong 106 is shown as having a single electrode 172 in the embodiment shown in FIGS. 5A-5B. Prong 106 can have any number of electrodes in alternate embodiments. Electrode 172 is positioned on distal end 162 of prong 106 to sense an electrical activity or physiological status of remote body component B. Electrode 172 can also provide therapeutic electrical stimulation to remote body component B.

Prong 106 is made of a stiff material so that it is capable of pushing through tissue in the body when subcutaneous device 100 in implanted into a patient. Prong 106 can be made out of nickel titanium, also known as Nitinol. Nitinol is a shape memory alloy with superelasticity, allowing prong 106 to go back to its original shape and position if prong 106 is deformed as subcutaneous device 100 is implanted into a patient. Prong 106 can also be made out of silicone, polyurethane, stainless steel, titanium, epoxy, polyurethane with metallic reinforcements, or any other material that is suitable for non-porous implants. As an example, prong 106 can be made out of a composite made of polyurethane and silicone and reinforced with metal to provide spring stiffness.

Spring portion 166 of prong 106 allows prong 106 to be flexible once it is positioned in the body. For example, if remote body component B is a heart of a patient and contact portion 170 of prong 106 is positioned against the heart, spring portion 166 of prong 106 allows prong 106 to move with up and down as the heart beats. This ensures that prong 106 does not puncture or damage the heart when contact portion 170 of prong 106 is in contact with the heart. Distal end 162 of prong 106 has a rounded shape to prevent prong 106 from puncturing or damaging the heart when contact portion 170 of prong 106 is in contact with the heart. The overall axial stiffness of prong 106 can be adjusted so that prong 106 gently presses against the heart and moves up and down in contact with the heart as the heart beats, but is not stiff or sharp enough to pierce or tear the pericardial or epicardial tissue.

Figure 6A:
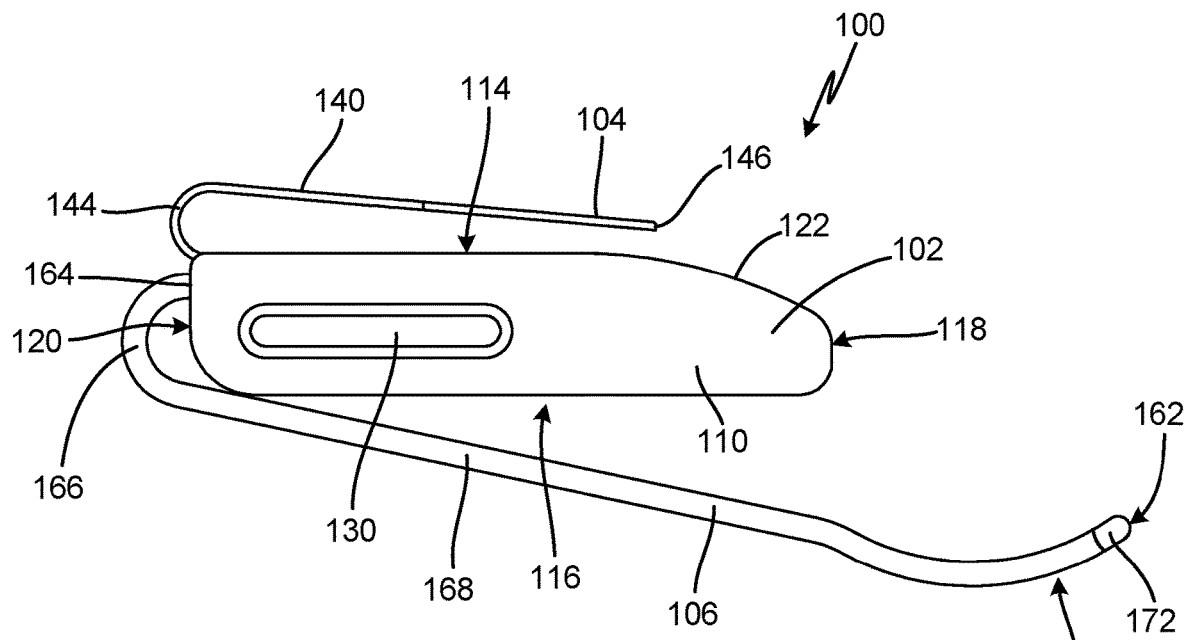
FIG. 6A is a side view of the first embodiment of the subcutaneous device.
Figure 6B:
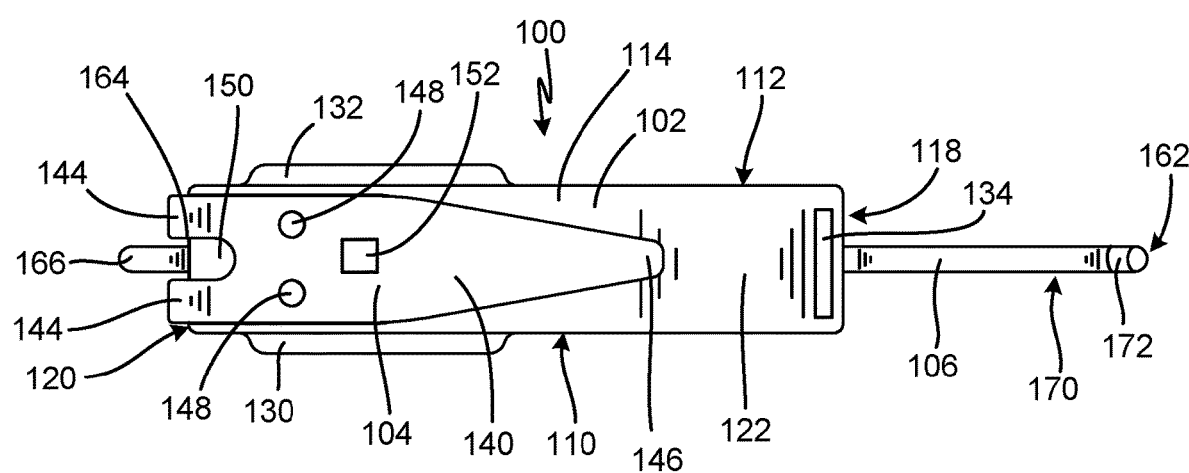
FIG. 6B is a top view of the first embodiment of the subcutaneous device.

FIG. 6A is a side view of subcutaneous device 100. FIG. 6B is a top view of subcutaneous device 100. FIG. 6C is a bottom view of subcutaneous device 100. FIG. 6D is a back view of subcutaneous device 100. FIG. 6E is a front view of subcutaneous device 100. Subcutaneous device 100 includes housing 102, clip 104, and prong 106. Housing 102 includes first side 110, second side 112, top side 114, bottom side 116, front end 118, back end 120, curved surface 122, recess 124, port 126, channel 128, first guide 130, second guide 132, electrode 134, and electrode 136. Clip 104 includes top portion 140, bottom portion 142, spring portion 144, tip 146, openings 148, slot 150, and electrode 152. Prong 106 includes proximal end 160, distal end 162, base portion 164, spring portion 166, arm portion 168, contact portion 170, and electrode 172.

Subcutaneous device 100 includes housing 102, clip 104, and prong 106. Housing 102 is described in detail in reference to FIGS. 3A-3E above. Clip 104 is described in detail in reference to FIGS. 4A-4E above. Prong 106 is described in detail in reference to FIGS. 6A-6B above.

Clip 104 is connected to top side 114 of housing 102 of subcutaneous device 100. Recess 124 of housing 102 is shaped to fit bottom portion 142 of clip 104. Bottom portion 142 is positioned in and connected to recess 124 of housing 102, for example by welding. Spring portion 144 of clip 104 is aligned with back side 120 of housing 102. Top portion 140 of clip 104 extends along top side 114 of housing 102. The spring bias in clip 104 will force tip 146 of clip 104 towards housing 102. Clip 104 can be expanded by lifting up tip 146 of clip 104 to position clip 104 on a bone, a muscle, or a tissue of a patient. When clip 104 is positioned on a muscle, a bone, or a tissue of a patient, the tension in spring portion 144 will force top portion 140 of clip 104 down onto the muscle, the bone, or the tissue. This tension will anchor clip 104, and thus subcutaneous device 100, to the muscle, the bone, or the tissue.

Prong 106 is connected to back side 120 of housing 102 of subcutaneous device 100. Port 126 of housing 102 is shaped to fit base portion 164 of prong 106. Base portion 164 of prong 106 is positioned in port 126 of housing 102. Base portion 164 of prong 106 is electrically connected to the internal components of housing 102, for example with a feedthrough. Base portion 164 of prong 106 is also hermetically sealed in port 126 of housing 102. Spring portion 166 of prong 106 curves around back side 120 of housing 102 and arm portion 168 extends underneath bottom side 116 of housing 102. Arm portion 168 extends past front end 118 of housing 102 so that contact portion 170 is positioned outwards from front end 118 of housing 102. In alternate embodiments, prong 106 can have different shapes and lengths. Further, prong 106 can extend from housing 102 in any direction.

Subcutaneous device 100 is shown in a deployed position in FIGS. 6A-6E. Subcutaneous device 100 will be in the deployed position when subcutaneous device 100 is implanted in a patient. In the deployed position, prong 106 only contacts housing 102 at base portion 164. Subcutaneous device also has a stowed position. Subcutaneous device 100 is in the stowed position when subcutaneous device 100 is loaded in a surgical instrument prior to delivery to the patient. In the stowed position, arm portion 168 of prong 106 is positioned in channel 128 of housing 102. Channel 128 of housing 102 holds arm portion 168 of prong 106 in a centered position with respect to housing 102 when subcutaneous device 100 is in a stowed position. When subcutaneous device is implanted in a patient, subcutaneous device 100 will deploy. The tension of spring portion 166 of prong 106 will force arm portion 168 outwards away from channel 128 of housing 102.

Subcutaneous device 100 can function as a pacemaker. Prong 106 can be shaped so that contact portion 170 of prong 106 contacts the right ventricle, left ventricle, right atrium, or left atrium of the heart. Subcutaneous device 100 can function as a unipolar pacemaker, utilizing electrode 172 on prong 106 and one of electrode 134 or electrode 136 on housing 102 or electrode 152 on clip 104. Further, subcutaneous device 100 can function as a bipolar pacemaker, utilizing electrode 172 on prong 106 and a second electrode also positioned on prong 106.

Figure 7:
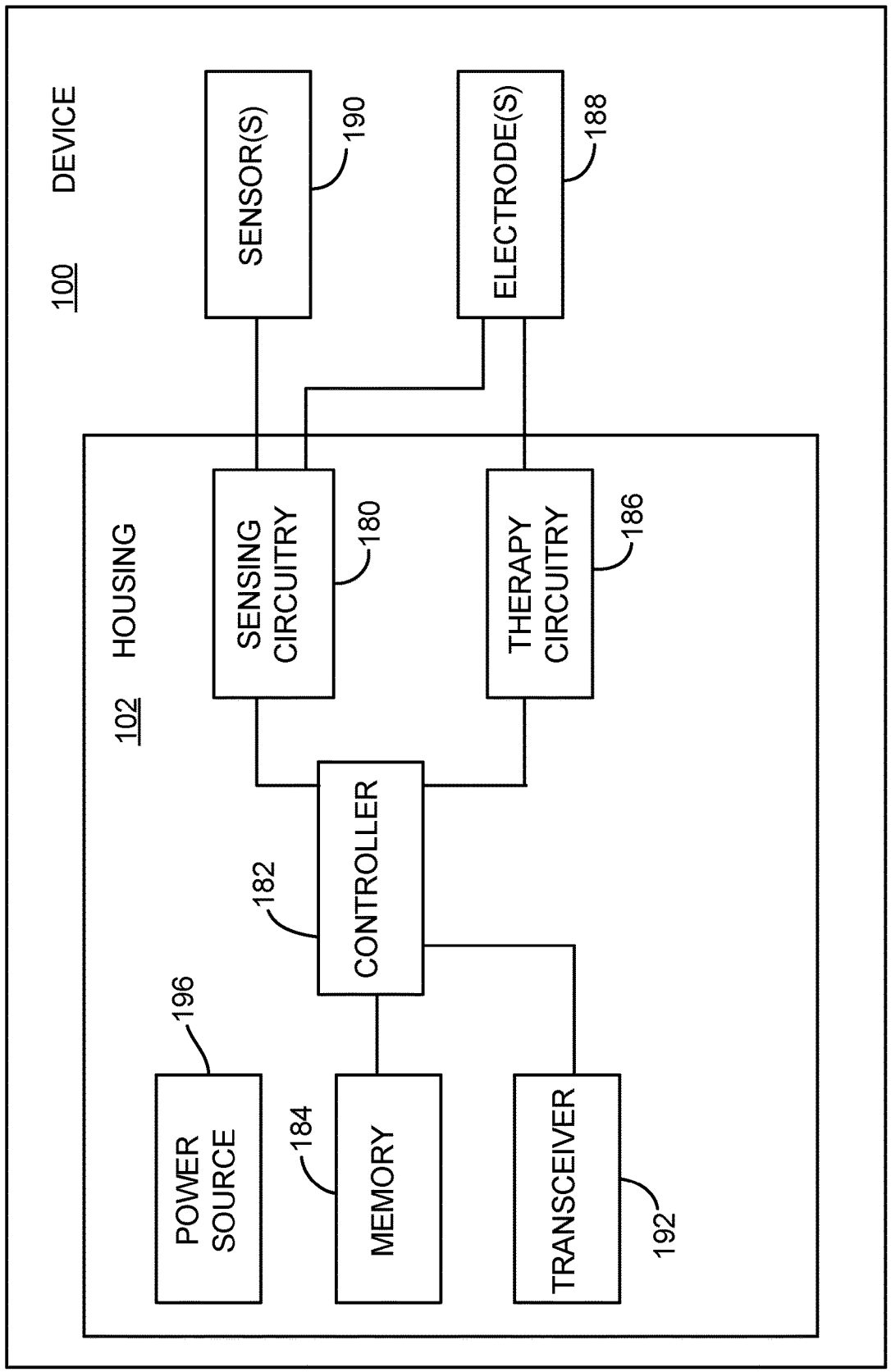
FIG. 7 is a functional block diagram of the first embodiment of the subcutaneous device.

FIG. 7 is a functional block diagram of subcutaneous device 100. Subcutaneous device 100 includes housing 102, sensing circuitry 180, controller 182, memory 184, therapy circuitry 186, electrode(s) 188, sensor(s) 190, transceiver 192, and power source 194.

Housing 102 contains sensing circuitry 180, controller 182, memory 184, and therapy circuitry 186. Sensing circuitry 180 receives electrical signals from the heart and communicates the electrical signals to controller 182. Controller 182 analyzes the electrical signals and executes instructions stored in memory 184 to determine if there is an arrhythmia in the patient's heart rate. If controller 182 determines that there is an arrhythmia, controller 182 will send instructions to therapy circuitry 186 to send electrical stimulation to the heart to regulate the heart rate of the patient. Sensing circuitry 180 and therapy circuitry 186 are both in communication with electrode(s) 188. Electrode(s) 188 can be positioned in housing 102, clip 104, and/or prong 106 and are in contact with an organ, a nerve, or a tissue when subcutaneous device 100 is implanted in a patient. Electrode(s) 188 sense electrical signals from the organ, the nerve, or the tissue and provide electrical stimulation to the heart.

Controller 182 is also in communication with sensor(s) 190 through sensing circuitry 180. Sensor(s) 190 can be positioned in housing 102 and/or prong 106. Sensor(s) 190 can be used with controller 182 to determine physiological parameters of the patient. Controller 182 is further in communication with transceiver 192 that is positioned in housing 102. Transceiver 192 can receive information and instructions from outside of subcutaneous device 100 and send information gathered in subcutaneous device 100 outside of subcutaneous device 100. Power source 194 is also positioned in housing 102 and provides power to the components in housing 102, clip 104, and prong 106, as needed. Power source 194 can be a battery that provides power to the components in housing 102.

Sensing circuitry 180 is electrically coupled to electrode(s) 188 via conductors extending through prong 106 and into housing 102. Sensing circuitry 180 is configured to receive a sensing vector formed by electrode(s) 188 and translate the sensing vector into an electrical signal that can be communicated to controller 182. Sensing circuitry 180 can be any suitable circuitry, including electrodes (including positive and negative ends), analog circuitry, analog to digital converters, amps, microcontrollers, and power sources.

Controller 182 is configured to implement functionality and/or process instructions for execution within subcutaneous device 100. Controller 182 can process instructions stored in memory 184. Examples of controller 182 can include any one or more of a microcontroller, a microprocessor, a digital signal processor (DSP), an application specific integrated circuit (ASIC), a field-programmable gate array (FPGA), or other equivalent discrete or integrated logic circuitry.

Memory 184 can be configured to store information within subcutaneous device 100 during operation. Memory 184, in some examples, is described as computer-readable storage media. In some examples, a computer-readable storage medium can include a non-transitory medium. The term "non-transitory" can indicate that the storage medium is not embodied in a carrier wave or a propagated signal. In certain examples, a non-transitory storage medium can store data that can, over time, change (e.g., in RAM or cache). In some examples, memory 184 is a temporary memory, meaning that a primary purpose of memory 184 is not long-term storage. Memory 184, in some examples, is described as volatile memory, meaning that memory 184 does not maintain stored contents when power to subcutaneous device 100 is turned off. Examples of volatile memories can include random access memories (RAM), dynamic random access memories (DRAM), static random access memories (SRAM), and other forms of volatile memories. In some examples, memory 184 is used to store program instructions for execution by controller 182. Memory 184, in one example, is used by software or applications running on subcutaneous device 100 to temporarily store information during program execution.

Memory 184, in some examples, also includes one or more computer-readable storage media. Memory 184 can be configured to store larger amounts of information than volatile memory. Memory 184 can further be configured for long-term storage of information. In some examples, memory 184 can include non-volatile storage elements. Examples of such non-volatile storage elements can include magnetic hard discs, optical discs, floppy discs, flash memories, or forms of electrically programmable memories (EPROM) or electrically erasable and programmable (EEPROM) memories.

Controller 182 can receive electrical signals from sensing circuitry 180, analyze the electrical signals, and execute instructions stored in memory 184 to determine whether an arrhythmia is present in the heart rate of a patient. If an arrhythmia is detected, controller 182 can send instructions to therapy circuitry 186 to deliver an electrical stimulation to the heart via electrode(s) 188.

Therapy circuitry 186 is electrically coupled to electrode(s) 188 via conductors extending through prong 106 and into housing 102. Therapy circuitry 186 is configured to deliver an electrical stimulation to the heart via electrode(s) 188. Therapy circuitry 186 will include a capacitor to generate the electrical stimulation. Therapy circuitry 180 can be any suitable circuitry, including microcontroller, power sources, capacitors, and digital to analog converters.

Controller 182 can also receive information from sensor(s) 190. Sensor(s) 190 can include any suitable sensor, including, but not limited to, temperature sensors, accelerometers, pressure sensors, proximity sensors, infrared sensors, optical sensors, and ultrasonic sensors. The information from sensor(s) 190 allows subcutaneous device 100 to sense physiological parameters of a patient. For example, the data from the sensors can be used to calculate heart rate, heart rhythm, respiration rate, respiration waveform, activity, movement, posture, oxygen saturation, photoplethysmogram (PPG), blood pressure, core body temperature, pulmonary edema, and pulmonary wetness. The accelerometer can also be used for rate responsive pacing.

Subcutaneous device 100 also includes transceiver 192. Subcutaneous device 100, in one example, utilizes transceiver 192 to communicate with external devices via wireless communication. Subcutaneous device 100, in a second example, utilizes transceiver 192 to communication with other devices implanted in the patient via wireless communication. Transceiver 192 can be a network interface card, such as an Ethernet card, an optical transceiver, a radio frequency transceiver, or any other type of device that can send and receive information. Other examples of such network interfaces can include Bluetooth, 3G, 4G, WiFi radio computing devices, Universal Serial Bus (USB), standard inductive coupling, low frequency medical frequency radio (MICS), ultra-wide band radio, standard audio, and ultrasonic radio. Examples of external devices that transceiver 192 can communicate with include laptop computers, mobile phones (including smartphones), tablet computers, personal digital assistants (PDAs), desktop computers, servers, mainframes, cloud servers, or other devices. Other devices implanted in the body can include other implantable medical devices, such as other pacemakers, implantable cardioversion-defibrillators, nerve stimulators, and the like. Transceiver 192 can also be connected to an antenna.

Subcutaneous device 100 includes power source 194 positioned in housing 102. Subcutaneous device 100 can also include a battery or device outside of housing 102 that transmits power and data to subcutaneous device 100 through wireless coupling or RF. Further, power source 194 can be a rechargeable battery.

The internal components of subcutaneous device 100 described above in reference to FIG. 7 is intended to be exemplary. Subcutaneous device 100 can include more, less, or other suitable components. For example, when subcutaneous device 100 is only used for diagnostics, subcutaneous device 100 will not include therapy circuitry 186. As a further example, subcutaneous device 100 can function as a pacemaker without sensor(s) 190.

Figure 8:
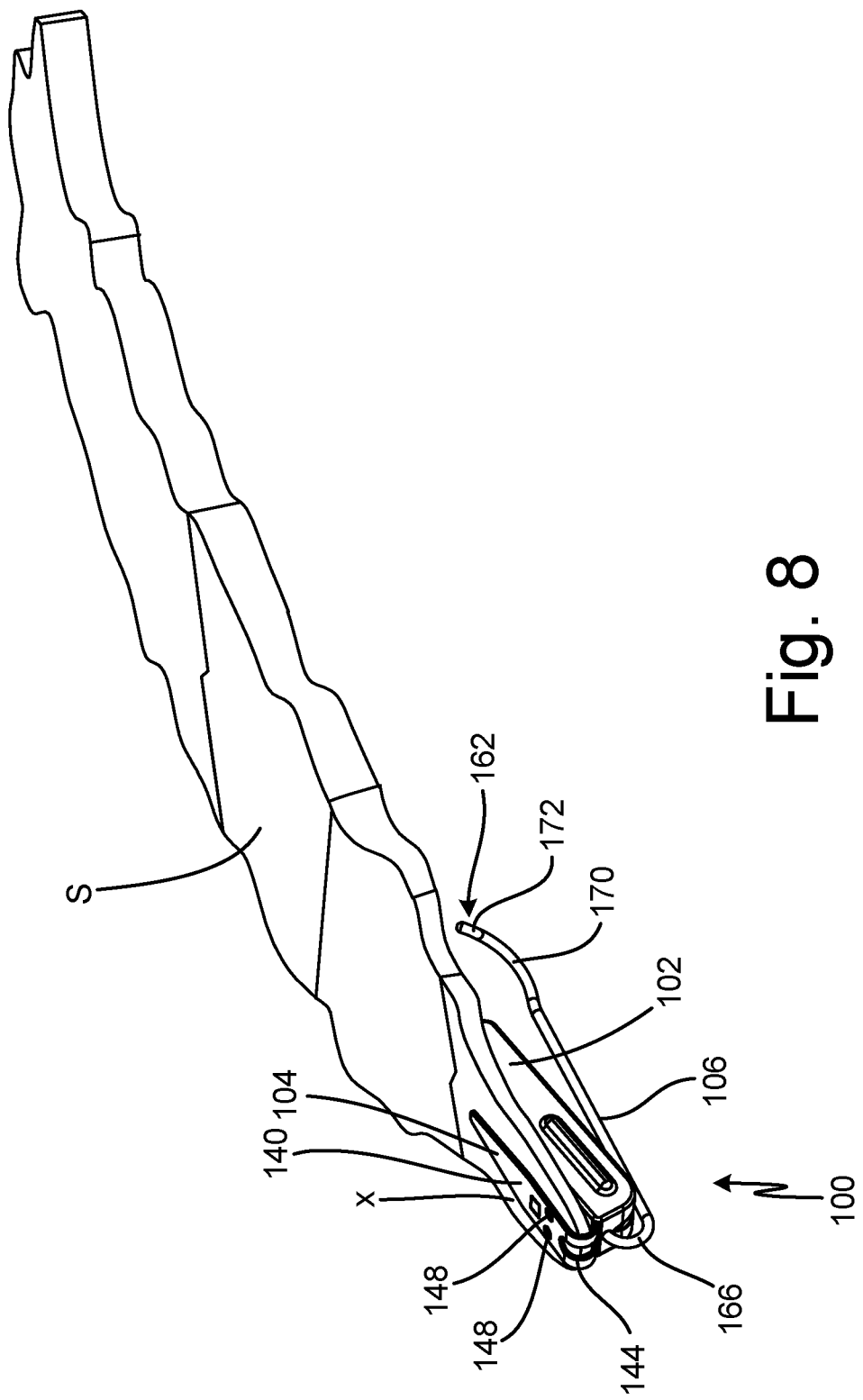
FIG. 8 is a perspective view of the first embodiment of the subcutaneous device positioned on a xiphoid process and a sternum.
Figure 9A:
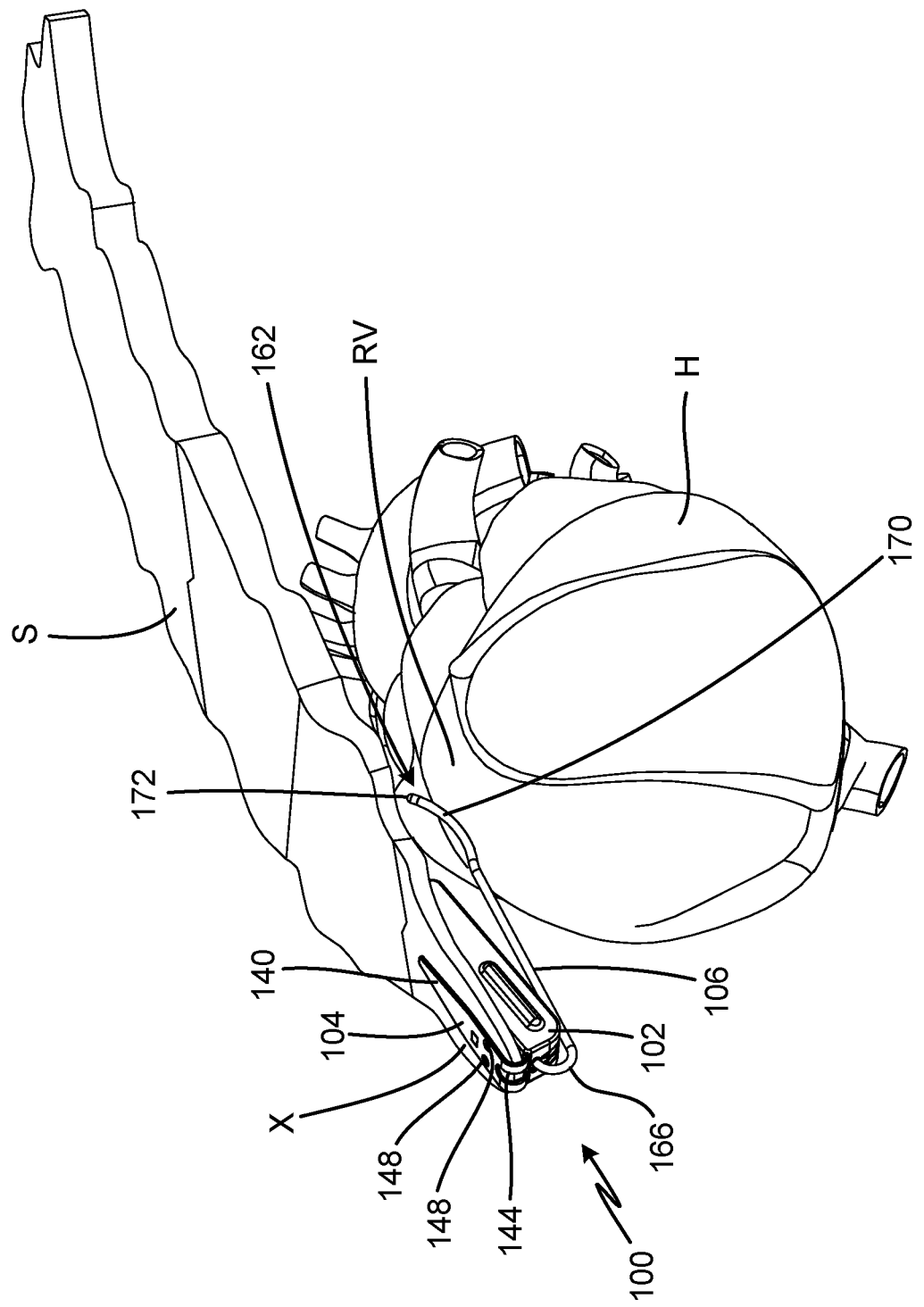
FIG. 9A is a perspective view of the first embodiment of the subcutaneous device positioned on the xiphoid process and the sternum and showing a positioning of a prong on a heart.
Figure 9B:
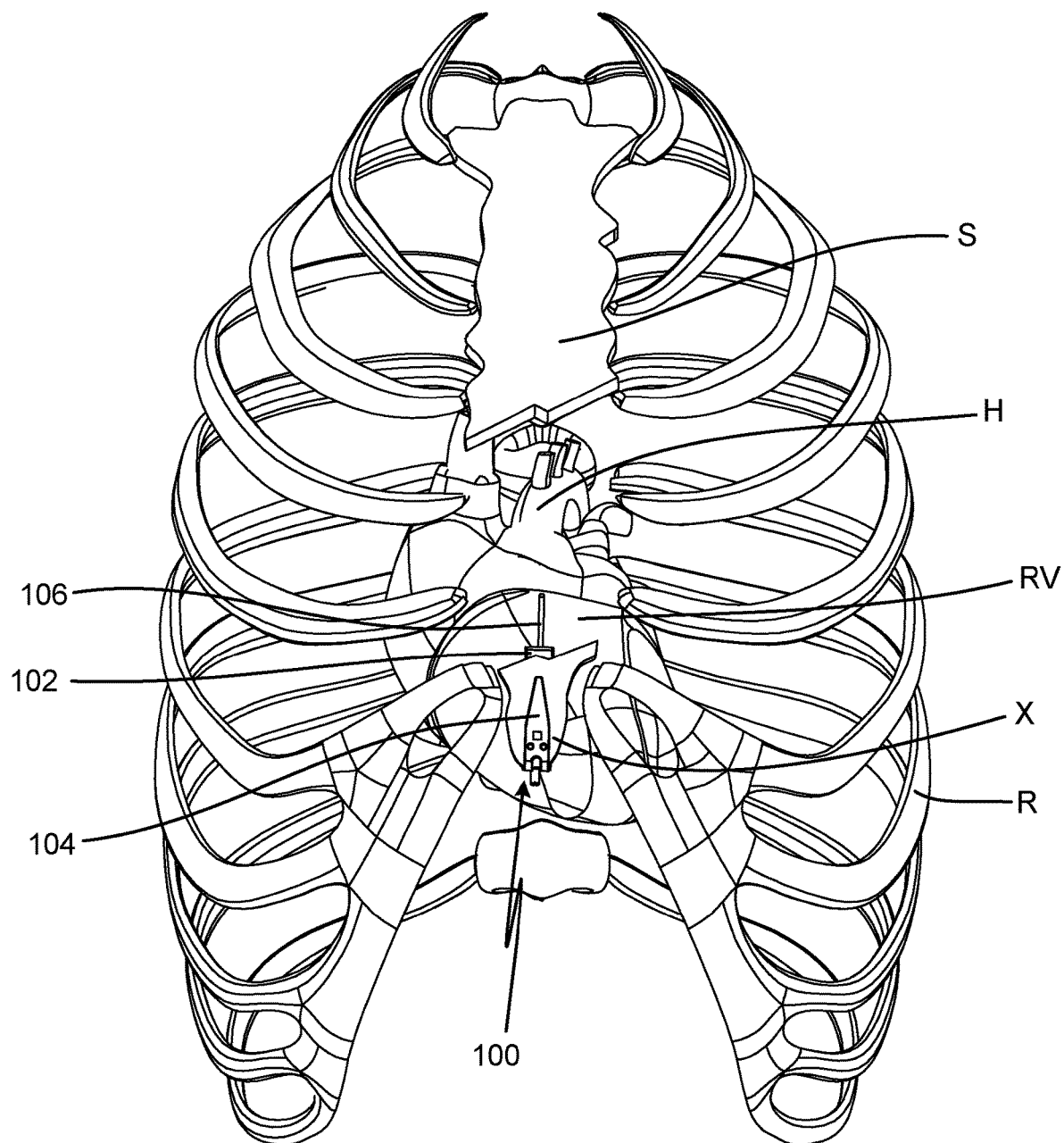
FIG. 9B is a front cut away view of the first embodiment of the subcutaneous device positioned on the xiphoid process and the sternum and showing a positioning of the prong on the heart.
Figure 9C:
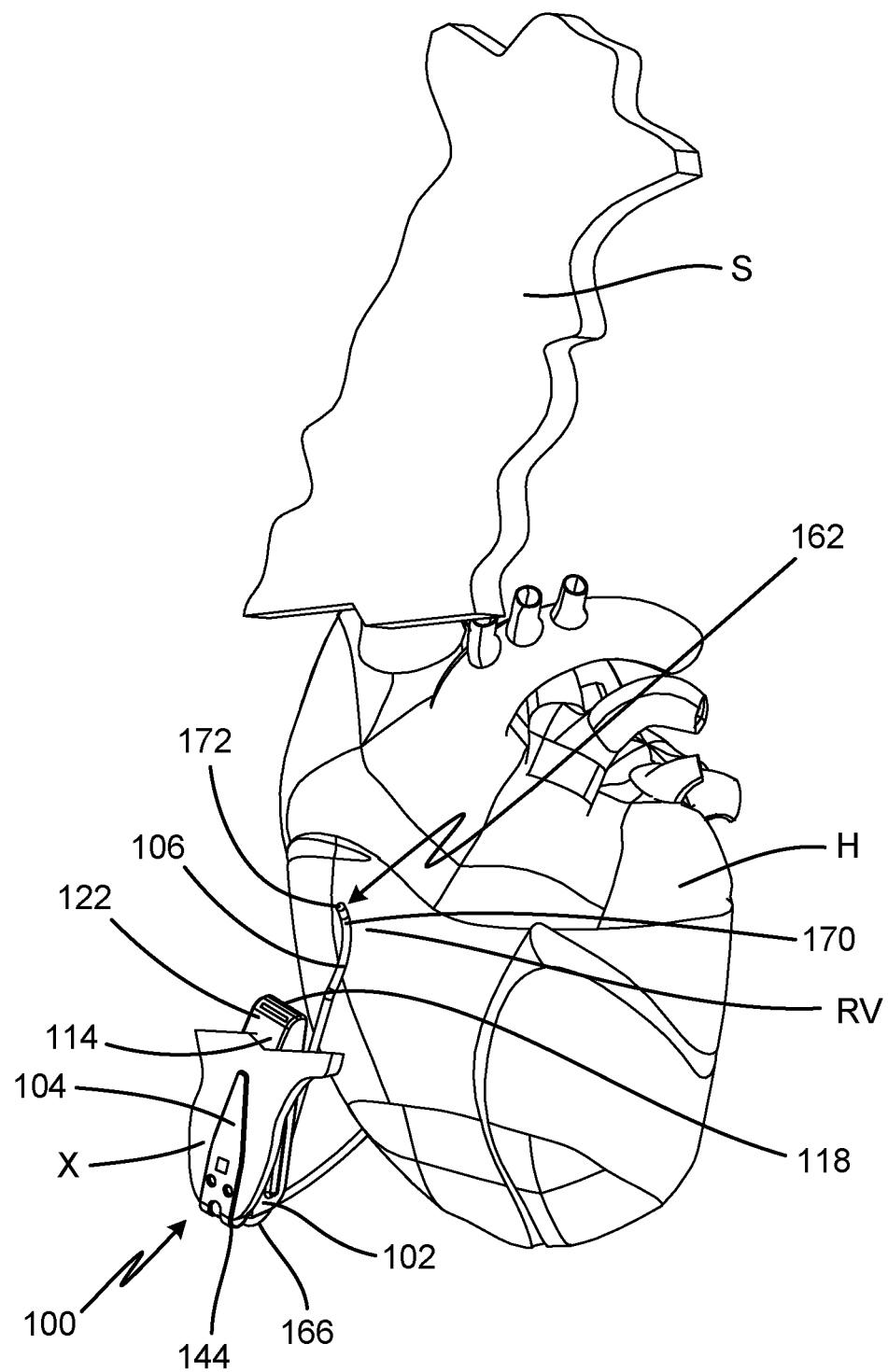
FIG. 9C is a perspective cut away view of the first embodiment of the subcutaneous device positioned on the xiphoid process and the sternum and showing a positioning of the prong on the heart.

FIG. 8 is a perspective view of subcutaneous device 100 positioned on xiphoid process X and sternum S. FIG. 9A is a perspective view of subcutaneous device 100 positioned on xiphoid process X and sternum S and showing a positioning of prong 104 on heart H. FIG. 9B is a front cut away view of subcutaneous device 100 positioned on xiphoid process X and sternum S and showing a positioning of prong 104 on heart H. FIG. 9C is a perspective cut away view of subcutaneous device 100 positioned on xiphoid process X and sternum S and showing a positioning of prong 104 on heart H. Subcutaneous device 100 includes housing 102, clip 104, and prong 106. Housing 102 includes top side 114, front end 118, and curved surface 122. Clip 104 includes top portion 140, spring portion 144, and openings 148. Prong 106 includes distal end 162, spring portion 166, contact portion 170, and electrode 172. FIGS. 8-9C show xiphoid process X and sternum S. FIGS. 9A-9C further show heart H and right ventricle RV. FIG. 9B also shows ribs R.

FIGS. 8-9C show xiphoid process X and sternum S. FIG. 9B further shows xiphoid process X and sternum S in relation to ribs R. Subcutaneous device 100 can be anchored to xiphoid process X and sternum S of a patient. Xiphoid process X is a process extending from a lower end of sternum S. When subcutaneous device 100 is anchored to xiphoid process X, housing 102 of subcutaneous device 100 will be partially positioned underneath sternum S of the patient. In some patients, xiphoid process X is absent, small, narrow, or elongated, and subcutaneous device 100 can be attached directly to a distal end of sternum S. Subcutaneous device will be positioned in the anterior mediastinum of the patient when it is anchored to the xiphoid process X and sternum S. The anterior mediastinum is an area that is anterior to the pericardium, posterior to sternum S, and inferior to the thoracic plane. The anterior mediastinum includes loose connective tissues, lymph nodes, and substernal musculature.

When subcutaneous device 100 is deployed onto xiphoid process X and sternum S, housing 102 and prong 106 of subcutaneous device 100 will move through the anterior mediastinum. Curved surface 122 on top side 114 of housing 102 creates a tapered front end 118 of housing 102 to help subcutaneous device 100 push through the tissue in the anterior mediastinum. Further, prong 106 is made of a stiff material to allow it to push through the tissue in the anterior mediastinum.

Subcutaneous device 100 can be anchored to xiphoid process X and sternum S with clip 104. When clip 104 is positioned on xiphoid process X, top portion 140 of clip 104 will be positioned superior to xiphoid process X and sternum S. Spring portion 144 of clip 104 will put tension on top portion 140 of clip 104 to push top portion 140 down onto xiphoid process X and sternum S. Clip 104 will hold subcutaneous device 100 in position on xiphoid process X and sternum S. Further, openings 148 in top portion 140 of clip 104 can be used to suture clip 104 to xiphoid process X and sternum S, or openings 148 can receive additional fixation mechanisms, such as tines, pins, or screws. This will further anchor subcutaneous device 100 to xiphoid process X and sternum S.

When subcutaneous device 100 is anchored to xiphoid process X and sternum S, prong 106 will extend from housing 102 and come into contact with heart H of the patient. Specifically, contact portion 170 and electrode 172 of prong 106 will come into contact with the pericardium. The pericardium is the fibrous sac that surrounds heart H. Electrode 172 will be positioned on the portion of the pericardium that surrounds right ventricle RV of heart H. An electrical stimulation can be applied to right ventricle RV of heart H, causing heart H to contract, by transmitting the electrical signal from electrode 172 on distal end 162 of prong 106 through the pericardium and epicardium and into the myocardium of heart H. Prong 106 can also sense electrical signals from heart H to determine a surface ECG of heart H.

As heart H beats, it will move in a vertical and a three-dimensional pattern. Spring portion 166 of prong 106 provides some flexibility to prong 106 to allow prong 106 to move with heart H as it beats. This will ensure that prong 106 does not puncture or damage heart H.

Anchoring subcutaneous device 100 to xiphoid process X and sternum S ensures that subcutaneous device 100 will not migrate in the patient's body. Maintaining the position of subcutaneous device 100 in the body ensures that prong 106 is properly positioned and will not lose contact with heart H. Further, subcutaneous device 100 is able to accurately and reliably determine a heart rate and other physiological parameters of the patient, as subcutaneous device 100 will not move in the patient's body. For instance, the ECG morphology will not change due to movement of subcutaneous device 100 within the patient's body.

Subcutaneous device 100 can be implanted with a simple procedure where subcutaneous device 100 is injected onto xiphoid process X using a surgical instrument. The surgical procedure for implanting subcutaneous device 100 is less invasive than the surgical procedure required for more traditional pacemaker devices, as subcutaneous device is placed subcutaneously in the body. No leads need to be positioned in the vasculature of the patient, lowering the risk of thrombosis to the patient. A surgical instrument and a method for implanting subcutaneous device 100 are described in greater details below.

Injectable Tool 200

FIG. 10A is a perspective view of surgical instrument 200 in a first position. FIG. 10B is a cross-sectional perspective view of surgical instrument 200 in the first position. Surgical instrument 200 includes body 202, slider 204, blade 206, bolt 208, and screw 210.

Surgical instrument 200 can be used to implant a medical device in a patient. In the following discussion, subcutaneous device 100 (shown in FIGS. 1-9) will be used as an example of a device that can be implanted in a patient using surgical instrument 200. However, surgical instrument 200 can be used to implant any suitable medical device in a patient, including any of subcutaneous devices 400, 500, 600, 700, 800, 900, 1000, 1100, 1200, 1300, 1400, and 1500 shown in FIGS. 20-37.

Surgical instrument 200 includes body 202 that can be grasped by a user to hold and maneuver surgical instrument 200. Surgical instrument 200 further includes slider 204 and blade 206 that are attached to body 202. Bolt 208 extends through body 202 and slider 204 to hold slider 204 in position in surgical instrument 200. Slider 204 is configured to deploy a subcutaneous device into a body of a patient when a subcutaneous device is stowed in surgical instrument 200. Screw 210 extends through blade 206 and into body 202 to mount blade 206 to body 202. Blade 206 is configured to extend past a front end of surgical instrument 200 and can be used to cut through tissue prior to deploying a subcutaneous device that is stowed in surgical instrument 200 into a patient. In an alternate embodiment, blade 206 can be a separate blade that is not connected to surgical instrument 200.

Surgical instrument 200 in shown in a first position in FIGS. 10A-10B. In the first position, slider 204 is positioned to abut body 202 and subcutaneous device 100 (shown in FIGS. 1-9) can be loaded into surgical instrument 200. Surgical instrument 200 can be used to inject subcutaneous device 100 onto a bone, a muscle, or a tissue of a patient. In one example, surgical instrument 200 can be used to inject subcutaneous device 100 onto a xiphoid process and a sternum of a patient.

FIG. 11A is a perspective view of body 202 of surgical instrument 200. FIG. 11B is a side view of body 202 of surgical instrument 200. FIG. 11C is a bottom view of body 202 of surgical instrument 200. FIG. 11D is a front view of body 202 of surgical instrument 200. Body 202 includes base 220, handle 222, upper arm 224, lower arm 226, slider slot 228, bolt aperture 230, bolt aperture 232, blade slot 234, screw aperture 236, guide track 238, guide track 240, and prong track 242.

Body 202 includes base 220, handle 222, upper arm 224, and lower arm 226 that are integral with one another to form body 202. Base 220 forms a support portion in the middle of body 202. Handle 220 extends away from a back end of base 220. Handle 220 can be grasped by a user to grasp body 202 of surgical instrument 200. Upper arm 224 and lower arm 226 extend away from a front end of base 220. Upper arm 224 is positioned on an upper side of base 220, and lower arm 226 is positioned on a lower side of base 220. Body 202 can be made out of any suitable metallic or plastic material.

Upper arm 224 includes slider slot 228 that forms an opening in upper arm 224. Slider slot 228 is configured to allow slider 204 of surgical instrument 200 (shown in FIGS. 10A-10B) to slide through upper arm 224. Upper arm 224 further includes bolt aperture 230 that extends through a front end of upper arm 224. Bolt aperture 230 of upper arm 224 is configured to receive bolt 208 of surgical instrument 200 (shown in FIGS. 10A-10B). Bolt aperture 230 has a recessed portion that is configured to receive a head of bolt 208 so that bolt 208 is flush with a front end of body 202.

Base 210 includes bolt aperture 232 that extends into an upper end of base 210. Bolt aperture 232 of base 210 is configured to receive bolt 208 of surgical instrument 200 (shown in FIGS. 10A-10B). Bolt aperture 232 is threaded to receive threads on bolt 208. Base 210 further includes blade slot 234 that extends into a middle of base 210. Blade slot 234 of base 210 is configured to receive blade 206 of surgical instrument 200 (shown in FIGS. 10A-10B). Base 210 also includes screw aperture 236 extending up into base 210 from a bottom side of base 210. Screw aperture 236 is configured to receive screw 210 of surgical instrument 200 (shown in FIGS. 10A-10B). Blade slot 234 extends into screw aperture 236 so that screw 210 can extend through blade 206 to mount blade 206 to surgical instrument 200.

Lower arm 226 includes first guide track 238 and second guide track 240. First guide track 238 is a groove extending along an inner surface of a first side of lower arm 226, and second guide track 240 is a groove extending along an inner surface of a second side of lower arm 226. First guide track 238 and second guide track 240 are configured to receive first guide 130 and second guide 132 of housing 102 of subcutaneous device 100 (shown in FIGS. 3A-3D and 6A-6E), respectively. Lower arm 226 further includes prong track 242. Prong track 242 is a groove extending along a top surface of lower arm 226. Prong track 242 is configured to receive prong 106 of subcutaneous device 100.

FIG. 12A is a perspective view of slider 204 of surgical instrument 200. FIG. 12B is a front view of slider 204 of surgical instrument 200. FIG. 12C is a side view of slider 204 of surgical instrument 200. FIG. 12D is a bottom view of slider 204 of surgical instrument 200. Slider 204 includes base 250, knob 252, shaft 254, first guide 256, second guide 258, third guide 260, fourth guide 262, bolt aperture 264, blade slot 266, first shoulder 268, second shoulder 270, and device notch 272.

Slider 204 includes base 250, knob 252, and shaft 254 that are integral with one another to form slider 204. Base 250 form a support portion in the middle of slider 204. Knob 252 extends upwards from base 250. Knob 252 can be grasped by a user to slide slider 204 within surgical instrument 200. Shaft 254 extends downwards from base 250.

Base 250 includes first guide 256 and second guide 258 on a bottom surface of base 250. First guide 256 is positioned on a first side of base 250 and extends from a front end to a back end of base 250, and second guide 258 is positioned on a second side of base 250 and extends from a front end to a back end of base 250. Shaft 254 includes third guide 260 and fourth guide 262. Third guide 260 extends from a front end to a back end of shaft 254 on a first side of shaft 254, and fourth guide 262 extends from a front end to a back end of shaft 254 on a second side of shaft 254. First guide 256, second guide 258, third guide 260, and fourth guide 262 are configured to reduce friction as slider 204 slides through surgical instrument 200 (shown in FIGS. 10A-10B).

Shaft 254 also includes bolt aperture 264 that extends from a front end to a back end of slider 204. Bolt aperture 264 is configured to receive a portion of bolt 208 of surgical instrument 200 (shown in FIGS. 10A-10B). Shaft 254 further includes blade slot 266 that extends from a front end to a back end of slider 204. Blade slot 266 is configured to receive a portion of blade 206 of surgical instrument 200 (shown in FIGS. 10A-10B). Shaft 254 also includes first shoulder 268 and second shoulder 270. First shoulder 268 is a ridge on a first side of slider 204, and second shoulder 270 is a ridge on a second side of slider 204. First shoulder 268 and second shoulder 270 are configured to slide along lower arm 226 of body 202. Shaft 254 additionally includes device notch 272. Device notch 272 is a groove on a front end of shaft 254. Device notch 272 is configured to receive a portion of subcutaneous device 100 (shown in FIGS. 1-9).

FIG. 13A is a perspective view of blade 206 of surgical instrument 200. FIG. 13B is a side view of blade 206 of surgical instrument 200. Blade 206 includes base 280, shaft 282, tip 284, and opening 286.

Blade 206 includes base 280, shaft 282, and tip 284. Base 280 forms a back end of blade 206. A back end of shaft 282 is connected to base 280. Tip 284 is connected to a front end of shaft 282. Tip 284 is a blade tip. Blade 206 also includes opening 286 that extends through base 280 of blade 206. Opening 286 is configured to receive screw 210 of surgical instrument 200 (shown in FIGS. 10A-10B) to mount blade 206 in surgical instrument 200.

FIG. 14A is a perspective view of surgical instrument 200. FIG. 14B is a cross-sectional view of surgical instrument 200. Surgical instrument 200 includes body 202, slider 204, blade 206, bolt 208, and screw 210. Body 202 includes base 220, handle 222, upper arm 224, lower arm 226, slider slot 228, bolt aperture 230, bolt aperture 232, blade slot 234, screw aperture 236, guide track 238, guide track 240, and prong track 242. Slider 204 includes base 250, knob 252, shaft 254, first guide 256, second guide 258, third guide 260, fourth guide 262, bolt aperture 264, blade slot 266, first shoulder 268, second shoulder 270, and device notch 272. Blade 206 includes base 280, shaft 282, tip 284, and opening 286.

Surgical instrument 200 includes body 202, slider 204, blade 206, bolt 208, and screw 210. Body 202 is described in reference to FIGS. 11A-11D above. Slider 204 is described in reference to FIGS. 12A-12D above. Blade 206 is described in reference to FIGS. 13A-13B above.

Slider 204 is positioned in and is capable of sliding in slider slot 228 of body 202 of surgical instrument 200. Base 250 of slider 204 slides along on upper arm 224 of body 202 as slider 204 slides through slider slot 228 of body 202. Bolt 208 extends through bolt aperture 230 in body 202, bolt aperture 264 in slider 204, and into bolt aperture 232 in body 202. Slider 204 can slide along bolt 208 as it slides through slider slot 228 of body 202. In an alternate embodiment, bolt 208 can be a shaft or any other suitable mechanism upon which slider 204 can slide. Further, blade 206 extends through blade slot 266 of slider 204. Slider 204 can slide along blade 206 as it slides through slider slot 228 of body 202. Slider 204 also includes first shoulder 268 and second shoulder 270 that abut and slide along upper sides of lower arm 226 as slider 204 slides through slider slot 228 of body 202.

Slider 204 is a mechanism that can be manually pushed by a surgeon to deploy a device pre-loaded in surgical instrument 200 out of surgical instrument 200. In an alternate embodiment, slider 204 can be automatic and the device pre-loaded in surgical instrument 200 can be automatically deployed out of surgical instrument 200.

Blade 206 is positioned in and mounted to body 202 of surgical instrument 200. Base 150 of blade 206 is positioned in blade slot 234 of body 202 so that opening 286 in base 150 of blade 206 is aligned with screw aperture 236 in body 202. Screw 210 can be inserted through opening 286 in base 280 of blade 206 and then screwed into screw aperture 236 of body 202 to mount blade 206 to body 202 of surgical instrument 200. When blade 206 is mounted in surgical instrument 202, tip 284 of blade 206 will extend past a front end of surgical instrument 200 so that a surgeon can use tip 284 of blade 206 to cut through tissue in a patient. In an alternate embodiment, blade 206 can include a blunt edge that a surgeon can use to ensure that a pocket that is created for subcutaneous device 100 is a correct width and depth.

Surgical instrument 200 can be used to implant subcutaneous device 100 in a patient. Slider 204 of surgical instrument 200 acts as an injection mechanism to inject subcutaneous device 100 onto a bone, a muscle, or a tissue of a patient. When surgical instrument 200 is positioned adjacent to the bone, the muscle, or the tissue, a surgeon pushes slider 204 of surgical instrument 200 forward to inject subcutaneous device 100 onto the bone, the muscle, or the tissue. A method for injecting the subcutaneous device 100 onto the bone, the muscle, or the tissue is described in greater detail below with reference to FIGS. 15-19.

Method 300

FIG. 15 is a flow chart showing method 300 for implanting subcutaneous device 100 using surgical instrument 200. FIGS. 16A-19 show subcutaneous device 100 at different positions in surgical instrument 200 as subcutaneous device 100 is being implanted with surgical instrument 200. FIG. 16A is a perspective view of subcutaneous device 100 in a first position in surgical instrument 200. FIG. 16B is a cross-sectional view of subcutaneous device 100 in the first position in surgical instrument 200. FIG. 17A is a perspective view of subcutaneous device 100 in a second position in surgical instrument 200 as the subcutaneous device is being implanted. FIG. 17B is a cross-sectional view of subcutaneous device 100 in the second position in surgical instrument 200 as subcutaneous device 100 is being implanted. FIG. 17C is a cross-sectional view of subcutaneous device 100 in the second position in surgical instrument 200 as subcutaneous device 100 is being implanted. FIG. 18A is a perspective view of subcutaneous device 100 in a third position in surgical instrument 200 as subcutaneous device 100 is being implanted. FIG. 18B is a cross-sectional view of subcutaneous device 100 in the third position in surgical instrument 200 as subcutaneous device 100 is being implanted. FIG. 19 is a perspective view of subcutaneous device 100 after it has been deployed from surgical instrument 200. Subcutaneous device 100 includes housing 102, clip 104, and prong 106. Clip 104 includes top portion 140, bottom portion 142, spring portion 144, and slot 150. Prong 106 includes spring portion 144. Surgical instrument 200 includes body 202, slider 204, blade 206, bolt 208, and screw 210. Body 202 includes base 220, handle 222, and slider slot 228. Slider 204 includes shaft 254 and knob 252. Blade 206 includes tip 284. Method 300 includes steps 302-314.

Method 300 is described here in relation to implanting subcutaneous device 100 (shown in FIGS. 1-9) on a xiphoid process and a sternum of a patient. However, method 300 can be used to implant any suitable medical device (including any of subcutaneous devices 400, 500, 600, 700, 800, 900, 1000, 1100, 1200, 1300, 1400, and 1500 shown in FIGS. 20-37) on any bone, muscle, or tissue in a patient. Further, method 300 is described here in relation to using surgical instrument 200 (shown in FIGS. 10A-14B) to implant subcutaneous device 100. However, any suitable surgical instrument 200 can be used to implant subcutaneous device 100.

Step 302 includes making a small incision in a patient below a xiphoid process. The patient may be under local or general anesthesia. A surgeon can make a small incision through the skin right below the xiphoid process using a scalpel.

Step 304 includes inserting surgical instrument 200 through the small incision. Surgical instrument 200 will be pre-loaded with subcutaneous device 100 when it is inserted through the small incision, as shown in FIGS. 16A-16B. When surgical instrument 200 is pre-loaded with subcutaneous device 100, surgical instrument 200 will be in a first position. In the first position, shaft 254 of slider 204 of surgical instrument 200 will abut base 220 of body 202 of surgical instrument 200. Subcutaneous device 100 is loaded into surgical instrument 200 so that a front end of subcutaneous device 100 is aligned with a front end of surgical instrument 200. A back end of subcutaneous device 100 will abut slider 204 of surgical instrument 200. Spring portion 144 of clip 104 of subcutaneous device 100 will be positioned in device notch 272 of slider 204 of surgical instrument 200. First guide 130 and second guide 132 of housing 102 of subcutaneous device 100 sit in guide track 238 and guide track 240 of body 202 of surgical instrument 200, respectively. Blade 206 of surgical instrument 200 will extend through slot 150 of clip 104 of subcutaneous device 100. Tip 284 of blade 206 will extend past a front end of subcutaneous device 100, allowing tip 284 of blade 206 to be used to cut tissue in the patient.

Step 306 includes advancing surgical instrument 200 to the xiphoid process and a distal end of the sternum. A surgeon who is holding handle 222 of body 202 of surgical instrument 200 can move surgical instrument 200 into and through the patient. The surgeon can manipulate surgical instrument 200 to use tip 284 of blade 206 of surgical instrument 200 to cut tissue in the patient to provide a pathway to the xiphoid process and the distal end of the sternum.

Step 308 includes removing tissue from the xiphoid process and a distal end of the sternum using blade 206 of surgical instrument 200. A surgeon can manipulate surgical instrument 200 to use tip 284 of blade 206 of surgical instrument 200 to scrape tissue on the xiphoid process and the distal end of the sternum off to expose the xiphoid process and the distal end of the sternum. In an alternate embodiment, a surgeon can use a scalpel or other surgical instrument to scrape tissue off of the xiphoid process and the distal end of the sternum.

Step 310 includes positioning surgical instrument 200 to deploy subcutaneous device 100 onto the xiphoid process and the distal end of the sternum. After the xiphoid process and the distal end of the sternum have been exposed, the surgeon can position surgical instrument 200 in the patient so that blade 206 of surgical instrument 200 is positioned to abut the top side of the xiphoid process and the distal end of the sternum. In this position, prong 206 of subcutaneous device 100 will be positioned beneath the xiphoid process and the distal end of the sternum. Further, the surgeon can adjust the position of subcutaneous device 100 with surgical instrument 200 to ensure that prong 106 has good contact with the pericardium, fat, muscle, or tissue.

Step 312 includes pushing subcutaneous device 100 onto the xiphoid process and the distal end of the sternum using surgical instrument 200. Subcutaneous device 100 is pushed out of surgical instrument 200 and onto the xiphoid process and the distal end of the sternum by pushing slider 204 of surgical instrument 200. FIGS. 17A-17C show surgical instrument 200 in a second position. In the second position, slider 204 of surgical instrument 200 has been pushed halfway through slider slot 228 of body 202 of surgical instrument 200. Further, in the second position, subcutaneous device 100 is pushed partially out of surgical instrument 200. FIGS. 18A-18B show surgical instrument 200 in a third position. In the third position, slider 204 of surgical instrument 200 has been pushed to the front end slider slot 228 of body 202 of surgical instrument 200. Further, in the third position, subcutaneous device 100 is pushed almost fully out of surgical instrument 100.

The surgeon will push knob 252 of slider 204 of surgical instrument 200 along slider slot 228 of body 202 of surgical instrument 200. As slider 204 is pushed through surgical instrument 200, subcutaneous device 100 is pushed out of surgical instrument 200. As subcutaneous device 100 is pushed out of surgical instrument 200, first guide 130 and second guide 132 of housing 102 of subcutaneous device 100 slide along guide track 238 and guide track 240 of body 202 of surgical instrument 200, respectively, as shown in FIG. 17C. As subcutaneous device 100 is pushed out of surgical instrument 200, subcutaneous device 100 will be pushed on the xiphoid process and the distal end of the sternum of the patient. In an alternate embodiment, surgical instrument 200 can be configured to automatically advance subcutaneous device 100 out of surgical instrument 200 and onto the xiphoid process and the distal end of the sternum.

Step 314 includes anchoring subcutaneous device 100 onto the xiphoid process and the distal end of the sternum. As subcutaneous device 100 is pushed out of surgical instrument 200, top portion 140 of clip 104 of subcutaneous device 100 will be pushed on top of the xiphoid process and the distal end of the sternum, and bottom portion 142 of clip 104, housing 102, and prong 106 of subcutaneous device 100 will be pushed underneath the xiphoid process and the distal end of the sternum. Subcutaneous device 100 will be pushed onto the xiphoid process and the distal end of the sternum until spring portion 144 of clip 104 of subcutaneous device 100 abuts the xiphoid process. The tension in spring portion 144 of clip 104 of subcutaneous device 100 will force top portion 140 of clip 104 of subcutaneous device 100 down onto the xiphoid process and the distal end of the sternum. This tension will anchor subcutaneous device 100 onto the xiphoid process and the distal end of the sternum.

When subcutaneous device 100 is stowed in surgical instrument 200, prong 106 of subcutaneous device 100 is positioned in channel 128 of housing 102 of subcutaneous device 100. When subcutaneous device 100 is deployed and anchored to the xiphoid process and the distal end of the sternum, spring portion 166 of prong 106 will push arm portion 168 and contact portion 170 downwards and away from housing 102. As subcutaneous device 100 is implanted onto the xiphoid process and the distal end of the sternum, prong 106 will push through tissue in the anterior mediastinum. When subcutaneous device 100 is implanted on the xiphoid process and the distal end of the sternum, contact portion 170 of prong 106 should be positioned on the right ventricle of the heart. A surgeon can check and adjust the placement of prong 106 as needed during implantation of subcutaneous device 100.

Step 316 includes removing surgical instrument 200 from the small incision in the patient. After subcutaneous device 100 has been anchored onto the xiphoid process and the distal end of the sternum, surgical instrument 200 can be removed from the small incision in the patient, as shown in FIG. 19. When surgical instrument 200 is removed, subcutaneous device 100 will remain anchored to the xiphoid process and the distal end of the sternum.

Subcutaneous device 100 remains anchored to the xiphoid process and the distal end of the sternum due to the tension being put on top portion 140 of clip 104 from spring portion 144 of clip 104. The tension of clip 104 will hold subcutaneous device 100 in position on the xiphoid process and the distal end of the sternum, with little risk that subcutaneous device 100 will move. Two to four weeks post-surgery, fibrosis will begin to develop around subcutaneous device 100. The fibrosis that develops around subcutaneous device 100 will further hold subcutaneous device 100 in position in the patient.

If subcutaneous device 100 needs to be removed from the patient within two to four weeks post-surgery and before fibrosis has formed around subcutaneous device 100, a surgeon can make a small incision below the xiphoid process and insert an instrument through the small incision to pull subcutaneous device 100 out of the patient. The instrument will lift top portion 140 of clip 104 of subcutaneous device 100 and pull clip 104 of subcutaneous device 100 off of the xiphoid process and the distal end of the sternum, thus removing subcutaneous device 100 from the patient. The instrument that is used to remove subcutaneous device 100 can be the same instrument used to insert subcutaneous device 100 or a separate instrument.

If subcutaneous device 100 needs to be removed from the patient after fibrosis has formed around subcutaneous device 100, a surgeon can use a scalpel and other surgical instruments to cut through the skin, tissue, and fibrosis to access subcutaneous device 100. The surgeon can then use any suitable instrument to remove subcutaneous device 100 from the patient.

Method 300 is a non-invasive surgery. Leads are not implanted in the vasculature of the patient using invasive techniques. Rather, subcutaneous device 100 is anchored to the xiphoid process and the distal end of the sternum using surgical instrument 200 and prong 106 extends through the anterior mediastinum and comes into contact with the heart. This lowers the risk of infection, complications during surgery, and potential failure of the device. Method 300 can be used to implant subcutaneous device 300 on any bone, muscle, or tissue in the body of a patient. In an alternate embodiment, any suitable method, including traditional surgical methods, and any suitable instrument can be used to implant subcutaneous device 100.

FIGS. 20-37 below show different embodiments of subcutaneous device 100. These embodiments are intended to be exemplary. Subcutaneous device 100 can have any suitable design and function. Each of the embodiments shown in FIGS. 20-37 below can be implanted into the patient using surgical instrument 200 shown in FIGS. 10A-14B and/or using method 300 shown in FIGS. 15-19. As shown in the different embodiments of subcutaneous device 100 shown in FIGS. 20-37 below, subcutaneous device 100 can include any suitable number of prongs 106. Prongs 106 can have any suitable length and shape to be positioned and/or come into contact with various organs, nerves, and tissues in the patient's body. Further, subcutaneous device 100 can function as a monitoring device, a diagnostic device, a pacemaker device, a defibrillator device, or any combinations thereof.

Subcutaneous Device 400

FIG. 20 is a perspective view of subcutaneous device 400. Subcutaneous device 400 includes housing 402, clip 404, and prong 406. Housing 402 includes first side 410, second side 412, top side 414, bottom side 416, front end 418, back end 420, curved surface 422, recess 424, port 426, channel 428, first guide 430 (not shown in FIG. 20), second guide 432, electrode 434, and electrode 436. Clip 404 includes top portion 440, bottom portion 442, spring portion 444, tip 446, openings 448, slot 450, and electrode 452. Prong 406 includes proximal end 460 (not shown in FIG. 20), distal end 462, base portion 464, spring portion 466, arm portion 468, contact portion 470, and electrode 472.

Subcutaneous device 400 includes housing 402, clip 404, and prong 406. Housing 402 has the same general structure and design as housing 102 of subcutaneous device 100 shown in FIGS. 1-9C. Clip 404 has the same general structure and design as clip 104 of subcutaneous device 100 shown in FIGS. 1-9C. The reference numerals that refer to the parts of housing 402 and clip 404 are incremented by three-hundred compared to the reference numerals that refer to the parts of housing 102 and clip 104 of subcutaneous device 100 shown in FIGS. 1-9C.

Prong 406 includes the same parts as prong 106 of subcutaneous device 100 as shown in FIGS. 1-9C, and the reference numerals that refer to the parts of prong 406 are incremented by three-hundred compared to the reference numerals that refer to the parts of prong 106 of subcutaneous device 100 shown in FIGS. 1-9C. However, prong 406 has a different shape. Spring portion 466 and arm portion 468 extend away from first side 410 of housing 402. Contact portion 470 is a portion of prong 406 adjacent to distal end 462 of prong 406 that is configured to come into contact with a left ventricle of a patient's heart. Electrode 472 positioned on contact portion 470 will also come into contact with a left ventricle of a patient's heart.

In one example, subcutaneous device 400 can be anchored to a xiphoid process and a sternum of a patient. Clip 404 is configured to anchor subcutaneous device 400 to the xiphoid process and the sternum. Clip 404 will expand as it is slid around the xiphoid process and the sternum. Spring portion 444 acts as a spring for clip 404 and is under tension. Top portion 440 acts as a tension arm and the forces from spring portion 444 translate to and push down on top portion 440. When clip 404 is positioned on the xiphoid process and the sternum, the tension in spring portion 444 will force top portion 440 down onto the xiphoid process and the sternum to anchor clip 404 to the xiphoid process and the sternum. Further, sutures, tines, pins, or screws can be inserted through openings 448 on top portion 440 of clip 404 to further anchor subcutaneous device 400 to the xiphoid process and the sternum.

Subcutaneous device 400 can include a power source, a controller, a memory, a transceiver, sensors, sensing circuitry, therapeutic circuitry, electrodes, and/or any other component of a medical device. In the embodiment shown in FIG. 20, subcutaneous device 400 is configured to be a single chamber pacemaker. Any one or combination of electrode 434, electrode 436, electrode 452, and electrode 472 can sense the electrical activity of a heart. The sensed electrical activity can be transmitted to the sensing circuitry and the controller in housing 402 of subcutaneous device 400. The controller can determine the heart rate of the patient and can detect whether an arrhythmia is present. If an arrhythmia is detected, the controller can send instructions to therapeutic circuitry to provide a therapeutic electrical stimulation to the heart. Specifically, a therapeutic electrical stimulation can be provided to the left ventricle. In this manner, subcutaneous device 400 functions as a monitoring device, a diagnostic device, and a therapeutic device. In alternate embodiments, subcutaneous device 400 can function only as a monitoring device, a diagnostic device, a therapeutic device, or any combinations thereof.

Subcutaneous Device 500

FIG. 21A is a perspective view of subcutaneous device 500. FIG. 21B is a side view of subcutaneous device 500. Subcutaneous device 500 includes housing 502, clip 504, and prong 506. Housing 502 includes first side 510, second side 512, top side 514, bottom side 516, front end 518, back end 520, curved surface 522, recess 524, port 526, channel 528, first guide 530, second guide 532, electrode 534, and electrode 536. Clip 504 includes top portion 540, bottom portion 542, spring portion 544, tip 546, openings 548, slot 550, and electrode 552. Prong 506 includes proximal end 560 (not shown in FIGS. 21A-21B), distal end 562, base portion 564, spring portion 566, arm portion 568, contact portion 570, and defibrillator coil 574.

Subcutaneous device 500 includes housing 502, clip 504, and prong 506. Housing 502 has the same general structure and design as housing 102 of subcutaneous device 100 shown in FIGS. 1-9C. Clip 504 has the same general structure and design as clip 104 of subcutaneous device 100 shown in FIGS. 1-9C. The reference numerals that refer to the parts of housing 502 and clip 504 are incremented by four-hundred compared to the reference numerals that refer to the parts of housing 102 and clip 104 of subcutaneous device 100 shown in FIGS. 1-9C.

Prong 506 generally includes the same parts as prong 106 of subcutaneous device 100 as shown in FIGS. 1-9C, and the reference numerals that refer to the parts of prong 506 are incremented by four-hundred compared to the reference numerals that refer to the parts of prong 106 of subcutaneous device 100 shown in FIGS. 1-9C. However, prong 406 has a different shape and includes defibrillator coil 574 instead of an electrode at distal end 562. Spring portion 566 and arm portion 568 extend away from bottom side 520 of housing 502. Contact portion 570 is a portion of prong 506 adjacent to distal end 562 of prong 506 that is configured to come into contact with tissue inferior to a patient's heart. Defibrillator coil 574 is positioned on contact portion 570 adjacent to distal end 562 of prong 506. When an electrical signal is delivered to defibrillator coil 574, defibrillator coil 574 will create a vector with electrode 534 on front end 518 of housing 502. In the embodiment shown, defibrillator coil 574 serves as the negative electrode and electrode 534 serves as the positive electrode. However, in alternate embodiments this can be reversed. Prong 506 is positioned so that distal end 562, and thus contact portion 570 and defibrillator coil 574, are positioned inferior to the heart. Thus, the vector created between defibrillator coil 574 and electrode 534 will pass through a patient's heart to provide a high voltage electrical shock to the patient's heart.

In one example, subcutaneous device 500 can be anchored to a xiphoid process and a sternum of a patient. Clip 504 is configured to anchor subcutaneous device 500 to the xiphoid process and the sternum. Clip 504 will expand as it is slid around the xiphoid process and the sternum. Spring portion 544 acts as a spring for clip 504 and is under tension. Top portion 540 acts as a tension arm and the forces from spring portion 544 translate to and push down on top portion 540. When clip 504 is positioned on the xiphoid process and the sternum, the tension in spring portion 544 will force top portion 540 down onto the xiphoid process and the sternum to anchor clip 504 to the xiphoid process and the sternum. Further, sutures, tines, pins, or screws can be inserted through openings 548 on top portion 540 of clip 504 to further anchor subcutaneous device 500 to the xiphoid process and the sternum.

Subcutaneous device 500 can include a power source, a controller, a memory, a transceiver, sensors, sensing circuitry, therapeutic circuitry, electrodes, and/or any other component of a medical device. In the embodiment shown in FIGS. 21A-21B, subcutaneous device 500 is configured to be a defibrillator. Any one or combination of electrode 534, electrode 536, and electrode 552 can sense the electrical activity of a heart. Further, defibrillator coil 574 can act as an electrode that senses the electrical activity of the heart. The sensed electrical activity can be transmitted to the sensing circuitry and the controller in housing 502 of subcutaneous device 500. The controller can determine the heart rate of the patient and can detect whether an abnormality is present. If an abnormality is detected, the controller can send instructions to therapeutic circuitry to provide a high voltage electrical shock to the heart using defibrillator coil 574. In this manner, subcutaneous device 500 functions as a monitoring device, a diagnostic device, and a therapeutic device. In alternate embodiments, subcutaneous device 500 can function only as a monitoring device, a diagnostic device, or a therapeutic device, or any combinations thereof.

Subcutaneous Device 600

FIG. 22A is a perspective view of subcutaneous device 600. FIG. 22B is a top view of subcutaneous device 600. FIG. 22C is a bottom view of subcutaneous device 600. FIG. 22D is a side view of subcutaneous device 600. FIG. 22E is a back view of subcutaneous device 600. FIG. 23A is a perspective view of subcutaneous device 600 positioned on xiphoid process X and sternum S and showing a positioning of prongs 606A and 606B on left lung LL and right lung RL. FIG. 23B is a front view of subcutaneous device 600 positioned on xiphoid process X and sternum S and showing a positioning of prongs 606A and 606B on left lung LL and right lung RL. FIG. 23C is a side view of subcutaneous device 600 positioned on xiphoid process X and sternum S and showing a positioning of prongs 606A and 606B on left lung LL and right lung RL. Subcutaneous device 600 includes housing 602, clip 604, prong 606A, and prong 606B. Housing 602 includes first side 610, second side 612, top side 614, bottom side 616, front end 618, back end 620, curved surface 622, recess 624, port 626A, port 626B, channel 628A, channel 628B, first guide 630, second guide 632, electrode 634, and electrode 636. Clip 604 includes top portion 640, bottom portion 642, spring portion 644, tip 646, openings 648, slot 650, and electrode 652. Prong 606A includes proximal end 660A (not shown in FIGS. 22A-22B), distal end 662A, base portion 664A, spring portion 666A, arm portion 668A, contact portion 670A, and electrode 672A. Prong 606B includes proximal end 660B (not shown in FIGS. 22A-22B), distal end 662B, base portion 664B, spring portion 666B, arm portion 668B, contact portion 670B, and electrode 672B. FIGS. 23A-23C show xiphoid process X, sternum S, left lung LL, and right lung RL. FIG. 23B also shows ribs R.

Subcutaneous device 600 includes housing 602, clip 604, prong 606A, and prong 606B. Housing 602 has the same general structure and design as housing 102 of subcutaneous device 100 shown in FIGS. 1-9C. However, housing 602 includes two ports, including port 626A and port 626B, and two channels, including channel 628A and channel 628B. The reference numerals that refer to the parts of housing 602 are incremented by five-hundred compared to the reference numerals that refer to the parts of housing 102 of subcutaneous device 100 shown in FIGS. 1-9C. Port 626A and port 626B are positioned next to one another on housing 602, and channel 628A and channel 628B are positioned next to one another on housing 602. Prong 606A is configured to be connected to port 626A and can be positioned in channel 628A when subcutaneous device 600 is in a stowed position. Prong 606B is configured to be connected to port 626B and can be positioned in channel 628B when subcutaneous device 600 is in a stowed position.

Clip 604 has the same general structure and design as clip 104 of subcutaneous device 100 shown in FIGS. 1-9C. The reference numerals that refer to the parts of clip 604 are incremented by five-hundred compared to the reference numerals that refer to the parts of clip 104 of subcutaneous device 100 shown in FIGS. 1-9C.

Prong 606A and prong 606B each include the same parts as prong 106 of subcutaneous device 100 as shown in FIGS. 1-9C, and the reference numerals that refer to the parts of prong 606A and prong 606B are incremented by five-hundred compared to the reference numerals that refer to the parts of prong 106 of subcutaneous device 100 shown in FIGS. 1-9C. However, prong 606A and 606B have different shapes than prong 106 shown in FIGS. 1-9C. Spring portion 666A and arm portion 668A of prong 606A extend away from first side 610 of housing 602. Contact portion 670A is a portion of prong 606A adjacent to distal end 662A of prong 606A that is configured to come into contact with left lung LL of a patient. Electrode 672A positioned on contact portion 670A will also come into contact with left lung LL. Spring portion 666B and arm portion 668B of prong 606B extend away from second side 612 of housing 602. Contact portion 670B is a portion of prong 606B adjacent to distal end 662B of prong 606B that is configured to come into contact with right lung RL of a patient. Electrode 672B positioned on contact portion 670B will also come into contact with right lung RL.

In one example, subcutaneous device 600 can be anchored to xiphoid process X and sternum S of a patient. Clip 604 is configured to anchor subcutaneous device 600 to xiphoid process X and sternum S. Clip 604 will expand as it is slid around xiphoid process X and sternum S. Spring portion 644 acts as a spring for clip 604 and is under tension. Top portion 640 acts as a tension arm and the forces from spring portion 644 translate to and push down on top portion 640. When clip 604 is positioned on xiphoid process X and sternum S, the tension in spring portion 644 will force top portion 640 down onto xiphoid process X and sternum S to anchor clip 604 to xiphoid process X and sternum S. Further, sutures, tines, pins, or screws can be inserted through openings 648 on top portion 640 of clip 604 to further anchor subcutaneous device 600 to xiphoid process X and sternum S.

Subcutaneous device 600 can include a power source, a controller, a memory, a transceiver, sensors, sensing circuitry, electrodes, and/or any other component of a medical device. In the embodiment shown in FIGS. 22A-23C, subcutaneous device 600 is configured to be a pulmonary monitoring and diagnostic device. Any one or combination of electrode 634, electrode 636, electrode 652, electrode 672A, and electrode 672B can sense the electrical activity of left lung LL, right lung RL, and tissue surrounding left lung LL and right lung RL. The sensed electrical activity can be transmitted to the sensing circuitry and the controller in housing 602 of subcutaneous device 600. The controller can determine physiological parameters of the patient for monitoring and diagnostic purposes. In this manner, subcutaneous device 600 functions as a monitoring device and a diagnostic device. In alternate embodiments, subcutaneous device 600 can function only as a monitoring device or a diagnostic device.

Subcutaneous Device 700

FIG. 24A is a top view of subcutaneous device 700. FIG. 24B is a bottom view of subcutaneous device 700. FIG. 24C is a side view of subcutaneous device 700. FIG. 24D is a front view of subcutaneous device 700. FIG. 25A is a front view of subcutaneous device 700 positioned on xiphoid process X and sternum S and showing a positioning of prongs 706A and 706B around heart H. FIG. 25B is a perspective view of subcutaneous device 700 positioned on xiphoid process X and sternum S and showing a positioning of prongs 706A and 706B around heart H. Subcutaneous device 700 includes housing 702, clip 704, prong 706A, and prong 706B. Housing 702 includes first side 710, second side 712, top side 714, bottom side 716, front end 718, back end 720, curved surface 722, recess 724, port 726A, port 726B, channel 728A, channel 728B, first guide 730, second guide 732, electrode 734, and electrode 736. Clip 704 includes top portion 740, bottom portion 742, spring portion 744, tip 746, openings 748, slot 750, and electrode 752. Prong 706A includes proximal end 760A (not shown in FIGS. 24A-25B), distal end 762A, base portion 764A, spring portion 766A, arm portion 768A, contact portion 770A, and electrode 772A. Prong 706B includes proximal end 760B (not shown in FIGS. 24A-25B), distal end 762B, base portion 764B, spring portion 766B, arm portion 768B, contact portion 770B, and electrode 772B. FIGS. 25A-25B show xiphoid process X, sternum S, and heart H.

Subcutaneous device 700 includes housing 702, clip 704, prong 706A, and prong 706B. Housing 702 has the same general structure and design as housing 102 of subcutaneous device 100 shown in FIGS. 1-9C. However, housing 702 includes two ports, including port 726A and port 726B, and two channels, including channel 728A and channel 728B. The reference numerals that refer to the parts of housing 702 are incremented by six-hundred compared to the reference numerals that refer to the parts of housing 102 of subcutaneous device 100 shown in FIGS. 1-9C. Port 726A and port 726B are positioned next to one another on housing 702, and channel 728A and channel 728B are positioned next to one another on housing 702. Prong 706A is configured to be connected to port 726A and can be positioned in channel 728A when subcutaneous device 700 is in a stowed position. Prong 706B is configured to be connected to port 726B and can be positioned in channel 728B when subcutaneous device 700 is in a stowed position.

Clip 704 has the same general structure and design as clip 104 of subcutaneous device 100 shown in FIGS. 1-9C. The reference numerals that refer to the parts of clip 704 are incremented by six-hundred compared to the reference numerals that refer to the parts of clip 104 of subcutaneous device 100 shown in FIGS. 1-9C.

Prong 706A and prong 706B each include the same parts as prong 106 of subcutaneous device 100 as shown in FIGS. 1-9C, and the reference numerals that refer to the parts of prong 706A and prong 706B are incremented by six-hundred compared to the reference numerals that refer to the parts of prong 106 of subcutaneous device 100 shown in FIGS. 1-9C. However, prong 706A and 706B have a different shape than prong 106 shown in FIGS. 1-9C. Spring portion 766A and arm portion 768A of prong 706A extend away from first side 710 of housing 702. Contact portion 770A is a portion of prong 706A adjacent to distal end 762A of prong 706A that is configured to come into contact with tissue surrounding heart H of a patient. Electrode 772A positioned on contact portion 770A will also come into contact with tissue surrounding heart H of a patient. Spring portion 766B and arm portion 768B of prong 706B extend away from second side 712 of housing 702. Contact portion 770B is a portion of prong 706B adjacent to distal end 762B of prong 706B that is configured to come into contact with tissue surrounding heart H of a patient. Electrode 772B positioned on contact portion 770B will also come into contact with tissue surrounding heart H of a patient.

In one example, subcutaneous device 700 can be anchored to xiphoid process X and sternum S of a patient. Clip 704 is configured to anchor subcutaneous device 700 to xiphoid process X and sternum S. Clip 704 will expand as it is slid around xiphoid process X and sternum S. Spring portion 744 acts as a spring for clip 704 and is under tension. Top portion 740 acts as a tension arm and the forces from spring portion 744 translate to and push down on top portion 740. When clip 704 is positioned on xiphoid process X and sternum S, the tension in spring portion 744 will force top portion 740 down onto xiphoid process X and sternum S to anchor clip 704 to xiphoid process X and sternum S. Further, sutures, tines, pins, or screws can be inserted through openings 748 on top portion 740 of clip 704 to further anchor subcutaneous device 700 to xiphoid process X and sternum S.

Subcutaneous device 700 can include a power source, a controller, a memory, a transceiver, sensors, sensing circuitry, electrodes, and/or any other component of a medical device. In the embodiment shown in FIGS. 24A-25B, subcutaneous device 700 is configured to be a cardiac monitoring and diagnostic device. Any one or combination of electrode 734, electrode 736, electrode 752, electrode 772A, and electrode 772B can sense the electrical activity of tissue surrounding heart H. The sensed electrical activity can be transmitted to the sensing circuitry and the controller in housing 702 of subcutaneous device 700. The controller can determine physiological parameters of the patient for monitoring and diagnostic purposes. In this manner, subcutaneous device 700 functions as a monitoring device and a diagnostic device. In alternate embodiments, subcutaneous device 700 can function only as a monitoring device or a diagnostic device.

Specifically, in the embodiment shown in FIGS. 24A-25B, a surface ECG of heart H can be determined using electrode 734, electrode 736, electrode 772A, and electrode 772B. A first lead can be determined between electrode 734 and electrode 736 on housing 702 of subcutaneous device 700. A second lead can be determined between electrode 772A on first prong 706A and electrode 772B on second prong 706B. The information gathered from these two leads can then be extrapolated to give the surface ECG across six leads. Anchoring subcutaneous device 700 to xiphoid process X and sternum S allows for consistency and accuracy in the surface ECG readings, as subcutaneous device 700 is not moving within the body and causing the ECG morphology to change.

Subcutaneous Device 800

FIG. 26 is a perspective view of subcutaneous device 800. Subcutaneous device 800 includes housing 802, clip 804, prong 806A, and prong 806B. Housing 802 includes first side 810, second side 812, top side 814, bottom side 816, front end 818, back end 820, curved surface 822, recess 824, port 826A, port 826B, channel 828A, channel 828B, first guide 830 (now shown in FIG. 26) second guide 832, electrode 834, and electrode 836. Clip 804 includes top portion 840, bottom portion 842, spring portion 844, tip 846, openings 848, slot 850, and electrode 852. Prong 806A includes proximal end 860A (not shown in FIG. 26), distal end 862A, base portion 864A, spring portion 866A, arm portion 868A, contact portion 870A, and electrode 872A. Prong 806B includes proximal end 860B (not shown in FIG. 26), distal end 862B, base portion 864B, spring portion 866B, arm portion 868B, contact portion 870B, and electrode 872B.

Subcutaneous device 800 includes housing 802, clip 804, prong 806A, and prong 806B. Housing 802 has the same general structure and design as housing 102 of subcutaneous device 100 shown in FIGS. 1-9C. However, housing 802 includes two ports, including port 826A and port 826B, and two channels, including channel 828A and channel 828B. The reference numerals that refer to the parts of housing 802 are incremented by seven-hundred compared to the reference numerals that refer to the parts of housing 102 of subcutaneous device 100 shown in FIGS. 1-9C. Port 826A and port 826B are positioned next to one another on housing 802, and channel 828A and channel 828B are positioned next to one another on housing 802. Prong 806A is configured to be connected to port 826A and can be positioned in channel 828A when subcutaneous device 800 is in a stowed position. Prong 806B is configured to be connected to port 826B and can be positioned in channel 828B when subcutaneous device 800 is in a stowed position.

Clip 804 has the same general structure and design as clip 104 of subcutaneous device 100 shown in FIGS. 1-9C. The reference numerals that refer to the parts of clip 804 are incremented by seven-hundred compared to the reference numerals that refer to the parts of clip 104 of subcutaneous device 100 shown in FIGS. 1-9C.

Prong 806A and prong 806B each include the same parts as prong 106 of subcutaneous device 100 as shown in FIGS. 1-9C, and the reference numerals that refer to the parts of prong 806A and prong 806B are incremented by seven-hundred compared to the reference numerals that refer to the parts of prong 106 of subcutaneous device 100 shown in FIGS. 1-9C. However, prong 806A has a different shape than prong 106 shown in FIGS. 1-9C. Spring portion 866A and arm portion 868A of prong 806A extend away from first side 810 of housing 802. Contact portion 870A is a portion of prong 806A adjacent to distal end 862A of prong 806A that is configured to come into contact with the left ventricle of the patient's heart. Electrode 872A positioned on contact portion 870A will also come into contact with the left ventricle of the patient's heart. Prong 806B has the same shape as prong 106 shown in FIGS. 1-9C. Spring portion 866B and arm portion 868B of prong 806B extend underneath bottom side 816 of housing 802. Contact portion 870B is a portion of prong 806B adjacent to distal end 862B of prong 806B that is configured to come into contact with the right ventricle of a patient's heart. Electrode 872B positioned on contact portion 870B will also come into contact with the right ventricle of patient's heart.

In one example, subcutaneous device 800 can be anchored to a xiphoid process and a sternum of a patient. Clip 804 is configured to anchor subcutaneous device 800 to the xiphoid process and the sternum. Clip 804 will expand as it is slid around the xiphoid process and the sternum. Spring portion 844 acts as a spring for clip 804 and is under tension. Top portion 840 acts as a tension arm and the forces from spring portion 844 translate to and push down on top portion 840. When clip 804 is positioned on the xiphoid process and the sternum, the tension in spring portion 844 will force top portion 840 down onto the xiphoid process and the sternum to anchor clip 804 to the xiphoid process and the sternum. Further, sutures, tines, pins, or screws can be inserted through openings 848 on top portion 840 of clip 804 to further anchor subcutaneous device 800 to the xiphoid process and the sternum.

Subcutaneous device 800 can include a power source, a controller, a memory, a transceiver, sensors, sensing circuitry, therapeutic circuitry, electrodes, and/or any other component of a medical device. In the embodiment shown in FIG. 26, subcutaneous device 800 is configured to be a dual chamber pacemaker. Any one or combination of electrode 834, electrode 836, electrode 852, electrode 872A, and electrode 872B can sense the electrical activity of a heart. The sensed electrical activity can be transmitted to the sensing circuitry and the controller in housing 802 of subcutaneous device 800. The controller can determine the heart rate of the patient and can detect whether an arrhythmia is present. If an arrhythmia is detected, the controller can send instructions to therapeutic circuitry to provide a therapeutic electrical stimulation to the heart. Specifically, a therapeutic electrical stimulation can be provided to the right ventricle and the left ventricle. In this manner, subcutaneous device 800 functions as a monitoring device, a diagnostic device, and a therapeutic device. In alternate embodiments, subcutaneous device 800 can function only as a monitoring device, a diagnostic device, or a therapeutic device, or any combinations thereof.

Subcutaneous Device 900

FIG. 27 is a perspective view of subcutaneous device 900. FIG. 28 is a cut-away perspective view of subcutaneous device 900 positioned on xiphoid process X and sternum S and showing a positioning of prongs 906A and 906B on heart H. Subcutaneous device 900 includes housing 902, clip 904, prong 906A, and prong 906B. Housing 902 includes first side 910, second side 912, top side 914, bottom side 916, front end 918, back end 920, curved surface 922, recess 924, port 926A, port 926B, channel 928A, channel 928B, first guide 930 (not shown in FIG. 27), second guide 932, electrode 934, and electrode 936. Clip 904 includes top portion 940, bottom portion 942, spring portion 944, tip 946, openings 948, slot 950, and electrode 952. Prong 906A includes proximal end 960A (not shown in FIGS. 27-28), distal end 962A, base portion 964A, spring portion 966A, arm portion 968A, contact portion 970A, and electrode 972A. Prong 906B includes proximal end 960B (not shown in FIGS. 27-28), distal end 962B, base portion 964B, spring portion 966B, arm portion 968B, contact portion 970B, and electrode 972B. FIG. 28 shows xiphoid process X, sternum S, heart H, right ventricle RV, and right atrium RA.

Subcutaneous device 900 includes housing 902, clip 904, prong 906A, and prong 906B. Housing 902 has the same general structure and design as housing 102 of subcutaneous device 100 shown in FIGS. 1-9C. However, housing 902 includes two ports, including port 926A and port 926B, and two channels, including channel 928A and channel 928B. The reference numerals that refer to the parts of housing 902 are incremented by eight-hundred compared to the reference numerals that refer to the parts of housing 102 of subcutaneous device 100 shown in FIGS. 1-9C. Port 926A and port 926B are positioned next to one another, and channel 928A and channel 928B are positioned next to one another. Prong 906A is configured to be connected to port 926A and can be positioned in channel 928A when subcutaneous device 900 is in a stowed position. Prong 906B is configured to be connected to port 926B and can be positioned in channel 928B when subcutaneous device 900 is in a stowed position.

Clip 904 has the same general structure and design as clip 104 of subcutaneous device 100 shown in FIGS. 1-9C. The reference numerals that refer to the parts of clip 904 are incremented by eight-hundred compared to the reference numerals that refer to the parts of clip 104 of subcutaneous device 100 shown in FIGS. 1-9C.

Prong 906A and prong 906B each include the same parts as prong 106 of subcutaneous device 100 as shown in FIGS. 1-9C, and the reference numerals that refer to the parts of prong 906A and prong 906B are incremented by eight-hundred compared to the reference numerals that refer to the parts of prong 106 of subcutaneous device 100 shown in FIGS. 1-9C. Prong 906A has the same shape as prong 106 shown in FIGS. 1-9C. Spring portion 966A and arm portion 968A of prong 906A extend underneath bottom side 916 of housing 902. Contact portion 970A is a portion of prong 906A adjacent to distal end 962A of prong 906A that is configured to come into contact with right ventricle RV of heart H of the patient. Electrode 972A positioned on contact portion 970A will also come into contact with right ventricle RV of heart H of the patient. However, 906B has a different shape than prong 106 shown in FIGS. 1-9C. Spring portion 966B and arm portion 968B of prong 906B extend away from second side 912 of housing 902. Contact portion 970B is a portion of prong 906B adjacent to distal end 962B of prong 906B that is configured to come into contact with right atrium RA of heart H of the patient. Electrode 972B positioned on contact portion 970B will also come into contact with right atrium RA of heart H of the patient.

In one example, subcutaneous device 900 can be anchored to xiphoid process X and sternum S of a patient. Clip 904 is configured to anchor subcutaneous device 900 to xiphoid process X and sternum S. Clip 904 will expand as it is slid around xiphoid process X and sternum S. Spring portion 944 acts as a spring for clip 904 and is under tension. Top portion 940 acts as a tension arm and the forces from spring portion 944 translate to and push down on top portion 940. When clip 904 is positioned on xiphoid process X and sternum S, the tension in spring portion 944 will force top portion 940 down onto xiphoid process X and sternum S to anchor clip 904 to xiphoid process X and sternum S. Further, sutures, tines, pins, or screws can be inserted through openings 948 on top portion 940 of clip 904 to further anchor subcutaneous device 900 to xiphoid process X and sternum S.

Subcutaneous device 900 can include a power source, a controller, a memory, a transceiver, sensors, sensing circuitry, therapeutic circuitry, electrodes, and/or any other component of a medical device. In the embodiment shown in FIGS. 27-28, subcutaneous device 900 is configured to be a dual chamber pacemaker. Any one or combination of electrode 934, electrode 936, electrode 952, electrode 972A, and electrode 972B can sense the electrical activity of heart H. The sensed electrical activity can be transmitted to the sensing circuitry and the controller in housing 902 of subcutaneous device 900. The controller can determine the heart rate of the patient and can detect whether an arrhythmia is present. If an arrhythmia is detected, the controller can send instructions to therapeutic circuitry to provide a therapeutic electrical stimulation to heart H. Specifically, a therapeutic electrical stimulation can be provided to the right ventricle and the right atrium. In this manner, subcutaneous device 900 functions as a monitoring device, a diagnostic device, and a therapeutic device. In alternate embodiments, subcutaneous device 900 can function only as a monitoring device, a diagnostic device, or a therapeutic device, or any combinations thereof.

Subcutaneous Device 1000

FIG. 29 is a perspective view of subcutaneous device 1000. Subcutaneous device 1000 includes housing 1002, clip 1004, prong 1006A, and prong 1006B. Housing 1002 includes first side 1010, second side 1012, top side 1014, bottom side 1016, front end 1018, back end 1020, curved surface 1022, recess 1024, port 1026A, port 1026B, channel 1028A, channel 1028B, first guide 1030 (not shown in FIG. 29), second guide 1032, electrode 1034, and electrode 1036. Clip 1004 includes top portion 1040, bottom portion 1042, spring portion 1044, tip 1046, openings 1048, slot 1050, and electrode 1052. Prong 1006A includes proximal end 1060A (not shown in FIG. 29), distal end 1062A, base portion 1064A, spring portion 1066A, arm portion 1068A, contact portion 1070A, and electrode 1072A. Prong 1006B includes proximal end 1060B (not shown in FIG. 29), distal end 1062B, base portion 1064B, spring portion 1066B, arm portion 1068B, contact portion 1070B, and electrode 1072B.

Subcutaneous device 1000 includes housing 1002, clip 1004, prong 1006A, and prong 1006B. Housing 1002 has the same general structure and design as housing 102 of subcutaneous device 100 shown in FIGS. 1-9C. However, housing 1002 includes two ports, including port 1026A and port 1026B, and two channels, including channel 1028A and channel 1028B. The reference numerals that refer to the parts of housing 1002 are incremented by nine-hundred compared to the reference numerals that refer to the parts of housing 102 of subcutaneous device 100 shown in FIGS. 1-9C. Port 1026A and port 1026B are positioned next to one another on housing 1002, and channel 1028A and channel 1028B are positioned next to one another on housing 1002. Prong 1006A is configured to be connected to port 1026A and can be positioned in channel 1028A when subcutaneous device 1000 is in a stowed position. Prong 1006B is configured to be connected to port 1026B and can be positioned in channel 1028B when subcutaneous device 1000 is in a stowed position.

Clip 1004 has the same general structure and design as clip 104 of subcutaneous device 100 shown in FIGS. 1-9C. The reference numerals that refer to the parts of clip 1004 are incremented by nine-hundred compared to the reference numerals that refer to the parts of clip 104 of subcutaneous device 100 shown in FIGS. 1-9C.

Prong 1006A and prong 1006B each include the same parts as prong 106 of subcutaneous device 100 as shown in FIGS. 1-9C, and the reference numerals that refer to the parts of prong 1006A and prong 1006B are incremented by nine-hundred compared to the reference numerals that refer to the parts of prong 106 of subcutaneous device 100 shown in FIGS. 1-9C. However, prong 1006A and 1006B have a different shape than prong 106 shown in FIGS. 1-9C. Spring portion 1066A and arm portion 1068A of prong 1006A extend away from first side 1010 of housing 1002. Contact portion 1070A is a portion of prong 1006A adjacent to distal end 1062A of prong 1006A that is configured to come into contact with the left ventricle of the patient's heart. Electrode 1072A positioned on contact portion 1070A will also come into contact with the left ventricle of the patient's heart. Spring portion 1066B and arm portion 1068B of prong 1006B extend away from second side 1012 of housing 1002. Contact portion 1070B is a portion of prong 1006B adjacent to distal end 1062B of prong 1006B that is configured to come into contact with the right atrium of a patient's heart. Electrode 1072B positioned on contact portion 1070B will also come into contact with the right atrium of patient's heart.

In one example, subcutaneous device 1000 can be anchored to a xiphoid process and a sternum of a patient. Clip 1004 is configured to anchor subcutaneous device 1000 to the xiphoid process and the sternum. Clip 1004 will expand as it is slid around the xiphoid process and the sternum. Spring portion 1044 acts as a spring for clip 1004 and is under tension. Top portion 1040 acts as a tension arm and the forces from spring portion 1044 translate to and push down on top portion 1040. When clip 1004 is positioned on the xiphoid process and the sternum, the tension in spring portion 1044 will force top portion 1040 down onto the xiphoid process and the sternum to anchor clip 1004 to the xiphoid process and the sternum. Further, sutures, tines, pins, or screws can be inserted through openings 1048 on top portion 1040 of clip 1004 to further anchor subcutaneous device 1000 to the xiphoid process and the sternum.

Subcutaneous device 1000 can include a power source, a controller, a memory, a transceiver, sensors, sensing circuitry, therapeutic circuitry, electrodes, and/or any other component of a medical device. In the embodiment shown in FIG. 29, subcutaneous device 1000 is configured to be a dual chamber pacemaker. Any one or combination of electrode 1034, electrode 1036, electrode 1052, electrode 1072A, and electrode 1072B can sense the electrical activity of a heart. The sensed electrical activity can be transmitted to the sensing circuitry and the controller in housing 1002 of subcutaneous device 1000. The controller can determine the heart rate of the patient and can detect whether an arrhythmia is present. If an arrhythmia is detected, the controller can send instructions to therapeutic circuitry to provide a therapeutic electrical stimulation to the heart. Specifically, a therapeutic electrical stimulation can be provided to the left ventricle and the right atrium. In this manner, subcutaneous device 1000 functions as a monitoring device, a diagnostic device, and a therapeutic device. In alternate embodiments, subcutaneous device 1000 can function only as a monitoring device, a diagnostic device, a therapeutic device, or any combinations thereof.

Subcutaneous Device 1100

FIG. 30 is a perspective view of subcutaneous device 1100. Subcutaneous device 1100 includes housing 1102, clip 1104, prong 1106A, and prong 1106B. Housing 1102 includes first side 1110, second side 1112, top side 1114, bottom side 1116, front end 1118, back end 1120, curved surface 1122, recess 1124, port 1126A, port 1126B, channel 1128A, channel 1128B, first guide 1130 (not shown in FIG. 30), second guide 1132, electrode 1134, and electrode 1136. Clip 1104 includes top portion 1140, bottom portion 1142, spring portion 1144, tip 1146, openings 1148, slot 1150, and electrode 1152. Prong 1106A includes proximal end 1160A (not shown in FIG. 30), distal end 1162A, base portion 1164A, spring portion 1166A, arm portion 1168A, contact portion 1170A, and electrode 1172A. Prong 1106B includes proximal end 1160B (not shown in FIG. 30), distal end 1162B, base portion 1164B, spring portion 1166B, arm portion 1168B, contact portion 1170B, and defibrillator coil 1174B.

Subcutaneous device 1100 includes housing 1102, clip 1104, prong 1106A, and prong 1106B. Housing 1102 has the same general structure and design as housing 102 of subcutaneous device 100 shown in FIGS. 1-9C. However, housing 1102 includes two ports, including port 1126A and port 1126B, and two channels, including channel 1128A and channel 1128B. The reference numerals that refer to the parts of housing 1102 are incremented by ten-hundred compared to the reference numerals that refer to the parts of housing 102 of subcutaneous device 100 shown in FIGS. 1-9C. Port 1126A and port 1126B are positioned next to one another on housing 1102, and channel 1128A and channel 1128B are positioned next to one another on housing 1102. Prong 1106A is configured to be connected to port 1126A and can be positioned in channel 1128A when subcutaneous device 1100 is in a stowed position. Prong 1106B is configured to be connected to port 1126B and can be positioned in channel 1128B when subcutaneous device 1100 is in a stowed position.

Clip 1104 has the same general structure and design as clip 104 of subcutaneous device 100 shown in FIGS. 1-9C. The reference numerals that refer to the parts of clip 1104 are incremented by ten-hundred compared to the reference numerals that refer to the parts of clip 104 of subcutaneous device 100 shown in FIGS. 1-9C.

Prong 1106A and prong 1106B generally include the same parts as prong 106 of subcutaneous device 100 as shown in FIGS. 1-9C, and the reference numerals that refer to the parts of prong 1106A and 1106B are incremented by ten-hundred compared to the reference numerals that refer to the parts of prong 106 of subcutaneous device 100 shown in FIGS. 1-9C. Prong 1106A has the same shape as prong 106 shown in FIGS. 1-9C. Spring portion 1166A and arm portion 1168A extend away from bottom side 1120 of housing 1102. Contact portion 1170A is a portion of prong 1106A adjacent to distal end 1162A of prong 1106A that is configured to come into contact with the right ventricle of the patient's heart. Electrode 1172A positioned on contact portion 1170A will also come into contact with the right ventricle of the patient's heart. However, prong 1106B has a different shape than prong 106 shown in FIGS. 1-9C and includes defibrillator coil 1174B instead of an electrode. Spring portion 1166B and arm portion 1168B extend away from bottom side 1120 of housing 1102. Contact portion 1170B is a portion of prong 1106B adjacent to distal end 1162B of prong 1106B that is configured to come into contact with tissue inferior to a patient's heart. Defibrillator coil 1174B is positioned on contact portion 1170B adjacent to distal end 1162B of prong 1106B. When an electrical signal is delivered to defibrillator coil 1174B, defibrillator coil 1174B will create a vector with electrode 1134 on front end 1118 of housing 1102. In the embodiment shown, defibrillator coil 1174B serves as the negative electrode and electrode 1134 serves as the positive electrode. However, in alternate embodiments this can be reversed. Prong 1106B is positioned so that distal end 1162B, and thus contact portion 1170B and defibrillator coil 1174B, are positioned inferior to the heart. Thus, the vector created between defibrillator coil 1174B and electrode 1134 will pass through a patient's heart to provide a high voltage electrical shock to the patient's heart.

In one example, subcutaneous device 1100 can be anchored to a xiphoid process and a sternum of a patient. Clip 1104 is configured to anchor subcutaneous device 1100 to the xiphoid process and the sternum. Clip 1104 will expand as it is slid around the xiphoid process and the sternum. Spring portion 1144 acts as a spring for clip 1104 and is under tension. Top portion 1140 acts as a tension arm and the forces from spring portion 1144 translate to and push down on top portion 1140. When clip 1104 is positioned on the xiphoid process and the sternum, the tension in spring portion 1144 will force top portion 1140 down onto the xiphoid process and the sternum to anchor clip 1104 to the xiphoid process and the sternum. Further, sutures, tines, pins, or screws can be inserted through openings 1148 on top portion 1140 of clip 1104 to further anchor subcutaneous device 1100 to the xiphoid process and the sternum.

Subcutaneous device 1100 can include a power source, a controller, a memory, a transceiver, sensors, sensing circuitry, therapeutic circuitry, electrodes, and/or any other component of a medical device. In the embodiment shown in FIG. 30, subcutaneous device 1100 is configured to be a single chamber pacemaker and a defibrillator. Any one or combination of electrode 1134, electrode 1136, electrode 1152, and electrode 1172A can sense the electrical activity of a heart. Further, defibrillator coil 1174B can act as an electrode that senses the electrical activity of the heart. The sensed electrical activity can be transmitted to the sensing circuitry and the controller in housing 1102 of subcutaneous device 1100. The controller can determine the heart rate of the patient and can detect whether an arrhythmia or abnormality is present. If an arrhythmia is detected, the controller can send instructions to therapeutic circuitry to provide a therapeutic stimulation to the heart with electrode 1172A. If an abnormality is detected, the controller can send instructions to therapeutic circuitry to provide a high voltage electrical shock to the heart with defibrillator coil 1174B. In this manner, subcutaneous device 1100 functions as a monitoring device, a diagnostic device, and a therapeutic device. In alternate embodiments, subcutaneous device 1100 can function only as a monitoring device, a diagnostic device, or a therapeutic device, or any combinations thereof.

Subcutaneous Device 1200

FIG. 31A is a perspective view of subcutaneous device 1200. FIG. 31B is a side view of subcutaneous device 1200. FIG. 31C is a top view of subcutaneous device 1200. FIG. 31D is a front view of subcutaneous device 1200. FIG. 31E is a back view of subcutaneous device 1200. FIG. 32A is a cut-away perspective view of subcutaneous device 1200 positioned on xiphoid process X and sternum S and showing a positioning of prongs 1206A, 1206B, and 1206C on heart H. FIG. 32B is a cut-away front view of subcutaneous device 1200 positioned on xiphoid process X and sternum S and showing a positioning of 1206A, 1206B, and 1206C on heart H. FIG. 32C is a cut-away front view of subcutaneous device 1200 positioned on xiphoid process X and sternum S and showing a positioning of prongs 1206A, 1206B, and 1206C on heart H. Subcutaneous device 1200 includes housing 1202, clip 1204, prong 1206A, prong 1206B, and prong 1206C. Housing 1202 includes first side 1210, second side 1212, top side 1214, bottom side 1216, front end 1218, back end 1220, curved surface 1222, recess 1224, port 1226A, port 1226B, port 1226C, channel 1228A, channel 1228B, channel 1228C, first guide 1230, second guide 1232, electrode 1234, and electrode 1236. Clip 1204 includes top portion 1240, bottom portion 1242, spring portion 1244, tip 1246, openings 1248, slot 1250, and electrode 1252. Prong 1206A includes proximal end 1260A (not shown in FIGS.

31A-32C), distal end 1262A, base portion 1264A, spring portion 1266A, arm portion 1268A, contact portion 1270A, and electrode 1272A. Prong 1206B includes proximal end 1260B (not shown in FIGS. 31A-32C), distal end 1262B, base portion 1264B, spring portion 1266B, arm portion 1268B, contact portion 1270B, and electrode 1272B. Prong 1206C includes proximal end 1260C (not shown in FIGS. 31A-32C), distal end 1262C, base portion 1264C, spring portion 1266C, arm portion 1268C, contact portion 1270C, and electrode 1272C. FIGS. 32A-32C include xiphoid process X, sternum S, heart H, left ventricle LV, right ventricle RV, and right atrium RA. FIG. 32C also show ribs R.

Subcutaneous device 1200 includes housing 1202, clip 1204, prong 1206A, prong 1206B, and prong 1206C. Housing 1202 has the same general structure and design as housing 102 of subcutaneous device 100 shown in FIGS. 1-9C. However, housing 1202 includes three ports, including port 1226A, port 1226B, and port 1226C, and three channels, including channel 1228A, channel 1228B, and channel 1228C. The reference numerals that refer to the parts of housing 1202 are incremented by eleven-hundred compared to the reference numerals that refer to the parts of housing 102 of subcutaneous device 100 shown in FIGS. 1-9C. Port 1226A, port 1226B, and port 1228C are positioned next to one another on housing 1202, and channel 1228A, channel 1228B, and channel 1228C are positioned next to one another on housing 1202. Prong 1206A is configured to be connected to port 1226A and can be positioned in channel 1228A when subcutaneous device 1200 is in a stowed position. Prong 1206B is configured to be connected to port 1226B and can be positioned in channel 1228B when subcutaneous device 1200 is in a stowed position. Prong 1206C is configured to be connected to port 1226C and can be positioned in channel 1228C when subcutaneous device 1200 is in a stowed position.

Clip 1204 has the same general structure and design as clip 104 of subcutaneous device 100 shown in FIGS. 1-9C. The reference numerals that refer to the parts of clip 1204 are incremented by eleven-hundred compared to the reference numerals that refer to the parts of clip 104 of subcutaneous device 100 shown in FIGS. 1-9C.

Prong 1206A, prong 1206B, and prong 1206C each include the same parts as prong 106 of subcutaneous device 100 as shown in FIGS. 1-9C, and the reference numerals that refer to the parts of prong 1206A, prong 1206B, and prong 1206C are incremented by eleven-hundred compared to the reference numerals that refer to the parts of prong 106 of subcutaneous device 100 shown in FIGS. 1-9C. However, prong 1206A and prong 1206C have a different shape than prong 106 shown in FIGS. 1-9C. Spring portion 1266A and arm portion 1268A of prong 1206A extend away from first side 1210 of housing 1202. Contact portion 1270A is a portion of prong 1206A adjacent to distal end 1262A of prong 1206A that is configured to come into contact with left ventricle LV of heart H of the patient. Electrode 1272A positioned on contact portion 1270A will also come into contact with left ventricle LV of heart H of the patient. Spring portion 1266C and arm portion 1268C of prong 1206C extend away from second side 1212 of housing 1202. Contact portion 1270C is a portion of prong 1206C adjacent to distal end 1262C of prong 1206C that is configured to come into contact with right atrium RA of heart H of the patient. Electrode 1272C positioned on contact portion 1270C will also come into contact with right atrium RA of heart H of the patient. Prong 1206B has the same shape as prong 106 shown in FIGS. 1-9C. Spring portion 1266B and arm portion 1268B of prong 1206B extend underneath bottom side 1216 of housing 1202. Contact portion 1270B is a portion of prong 1206B adjacent to distal end 1262B of prong 1206B that is configured to come into contact with right ventricle RV of heart H of the patient. Electrode 1272B positioned on contact portion 1270B will also come into contact with right ventricle RV of heart H of the patient.

In one example, subcutaneous device 1200 can be anchored to xiphoid process X and sternum S of a patient. Clip 1204 is configured to anchor subcutaneous device 1200 to xiphoid process X and sternum S. Clip 1204 will expand as it is slid around xiphoid process X and sternum S. Spring portion 1244 acts as a spring for clip 1204 and is under tension. Top portion 1240 acts as a tension arm and the forces from spring portion 1244 translate to and push down on top portion 1240. When clip 1204 is positioned on xiphoid process X and sternum S, the tension in spring portion 1244 will force top portion 1240 down onto xiphoid process X and sternum S to anchor clip 1204 to xiphoid process X and sternum S. Further, sutures, tines, pins, or screws can be inserted through openings 1248 on top portion 1240 of clip 1204 to further anchor subcutaneous device 1200 to xiphoid process S and sternum S.

Subcutaneous device 1200 can include a power source, a controller, a memory, a transceiver, sensors, sensing circuitry, therapeutic circuitry, electrodes, and/or any other component of a medical device. In the embodiment shown in FIGS. 31A-32C, subcutaneous device 1200 is configured to be a triple chamber pacemaker. Any one or combination of electrode 1234, electrode 1236, electrode 1252, electrode 1272A, electrode 1274B, and electrode 1274C can sense the electrical activity of heart H. The sensed electrical activity can be transmitted to the sensing circuitry and the controller in housing 1202 of subcutaneous device 1200. The controller can determine the heart rate of the patient and can detect whether an arrhythmia is present. If an arrhythmia is detected, the controller can send instructions to therapeutic circuitry to provide a therapeutic electrical stimulation to heart H. Specifically, a therapeutic electrical stimulation can be provided to the right ventricle, the left ventricle, and the right atrium. In this manner, subcutaneous device 1200 functions as a monitoring device, a diagnostic device, and a therapeutic device. In alternate embodiments, subcutaneous device 1200 can function only as a monitoring device, a diagnostic device, or a therapeutic device, or any combinations thereof.

Subcutaneous Device 1300

FIG. 33 is a perspective view of subcutaneous device 1300. Subcutaneous device 1300 includes housing 1302, clip 1304, prong 1306A, prong 1306B, and prong 1306C. Housing 1302 includes first side 1310, second side 1312, top side 1314, bottom side 1316, front end 1318, back end 1320, curved surface 1322, recess 1324, port 1326A, port 1326B, port 1326C, channel 1328A (not shown in FIG. 33), channel 1328B, channel 1328C, first guide 1330 (not shown in FIG. 33), second guide 1332, electrode 1334, and electrode 1336. Clip 1304 includes top portion 1340, bottom portion 1342, spring portion 1344, tip 1346, openings 1348, slot 1350, and electrode 1352. Prong 1306A includes proximal end 1360A (not shown in FIG. 33), distal end 1362A, base portion 1364A, spring portion 1366A, arm portion 1368A, contact portion 1370A, and electrode 1372A. Prong 1306B includes proximal end 1360B (not shown in FIG. 33), distal end 1362B, base portion 1364B, spring portion 1366B, arm portion 1368B, contact portion 1370B, and electrode 1372B. Prong 1306C includes proximal end 1360C (not shown in FIG. 33), distal end 1362C, base portion 1364C, spring portion 1366C, arm portion 1368C, contact portion 1370C, and defibrillator coil 1374C.

Subcutaneous device 1300 includes housing 1302, clip 1304, prong 1306A, prong 1306B, and prong 1306C. Housing 1302 has the same general structure and design as housing 102 of subcutaneous device 100 shown in FIGS. 1-9C. However, housing 1302 includes three ports, including port 1326A, port 1326B, and port 1326C, and three channels, including channel 1328A, channel 1328B, and channel 1328C. The reference numerals that refer to the parts of housing 1302 are incremented by twelve-hundred compared to the reference numerals that refer to the parts of housing 102 of subcutaneous device 100 shown in FIGS. 1-9C. Port 1326A, port 1326B, and port 1326C are positioned next to one another on housing 1302, and channel 1328A, channel 1328B, and channel 1328C are positioned next to one another on housing 1302. Prong 1306A is configured to be connected to port 1326A and can be positioned in channel 1328A when subcutaneous device 1300 is in a stowed position. Prong 1306B is configured to be connected to port 1326B and can be positioned in channel 1328B when subcutaneous device 1300 is in a stowed position. Prong 1306C is configured to be connected to port 1326C and can be positioned in channel 1328C when subcutaneous device 1300 is in a stowed position.

Clip 1304 has the same general structure and design as clip 104 of subcutaneous device 100 shown in FIGS. 1-9C. The reference numerals that refer to the parts of clip 1304 are incremented by twelve-hundred compared to the reference numerals that refer to the parts of clip 104 of subcutaneous device 100 shown in FIGS. 1-9C.

Prong 1306A, prong 1306B, and prong 1306C generally include the same parts as prong 106 of subcutaneous device 100 as shown in FIGS. 1-9C, and the reference numerals that refer to the parts of prong 1306A, prong 1306B, and prong 1306C are incremented by twelve-hundred compared to the reference numerals that refer to the parts of prong 106 of subcutaneous device 100 shown in FIGS. 1-9C. However, prong 1306A and prong 1306C have a different shape than prong 106 shown in FIGS. 1-9C, and prong 1306C includes defibrillator coil 1374C instead of an electrode. Spring portion 1366A and arm portion 1368A extend away from first side 1310 of housing 1302. Contact portion 1370A is a portion of prong 1306A adjacent to distal end 1362A of prong 1306A that is configured to come into contact with the left ventricle of the patient's heart. Electrode 1372A positioned on contact portion 1370A will also come into contact with the left ventricle of the patient's heart. Spring portion 1366C and arm portion 1368C extend away from bottom side 1320 of housing 1302. Contact portion 1370C is a portion of prong 1306C adjacent to distal end 1362C of prong 1306C that is configured to come into contact with tissue inferior to a patient's heart. Defibrillator coil 1374C is positioned on contact portion 1370C adjacent to distal end 1362C of prong 1306C. When an electrical signal is delivered to defibrillator coil 1374C, defibrillator coil 1374C will create a vector with electrode 1334 on front end 1318 of housing 1302. In the embodiment shown, defibrillator coil 1374C serves as the negative electrode and electrode 1334 serves as the positive electrode. However, in alternate embodiments this can be reversed. Prong 1306C is positioned so that distal end 1362C, and thus contact portion 1370C and defibrillator coil 1374C, are positioned inferior to the heart. Thus, the vector created between defibrillator coil 1374C and electrode 1334 will pass through a patient's heart to provide a high voltage electrical shock to the patient's heart. Prong 1306B has the same shape as prong 106 shown in FIGS. 1-9C. Spring portion 1366B and arm portion 1368B extend away from bottom side 1320 of housing 1302. Contact portion 1370B is a portion of prong 1306B adjacent to distal end 1362B of prong 1306B that is configured to come into contact with the left ventricle of the patient's heart. Electrode 1372B positioned on contact portion 1370B will also come into contact with the left ventricle of the patient's heart.

In one example, subcutaneous device 1300 can be anchored to a xiphoid process and a sternum of a patient. Clip 1304 is configured to anchor subcutaneous device 1300 to the xiphoid process and the sternum. Clip 1304 will expand as it is slid around the xiphoid process and the sternum. Spring portion 1344 acts as a spring for clip 1304 and is under tension. Top portion 1340 acts as a tension arm and the forces from spring portion 1344 translate to and push down on top portion 1340. When clip 1304 is positioned on the xiphoid process and the sternum, the tension in spring portion 1344 will force top portion 1340 down onto the xiphoid process and the sternum to anchor clip 1304 to the xiphoid process and the sternum. Further, sutures, tines, pins, or screws can be inserted through openings 1348 on top portion 1340 of clip 1304 to further anchor subcutaneous device 1300 to the xiphoid process and the sternum.

Subcutaneous device 1300 can include a power source, a controller, a memory, a transceiver, sensors, sensing circuitry, therapeutic circuitry, electrodes, and/or any other component of a medical device. In the embodiment shown in FIG. 33, subcutaneous device 1300 is configured to be a two chamber pacemaker and a defibrillator. Any one or combination of electrode 1334, electrode 1336, electrode 1352, electrode 1372A, and electrode 1372B can sense the electrical activity of a heart. Further, defibrillator coil 1374C can act as an electrode that senses the electrical activity of the heart. The sensed electrical activity can be transmitted to the sensing circuitry and the controller in housing 1302 of subcutaneous device 1300. The controller can determine the heart rate of the patient and can detect whether an arrhythmia or an abnormality is present. If an arrhythmia is detected, the controller can send instructions to therapeutic circuitry to provide a therapeutic electrical stimulation to the heart with electrode 1372A and electrode 137B. Specifically, a therapeutic electrical stimulation can be provided to the right ventricle and the left ventricle. If an abnormality is detected, the controller can send instructions to therapeutic circuitry to provide a high voltage electrical shock to the heart with defibrillator coil 1374C. In this manner, subcutaneous device 1300 functions as a monitoring device, a diagnostic device, and a therapeutic device. In alternate embodiments, subcutaneous device 1300 can function only as a monitoring device, a diagnostic device, or a therapeutic device, or any combinations thereof.

Subcutaneous Device 1400

FIG. 34A is a perspective view of subcutaneous device 1400. FIG. 34B is a perspective view of subcutaneous device 1400. FIG. 34C is a side view of subcutaneous device 1400. Subcutaneous device 1400 includes housing 1402, clip 1404, prong 1406A, prong 1406B, prong 1406C, and prong 1406D. Housing 1402 includes first side 1410, second side 1412, top side 1414, bottom side 1416, front end 1418, back end 1420, curved surface 1422, recess 1424, port 1426A, port 1426B, port 1426C, port 1426D, channel 1428A (not shown in FIGS. 34A-34C), channel 1428B, channel 1428C, channel 1428D, first guide 1430, second guide 1432, electrode 1434, and electrode 1436. Clip 1404 includes top portion 1440, bottom portion 1442, spring portion 1444, tip 1446, openings 1448, slot 1450, and electrode 1452. Prong 1406A includes proximal end 1460A (not shown in FIGS. 34A-34C), distal end 1462A, base portion 1464A, spring portion 1466A, arm portion 1468A, contact portion 1470A, and defibrillator coil 1474A. Prong 1406B includes proximal end 1460B (not shown in FIGS. 34A-34C), distal end 1462B, base portion 1464B, spring portion 1466B, arm portion 1468B, contact portion 1470B, and defibrillator coil 1474B. Prong 1406C includes proximal end 1460C (not shown in FIGS. 34A-34C), distal end 1462C, base portion 1464C, spring portion 1466C, arm portion 1468C, contact portion 1470C, and electrode 1474C. Prong 1406D includes proximal end 1460D (not shown in FIGS. 34A-34C), distal end 1462D, base portion 1464D, spring portion 1466D, arm portion 1468D, contact portion 1470D, and defibrillator coil 1474D.

Subcutaneous device 1400 includes housing 1402, clip 1404, prong 1406A, prong 1406B, prong 1406C, and prong 1406D. Housing 1402 has the same general structure and design as housing 102 of subcutaneous device 100 shown in FIGS. 1-9C. However, housing 1402 includes four ports, including port 1426A, port 1426B, port 1426C, and port 1426D, and four channels, including channel 1428A, channel 1428B, channel 1428C, and channel 1428D. The reference numerals that refer to the parts of housing 1402 are incremented by thirteen-hundred compared to the reference numerals that refer to the parts of housing 102 of subcutaneous device 100 shown in FIGS. 1-9C. Port 1426A, port 1426B, port 1426C, and port 1426D are positioned next to one another on housing 1402, and channel 1428A, channel 1428B, channel 1428C, and channel 1428D are positioned next to one another on housing 1402. Prong 1406A is configured to be connected to port 1426A and can be positioned in channel 1428A when subcutaneous device 1400 is in a stowed position. Prong 1406B is configured to be connected to port 1426B and can be positioned in channel 1428B when subcutaneous device 1400 is in a stowed position. Prong 1406C is configured to be connected to port 1426C and can be positioned in channel 1428C when subcutaneous device 1400 is in a stowed position. Prong 1406D is configured to be connected to port 1426D and can be positioned in channel 1428D when subcutaneous device 1400 is in a stowed position.

Clip 1404 has the same general structure and design as clip 104 of subcutaneous device 100 shown in FIGS. 1-9C. The reference numerals that refer to the parts of clip 1404 are incremented by thirteen-hundred compared to the reference numerals that refer to the parts of clip 104 of subcutaneous device 100 shown in FIGS. 1-9C.

Prong 1406A, prong 1406B, prong 1406C, and prong 1406D generally include the same parts as prong 106 of subcutaneous device 100 as shown in FIGS. 1-9C, and the reference numerals that refer to the parts of prong 1406A, prong 1406B, prong 1406C, and prong 1406D are incremented by thirteen-hundred compared to the reference numerals that refer to the parts of prong 106 of subcutaneous device 100 shown in FIGS. 1-9C. However, prong 1406A, prong 1406B, and prong 1406D have a different shape than prong 106 shown in FIGS. 1-9C and include defibrillator coil 1474A, defibrillator coil 1474B, and defibrillator coil 1474D, respectively, instead of an electrode.

Spring portion 1466A and arm portion 1468A extend along first side 1410 of housing 1402. Contact portion 1470A is a portion of prong 1406A adjacent to distal end 1462A of prong 1406A that is configured to come into contact with tissue on first side 1410 of housing 1402. Defibrillator coil 1474A is positioned on contact portion 1470A adjacent to distal end 1462A of prong 1406A. Defibrillator coil 1474A is configured to create a vector with defibrillator coil 1474B. Spring portion 1466D and arm portion 1468D extend along second side 1412 of housing 1402. Contact portion 1470D is a portion of prong 1406D adjacent to distal end 1462D of prong 1406D that is configured to come into contact with tissue on second side 1412 of housing 1402. Defibrillator coil 1474D is positioned on contact portion 1470D adjacent to distal end 1462D of prong 1406D. Defibrillator coil 1474D is configured to create a vector with defibrillator coil 1474B.

Spring portion 1466B and arm portion 1468B extend away from bottom side 1420 of housing 1402. Contact portion 1470B is a portion of prong 1406B adjacent to distal end 1462B of prong 1406B that is configured to come into contact with tissue inferior to a patient's heart. Defibrillator coil 1474B is positioned on contact portion 1470B adjacent to distal end 1462B of prong 1406B. When an electrical signal is delivered to defibrillator coil 1474B, defibrillator coil 1474B will create a first vector with electrode 1434 on front end 1418 of housing 1402, a second vector with defibrillator coil 1474A on prong 1406A, and a third vector with defibrillator coil 1474D on prong 1406D. In the embodiment shown, defibrillator coil 1474B serves as the negative electrode and electrode 1434, defibrillator coil 1474A, and defibrillator coil 1474D serve as the positive electrodes. However, in alternate embodiments this can be reversed. Prong 1406B is positioned so that distal end 1462B, and thus contact portion 1470B and defibrillator coil 1474B, are positioned inferior to the heart. Thus, the vectors created between defibrillator coil 1474B and electrode 1434, defibrillator coil 1474A, and defibrillator coil 1474D will pass through a patient's heart to provide a high voltage electrical shock to the patient's heart.

Prong 1406C has the same shape as prong 106 shown in FIGS. 1-9C. Spring portion 1466C and arm portion 1468C extend away from bottom side 1420 of housing 1402. Contact portion 1470C is a portion of prong 1406C adjacent to distal end 1462C of prong 1406C that is configured to come into contact with the left ventricle of the patient's heart. Electrode 1472C positioned on contact portion 1470C will also come into contact with the left ventricle of the patient's heart.

In one example, subcutaneous device 1400 can be anchored to a xiphoid process and a sternum of a patient. Clip 1404 is configured to anchor subcutaneous device 1400 to the xiphoid process and the sternum. Clip 1404 will expand as it is slid around the xiphoid process and the sternum. Spring portion 1444 acts as a spring for clip 1404 and is under tension. Top portion 1440 acts as a tension arm and the forces from spring portion 1444 translate to and push down on top portion 1440. When clip 1404 is positioned on the xiphoid process and the sternum, the tension in spring portion 1444 will force top portion 1440 down onto the xiphoid process and the sternum to anchor clip 1404 to the xiphoid process and the sternum. Further, sutures, tines, pins, or screws can be inserted through openings 1448 on top portion 1440 of clip 1404 to further anchor subcutaneous device 1400 to the xiphoid process and the sternum.

Subcutaneous device 1400 can include a power source, a controller, a memory, a transceiver, sensors, sensing circuitry, therapeutic circuitry, electrodes, and/or any other component of a medical device. In the embodiment shown in FIGS. 34A-34C, subcutaneous device 1400 is configured to be a single chamber pacemaker and a multi-vector defibrillator. Any one or combination of electrode 1434, electrode 1436, electrode 1452, and electrode 1472C can sense the electrical activity of a heart. Further, defibrillator coil 1474A, defibrillator coil 1474B, and defibrillator coil 1474D can act as an electrode that senses the electrical activity of the heart. The sensed electrical activity can be transmitted to the sensing circuitry and the controller in housing 1402 of subcutaneous device 1400. The controller can determine the heart rate of the patient and can detect whether an arrhythmia or abnormality is present. If an arrhythmia is detected, the controller can send instructions to therapeutic circuitry to provide a therapeutic electrical shock to the heart with electrode 1472C. If an abnormality is detected, the controller can send instructions to therapeutic circuitry to provide a high voltage electrical shock to the heart with defibrillator coil 1474B. In this manner, subcutaneous device 1400 functions as a monitoring device, a diagnostic device, and a therapeutic device. In alternate embodiments, subcutaneous device 1400 can function only as a monitoring device, a diagnostic device, a therapeutic device, or any combinations thereof.

Subcutaneous Device 1500

FIG. 35A is a perspective view of subcutaneous device 1500. FIG. 35B is a perspective view of subcutaneous device 1500. FIG. 35C is a bottom view of subcutaneous device 1500. FIG. 35D is a side view of subcutaneous device 1500. FIG. 35E is a back view of subcutaneous device 1500. FIG. 35F is a front view of subcutaneous device 1500. FIG. 36A is a schematic diagram of subcutaneous device 1500. FIG. 36B is a sectional diagram illustrating portions of subcutaneous device 1500 from the side. FIG. 36C is a sectional diagram illustrating portions of subcutaneous device 1500 from the bottom. FIG. 37 is a perspective view of subcutaneous device 1500 positioned on xiphoid process X and sternum S. Subcutaneous device 1500 includes housing 1502, clip 1504, prong 1506A, and prong 1506B. Housing 1502 includes first side 1510, second side 1512, top side 1514, bottom side 1516, front end 1518, back end 1520, curved surface 1522, recess 1524, port 1526A, port 1526B, first guide 1530, second guide 1532, electrode 1534, and electrode 1536. Clip 1504 includes top portion 1540, bottom portion 1542, spring portion 1544, tip 1546, openings 1548, slot 1550, and electrode 1552. Prong 1506A includes proximal end 1560A, distal end 1562A, base portion 1564A, spring portion 1566A, arm portion 1568A, contact portion 1570A, opening 1576A, and lumen 1578A. Prong 1508B includes proximal end 1560B, distal end 1562B, base portion 1564B, spring portion 1566B, arm portion 1568B, opening 1576B, and lumen 1578B. Subcutaneous device 1500 further includes drug reservoir 1580, drug pump 1582, fluid connector 1584, fluid connector 1586, fluid connector 1588, electronic components 1590, and battery 1592. FIG. 37 shows xiphoid process X and sternum S.

Subcutaneous device 1500 includes housing 1502, clip 1504, prong 1506A, and prong 1506B. Housing 1502 has the same general structure and design as housing 102 of subcutaneous device 100 shown in FIGS. 1-9C. However, housing 1502 includes two ports, including port 1526A and port 1526B. The reference numerals that refer to the parts of housing 1502 are incremented by fourteen-hundred compared to the reference numerals that refer to the parts of housing 102 of subcutaneous device 100 shown in FIGS. 1-9C. Port 1526A and port 1526B are positioned next to one another on housing 1502. Prong 1506A is configured to be connected to port 1526A. Prong 1506B is configured to be connected to port 1526B.

Clip 1504 has the same general structure and design as clip 104 of subcutaneous device 100 shown in FIGS. 1-9C. The reference numerals that refer to the parts of clip 1504 are incremented by fourteen-hundred compared to the reference numerals that refer to the parts of clip 104 of subcutaneous device 100 shown in FIGS. 1-9C.

Prong 1506A and prong 1506B generally include the same parts as prong 106 of subcutaneous device 100 as shown in FIGS. 1-9C, and the reference numerals that refer to the parts of prong 1506A and prong 1506B are incremented by fourteen-hundred compared to the reference numerals that refer to the parts of prong 106 of subcutaneous device 100 shown in FIGS. 1-9C. However, prong 1506A and prong 1506B have a different shape than prong 106 shown in FIGS. 1-9C, and include opening 1576A and lumen 1578A, and opening 1576B and lumen 1578B, respectively. Spring portion 1566A and arm portion 1568A extend underneath bottom side 1516 of housing 1502. Contact portion 1570A is a portion of prong 1506A adjacent to distal end 1562A of prong 1506A that is configured to come into contact with an organ, a nerve, or a tissue. Prong 1506A has opening 1576A at distal end 1562A and includes lumen 1578A extending from proximal end 1560A to distal end 1562A. Spring portion 1566B and arm portion 1568B extend upwards along back side 1520 of housing 1502. Prong 1506B has opening 1576B at distal end 1562B and includes lumen 1578B extending from proximal end 1560B to distal end 1562B.

In one example, subcutaneous device 1500 can be anchored to xiphoid process X and sternum S of a patient. Clip 1504 is configured to anchor subcutaneous device 1500 to xiphoid process X and sternum S. Clip 1504 will expand as it is slid around xiphoid process X and sternum S. Spring portion 1544 acts as a spring for clip 1504 and is under tension. Top portion 1540 acts as a tension arm and the forces from spring portion 1544 translate to and push down on top portion 1540. When clip 1504 is positioned on xiphoid process X and sternum S, the tension in spring portion 1544 will force top portion 1540 down onto xiphoid process X and sternum S to anchor clip 1504 to xiphoid process X and sternum S. Further, sutures, tines, pins, or screws can be inserted through openings 1548 on top portion 1540 of clip 1504 to further anchor subcutaneous device 1500 to xiphoid process X and sternum S.

Subcutaneous device 1500 can include a power source, a controller, a memory, a transceiver, sensors, sensing circuitry, therapeutic circuitry, electrodes, and/or any other component of a medical device. In the embodiment shown in FIGS. 35A-37, subcutaneous device 1500 is configured to be a drug delivery device. As shown in FIGS. 36A-36C, subcutaneous device 1500 includes drug reservoir 1580 and drug pump 1582 positioned in housing 1502. Drug reservoir 1580 includes fluid connector 1584 that fluidly connects drug reservoir 1580 to prong 1506B and fluid connector 1586 that fluidly connects drug reservoir 1580 to drug pump 1582. Drug pump 1582 also includes fluid connector 1588 that fluidly connects drug pump 1582 to prong 1506A. A drug can be inserted into opening 1576B of prong 1506B and then travel through lumen 1578B of prong 1506B to drug reservoir 1580. In this way, drug reservoir 1580 can be replenished and refilled as needed. An injector can be positioned in opening 1578B to inject the drug into prong 1506B. The drug in drug reservoir 1580 can then be pumped out of drug reservoir 1580 with drug pump 1582. Drug pump 1582 will pump the drug in drug reservoir 1580 through fluid connector 1586, drug pump 1582, fluid connector 1588, and into prong 1506A. The drug in prong 1506A can travel through lumen 1578A of prong 1506A and exit prong 1506A at opening 1576A. Opening 1576A is positioned to contact an organ, a nerve, or a tissue, so the drug can be applied to the organ, the nerve, or the tissue. FIGS. 36A-36C also show electronic components 1590, which can include a controller, a memory, a transceiver, sensors, sensing circuitry, therapeutic circuitry, electrodes, and/or any other component of a medical device, and battery 1592. Battery 1592 powers subcutaneous device 1500, including electronic components 1590 and drug pump 1592. Electronic components 1590 can specifically include therapeutic circuitry that can send a signal to drug pump 1592 to administer a drug to the patient through prong 1506A. In this manner, subcutaneous device 1500 functions as a drug delivery device that is capable of providing a targeted or systemic therapeutic drug to an organ, a nerve, or a tissue. Providing a targeted or systemic therapeutic drug can be used to treat cancer, diabetes, and hypertension. Treating cancer with targeted or systemic therapeutic drug can reduce side effects. In alternate embodiments, subcutaneous device 1500 can include components to allow it to also function as a monitoring and diagnostic device, as a pacemaker device, or as a defibrillator device.

Subcutaneous Device 1600

FIG. 38 is a side view of subcutaneous device 1600 anchored to structural body component A. Subcutaneous device 1600 includes housing 1602, clip 1604, and prong 1606.

Subcutaneous device 1600 is a medical device that is configured to be anchored to structural body component A. Structural body component A may be a muscle, a bone, or a tissue of a patient. Subcutaneous device 1600 can be a monitoring device, a diagnostic device, a therapeutic device, or any combination thereof. For example, subcutaneous device 1600 can be a pacemaker device that is capable of monitoring a patient's heart rate, diagnosing an arrhythmia of the patient's heart, and providing therapeutic electrical stimulation to the patient's heart. Subcutaneous device 1600 includes housing 1602. Housing 1602 of subcutaneous device 1600 may include sensing circuitry 180, controller 182, memory 184, therapy circuitry 186, electrode(s) 188, sensor(s) 190, transceiver 192, and power source 194 as described with respect to FIG. 7 and/or any other component of a medical device.

Clip 1604 is attached to housing 1602. Clip 1604 is configured to anchor subcutaneous device 1600 to structural body component A. Clip 1604 will expand as it is advanced around structural body component A. Clip 1604 can be a passive clip or an active clip. A passive clip only uses the stiffness of clamping components to attach to the bone, the muscle, or the tissue. This stiffness can be the result of design or active crimping during the implant procedure. An active clip may additionally use an active fixation method such as sutures, tines, pins, or screws to secure the clip to the bone, the muscle, or the tissue. In the embodiment shown in FIG. 38, clip 1604 has a spring bias that will put tension on structural body component A when it is expanded and fit onto structural body component A. The spring bias of clip 1604 will anchor subcutaneous device 1600 to structural body component A.

Prong 1606 is connected to and extends away from housing 1602 of subcutaneous device 1600. Prong 1606 is configured to contact remote body component B that is positioned away from structural body component A. Remote body component B may be an organ, a nerve, or tissue of the patient. For example, remote body component B can include a heart, a lung, or any other suitable organ in the body. Prong 1606 includes an electrode that is capable of sensing an electrical activity or physiological parameter of remote body component B and/or providing therapeutic electrical stimulation to remote body component B.

In one example, subcutaneous device 1600 can be a pacemaker and the electrode on prong 1606 of subcutaneous device 1600 can sense the electrical activity of a heart. The sensed electrical activity can be transmitted to sensing circuitry and a controller in housing 1602 of subcutaneous device 1600. The controller can determine the heart rate of the patient and can detect whether an arrhythmia is present. If an arrhythmia is detected, the controller can send instructions to therapeutic circuitry to provide a therapeutic electrical stimulation to the heart. In this manner, subcutaneous device 1600 functions as a monitoring device, a diagnostic device, and a therapeutic device.

Subcutaneous device 1600 will be discussed in greater detail in relation to FIGS. 39A-45 below. Subcutaneous device 1600 will be discussed as a pacemaker that can be used for monitoring, diagnostics, and therapeutics in the discussion of FIGS. 39A-45 below. In this embodiment, subcutaneous device 1600 is a unipolar pacemaker. In alternate embodiments, subcutaneous device 1600 may be a bipolar pacemaker. Subcutaneous device 1600 can also be a monitoring device, a diagnostic device, an implantable cardioverter-defibrillator, a general organ/nerve/tissue stimulator, and/or a drug delivery device.

FIG. 39A is a side view of subcutaneous device 1600. FIG. 39B is a top view of subcutaneous device 1600. FIG. 39C is a bottom view of subcutaneous device 1600. FIG. 39D is a back view of subcutaneous device 1600. FIG. 39E is a front view of subcutaneous device 1600. FIGS. 39A-39E will be discussed together. Subcutaneous device 1600 includes housing 1602, clip 1604, and prong 1606. Housing 1602 includes first side 1610, second side 1612, top side 1614, bottom side 1616, front end 1618, back end 1620, first housing clip 1622, second housing clip 1624, and guide 1630. Clip 1604 includes top portion 1640, bottom portion 1642, spring portion 1644, and openings 1648. Prong 1606 includes proximal end 1660, distal end 1662, base portion 1664, arm portion 1668, contact portion 1670, and electrode 1672.

Subcutaneous device 1600 includes housing 1602, clip 1604, and prong 1606 as described in reference to FIG. 38. Housing 1602 can be made out of stainless steel, titanium, nitinol, epoxy, silicone, polyurethane with metallic reinforcements, or any other material that is suitable for non-porous implants. Housing 1602 can also include an exterior coating. Clip 1604 can be made out of stainless steel, titanium, nitinol, epoxy, silicone, polyurethane with metallic reinforcements, or any other material that is suitable for non-porous implants. Prong 1606 can be made out of nickel titanium, also known as Nitinol. Nitinol is a shape memory alloy with superelasticity, allowing prong 1606 to go back to its original shape and position if prong 1606 is deformed as subcutaneous device 1600 is implanted into a patient. Prong 1606 can also be made out of silicone, polyurethane, stainless steel, titanium, epoxy, polyurethane with metallic reinforcements, or any other material that is suitable for non-porous implants. As an example, prong 1606 can be made out of a composite made of polyurethane and silicone and reinforced with metal to provide spring stiffness.

Housing 1602 includes first side 1610, second side 1612, top side 1614, bottom side 1616, front end 1618, back end 1620, first housing clip 1622, second housing clip 1624, and guide 1630. First side 1610 is opposite of second side 1612. Top side 1614 is a top of housing 1602 opposite of bottom side 1616, which is a bottom of housing 1602. Front end 1618 is opposite of back end 1620. Housing 1602 is substantially rectangular-shaped in the embodiment shown. In alternate embodiments, housing 1602 can be shaped as a cone, frustum, or cylinder. Housing 1602 can be made out of stainless steel, titanium, nitinol, epoxy, silicone, polyurethane with metallic reinforcements, or any other material that is suitable for non-porous implants. Housing 1602 can also include an exterior coating.

First housing clip 1622 is U-shaped and has a first end and a second end attached to bottom side 1616 of housing 1602. First housing clip 1622 is adjacent back end 1620 of housing. First housing clip 1622 is configured to attach prong 1606 to bottom side 1616 of housing 1602. Second housing clip 1624 is U-shaped and has a first end and a second end attached to bottom side 1616 of housing 1602. Second housing clip 1624 is spaced from first housing clip 1622. As such, second housing clip 1624 is closer to front end 1618 of housing than first housing clip 1622. Second housing clip 1624 is configured to attach prong 1606 to bottom side 1616 of housing 1602. Guide 1630 is an L-shaped rod that is connected to back end 1620 and first side 1610 of housing 1602. In this embodiment, guide 1630 is closer to top side 1614 than bottom side 1616 of housing 1602. Guide 1630 is configured to guide housing 1602 of subcutaneous device 1600 through a surgical instrument used to implant subcutaneous device 1600 into a patient.

Clip 1604 includes top portion 1640, bottom portion 1642, spring portion 1644, and openings 1648. Top portion 1640 is a flat portion that forms a top of clip 1604, and bottom portion 1642 is a flat portion that forms a bottom of clip 1604. Bottom portion 1642 is configured to be attached to housing 1602 of subcutaneous device 1600. Bottom portion 1642 of clip 1604 may also be integrally formed with housing 1602 and/or housing 1602 can form bottom portion 1642 of clip 1604. Spring portion 1644 is a curved portion positioned on a back end of clip 1604 that extends between and connects top portion 1640 to bottom portion 1642. Clip 1604 can be made out of stainless steel, titanium, nitinol, epoxy, silicone, polyurethane with metallic reinforcements, or any other material that is suitable for non-porous implants.

Top portion 1640 of clip 1604 includes openings 1648. Openings 1648 extend through top portion 1640. In the embodiment shown in FIGS. 39A-39F, ten openings 1648 extend through top portion 1640. In alternate embodiments, any suitable number of openings 1648 may extend through top portion 1640. Openings 1648 are configured to allow clip 1604 to be sutured to a muscle, a bone, or a tissue in a patient to secure subcutaneous device 1600 to the muscle, the bone, or the tissue. Further, openings 1648 can receive additional fixation mechanisms, such as tines, pins, or screws, to secure subcutaneous device 1600 to the muscle, the bone, or the tissue. These additional fixation mechanisms can be made from bioabsorbable materials.

Clip 1604 is connected to back end 1620 of housing 1602 to align bottom portion 1642 of clip 1606 with top side 1614 of housing 1602 of subcutaneous device 1600. Bottom portion 1642 of clip 1604 is connected to back end 1620 of housing 1602 adjacent top side 1614 of housing such that bottom portion 1642 extends beyond back end 1620 of housing. Spring portion 1644 of clip 1604 is positioned beyond back end 1620 of housing 1602. A portion of top portion 1640 of clip 1604 extends along top side 1614 of housing 1602.

Spring portion 1644 acts as a spring for clip 1604 and is under tension. Top portion 1640 acts as a tension arm and the forces from spring portion 1644 translate to and push down on top portion 1640. In its natural state, a spring bias of spring portion 1644 forces the tip of top portion 1640, which is at the end of top portion 1640 positioned over top side 1614 of housing 1602, towards bottom portion 1642 of clip 1604 and top side 1614 of housing 1602. The tip of top portion 1640 of clip 1604 can be lifted up to expand clip 1604, and clip 1604 can be positioned on a muscle, a bone, or tissue of a patient. When clip 1604 is positioned on a muscle, a bone, or tissue of a patient, the tension in spring portion 1644 will force top portion 1640 down onto the muscle, the bone, or the tissue. This tension will anchor clip 1604 to the muscle, the bone, or the tissue. Additional fixation mechanisms, such as tines, pins, or screws can also be used to anchor clip 1604 to the bone, the muscle, or the tissue.

Prong 1606 includes proximal end 1660 and distal end 1662, which is opposite of proximal end 1660. Prong 1606 includes base portion 1664, arm portion 1668, and contact portion 1670. A first end of base portion 1664 is aligned with proximal end 1660 of prong 1606, and a second end of base portion 1664 is connected to a first end of arm portion 1668. Base portion 1664 is a straight, planar portion that is positioned against and extends along bottom side 1616 of housing 1602. Base portion 1664 is attached to housing 1602. First housing clip 1622 and second housing clip 1624 extend around base portion 1664 of prong 1606 to secure base portion 1664 of prong 1606 to housing 1602. Base portion 1664 extends through first housing clip 1622 and second housing clip 1624. As such, proximal end 1660 of prong 1606 is attached to housing 1602. Base portion 1664 of prong 106 is electrically connected to the internal components of housing 1602, for example with a feedthrough.

The first end of arm portion 1668 is connected to the second end of base portion 1664, and a second end of arm portion 1668 is connected to a first end of contact portion 1670. As such, arm portion 1668 extends from base portion 1664 so as to define a first plane that includes opposite ends, or first end and second end, of arm portion 1668 and is perpendicular to the horizontal plane of housing 1602 such that the first plane is a vertical plane that bisects housing 1602 longitudinally from front end 1618 to back end 1620 and is perpendicular to top side 1614 and bottom side 1616. Arm portion 1668 also extends past front end 1618 of housing 1602 so that contact portion 1670 is positioned outwards from front end 1618 of housing 1602. Arm portion 1668 is a predominantly straight portion that is angled with respect to housing 1602. In this embodiment, arm portion 1668 is angled away, or extends away, from bottom side 1616 of housing 1602. For example, arm portion 1668 may be angled about 30 degrees to about 60 degrees down from a horizontal defined by a bottom side 1616 of housing 1602. The first end of arm portion 1668 acts as a spring for prong 1606 and is under tension. Arm portion 1668 acts as a tension arm and the forces from the first end of arm portion 1668 translate to and push down on the second end of arm portion 1668. In its natural state, a spring bias of arm portion 1668 forces distal end 1662 of prong 1606 away from bottom side 1616 of housing 1602. As such, prong 1606 undergoes spring action in both a horizontal plane parallel to the horizontal plane of housing 1602 and in a vertical plane perpendicular to the horizontal plane of housing 1602. In alternate embodiments, arm portion 1668 of prong 1606 can extend from housing 1602 in any direction or directions.

The first end of contact portion 1670 is connected to the second end of arm portion 1668, and a second end of contact portion 1670 is aligned with distal end 1662 of prong 1606. As such, arm portion 1668 is between base portion 1664 and contact portion 1670. Arm portion 1668 extends beyond front end 1618 of housing 1602 so that contact portion 1670 is positioned beyond front end 1618 of housing 1602.

Contact portion 1670 can be positioned such that distal end 1662 of prong 1606 contacts remote body component B (shown in FIG. 38). Contact portion 1670 is angled with respect to housing 1602 and arm portion 1668. Contact portion 1670 is angled away from the first plane defined with respect to arm portion 1668 and housing 1602. In this embodiment, contact portion 1670 is further angled away from bottom side 1616 of housing 1602. Contact portion is also curved, or angled, away from first side 1610 of housing 1602. Contact portion 1670 extends away from bottom side 1616 of housing 1602 and extends away from first side 1610 of housing 1602 so that distal end 1662 of prong 1606 is positioned below and away from housing 1602 and arm portion 1668. In alternate embodiments, contact portion 1670 may be angled in any direction with respect to bottom side 1616 of housing 1602 and in any direction with respect to first side 1610 and second side 1612 of housing 1602 depending on the location of remote body component B with respect to structural body component A. Contact portion 1670 is angled toward remote body component B. Contact portion 1670 may also have any angle depending on the location of remote body component B with respect to structural body component A. For example, when remote body component B is a lung or a kidney, contact portion 1670 is angled toward the lung or the kidney. Contact portion 1670 may be angled about 45 degrees to about 60 degrees from the first vertical plane defined with respect to arm portion 1668 and housing 1602. Contact portion 1670 can be angled up to 90 degrees.

Prong 1606 further includes electrode 1672. Electrode 1672 is at distal end 1662 of prong 1606. As such, electrode 1672 makes up the second end of contact portion 1670. Electrode 1672 has a rounded end. Prong 1606 has a single electrode 1672 in the embodiment shown in FIGS. 39A-39F. Prong 1606 can have any number of electrodes in alternate embodiments. Electrode 1672 is positioned at distal end 1662 of prong 1606 to sense an electrical activity or physiological status of remote body component B. Electrode 1672 can also provide therapeutic electrical stimulation to remote body component B.

Prong 1606 is angled with respect to housing 1602 to improve contact of electrode 1672 with remote body component B. Prong 1606 is angled so that contact portion 1670 pushes down against remote body component B, such as the heart. Electrode 1672 at distal end 1662 of prong 1606 contacts the heart and buries into the cardiac tissue. Further, because prong 1606 is angled down toward heart, prong 1606 applies pressure to the heart as the heart beats and moves up and down, without increasing the stiffness of prong 1606. As a result, electrode 1672 maintains contact with the heart without fixing electrode 1672 to the heart. For example, prong 1606 is prevented from bouncing off of the heart as the heart beats, which would cause intermittent contact that reduces functionality. Additionally, contact portion 1670 is angled away from bottom 1616 and first side 1610 of housing 1602 to ensure distal end 1662 of prong 1606 is positioned on the heart when subcutaneous device 1600 is attached to a xiphoid and/or sternum of a patient. As such, subcutaneous device 1600 can be inserted and deployed into a patient without requiring cardiac catheterization labs. Thus, the procedure for inserting the device is simple and only requires local anesthesia, which means it can be carried out in various environments, such as in an ambulance.

Arm portion 1668 of prong 1606 allows prong 1606 to be flexible once it is positioned in the body. The pivot point of arm portion 1668 is at second housing clip 1624, which securely attaches prong 1606 to housing 1602, thereby providing structural stability to prong 1606. For example, if remote body component B is the heart of the patient and contact portion 1670 of prong 1606 is positioned against the heart, arm portion 1668 of prong 1606 allows prong 1606 to move up and down with the heart as the heart beats. This ensures that prong 1606 does not puncture or damage the heart while contact portion 1670 of prong 1606 maintains contact with the heart. In this embodiment, electrode 1672 at distal end 1662 of prong 1606 has a rounded end to further prevent prong 1606 from puncturing or damaging the heart when contact portion 1670 of prong 1606 is in contact with the heart. The overall axial stiffness of prong 1606 can be adjusted so that prong 1606 gently presses against the heart and moves up and down in contact with the heart as the heart beats, but is not stiff or sharp enough to pierce or tear the pericardial or epicardial tissue. For example, the overall axial stiffness of prong 1606 can be adjusted by adjusting the material of prong 1606, the spring bias or mechanical resistance of prong 1606, the cross-sectional thickness of prong 1606, the angle of incidence of prong 1606 on remote body component B, the outer profile of prong 1606 where prong 1606 contacts remote body component B, and/or any other suitable characteristic of prong 1606.

Subcutaneous device 1600 can function as a pacemaker. Prong 1606 can be shaped so that contact portion 1670 of prong 1606 contacts the right ventricle, left ventricle, right atrium, or left atrium of the heart. Subcutaneous device 1600 can function as a unipolar pacemaker, utilizing electrode 1672 on prong 1606. Further, subcutaneous device 1600 can function as a bipolar pacemaker, utilizing more than one prong 1606 and electrode 1672.

FIG. 40A is a side view of subcutaneous device 1600 showing prong 1606. FIG. 40B is a top view of subcutaneous device 1600 showing prong 1606. FIG. 40C is a bottom view of subcutaneous device 1600 showing prong 1606. FIG. 40D is a back view of subcutaneous device 1600 showing prong 1606. FIG. 40E is a front view of subcutaneous device 1600 showing prong 1606. Prong 1606 includes proximal end 1660, distal end 1662, base portion 1664, arm portion 1668, contact portion 1670, electrode 1672, sleeve 1674 (which includes upper portion 1676 and lower portion 1678), wire 1680, structural tube 1682, and structural tube 1684. Sleeve 1674 of prong 1606 is shown as transparent in FIGS. 40A-40E.

Prong 1606 includes proximal end 1660, distal end 1662, base portion 1664, arm portion 1668, contact portion 1670, and electrode 1672 as described in reference to FIGS. 39A-39E. Sleeve 1674 is a hollow outer portion of prong 1606. Sleeve 1674 extends from proximal end 1660 of prong 1660 to contact portion 1670. A first end of sleeve is aligned with proximal end 1660 of prong 1606. Sleeve 1674 extends along base portion 1664, arm portion 1668, and a portion of contact portion 1670. A second end of sleeve 1674 is within contact portion 1670. As such, sleeve 1674 makes up the outer portions of base portion 1664, arm portion 1668, and a portion of contact portion 1670. Sleeve 1674 has upper portion 1676 opposite lower portion 1678. Upper portion 1676 and lower portion 1678 are flat, or planar, such that sleeve 1674 has a flat, or generally rectangular, cross-section. As such, a majority of prong 1606 has a flat, or generally rectangular, cross-section.

Wire 1680 extends through sleeve 1674, between upper portion 1676 and lower portion 1678, from proximal end 1660 of prong 1606 to contact portion 1670. Wire 1680 extends beyond the second end of sleeve 1674. A first end of wire 1680 is aligned with proximal end 1660 of prong 1606.

Wire 1680 extends along base portion 1664, arm portion 1668, and a portion of contact portion 1670. A second end of wire 1680 is connected to electrode 1672. As such, contact portion 1670 of prong 1606 is made up of sleeve 1674, wire 1680, and electrode 1672. Wire 1680 has the same overall shape and angle as sleeve 1674 and extends beyond the second end of sleeve 1674. As such, in this embodiment, wire 1680 is angled away from bottom side 1616 of housing 1602 and curved, or angled, away from first side 1610 of housing 1602.

Structural tubes 1682 and 1684 extend through sleeve 1674, between upper portion 1676 and lower portion 1678 and along wire 1680. Structural tubes 1682 and 1684 extend from proximal end 1660 of prong 1660 to the second end of arm portion 1668. First ends of structural tubes 1682 and 1684 are aligned with proximal end 1660 of prong 1606. Structural tubes 1682 and 1684 extend along base portion 1664 and arm portion 1668. Second ends of structural tubes 1682 and 1684 are aligned with the second end of arm portion 1668. In alternate embodiments, structural tubes 1682 and 1684 may extend into contact portion 1670 to the second end of sleeve 1674 such that second ends of structural tubes 1682 and 1684 are aligned with the second end of sleeve 1674. Structural tubes 1682 and 1684 have the same overall shape and angle as base portion 1664 and arm portion 1668. As such, in this embodiment, structural tubes 1682 and 1684 are angled away, or extend away, from bottom side 1616 of housing 1602 toward remote body component B.

First structural tube 1682 is on a first side of wire 1680, and second structural tube 1684 is on a second side of wire 1680 such that wire 1680 has structural tubes 1682 and 1684 on opposite sides of wire 1680. In alternate embodiments, prong 1606 may include any number of structural tubes 1682 and 1684 based on the desired stiffness of prong 1606. Structural tubes 1682 and 1684 may be hollow or solid. Structural tubes 1682 and 1684 can be any suitable size. For example, structural tubes 1682 and 1684 can have the same diameters as each other, can have the same diameter as wire 1680, or can have a smaller diameter than wire 1680. Structural tubes 1682 and 1684 can have any suitable thickness based on desired stiffness of prong 1606. Structural tubes 1682 and 1684 may be made of metal, polyurethane, silicone, any suitable plastic, a combination of metal and plastic, or any other suitable material. Structural tubes 1682 and 1684 are limited to an amount of metal that allows subcutaneous device 1600 to be MRI compatible. In alternate embodiments, prong 1606 may include any number of structural tubes 1682 and 1684. The size, shape, and material of structural tubes 1682 and 1684 may be selected based upon the desired stiffness of prong 1606. For example, prong 1606 may include five, seven, or any other suitable number of structural tubes 1682 and 1684 to make prong 1606 flatter and increase the stiffness of prong 1606.

The flat, or rectangular, cross-section of sleeve 1674 created by planar upper portion 1676 and planar lower portion 1678 provides stiffness to prong 1606, which makes prong 1606 more resistant to in-plane bending. Sleeve 1674 also provides space for wire 1680 to be surrounded by structural tubes 1682 and 1684. Structural tubes 1682 and 1684 also provide the desired structural stiffness to prong 1606. As a result, prong 1606 resists in-plane bending, or bending in any direction, to maintain positioning with respect to the heart, which ensures electrode 1672 maintains contact with the heart without requiring fluoroscopy or other visualization tools. In alternate embodiments, prong 1606 may include a pre-shaped spine made of shape-memory material, such as nitinol, to provide stiffness along with or instead of structural tubes 1682 and 1684. In these embodiments, prong 1606 may have the shape shown in FIG. 38, for example, or other suitable shapes or configurations.

Subcutaneous device 1600 is described here as having a single prong 1606. In alternate embodiments, subcutaneous device 1600 can include any number of prongs and those prongs can have any shape. For example, subcutaneous device 1600 can include any of the prongs shown and discussed in reference to FIGS. 1-37. Arm portion 1668 and contact portion 1670 can each have any angle with respect to bottom side 1616 and first side 1610 of housing 1602.

FIG. 41A is a partial perspective view of prong 1606 showing electrode 1672. FIG. 41B is a perspective view of electrode 1672. Prong 1606 includes distal end 1662, electrode 1672, and wire 1680. Electrode 1672 includes cylindrical portion 1686, ring portion 1688 and cone portion 1690.

Prong 1606 is described in reference to FIGS. 38-40E. Electrode 1672 is connected to the second end of wire 1680. Electrode 1672 is metal and conductive. Electrode 1672 has a conical shape. Electrode 1672 has cylindrical portion 1686 on a first end, cylindrical portion 1686 being connected to ring portion 1688. Ring portion 1688 has a larger diameter than cylindrical portion 1866. Electrode 1672 has cone portion 1690 on a second end, cone portion 1690 being connected to ring portion 1688. As such, a first end of ring portion 1688 is connected to cylindrical portion 1686 and a second end of ring portion 1688 is connected to cone portion 1690 such that ring portion 1688 is between cylindrical portion 1686 and cone portion 1690. Cylindrical portion 1686 of electrode 1672 is positioned within the second end of wire 1680. Ring portion 1688 and cone portion 1690 are positioned outside of wire 1680. The first end of ring portion 1688 connected to cylindrical portion 1686 abuts the second end of wire 1680. Cone portion 1690 has a conical shape with a rounded end. Cone portion 1690 defines distal end 1662 of prong 1606.

Cylindrical portion 1686 connects electrode 1672 to wire 1680. Ring portion 1688 positions electrode 1672 at the end of wire 1680, acting as a stop for electrode 1672. Cone portion 1690 is configured to contact remote body component B. For example, cone portion 1690 buries into the surface of the heart when subcutaneous device 1600 is positioned on the xiphoid process and/or sternum of a patient. Cone portion 1690 has a rounded end such that electrode 1672 is rounded and not sharp where electrode 1672 contacts remote body component B. For example, when electrode 1672 presses against the heart, electrode 1672 is not stiff or sharp enough to piece or tear the pericardial or epicardial tissue.

Electrode 1672 is conductive without significantly decreasing impedance and is shaped to allow for optimal contact with remote body component B without piercing remote body component B. The rounded end of cone portion 1690 of electrode 1672 prevents electrode 1672 from puncturing or damaging the heart. As such, prong 1606 can have sufficient stiffness and apply enough pressure to remote body component to maintain constant contact between electrode 1672 and remote body component B without causing damage to remote body component B. For example, when remote body component B is the heart, electrode 1672 does not puncture the heart and cause damage to the heart as the heart beats.

FIG. 42A is a partial perspective view of prong 1606A showing electrode 1672A. FIG. 42B is a perspective view of electrode 1672A. Prong 1606A includes distal end 1662A, electrode 1672A, and wire 1680A. Electrode 1672A includes cylindrical portion 1686A and spherical portion 1688A.

Prong 1606A has the same structure and function as prong 1606 described in reference to FIGS. 38-40E, except electrode 1672A has a different shape. Electrode 1672A is connected to the second end of wire 1680A. Electrode 1672A is metal and conductive. Electrode 1672A has a spherical shape. Electrode 1672A has cylindrical portion 1686A on a first end and spherical portion 1688A on a second end. Cylindrical portion 1686A is connected to spherical portion 1688A. Cylindrical portion 1686A of electrode 1672A is positioned within the second end of wire 1680A. Spherical portion 1688A is positioned outside of wire 1680A. Spherical portion 1688A defines distal end 1662A of prong 1606A.

Cylindrical portion 1686A connects electrode 1672A to wire 1680A. Spherical portion 1688A positions electrode 1672A at the end of wire 1680A, acting as a stop for electrode 1672A. Spherical portion 1688A is configured to contact remote body component B. For example, spherical portion 1688A buries into the surface of the heart when subcutaneous device 1600A is positioned on the xiphoid process and/or sternum of a patient. Spherical portion 1688A is rounded such that electrode 1672A is rounded and not sharp where electrode 1672A contacts remote body component B. For example, when electrode 1672A presses against the heart, electrode 1672A is not stiff or sharp enough to piece or tear the pericardial or epicardial tissue.

Electrode 1672A is conductive without significantly decreasing impedance and is shaped to allow for optimal contact with remote body component B without piercing remote body component B. Rounded spherical portion 1688A of electrode 1672A prevents electrode 1672A from puncturing or damaging the heart. As such, prong 1606A can have sufficient stiffness and apply enough pressure to remote body component to maintain constant contact between electrode 1672A and remote body component B without causing damage to remote body component B. For example, when remote body component B is the heart, electrode 1672A does not puncture the heart and cause damage to the heart as the heart beats.

FIG. 43A is a partial perspective view of prong 1606B showing electrode 1672B. FIG. 43B is a perspective view of electrode 1672B. Prong 1606B includes distal end 1662B, electrode 1672B, and wire 1680B. Electrode 1672B includes cylindrical portion 1686B and exterior cylindrical portion 1688B.

Prong 1606B has the same structure and function as prong 1606 described in reference to FIGS. 38-40E, except electrode 1672B has a different shape. Electrode 1672B is connected to the second end of wire 1680B. Electrode 1672B is metal and conductive. Electrode 1672B has a cylindrical shape. Electrode 1672B has cylindrical portion 1686B on a first end and exterior cylindrical portion 1688B on a second end. Cylindrical portion 1686B is connected to exterior cylindrical portion 1688B. Cylindrical portion 1686B of electrode 1672B is positioned within the second end of wire 1680B. Exterior cylindrical portion 1688B is positioned outside of wire 1680B. Exterior cylindrical portion 1688B defines distal end 1662B of prong 1606B.

Cylindrical portion 1686B connects electrode 1672B to wire 1680B. Exterior cylindrical portion 1688B is configured to contact remote body component B. For example, exterior cylindrical portion 1688B buries into the surface of the heart when subcutaneous device 1600B is positioned on the xiphoid process and/or sternum of a patient. Cylindrical portion 1688B has a rounded end such that electrode 1672B is not sharp where electrode 1672B contacts remote body component B. Because exterior cylindrical portion 1688B is entirely metal, exterior cylindrical portion 1688B is conductive wherever electrode 1672B contacts remote body component B, including at the most distal end of exterior cylindrical portion 1688B. For example, when electrode 1672B presses against the heart, electrode 1672B contacts the heart with a conductive surface.

Electrode 1672B is conductive without significantly decreasing impedance and is shaped to allow for optimal contact with remote body component B without piercing remote body component B. Exterior cylindrical portion 1688B of electrode 1672B ensures electrode 1672B contacts the remote body component B, such as the heart, with a conductive surface without being fixed to the remote body component B. As such, prong 1606B can have sufficient stiffness and apply enough pressure to remote body component B to maintain constant contact between a conductive surface of electrode 1672B and remote body component B. For example, when remote body component B is the heart, electrode 1672B maintains electrical contact with the heart as the heart beats.

FIG. 44A is a partial perspective view of prong 1606C showing electrode 1672C. FIG. 44B is a perspective view of electrode 1672C. Prong 1606C includes distal end 1662C, electrode 1672C, and wire 1680C. Electrode 1672C includes cylindrical portion 1686C, parallel portion 1688C, and perpendicular portion 1690C.

Prong 1606C has the same structure and function as prong 1606 described in reference to FIGS. 38-40E, except electrode 1672C has a different shape. Electrode 1672C is connected to the second end of wire 1680C. Electrode 1672C is metal and conductive. Electrode 1672C has a hammerhead shape. Electrode 1672C has cylindrical portion 1686C on a first end, cylindrical portion 1686C being connected to parallel portion 1688C. Electrode 1672C has perpendicular portion 1690C on a second end, perpendicular portion 1690C being connected to parallel portion 1688C. As such, a first end of parallel portion 1688C is connected to cylindrical portion 1686C and a second end of parallel portion 1688C is connected to perpendicular portion 1690C such that parallel portion 1688C is between cylindrical portion 1686C and perpendicular portion 1690C. Cylindrical portion 1686C of electrode 1672C is positioned within the second end of wire 1680C. Parallel portion 1688C and perpendicular portion 1690C are positioned outside of wire 1680 and form a screw head, or hammer head, shape. Parallel portion 1688C is cylindrical and is parallel and in alignment with cylindrical portion 1686C. Perpendicular portion 1690C is also cylindrical and is perpendicular to parallel portion 1688C. Perpendicular portion 1690C defines distal end 1662C of prong 1606C.

Cylindrical portion 1686C connects electrode 1672C to wire 1680C. Parallel portion 1688C positions perpendicular portion 1690C of electrode 1672C away from the end of wire 1680. Perpendicular portion 1690C is configured to contact remote body component B. For example, perpendicular portion 1690C buries into the surface of the heart when subcutaneous device 1600C is positioned on the xiphoid process and/or sternum of a patient. Perpendicular portion 1690C has a rounded end such that electrode 1672C is rounded and not sharp where electrode 1672C contacts remote body component B. Because parallel portion 1688C and perpendicular portion 1690C are entirely metal, parallel portion 1688C and perpendicular portion 1690C are conductive wherever electrode 1672C contacts remote body component B. For example, when electrode 1672C presses against the heart, electrode 1672C contacts the heart with a conductive surface.

Electrode 1672C is conductive without significantly decreasing impedance and is shaped to allow for optimal contact with remote body component B without piercing remote body component B. Parallel portion 1688C and perpendicular portion 1690C of electrode 1672C ensure electrode 1672C contacts the remote body component B, such as the heart, with a conductive surface without being fixed to the remote body component B. As such, prong 1606C can have sufficient stiffness and apply enough pressure to remote body component B to maintain constant contact between a conductive surface of electrode 1672C and remote body component B. For example, when remote body component B is the heart, electrode 1672C maintains electrical contact with the heart as the heart beats.

FIG. 45 is a perspective view of subcutaneous device 1600 positioned on xiphoid process X and/or sternum S and showing a positioning of prong 1606 on heart H. Subcutaneous device 1600 includes housing 1602, clip 1604, and prong 1606. Housing 1602 includes first side 1610 and bottom side 1616. Prong 1606 includes distal end 1662, arm portion 1668, electrode 1672, sleeve 1674, structural tube 1682, and structural tube 1684. FIG. 45 also shows xiphoid process X, sternum S, and heart H.

Subcutaneous device 1600 includes housing 1602, clip 1604, and prong 1606 as described above in reference to FIGS. 38-40E. In the embodiment shown in FIG. 45, subcutaneous device 1600 is configured to be a pacemaker used for cardiac monitoring, diagnostics, and/or therapeutics, such as subcutaneous device 100 described with respect to FIGS. 1-9C. In the embodiment shown in FIG. 45, subcutaneous device 1600 can be anchored to xiphoid process X and sternum S of a patient. Subcutaneous device 1600 can be implanted with a simple procedure where subcutaneous device 1600 is injected onto xiphoid process X and sternum S using a surgical instrument. For example, subcutaneous device 1600 can be anchored to xiphoid process X and sternum S using surgical instruments 1700, 1800, 1900, and 2000 and method 2100 described with respect to FIGS. 46A-51.

When subcutaneous device 1600 is anchored to xiphoid process X and sternum S via clip 1604, prong 1606 extends away from first side 1610 and bottom side 1616 of housing 1602. Arm portion 1668 extends away from bottom side 1616 of housing 1602, and contact portion 1670 extends away from bottom side 1616 and first side 1610 of housing 1602. As such, contact portion 1670 pushes down against heart H, and electrode 1672 at distal end 1662 of prong 1606 contacts heart H and maintains contact as heart H beats. Prong 1606 can be shaped so that prong 1606 contacts the right ventricle, left ventricle, right atrium, or left atrium of the heart. The overall desired stiffness of prong 1606 is achieved via structural tube 1682 and structural tube 1684 within sleeve 1674, which ensures that prong 1606 gently presses against heart H and moves up and down in contact with heart H as heart H beats, but is not stiff or sharp enough to pierce or tear the pericardial or epicardial tissue.

Prong 1606 is shaped to ensure prong 1606 is properly positioned against and will not lose contact with heart H. The surgical procedure for implanting subcutaneous device 1600 is less invasive than the surgical procedure required for more traditional pacemaker devices, as subcutaneous device is placed subcutaneously in the body. No leads need to be positioned in the vasculature of the patient, lowering the risk of thrombosis to the patient.

Surgical Instrument 1700

FIG. 46A is a perspective view of first surgical instrument 1700. FIG. 46B is a side view of first surgical instrument 1700. FIG. 46C is a top view of first surgical instrument 1700. FIG. 46D is a bottom view of first surgical instrument 1700. FIG. 46E is a back view of first surgical instrument 1700. FIG. 46F is a front view of first surgical instrument 1700. First surgical instrument 1700 includes proximal end 1702, distal end 1704, handle 1706 (having end 1706A and end 1706B), and dilation portion 1708 (having end 1708A and end 1708B). Dilation portion 1708 includes arm portion 1710 (having end 1710A and end 1710B), curved portion 1712 (having end 1712A and end 1712B), tip 1714, and marker 1716. Curved portion 1712 includes flattened portion 1718.

Surgical instrument 1700 can be used along with surgical instruments 1800, 1900, and 2000 (shown in FIGS. 47A-50) to implant a medical device in a patient. Surgical instruments 1700, 1800, and 1900 are used in a sequential manner to increasingly dilate tissue space to form a tunnel through which subcutaneous device 1600 is inserted via surgical instrument 2000. First surgical instrument 1700 spreads tissue to form a first space. Second surgical instrument 1800 spreads the tissue to form a second space that is larger than the first space. Finally, third surgical instrument 1900 spreads the tissue to form a third space that is larger than the second space. In alternate embodiments, any combination of surgical instruments 1700, 1800, and 1900 or none of surgical instruments 1700, 1800, and 1900 may be used along with surgical instrument 2000 to insert subcutaneous device 1600. In the following discussion, subcutaneous device 1600 (shown in FIGS. 38-45) will be used as an example of a device that can be implanted in a patient using surgical instruments 1700, 1800, 1900, and 2000. However, surgical instrument 1700 can be used to implant any suitable medical device in a patient, including any of subcutaneous devices 100, 400, 500, 600, 700, 800, 900, 1000, 1100, 1200, 1300, 1400, 1500, 2200, 2300, and 2400 shown in FIGS. 1-9C, 20-37 and 52-62E.

Surgical instrument 1700 has proximal end 1702 and distal end 1704. Surgical instrument 1700 is integrally formed such that surgical instrument 1700 is a single, continuous apparatus. Handle 1706 extends from proximal end 1702 such that end 1706A of handle 1706 defines proximal end 1702 of surgical instrument 1700. End 1706B of handle 1706 is connected to end 1708A of dilation portion 1708 such that dilation portion 1708 extends from handle 1706. Dilation portion 1708 has length L and width W. Dilation portion 1708 is primarily rod-like. Dilation portion 1708 has arm portion 1710 extending from handle 1706 such that end 1710A of arm portion 1710 is attached to end 1706B of handle 1706. Arm portion 1710 is rod-like. End 1710B of arm portion 1710 is adjacent to curved portion 1712 of dilation portion 1708 such that curved portion 1712 extends from arm portion 1710. End 1712A of curved portion 1712 is connected to arm portion 1710, and end 1712B of curved portion 1712 forms tip 1714 of dilation portion 1708 at end 1708B of dilation portion 1708 and distal end 1704 of surgical instrument 1700. Tip 1714 is located at distal end 1704 of surgical instrument 1700. As such, length L of dilation portion 1708 extends from end 1710A of arm portion 1710 to tip 1714. Curved portion 1712 is curved, or angled, up such that a top of curved portion 1712 is concave. Tip 1714 is rounded and smooth. Marker 1716 is a visual indicator on dilation portion 1708 positioned on arm portion 1710 near end 1710A of arm portion 1710 and adjacent handle 1706. In alternate embodiments, marker 1716 may be positioned at any suitable location on dilation portion 1708. Marker 1716 may be a line, an indentation, or any other suitable visual indicator. In this embodiment, surgical instrument 1700 has a single marker 1716. In alternate embodiments, surgical instrument 1700 may have multiple markers 1716. Curved portion 1712 includes flattened portion 1718 at a distal portion of curved portion 1712. Flattened portion 1718 has a flat cross-section such that curved portion 1712 has a flat top portion at a distal portion of curved portion 1712. Flattened portion 1718 extends to tip 1714. The diameter, or width W, of surgical instrument 1700 near distal end 1704 of surgical instrument 1700, such as at flattened portion 1718, corresponds to the diameter, or width, of prong 1606 of subcutaneous device 1600 near distal end 1662 of prong 1606.

Surgical instrument 1700 acts as an initial dilator and is the first of a series of surgical instruments used to spread tissue to create a tunnel for inserting subcutaneous device 1600. Distal end 1704 of surgical instrument 1700 is inserted into a patient. Anatomical markers can be used to insert surgical instrument 1700. For example, surgical instrument 1700 may be inserted into the patient and directed toward an intercostal space between the third intercostal space and the seventh intercostal space, or more specifically between the fifth and sixth ribs, to the left of the sternum. Handle 1706 can be grasped by a surgeon to hold and maneuver surgical instrument 1700. Surgical instrument 1700 is advanced into the patient such that dilation portion 1708 spreads tissue to form a tunnel. Pressure is directed to the top of handle 1706 such that the surgeon is pushing down on handle 1706 of surgical instrument 1700, ensuring dilation portion 1708 is being pushed up toward to the xiphoid process and/or the sternum and away from the heart. Surgical instrument 1700 is advanced into the patient up to marker 1716. Marker 1716 acts as an indicator for the surgeon to stop advancing surgical instrument 1700. [003%] Dilation portion 1708 of surgical instrument 1700 creates space in the tissue of the patient and forms a tunnel for the insertion of the subsequent surgical instrument, and ultimately through which subcutaneous device 1600 is to be inserted. Dilation portion 1708 has curved portion 1712 extending from distal end 1704 such that curved portion 1712 is angled up and away from the heart when surgical instrument 1700 is advanced into the patient, so that dilation portion 1708 does not poke the heart. Tip 1714 is smooth so that distal end 1704 of surgical instrument 1700 does not have sharp edges that could pierce the heart if surgical instrument 1700 is inserted too far and does contact the heart. Marker 1716 indicates when surgical instrument 1700 should not be advanced farther, which further ensures the surgeon does not poke and/or perforate the heart with surgical instrument 1700. As a result of flattened portion 1718, curved portion 1712 is narrower toward distal end 1704 of surgical instrument 1700, which opens up and spreads apart tissue, making it easier to push surgical instrument 1700 into the patient, and keeps the opening in the patient as small as possible. Curved portion 1712 not including flattened portion 1718 and arm portion 1710 create a larger space in the tissue than curved portion 1712 having flattened portion 1718.

The surgical procedure for implanting subcutaneous device 1600 with surgical instrument 1700 is less invasive than the surgical procedure required for more traditional pacemaker devices. Surgical instrument 1700 quickly creates an initial tunnel, or pocket, in the body of the patient without requiring fluoroscopy or any additional visualization tools. Marker 1716 indicates exactly how far surgical instrument 1700 should be inserted into the patient. As such, cardiac catheterization labs are not needed to utilize surgical instrument 1700. Because dilation portion 1708 has a small width W, surgical instrument 1700 creates a narrower tunnel that corresponds to the width or diameter of distal end 1662 of prong 1606, and subcutaneous device 1600 is not creating a new tunnel as subcutaneous device 1600 is inserted, which reduces trauma to the patient. Additionally, tissue is being spread by surgical instrument 1700 rather than cut, and surgical instrument 1700 is not being pushed through organs or muscle, which further reduces patient trauma. Surgical instrument 1700 also gives the surgeon control as to where the surgical device 1600 will be positioned, which is close to the skin of the patient. Curved portion 1712 and smooth tip 1714 act as safety features of surgical instrument 1700.

Surgical Instrument 1800

FIG. 47A is a perspective view of second surgical instrument 1800. FIG. 47B is a side view of second surgical instrument 1800. FIG. 47C is a top view of second surgical instrument 1800. FIG. 47D is a bottom view of second surgical instrument 1800. FIG. 47E is a back view of second surgical instrument 1800. FIG. 47F is a front view of second surgical instrument 1800. Second surgical instrument 1800 includes proximal end 1802, distal end 1804, handle 1806 (having end 1806A and end 1806B), and dilation portion 1808 (having end 1808A and end 1808B). Dilation portion 1808 includes arm portion 1810 (having end 1810A and end 1810B), curved portion 1812 (having end 1812A and end 1812B), tip 1814, marker 1816, and flattened portion 1818.

Surgical instrument 1800 has proximal end 1802 and distal end 1804. Surgical instrument 1800 is integrally formed such that surgical instrument 1800 is a single, continuous apparatus. Handle 1806 extends from proximal end 1802 such that end 1806A of handle 1806 defines proximal end 1802 of surgical instrument 1800. End 1806B of handle 1806 is connected to end 1808A of dilation portion 1808 such that dilation portion 1808 extends from handle 1806. Dilation portion 1808 has length L1, first width W1, and second width W2. Length L1 is shorter than length L of dilation portion 1708 of surgical instrument 1700. First width W1 and second width W2 are greater than width W of dilation portion 1708 of surgical instrument 1700. Dilation portion 1808 has a rounded bottom portion. Dilation portion 1808 has arm portion 1810 extending from handle 1806 such that end 1810A of arm portion 1810 is attached to end 1806B of handle 1806. Arm portion 1810 has a rounded bottom portion and height H1. End 1810B of arm portion 1810 is adjacent to curved portion 1812 of dilation portion 1808 such that curved portion 1812 extends from arm portion 1810. End 1812A of curved portion 1812 is connected to arm portion 1810, and end 1812B of curved portion 1812 forms tip 1814 of dilation portion 1808 at end 1808B of dilation portion 1808 and distal end 1804 of surgical instrument 1800. Tip 1814 is located at distal end 1804 of surgical instrument 1800. As such, length L1 of dilation portion 1808 extends from end 1810A of arm portion 1810 to tip 1814. Curved portion 1812 is curved, or angled, up such that a top of curved portion 1812 is concave. Curved portion 1812 has a rounded bottom portion, or is rounded where curved portion 1812 is convex. Curved portion 1812 is shaped to correspond to the shape of sleeve 1674 of prong 1606 of subcutaneous device 1600. Tip 1814 is also rounded and smooth. Curved portion 1812 has width W1, and arm portion 1810 has width W2. Width W2 of arm portion 1810 is greater than width W1 of curved portion 1812. Marker 1816 is a visual indicator on dilation portion 1808 positioned on arm portion 1810 near end 1810A of arm portion 1810 and adjacent handle 1806. In alternate embodiments, marker 1816 may be positioned at any suitable location on dilation portion 1808. Marker 1816 may be a line, an indentation, or any other suitable visual indicator. In this embodiment, surgical instrument 1800 has a single marker 1816. In alternate embodiments, surgical instrument 1800 may have multiple markers 1816. Dilation portion 1808 has flattened portion 1818 at the top of dilation portion 1808, extending from arm portion 1810 to tip 1814. Flattened portion 1818 has a flat cross-section. As such, flattened portion 1818 makes up the top of arm portion 1810 and the top, or concave side, of curved portion 1812. Flattened portion 1818 extends to tip 1814.

Surgical instrument 1800 acts as an intermediate dilator and is the second of a series of surgical instruments used to spread tissue to create a tunnel for inserting subcutaneous device 1600. Distal end 1804 of surgical instrument 1800 is inserted into the patient. Surgical instrument 1800 is inserted into the tunnel formed by surgical instrument 1700. For example, surgical instrument 1800 may be inserted into the opening formed in the patient by surgical instrument 1700 and directed toward the intercostal space between the fifth and sixth ribs, to the left of the sternum. Handle 1806 can be grasped by a surgeon to hold and maneuver surgical instrument 1800. Surgical instrument 1800 is advanced into the patient such that dilation portion 1808 spreads tissue to expand the tunnel formed by surgical instrument 1700. Pressure is directed to the top of handle 1806 such that the surgeon is pushing down on handle 1806 of surgical instrument 1800, ensuring dilation portion 1808 is being pushed up toward to the xiphoid process and/or the sternum and away from the heart. Surgical instrument 1800 is advanced into the patient up to marker 1816. Marker 1816 acts as an indicator for the surgeon to stop advancing surgical instrument 1800.

Dilation portion 1808 of surgical instrument 1800 creates a larger space in the tissue of the patient than was created by surgical instrument 1700 and thus forms a larger tunnel for the insertion of the subsequent surgical instrument, and ultimately through which subcutaneous device 1600 is to be inserted. Dilation portion 1808 has curved portion 1812 extending from distal end 1804 such that curved portion 1812 is angled up and away from the heart when surgical instrument 1800 is advanced into the patient, so that dilation portion 1808 does not poke the heart. Tip 1814 is smooth so that distal end 1804 of surgical instrument 1800 does not have sharp edges that could pierce the heart if surgical instrument 1800 is inserted too far and does contact the heart. Marker 1816 indicates when surgical instrument 1800 should not be advanced farther, which further ensures the surgeon does not poke and/or perforate the heart with surgical instrument 1800. As a result of flattened portion 1818, curved portion 1812 is narrower at distal end 1804 of surgical instrument 1800, which opens up and spreads apart tissue, making it easier to push surgical instrument 1800 into the patient. Because length L1 of dilation portion 1808 of surgical instrument 1800 is shorter than length L of dilation portion 1708 of surgical instrument 1700 and marker 1816 of surgical instrument 1800 is in the same location on handle 1806 as marker 1716 of surgical instrument 1700 is on handle 1706, the length of the tunnel is not increased and only a portion of the tunnel is enlarged via surgical instrument 1800. Because first width W1 of curved portion 1812 of surgical instrument 1800 is greater than width W of dilation portion 1708 of surgical instrument 1700, more space is opened in the patient to accommodate prong 1606 of subcutaneous device 1600, particularly sleeve 1674 of prong 1606. Because second width W2 of arm portion 1810 is greater than first width W1 of curved portion 1812 and arm portion 1810 has height H1, a larger space is created in the tissue of the patient where arm portion 1810 is inserted, which is closer to the skin of the patient and will accommodate housing 1602 of subcutaneous device 1600.

The surgical procedure for implanting subcutaneous device 1600 with surgical instrument 1800 is less invasive than the surgical procedure required for more traditional pacemaker devices. Surgical instrument 1800 quickly expands the initial tunnel, or pocket, that was created by surgical instrument 1700 in the body of the patient without requiring fluoroscopy or any additional visualization tools. Marker 1816 indicates exactly how far surgical instrument 1800 should be inserted into the patient. As such, cardiac catheterization labs are not needed to utilize surgical instrument 1800. Because dilation portion 1808 first width W1 and second width W2 that are larger than width W of dilation portion 1708, surgical instrument 1800 gradually creates a larger tunnel for accommodating housing 1602 and sleeve 1674 of prong 1606, which allows the tunnel to remain as narrow as possible. Further, subcutaneous device 1600 is prevented from creating a new tunnel as subcutaneous device 1600 is inserted, which reduces trauma to the patient. Curved portion 1812 has a smaller first width W1 than second width W2 of arm portion 1810 to tailor the space to fit prong 1606 of subcutaneous device 1600 rather than create excess space near the heart, or more space than necessary for inserting subcutaneous device 1600. Additionally, tissue is being spread by surgical instrument 1800 rather than cut, and surgical instrument 1800 is not being pushed through organs or muscle, which further reduces patient trauma. Surgical instrument 1800 also gives the surgeon control as to where the surgical device 1600 will be positioned, which is close to the skin of the patient. Curved portion 1812 and smooth tip 1814 act as safety features of surgical instrument 1800.

Surgical Instrument 1900

FIG. 48A is a perspective view of third surgical instrument 1900. FIG. 48B is a side view of third surgical instrument 1900. FIG. 48C is a top view of third surgical instrument 1900. FIG. 48D is a bottom view of third surgical instrument 1900. FIG. 48E is a back view of third surgical instrument 1900. FIG. 48F is a front view of third surgical instrument 1900. Third surgical instrument 1900 includes proximal end 1902, distal end 1904, handle 1906 (having end 1906A and end 1906B), and dilation portion 1908 (having end 1908A and end 1908B). Dilation portion 1908 includes arm portion 1910 (having end 1910A and end 1910B), curved portion 1912 (having end 1912A and end 1912B), tip 1914, marker 1916, and flattened portion 1918.

Surgical instrument 1900 has proximal end 1902 and distal end 1904. Surgical instrument 1900 is integrally formed such that surgical instrument 1900 is a single, continuous apparatus. Handle 1906 extends from proximal end 1902 such that end 1906A of handle 1906 defines proximal end 1902 of surgical instrument 1900. End 1906B of handle 1906 is connected to end 1908A of dilation portion 1908 such that dilation portion 1908 extends from handle 1706. Dilation portion 1908 has length L2, first width W3, and second width W4. Length L2 is shorter than length L1 of dilation portion 1808 of surgical instrument 1800. First width W3 is greater than first width W1 of dilation portion 1808 of surgical instrument 1800, and second width W4 is greater than second width W2 of dilation portion 1808 of surgical instrument 1800. Dilation portion 1908 has a rounded bottom portion. Dilation portion 1908 has arm portion 1910 extending from handle 1906 such that end 1910A of arm portion 1910 is attached to end 1906B of handle 1906. Arm portion 1910 has a rounded bottom portion and height H2. Height H2 is greater than height H1 of arm portion 1810 of surgical instrument 1800. End 1910B of arm portion 1910 is adjacent to curved portion 1912 of dilation portion 1908 such that curved portion 1912 extends from arm portion 1910. End 1912A of curved portion 1912 is connected to arm portion 1910, and end 1912B of curved portion 1912 forms tip 1914 of dilation portion 1908 at end 1908B of dilation portion 1908 and distal end 1904 of surgical instrument 1900. Tip 1914 is located at distal end 1904 of surgical instrument 1900. As such, length L2 of dilation portion 1908 extends from end 1910A of arm portion 1910 to tip 1914. Curved portion 1912 is curved, or angled, up such that a top of curved portion 1912 is concave. Curved portion 1912 has a rounded bottom portion, or is rounded where curved portion 1912 is convex. Tip 1914 is also rounded and smooth. Curved portion 1912 has width W3, and arm portion 1910 has width W4. Width W4 of arm portion 1910 is greater than width W3 of curved portion 1912. Width W4 corresponds to the width of housing 1602 of subcutaneous device 1600. Marker 1916 is a visual indicator on dilation portion 1908 positioned on arm portion 1910 near end 1910A of arm portion 1910 and adjacent handle 1906. In alternate embodiments, marker 1916 may be positioned at any suitable location on dilation portion 1908. Marker 1916 may be a line, an indentation, or any other suitable visual indicator. In this embodiment, surgical instrument 1900 has a single marker 1916. In alternate embodiments, surgical instrument 1900 may have multiple markers 1916. Dilation portion 1908 has flattened portion 1918 at the top of dilation portion 1908, extending from arm portion 1910 to tip 1914. Flattened portion 1918 has a flat cross-section. As such, flattened portion 1918 makes up the top of arm portion 1910 and the top, or concave side, of curved portion 1912. Flattened portion 1918 extends to tip 1914.

Surgical instrument 1900 acts as a final dilator and is the third of a series of surgical instruments used to spread tissue to create a tunnel for inserting subcutaneous device 1600. Distal end 1904 of surgical instrument 1900 is inserted into the patient. Surgical instrument 1900 is inserted into the tunnel formed by surgical instrument 1700 and surgical instrument 1800. For example, surgical instrument 1900 may be inserted into the opening formed in the patient by surgical instrument 1700 and surgical instrument 1900 and directed toward the intercostal space between the fifth and sixth ribs, to the left of the sternum. Handle 1906 can be grasped by a surgeon to hold and maneuver surgical instrument 1900. Surgical instrument 1900 is advanced into the patient such that dilation portion 1908 spreads tissue to expand the tunnel formed by surgical instrument 1800. Pressure is directed to the top of handle 1906 such that the surgeon is pushing down on handle 1906 of surgical instrument 1900, ensuring dilation portion 1908 is being pushed up toward to the xiphoid process and/or the sternum and away from the heart. Surgical instrument 1900 is advanced into the patient up to marker 1916. Marker 1916 acts as an indicator for the surgeon to stop advancing surgical instrument 1900.

Dilation portion 1908 of surgical instrument 1900 creates a larger space in the tissue of the patient than was created by surgical instrument 1800 and thus forms a larger tunnel for the insertion of the subsequent surgical instrument, and ultimately through which subcutaneous device 1600 is to be inserted. Dilation portion 1908 has curved portion 1912 extending from distal end 1904 such that curved portion 1912 is angled up and away from the heart when surgical instrument 1900 is advanced into the patient, so that dilation portion 1908 does not poke the heart. Tip 1914 is smooth so that distal end 1904 of surgical instrument 1900 does not have sharp edges that could pierce the heart if surgical instrument 1900 is inserted too far and does contact the heart. Marker 1916 indicates when surgical instrument 1900 should not be advanced farther, which further ensures the surgeon does not poke and/or perforate the heart with surgical instrument 1900. As a result of flattened portion 1918, curved portion 1912 is narrower at distal end 1904 of surgical instrument 1900, which opens up and spreads apart tissue, making it easier to push surgical instrument 1900 into the patient. Because length L2 of dilation portion 1908 of surgical instrument 1900 is shorter than length L1 of dilation portion 1808 of surgical instrument 1800 and marker 1916 of surgical instrument 1900 is in the same location on handle 1906 as marker 1816 of surgical instrument 1800 is on handle 1806, the length of the tunnel is not increased and only a portion of the tunnel is enlarged via surgical instrument 1900. Because first width W3 of curved portion 1912 of surgical instrument 1900 is greater than first width W1 of dilation portion 1808 of surgical instrument 1800, more space is opened in the patient to accommodate prong 1606 of subcutaneous device 1600, particularly sleeve 1674 of prong 1606. Because second width W4 of arm portion 1910 is greater than second width W2 of arm portion 1818 of subcutaneous device 1800 and arm portion 1910 has height H2 that is greater than height H1 of arm portion 1810 of subcutaneous device 1800, a larger space is created in the tissue of the patient where arm portion 1910 is inserted, which is closer to the skin of the patient and will accommodate housing 1602 of subcutaneous device 1600.

The surgical procedure for implanting subcutaneous device 1600 with surgical instrument 1900 is less invasive than the surgical procedure required for more traditional pacemaker devices. Surgical instrument 1900 quickly expands the tunnel, or pocket, that was created by surgical instrument 1800 in the body of the patient without requiring fluoroscopy or any additional visualization tools. Marker 1916 indicates exactly how far surgical instrument 1900 should be inserted into the patient. As such, cardiac catheterization labs are not needed to utilize surgical instrument 1900. Because dilation portion 1908 first width W3, second width W4, and second height H2 that are larger than first width W1, second width W2, and first height H1, respectively, of dilation portion 1808, surgical instrument 1900 gradually creates a larger tunnel for accommodating housing 1602 and sleeve 1674 of prong 1606, which allows the tunnel to remain as narrow as possible. Further, subcutaneous device 1600 is prevented from creating a new tunnel as subcutaneous device 1600 is inserted, which reduces trauma to the patient. Curved portion 1912 has a smaller first width W3 than second width W4 of arm portion 1910 to tailor the space to fit prong 1606 of subcutaneous device 1600 rather than create excess space near the heart, or more space than necessary for inserting subcutaneous device 1600. Additionally, tissue is being spread by surgical instrument 1900 rather than cut, and surgical instrument 1900 is not being pushed through organs or muscle, which further reduces patient trauma. Surgical instrument 1900 also gives the surgeon control as to where the subcutaneous device 1600 will be positioned, which is close to the skin of the patient. Curved portion 1912 and smooth tip 1914 act as safety features of surgical instrument 1900.

Surgical Instrument 2000

FIG. 49A is a perspective view of fourth surgical instrument 2000. FIG. 49B is a side view of fourth surgical instrument 2000. FIG. 49C is a top view of fourth surgical instrument 2000. FIG. 49D is a bottom view of fourth surgical instrument 2000. FIG. 49E is a back view of fourth surgical instrument 2000. FIG. 49F is a front view of fourth surgical instrument 2000. FIG. 50 is a perspective view of subcutaneous device 1600 positioned in the fourth surgical instrument. Subcutaneous device 1600 includes housing 1602, clip 1604, prong 1606, and guide 1630. Prong 1606 includes electrode 1642, sleeve 1674, and wire 1680. Fourth surgical instrument 2000 includes proximal end 2002, distal end 2004, handle 2006 (having end 2006A and end 2006B), and insertion portion 2008 (having end 2008A and end 2008B). Insertion portion 2008 includes arm portion 2010 (having end 2010A and end 2010B), curved portion 2012 (having end 2012A and end 2012B), tip 2014, and prong track 2016. Arm portion 2010 includes guide track 2018.

Surgical instrument 2000 has proximal end 2002 and distal end 2004. Surgical instrument 2000 is integrally formed such that surgical instrument 2000 is a single, continuous apparatus. Handle 2006, or insertion handle 2006, extends from proximal end 2002 such that end 2006A of handle 2006 defines proximal end 2002 of surgical instrument 2000. End 2006B of handle 2006 is connected to end 2008A of insertion portion 2008 such that insertion portion 2008 extends from handle 2006. Insertion portion 2008 has length L3, first width W5, and second width W6. Length L3 is the same length as length L2 of dilation portion 1908 of surgical instrument 1900. First width W5 is the same width as first width W3 of dilation portion 1908 of surgical instrument 1900, and second width W6 is the same width as second width W4 of dilation portion 1908 of surgical instrument 1900. Insertion portion 2008 has a rounded bottom portion. Insertion portion 2008 has arm portion 2010 extending from handle 2006 such that end 2010A of arm portion 2010 is attached to end 2006B of handle 2006. Arm portion 2010 has a rounded bottom portion and height H3. Height H3 is the same height as height H2 of arm portion 1910 of surgical instrument 1900. End 2010B of arm portion 2010 is adjacent to curved portion 2012 of insertion portion 2008 such that curved portion 2012 extends from arm portion 2010. End 2010A of curved portion 2012 is connected to arm portion 2010, and end 2010B of curved portion 2012 forms tip 2014 of insertion portion 2008 at end 2010B of insertion portion 2008 and distal end 2004 of surgical instrument 2000. Tip 2014 is located at distal end 2004 of surgical instrument 2000. As such, length L3 of insertion portion 2008 extends from end 2010A of arm portion 2010 to tip 2014. Curved portion 2012 is curved, or angled, up such that a top of curved portion 2012 is concave. Curved portion 2012 has a rounded bottom portion, or is rounded where curved portion 2012 is convex. Tip 2014 is also rounded and smooth. Curved portion 2012 has width W5, and arm portion 2010 has width W6. Width W6 of arm portion 2010 is greater than width W5 of curved portion 2012. Prong track 2016 extends along the top of arm portion 2010 and the top, or concave side, of curved portion 2012 of insertion portion 2008. Prong track 2016 is shaped to fit prong 1606 of subcutaneous device 1600. Guide track 2018 extends along a side of arm portion 2010 of insertion portion 2008. Guide track 2018 is shaped to fit guide 1630 of subcutaneous device 1600.

Surgical instrument 2000 acts as an insertion device, or introducer, for subcutaneous device 1600 and is the fourth and final surgical instrument in a series of surgical instruments used to the create a tunnel and insert subcutaneous device 1600. Subcutaneous device 1600 is loaded onto surgical instrument 2000. Subcutaneous device 1600 is positioned in insertion portion 2008 of surgical instrument 2000. Insertion portion 2008 releasably holds subcutaneous device 1600 to implant subcutaneous device 1600 for anchoring to the muscle, the bone, or the tissue of the patient. As seen in FIG. 50, housing 1602 fits within arm portion 2010, guide 1630 being positioned in guide track 2018. Prong 1606 fits within and is cradled by arm portion 2010 and curved portion 2012, prong 1606 being positioned in prong track 2016. Curved portion 2012 bends prong 1606 up toward bottom side 1616 of housing 1602. As such, prong 1606 is pushed up when subcutaneous device 1600 is loaded in surgical instrument 2000. Distal end 2004 of surgical instrument 2000 is inserted into the patient. More specifically, prong 1606 of subcutaneous device 1606 extends past distal end 2004 and is inserted first. Surgical instrument 2000 with subcutaneous device 1606 is inserted into the tunnel formed by surgical instruments 1700, 1800, and 1900. For example, surgical instrument 2000 may be inserted into the opening formed in the patient by surgical instruments 1700, 1800, and 1900 and directed toward the intercostal space between the fifth and sixth ribs, to the left of the sternum. Handle 2006 can be grasped by a surgeon to hold and maneuver surgical instrument 2000 with subcutaneous device 1600. Surgical instrument 2000 with subcutaneous device 1600 is advanced into the patient such that surgical instrument 2000 and subcutaneous device 1600 fit into the tunnel formed by surgical instruments 1700, 1800, and 1900. Pressure is directed to the top of handle 2006 such that the surgeon is pushing down on handle 2006 of surgical instrument 2000, ensuring insertion portion 2008, along with housing 1602 and prong 1606, is being pushed up toward to the xiphoid process and/or the sternum and away from the heart. Surgical instrument 2000 is advanced into the patient until clip 1604 of subcutaneous device 1600 is attached to the xiphoid process and/or sternum, which secures subcutaneous device 1600 to the patient.

Insertion portion 2008 of surgical instrument 2000 has length L3, first width W5, second width W6, and height H3 that are the same as length L2, first width W3, second width W4, and height H2 of dilation portion 1908 of surgical instrument 1900. As such, surgical instrument 2000 fits into the space in the tissue of the patient created by surgical instrument 1900, allowing for the insertion of subcutaneous device 1600. Insertion portion 2008 has curved portion 2012 extending from distal end 2004 such that curved portion 2012 is angled up and away from the heart when surgical instrument 2000 is advanced into the patient, so that insertion portion 2008 does not poke the heart. Tip 2014 is smooth so that distal end 2004 of surgical instrument 2000 does not have sharp edges that could pierce the heart if surgical instrument 2000 is inserted too far and does contact the heart. Prong track 1916 allows for positioning of prong 1606 of subcutaneous device 1600 within surgical instrument 2000. When subcutaneous device 1600 is anchored to a xiphoid process and/or sternum of a patient and surgical instrument 2000 is removed, prong 1606 bends back down to its initial angle prior to being loaded in surgical instrument 2000, which forces prong 1606 to contact the heart and maintain such contact as the heart contracts and relaxes. Guide track 2018 allows for positioning of guide 1630 and housing 1602 within surgical instrument 2000. As a result, subcutaneous device 1600 is properly positioned within surgical instrument 2000 and is directed to the proper location within the patient.

The surgical procedure for implanting subcutaneous device 1600 with surgical instrument 2000 is less invasive than the surgical procedure required for more traditional pacemaker devices. Surgical instrument 2000 fits into the tunnel, or pocket, that was created by surgical instrument 1900 in the body of the patient without requiring fluoroscopy or any additional visualization tools. As such, cardiac catheterization labs are not needed to utilize surgical instrument 2000 and place subcutaneous device 1600 within a patient. Because insertion portion 2008 has length L3, first width W5, second width W6, and height H3 that are the same as length L2, first width W3, second width W4, and height H2, respectively, of dilation portion 1908, surgical instrument 2000 with subcutaneous device 1600 fits into the tunnel created by surgical instrument 1900 while allowing the tunnel to remain as narrow as possible. Further, subcutaneous device 1600 is prevented from creating a new tunnel as subcutaneous device 1600 is inserted, which reduces trauma to the patient. Additionally, because a narrow tunnel is created, prong 1606 of subcutaneous device 1600 stays in place as no excess space exists for movement. As the tissue was spread by surgical instruments 1700, 1800, and 1900 and not cut, the tissue of the patient relaxes around subcutaneous device 1600 within a few seconds of insertion of the device, which further holds subcutaneous device 1600 in place. Because prong 1606 cannot move in excess space near the heart, prong 1606 of subcutaneous device 1600 is positioned for proper contact with the heart. Surgical instrument 2000 also gives the surgeon control as to where subcutaneous device 1600 will be positioned, which is close to the skin of the patient, allowing for easier insertion of subcutaneous device 1600. Curved portion 2012 and smooth tip 2014 act as safety features of surgical instrument 2000.
Method 2100

FIG. 51 is a flow chart showing method 2100 for injecting and anchoring subcutaneous device 1600 using first surgical instrument 1700, second surgical instrument 1800, third surgical instrument 1900, and fourth surgical instrument 2000. FIGS. 46A-46F show first surgical instrument 1700. FIGS. 47A-47F show second surgical instrument 1800. FIGS. 48A-48F show third surgical instrument 1900. FIGS. 49A-49F show fourth surgical instrument 2000. FIG. 50 fourth surgical instrument 2000 loaded with subcutaneous device 1600. Subcutaneous device 1600 includes housing 1602, clip 1604, prong 1606, and guide 1630. Prong 1606 includes electrode 1642, sleeve 1674, and wire 1680. First surgical instrument 1700 includes distal end 1704, handle 1706, and dilation portion 1708, which includes marker 1716. Second surgical instrument 1800 includes distal end 1804, handle 1806, and dilation portion 1808, which includes marker 1816. Third surgical instrument 1900 includes distal end 1904, handle 1906, and dilation portion 1908, which includes marker 1916. Fourth surgical instrument 2000 includes distal end 2004, handle 2006, and insertion portion 2008, which includes arm portion 2010 and prong track 2016. Arm portion 2010 includes guide track 2018. Method 2100 includes steps 2102-2130.

Method 2100 is described here in relation to implanting subcutaneous device 1600 (shown in FIGS. 38-45) on a xiphoid process and a sternum of a patient. However, method 2100 can be used to implant any suitable medical device (including any of subcutaneous devices 100, 400, 500, 600, 700, 800, 900, 1000, 1100, 1200, 1300, 1400, 1500, 2200, 2300, and 2400 shown in FIGS. 1-9C, 20-37 and 52-62E) on any bone, muscle, or tissue in a patient. Further, method 2100 is described here in relation to using surgical instruments 1700, 1800, 1900, and 2000 (shown in FIGS. 46A-50) to implant subcutaneous device 1600. However, any suitable surgical instrument or combination of surgical instruments 1700, 1800, 1900, and 2000 can be used to implant subcutaneous device 1600.

Step 2102 includes making a small incision in a patient below a xiphoid process. The patient may be under local or general anesthesia. A surgeon can make a small incision through the skin right below the xiphoid process using a scalpel.

Step 2104 includes inserting surgical instrument 1700 through the small incision. Distal end 1704 of surgical instrument 1700 is inserted first. Anatomical markers can be used to insert surgical instrument 1700. For example, surgical instrument 1700 may be inserted into the patient between the fifth and sixth ribs, or the fourth and fifth ribs, to the left of the sternum.

Step 2106 includes advancing surgical instrument 1700 to marker 1716 on surgical instrument 1700. A surgeon who is holding handle 1706 of surgical instrument 1700 can move surgical instrument 1700 into and through the patient. Anatomical markers can be used to direct surgical instrument 1700. For example, surgical instrument 1700 may be directed toward the intercostal space between the fifth and sixth ribs, to the left of the sternum. A surgeon who is advancing surgical instrument 1700 directs pressure to a top of handle 1706 such that handle 1706 is being pushed down and dilation portion 1708 is being pushed up toward the xiphoid process and/or the sternum. Surgical instrument 1700 acts as an initial dilator. Dilation portion 1708 of surgical instrument 1700 spreads tissue to create an initial tunnel or opening in the patient.

Surgical instrument 1700 may be advanced into the patient at an angle to the sternum. For example, when subcutaneous device 1600 is used for single chamber pacing, surgical instrument 1700 is advanced into the intercostal space between the fifth and sixth ribs, or the fourth and fifth ribs, at an angle between about 20 degrees and about 30 degrees to the sternum to accommodate a prong 1606 that is between 70 mm and 100 mm. For another example, when subcutaneous device 2300 (described with respect to FIGS. 56-58) is used for dual chamber pacing, surgical instrument 1700 is advanced at an angle between about 45 degrees and about 60 degrees to the sternum to accommodate a prong 2306 that is between 70 mm and 80 mm and a prong 2306A that is between 90 mm and 110 mm and may cross the coronary sinus to reach the left ventricle.

Step 2108 includes removing surgical instrument 1700 from the small incision in the patient. After surgical instrument 1700 has been advanced to marker 1716, surgical instrument 1700 can be removed from the small incision in the patient. When surgical instrument 1700 is removed, the tunnel created by surgical instrument 1700 remains in the tissue of the patient.

Step 2110 includes inserting surgical instrument 1800 through the small incision. Distal end 1804 of surgical instrument 1800 is inserted first. Surgical instrument 1800 is inserted into the tunnel formed by surgical instrument 1700.

Step 2112 includes advancing surgical instrument 1800 to marker 1816 on surgical instrument 1800. A surgeon who is holding handle 1806 of surgical instrument 1800 can move surgical instrument 1800 into the tunnel formed by surgical instrument 1700. Anatomical markers can be used to direct surgical instrument 1800. For example, surgical instrument 1800 may be directed toward the intercostal space between the fifth and sixth ribs, to the left of the sternum. A surgeon who is advancing surgical instrument 1800 directs pressure to a top of handle 1806 such that handle 1806 is being pushed down and dilation portion 1808 is being pushed up toward the xiphoid process and/or the sternum. Surgical instrument 1800 acts as an intermediate dilator. Dilation portion 1808 of surgical instrument 1800 further spreads tissue to expand the width of the tunnel, or opening in the patient, that was formed by surgical instrument 1700. Surgical instrument 1800 does not increase the length of the tunnel.

Step 2114 includes removing surgical instrument 1800 from the small incision in the patient. After surgical instrument 1800 has been advanced to marker 1816, surgical instrument 1800 can be removed from the small incision in the patient. When surgical instrument 1800 is removed, the tunnel created by surgical instruments 1700 and 1800 remains in the tissue of the patient.

Step 2116 includes inserting surgical instrument 1900 through the small incision. Distal end 1904 of surgical instrument 1900 is inserted first. Surgical instrument 1900 is inserted into the tunnel formed by surgical instruments 1700 and 1800.

Step 2118 includes advancing surgical instrument 1900 to marker 1916 on surgical instrument 1900. A surgeon who is holding handle 1906 of surgical instrument 1900 can move surgical instrument 1900 into the tunnel formed by surgical instruments 1700 and 1800. Anatomical markers can be used to direct surgical instrument 1900. For example, surgical instrument 1900 may be directed toward the intercostal space between the fifth and sixth ribs, to the left of the sternum. A surgeon who is advancing surgical instrument 1900 directs pressure to a top of handle 1906 such that handle 1906 is being pushed down and dilation portion 1908 is being pushed up toward the xiphoid process and/or the sternum. Surgical instrument 1900 acts as final dilator. Dilation portion 1908 of surgical instrument 1900 further spreads tissue to expand the width of the tunnel, or opening in the patient, that was formed by surgical instrument 1800. Surgical instrument 1900 does not increase the length of the tunnel.

Step 2120 includes removing surgical instrument 1900 from the small incision in the patient. After surgical instrument 1900 has been advanced to marker 1916, surgical instrument 1900 can be removed from the small incision in the patient. When surgical instrument 1900 is removed, the tunnel created by surgical instruments 1700, 1800, and 1900 remains in the tissue of the patient.

Step 2122 includes inserting surgical instrument 2000 loaded with subcutaneous device 1600 through the small incision. Subcutaneous device 1600 is loaded onto surgical instrument 2000 so that housing 1602 is positioned within arm portion 2010, guide 1630 is positioned in guide track 2018, and prong 1606 is positioned in prong track 2016. Distal end 2004 of surgical instrument 2000 and prong 1606 are inserted first. Surgical instrument 2000 is inserted into the tunnel formed by surgical instruments 1700, 1800, and 1900.

Step 2124 includes advancing surgical instrument 2000 to the xiphoid process and/or a distal end of the sternum. A surgeon who is holding handle 2006 of surgical instrument 1900 can move surgical instrument 1900 into the tunnel formed by surgical instruments 1700, 1800, and 1900. Anatomical markers can be used to direct surgical instrument 2000. For example, surgical instrument 2000 may be directed toward the intercostal space between the fifth and sixth ribs, to the left of the sternum. As such, housing 1604 and prong 1606 are directed toward the intercostal space between the fifth and sixth ribs while clip 1604 is directed to the xiphoid process and/or sternum of the patient due to the angle (of about 15 degrees, for example) of clip 1604 with respect to housing 1602. A surgeon who is advancing surgical instrument 2000 directs pressure to a top of handle 2006 such that handle 2006 is being pushed down and insertion portion 2008 is being pushed up toward the xiphoid process and/or the sternum. Surgical instrument 2000 acts as an insertion device for subcutaneous device 1600. Surgical instrument 2000 is advanced into the tunnel, or opening in the patient, that was formed by surgical instruments 1700, 1800, and 1900 until clip 1604 of subcutaneous device 1600 reaches the xiphoid process and/or sternum.

Step 2126 includes positioning surgical instrument 2000 adjacent to the xiphoid process and/or the distal end of the sternum to deploy subcutaneous device 1600 onto the xiphoid process and/or the distal end of the sternum. Clip 1604 and housing 1602 surround xiphoid process and/or the distal end of the sternum such that the xiphoid process and/or distal end of the sternum is positioned between clip 1604 and housing 1602. Prong 1606 of subcutaneous device 1600 will be positioned beneath the xiphoid process and/or distal end of the sternum.

Step 2128 includes anchoring subcutaneous device 1600 to the xiphoid process and/or the distal end of the sternum. Clip 1604 may be fixed to the xiphoid process and/or distal end of the sternum to anchor subcutaneous device 1600. When subcutaneous device 1600 is implanted on the xiphoid process and/or distal end of the sternum, electrode 1642 of prong 1606 can, for example, be positioned on the right ventricle of the heart. For another example, when surgical instrument 2000 is loaded with subcutaneous device 2300 (described with respect to FIGS. 56-58 and step 2106), a prong 2306A drops down to contact the right ventricle of the heart and subsequently a prong 2306 drops down to contact the left ventricle in the same injection process as surgical instrument 2000 is removed. A surgeon can check and adjust the placement of prong 1606 as needed during implantation of subcutaneous device 1600.

Step 2130 includes removing surgical instrument 2000 from the small incision in the patient. After subcutaneous device 1600 has been anchored to the xiphoid process and/or distal end of the sternum, surgical instrument 2000 can be removed from the small incision in the patient. When surgical instrument 2000 is removed, subcutaneous device 1600 will remain anchored to the xiphoid process and/or distal end of the sternum. The tissue forming the tunnel created by surgical instruments 1700, 1800, and 1900 will relax around subcutaneous device 1600.

Method 2100 is a non-invasive surgery. Leads are not implanted in the vasculature of the patient using invasive techniques. Rather, subcutaneous device 1600 is inserted into the patient and anchored to the xiphoid process and/or distal end of the sternum using surgical instruments 1700, 1800, and 1900. Surgical instruments 1700, 1800, and 1900 are used to spread tissue to progressively create and expand a single tunnel within the tissue of the patient. Prong 1606 extends through the patient to contact remote body component B, such as through the anterior mediastinum to come into contact with the heart. Method 2100 can be carried out using localized anesthesia and does not require fluoroscopy or additional visualization tools. This lowers the risk of infection, complications during surgery, and potential failure of the device. Method 2100 can also be carried out in a variety of environments, such as in an ambulance or any other suitable location. Method 2100 can be used to implant subcutaneous device 1600 on any bone, muscle, or tissue in the body of a patient. In an alternate embodiment, any suitable method, including traditional surgical methods, and any suitable instrument can be used to implant subcutaneous device 1600.

Forming a tunnel in a step-wise fashion using a series of surgical instruments 1700, 1800, and 1900 quickly and safely creates a smaller, more tailored spaced for subcutaneous device 1600 prior to insertion of subcutaneous device 1600, which reduces trauma to the patient and properly positions subcutaneous device 1600. Further, a narrow tunnel reduces open space around the heart so that subcutaneous device 1600 cannot migrate. Additionally, surgical instruments 1700, 1800, and 1900 spread, rather than cut, the tissue. As a result, the tissue that has been spread to form the tunnel quickly and easily relaxes back around subcutaneous device 1600, which further holds subcutaneous device 1600 in place. Because subcutaneous device 1600 is anchored to the xiphoid process and/or sternum of the patient, which is close to the skin of the patient, insertion of surgical instruments 1700, 1800, and 1900 creates a tunnel near the xiphoid process, where space exists. Surgical instruments 1700, 1800, and 1900 are broader in areas where surgical instruments 1700, 1800, and 1900 will be advanced closer to the xiphoid process and/or sternum, where there is less tissue. Surgical instruments 1700, 1800, and 1900 are narrower in areas where surgical instruments 1700, 1800, and 1900 will be advanced closer to the heart, where there is more tissue. As such, surgical instruments 1700, 1800, 1900, and 2000 are shaped to enhance the safety of method 2100.

Subcutaneous Device 2200

FIG. 52 is a side view of subcutaneous device 2200 anchored to a structural body component A. Subcutaneous device 2200 includes housing 2202, clip 2204, and prong 2206.

Subcutaneous device 2200 is a medical device that is configured to be anchored to structural body component A, which may be a muscle, a bone, or a tissue of a patient. Subcutaneous device 2200 can be a monitoring device, a diagnostic device, a therapeutic device, or any combination thereof. For example, subcutaneous device 2200 can be a pacemaker device that is capable of monitoring a patient's heart rate, diagnosing an arrhythmia of the patient's heart, and providing therapeutic electrical stimulation to the patient's heart. Subcutaneous device 2200 includes housing 2202. Housing 2202 of subcutaneous device 2200 may include sensing circuitry 180, controller 182, memory 184, therapy circuitry 186, electrode(s) 188, sensor(s) 190, transceiver 192, and power source 194 as described with respect to FIG. 7 and/or any other component of a medical device.

Clip 2204 is attached to housing 2202. Clip 2204 is configured to anchor subcutaneous device 2200 to structural body component A. Clip 2204 moves vertically within housing 2202 between an open position and a closed position. Clip 2204 is moved vertically away from housing 2202 when clip 2204 is in an open position. Clip 2204 will be in an open position as it is advanced around structural body component A. Clip 2204 is an active clip. In addition to using the stiffness of clamping components to attach to the bone, the muscle, or the tissue, clip 2204 uses an active fixation method such as tines and/or screws, and/or any other suitable anchoring structure to secure clip 2204 to the bone, the muscle, or the tissue. Clip 2204 is moved vertically toward housing 2202 to change clip 2204 from an open position to a closed position. Clip 2204 is shown in FIG. 52 in a closed position around structural body component A to clamp around structural body component A and anchor subcutaneous device 2200 to structural body component A.

Prong 2206 is connected to and extends away from housing 2202 of subcutaneous device 2200. Prong 2206 is configured to contact remote body component B that is positioned away from structural body component A. Remote body component B may be an organ, a nerve, or tissue of the patient. For example, remote body component B can include a heart, a lung, or any other suitable organ in the body. Prong 2206 includes an electrode that is capable of sensing an electrical activity or physiological parameter of remote body component B and/or providing therapeutic electrical stimulation to remote body component B.

In one example, subcutaneous device 2200 can be a pacemaker and the electrode on prong 2206 of subcutaneous device 2200 can sense the electrical activity of a heart. The sensed electrical activity can be transmitted to sensing circuitry and a controller in housing 2202 of subcutaneous device 2200. The controller can determine the heart rate of the patient and can detect whether an arrhythmia is present. If an arrhythmia is detected, the controller can send instructions to therapeutic circuitry to provide a therapeutic electrical stimulation to the heart. In this manner, subcutaneous device 2200 functions as a monitoring device, a diagnostic device, and a therapeutic device.

Subcutaneous device 2200 will be discussed in greater detail in relation to FIGS. 53A-55B below. Subcutaneous device 2200 will be discussed as a pacemaker that can be used for monitoring, diagnostics, and therapeutics in the discussion of FIGS. 53A-55B below. In this embodiment, subcutaneous device 2200 is a unipolar pacemaker. In alternate embodiments, subcutaneous device 2200 may be a bipolar pacemaker. Subcutaneous device 2200 can also be a monitoring device, a diagnostic device, an implantable cardioverter-defibrillator, a general organ/nerve/tissue stimulator, and/or a drug delivery device.

FIG. 53A is a top perspective view of subcutaneous device 2200. FIG. 53B is a side view of subcutaneous device 2200. FIG. 53C is a top view of subcutaneous device 2200. FIG. 53D is a bottom view of subcutaneous device 2200. FIG. 53E is a back view of subcutaneous device 2200. FIG. 53F is a front view of subcutaneous device 2200. Subcutaneous device 2200 includes housing 2202, clip 2204, and prong 2206. Housing 2202 includes first side 2210, second side 2212, top side 2214, bottom side 2216, front end 2218, back end 2220, housing latch 2222, and guide 2230. Clip 2204 includes top portion 2240, bottom portion 2242, and tines 2244. Prong 2206 includes proximal end 2260, distal end 2262, base portion 2264, arm portion 2268, contact portion 2270, electrode 2272, sleeve 2274 (which includes upper portion 2276 and lower portion 2278), wire 2280, structural tube 2282, and structural tube 2284.

Subcutaneous device 2200 includes housing 2202, clip 2204, and prong 2206 as described in reference to FIG. 52. Housing 2202 can be made out of stainless steel, titanium, nitinol, epoxy, silicone, polyurethane with metallic reinforcements, or any other material that is suitable for non-porous implants. Housing 2202 can also include an exterior coating. Clip 2204 can be made out of stainless steel, titanium, nitinol, epoxy, silicone, polyurethane with metallic reinforcements, or any other material that is suitable for non-porous implants. Prong 2206 can be made out of nickel titanium, also known as Nitinol. Nitinol is a shape memory alloy with superelasticity, allowing prong 2206 to go back to its original shape and position if prong 2206 is deformed as subcutaneous device 2200 is implanted into a patient. Prong 2206 can also be made out of silicone, polyurethane, stainless steel, titanium, epoxy, polyurethane with metallic reinforcements, or any other material that is suitable for non-porous implants. As an example, prong 2206 can be made out of a composite made of polyurethane and silicone and reinforced with metal to provide spring stiffness.

Housing 2202 includes first side 2210, second side 2212, top side 2214, bottom side 2216, front end 2218, back end 2220, housing latch 2222, and guide 2230. First side 2210 is opposite of second side 2212. Top side 2214 is a top of housing 2202 opposite of bottom side 2216, which is a bottom of housing 2202. Front end 2218 is opposite of back end 2220. Housing 2202 is substantially rectangular-shaped in the embodiment shown. In alternate embodiments, housing 2202 can be shaped as a cone, frustum, or cylinder. Housing 2202 can be made out of stainless steel, titanium, Nitinol, epoxy, silicone, polyurethane with metallic reinforcements, or any other material that is suitable for non-porous implants. Housing 2202 can also include an exterior coating.

Housing latch 2222 is connected to back end 2220 of housing 2202. Housing latch 2222 has a top portion that extends along back end 2220 of housing and a bottom portion that extends along bottom side 2216 of housing 2220. The top portion of housing latch 2222 is configured to engage with clip 2204. The bottom portion of housing latch 2222 is curved to accept prong 2206. As such, housing latch 2222 engages with clip 2204 along back end 2220 of housing and with prong 2206 along bottom side 2216 of housing 2202. Housing latch 2222 is configured to attach prong 2206 to bottom side 2216 of housing 2202. Guide 2230 is an L-shaped rod that is connected to back end 2220 and first side 2210 of housing 2202. In this embodiment, guide 2230 is closer to top side 2214 than bottom side 2216 of housing 2202. Guide 2230 is configured to guide housing 2202 of subcutaneous device 2200 through a surgical instrument used to implant subcutaneous device 2200 into a patient.

Clip 2204 includes top portion 2240, bottom portion 2242, and tines 2244. Top portion 2240 is connected to bottom portion 2242. Top portion 2240 forms a top of clip 2204 and is a flat portion of clip 2204 that extends across top side 2214 of housing 2202. Bottom portion 2242 forms a bottom of clip 2204 and is a flat portion that extends along back end 2220 of housing 2202. Bottom portion 2242 of clip 2204 is configured to be attached to housing 2202 and mate with housing latch 2222. Bottom portion 2242 of clip 2204 has pins extending from a back end that are configured to engage with slots in the top portion of housing latch 2222. As such, clip 2204 is connected to housing 2202 via housing latch 2222. Tines 2244 extend from top portion 2240 of clip 2204. Tines 2244 have first ends connected to a center portion of top portion 2240 and second ends that extend away from top portion 2240 toward top side 2214 of housing 2202. Tines 2244 are curved and extend in different directions. Tines 2244 are thin and may be made of metal or any other suitable material. In this embodiment, clip 2204 has four tines 2244. In alternate embodiments, clip 2204 may have any number of tines 2244. Further, in alternate embodiments, any other suitable anchoring structures or active fixation methods may be used along with or instead of tines 2244. Tines 2244 are configured to pierce and anchor to structural body component A.

When clip 2204 is connected to back end 2220 of housing 2202, top portion 2240 of clip 2204 extends along top side 2214 of housing 2202. In this embodiment, top portion 2240 of clip 2204 extends at an angle to the length of housing 2202 from back end 2220 to front end 2218. In alternate embodiments, top portion 2240 of clip 2204 may extend at any angle to the length of housing 2202.

An opening is formed between top portion 2240 of clip 2204 and top side 2214 of housing 2202. Clip 2204 is movable between an open position and a closed position to change the height of the opening. When clip 2204 is in an open position, the opening is expanded and subcutaneous device 2200 is inserted into a patient such that the opening is positioned around the muscle, the bone, or the tissue. After subcutaneous device 2200 is positioned on the muscle, the bone, or the tissue, clip 2204 is moved into a closed position. When clip 2204 is in a closed position, the opening is reduced. Bottom portion 2242 of clip 2204 and housing latch 2222 form a ratchet mechanism to move clip 2204 into the open and closed positions. Top portion 2240 of clip 2204 is forced toward top side 2214 of housing 2202 and down onto the muscle, the bone, or the tissue. Tines 2244 attach to the muscle, the bone, or the tissue, which anchors clip 2204 to the muscle, the bone, or the tissue. Tines 2244 will pierce the muscle, the bone, or the tissue in response to pressure from the engagement of bottom portion 2242 of clip 2204 with housing latch 2222. Tines 2244 may contact top side 2214 of housing such that tines 2244 bend back around into the muscle, the bone, or the tissue and further secure and anchor clip 2204 and subcutaneous device 2200 to the muscle, the bone, or the tissue. Tines 2244 are also removable from the muscle, the bone, or the tissue, such that subcutaneous device 2200 is easily removable from structural body component A.

Prong 2206 includes proximal end 2260 and distal end 2262, which is opposite of proximal end 2260. Prong 2206 includes base portion 2264, arm portion 2268, and contact portion 2270. A first end of base portion 2264 is aligned with proximal end 2260 of prong 2206, and a second end of base portion 2264 is connected to a first end of arm portion 2268. Base portion 2264 is a straight, planar portion that is positioned against and extends along bottom side 2216 of housing 2202. Base portion 2264 is attached to housing 2202. Housing latch 2222 extends around base portion 2264 of prong 2206 to secure base portion 2264 of prong 2206 to housing 2202. Base portion 2264 extends through housing latch 2222. As such, proximal end 2260 of prong 2206 is attached to housing 2202. Base portion 2264 of prong 2206 is electrically connected to the internal components of housing 2202, for example with a feedthrough, to which prong 2206 is also connected.

The first end of arm portion 2268 is connected to the second end of base portion 2264, and a second end of arm portion 2268 is connected to a first end of contact portion 2270. As such, arm portion 2268 extends from base portion 2264 so as to define a first plane that includes opposite ends, or first end and second end, of arm portion 2268 and is perpendicular to the horizontal plane of housing 2202 such that the first plane is a vertical plane that bisects housing 2202 longitudinally from front end 2218 to back end 2220 and is perpendicular to top side 2214 and bottom side 2216. Arm portion 2268 also extends past front end 2218 of housing 2202 so that contact portion 2270 is positioned outwards from front end 2218 of housing 2202. In this embodiment, arm portion 2268 is a predominantly straight portion that is planar and aligned with base portion 2264. The first end of arm portion 2268 acts as a spring for prong 2206 and is under tension. Arm portion 2268 acts as a tension arm and the forces from the first end of arm portion 2268 translate to and push down on the second end of arm portion 2268. As such, prong 2206 undergoes spring action in a vertical plane perpendicular to the horizontal plane of housing 2202 and has a reduced spring action in a horizontal plane parallel to the horizontal plane of housing 2202 due to high lateral stiffness of the planar arm portion 2268. In alternate embodiments, arm portion 2268 of prong 2206 can extend from housing 2202 in any direction or directions.

The first end of contact portion 2270 is connected to the second end of arm portion 2268, and a second end of contact portion 2270 is aligned with distal end 2262 of prong 2206. As such, arm portion 2268 is between base portion 2264 and contact portion 2270. Arm portion 2268 extends beyond front end 2218 of housing 2202 so that contact portion 2270 is positioned beyond front end 2218 of housing 2202. Contact portion 2270 can be positioned such that distal end 2262 of prong 2206 contacts remote body component B (shown in FIG. 52). Contact portion 2270 is angled with respect to housing 2202 and arm portion 2268. Contact portion 2270 is angled away from the first plane defined with respect to the arm portion 2268 and housing 2202. In this embodiment, contact portion 2270 is angled away from bottom side 2216 of housing 2202. Contact portion 2270 is also curved, or angled, away from first side 2210 of housing 2202. Contact portion 2270 extends away from bottom side 2216 of housing 2202 and extends away from first side 2210 of housing 2202 so that distal end 2262 of prong 2206 is positioned below and away from housing 2202 and arm portion 2268. In alternate embodiments, contact portion 2270 may be angled in any direction with respect to bottom side 2216 of housing 2202 and in any direction with respect to first side 2210 and second side 2212 of housing 2202 depending on the location of remote body component B with respect to structural body component A. Contact portion 2270 is angled toward remote body component B. For example, when remote body component B is a lung or a kidney, contact portion 2270 is angled toward the lung or the kidney. In this embodiment, a first portion of contact portion 2270 is angled about 90 degrees from bottom side 2216 of housing 2202 and arm portion 2268, and a second portion of contact portion 2270 is angled about 90 degrees from first side 2210 of housing 2202 and arm portion 2268. Contact portion 2270 may be angled about 45 degrees to about 60 degrees from the first vertical plane defined with respect to arm portion 2268 and housing 2202.

Prong 2206 further includes electrode 2272. Electrode 2272 is at distal end 2262 of prong 2206. As such, electrode 2272 makes up the second end of contact portion 2270. Electrode 2272 has a rounded end and has the same shape as electrode 1672A described in reference to FIGS. 42A and 42B. In alternate embodiments, electrode 2272 may have any suitable shape, such as any of the shapes of electrodes 1672, 1672B, and 1672C. Prong 2206 has a single electrode 2272 in the embodiment shown in FIGS. 53A-53F. Prong 2206 can have any number of electrodes in alternate embodiments. Electrode 2272 is positioned at distal end 2262 of prong 2206 to sense an electrical activity or physiological status of remote body component B. Electrode 2272 can also provide therapeutic electrical stimulation to remote body component B.

Sleeve 2274 is a hollow outer portion of prong 2206. Sleeve 2274 extends from proximal end 2260 of prong 2260 to contact portion 2270. A first end of sleeve 2274 is aligned with proximal end 2260 of prong 2206. Sleeve 2274 extends along base portion 2264, arm portion 2268, and a first portion of contact portion 2270. A second end of sleeve 2274 is within contact portion 2270. As such, sleeve 2274 makes up the outer portions of base portion 2264, arm portion 2268, and the first portion of contact portion 2270. Sleeve 2274 has upper portion 2276 opposite lower portion 2278. Upper portion 2276 and lower portion 2278 are flat, or planar, such that sleeve 2274 has a flat, or generally rectangular, cross-section. As such, a majority of prong 2206 has a flat, or generally rectangular, cross-section.

Wire 2280 extends through sleeve 2274, between upper portion 2276 and lower portion 2278, from proximal end 2260 of prong 2206 to contact portion 2270. Wire 2280 extends beyond the second end of sleeve 2274. A first end of wire 2280 is aligned with proximal end 2260 of prong 2206. Wire 2280 extends along base portion 2264, arm portion 2268, and contact portion 2270. A second end of wire 2280 is connected to electrode 2272. As such, contact portion 2270 of prong 2206 is made up of sleeve 2274, wire 2280, and electrode 2272. Wire 2280 has the same overall shape and angle as sleeve 2274 and extends beyond the second end of sleeve 2274. Wire 2280 extends away from the second end of sleeve 2274 and first side 2210 of housing 2202. In this embodiment, wire 2280 extends about 90 degrees away from the second end of sleeve 2274. As such, in this embodiment, wire 2280 is angled away from bottom side 2216 of housing 2202 along with sleeve 2274 and curved, or angled, away from first side 2210 of housing 2202 beyond sleeve 2274.

Structural tubes 2282 and 2284 may be configured like structural tubes 1682 and 1684 as shown in FIGS. 40A-40E. Structural tubes 2282 and 2284 extend through sleeve 2274, between upper portion 2276 and lower portion 2278 and along wire 2280. Structural tubes 2282 and 2284 extend from proximal end 2260 of prong 2260 to the second end of arm portion 2268. First ends of structural tubes 2282 and 2284 are aligned with proximal end 2260 of prong 2206. Structural tubes 2282 and 2284 extend along base portion 2264 and arm portion 2268. Second ends of structural tubes 2282 and 2284 are aligned with the second end of arm portion 2268. In alternate embodiments, structural tubes 2282 and 2284 may extend into contact portion 2270 to the second end of sleeve 2274 such that second ends of structural tubes 2282 and 2284 are aligned with the second end of sleeve 2274. Structural tubes 2282 and 2284 have the same overall shape as base portion 2264 and arm portion 2268. As such, in this embodiment, structural tubes 2282 and 2284 are planar.

First structural tube 2282 is on a first side of wire 2280, and second structural tube 2284 is on a second side of wire 2280 such that wire 2280 has structural tubes 2282 and 2284 on opposite sides of wire 2280. In alternate embodiments, prong 2206 may include any number of structural tubes 2282 and 2284 based on the desired stiffness of prong 2206. Structural tubes 2282 and 2284 may be hollow or solid. Structural tubes 2282 and 2284 can be any suitable size. For example, structural tubes 2282 and 2284 can have the same diameters as each other, can have the same diameter as wire 2280, or can have a smaller diameter than wire 2280. Structural tubes 2282 and 2284 can have any suitable thickness based on desired stiffness of prong 2206. Structural tubes 2282 and 2284 may be made of metal, polyurethane, silicone, any suitable plastic, a combination of metal and plastic, or any other suitable material. Structural tubes 2282 and 2284 are limited to an amount of metal that allows subcutaneous device 2200 to be MRI compatible. In alternate embodiments, prong 2206 may include any number of structural tubes 2282 and 2284. The size, shape, and material of structural tubes 2282 and 2284 may be selected based upon the desired stiffness of prong 2206. For example, prong 2206 may include five, seven, or any other suitable number of structural tubes 2282 and 2284 to make prong 2206 flatter and increase the stiffness of prong 2206.

Prong 2206 is angled with respect to housing 2202 to improve contact of electrode 2272 with remote body component B. Prong 2206 is angled so that contact portion 2270 pushes down against remote body component B, such as the heart. Electrode 2272 at distal end 2262 of prong 2206 contacts the heart and buries into the cardiac tissue. Further, because prong 2206 is angled down toward heart, prong 2206 applies pressure to the heart as the heart beats and moves up and down, without increasing the stiffness of prong 2206. As a result, electrode 2272 maintains contact with the heart without fixing electrode 2272 to the heart. For example, prong 2206 is prevented from bouncing off of the heart as the heart beats, which would cause intermittent contact that reduces functionality. Additionally, contact portion 2270 is angled away from bottom 2216 and first side 2210 of housing 2202 to ensure distal end 2262 of prong 2206 is positioned on the heart when subcutaneous device 2200 is attached to a xiphoid and/or sternum of a patient. As such, subcutaneous device 2200 can be inserted and deployed into a patient without requiring cardiac catheterization labs. Thus, the procedure for inserting the device is simple and only requires local anesthesia, which means it can be carried out in various environments, such as in an ambulance.

Arm portion 2268 of prong 2206 allows prong 2206 to be flexible once it is positioned in the body. The pivot point of arm portion 2268 is adjacent the first end of arm portion 2268, which is connected to the second end of base portion 2264, and slightly closer to proximal end 2260 than front end 2218 of housing 2202 is to proximal end 2206, or where prong 2206 is secured to bottom side 2216 of housing 2202 by housing latch 2222. For example, if remote body component B is the heart of the patient and contact portion 2270 of prong 2206 is positioned against the heart, arm portion 2268 of prong 2206 allows prong 2206 to move up and down with the heart as the heart beats. This ensures that prong 2206 does not puncture or damage the heart while contact portion 2270 of prong 2206 maintains contact with the heart. In this embodiment, electrode 2272 at distal end 2262 of prong 2206 has a rounded end to further prevent prong 2206 from puncturing or damaging the heart when contact portion 2270 of prong 2206 is in contact with the heart. The overall axial stiffness of prong 2206 can be adjusted so that prong 2206 gently presses against the heart and moves up and down in contact with the heart as the heart beats, but is not stiff or sharp enough to pierce or tear the pericardial or epicardial tissue. For example, the overall axial stiffness of prong 2206 can be adjusted by adjusting the material of prong 2206, the spring bias or mechanical resistance of prong 2206, the cross-sectional thickness of prong 2206, the angle of incidence of prong 2206 on remote body component B, the outer profile of prong 2206 where prong 2206 contacts remote body component B, and/or any other suitable characteristic of prong 2206.

The flat, or rectangular, cross-section of sleeve 2274 created by planar upper portion 2276 and planar lower portion 2278 provides stiffness to prong 2206, which makes prong 2206 more resistant to in-plane bending. Sleeve 2274 also provides space for wire 2280 to be surrounded by structural tubes 2282 and 2284. Structural tubes 2282 and 2284 also provide the desired structural stiffness to prong 2206. As a result, prong 2206 resists in-plane bending, or bending in any direction, to maintain positioning with respect to the heart, which ensures electrode 2272 maintains contact with the heart without requiring fluoroscopy or other visualization tools. In alternate embodiments, prong 2206 may include a pre-shaped spine made of shape-memory material, such as nitinol, to provide stiffness along with or instead of structural tubes 2282 and 2284. In these embodiments, prong 2206 may have the shape shown in FIG. 52, for example, or other suitable shapes or configurations.

Subcutaneous device 2200 is described here as having a single prong 2206. In alternate embodiments, subcutaneous device 2200 can include any number of prongs and those prongs can have any shape. For example, subcutaneous device 2200 can include any of the prongs shown and discussed in reference to FIGS. 1-37. Contact portion 2270 can have any angle with respect to bottom side 2216, first side 2210, and second side 2212 of housing 2202.

Subcutaneous device 2200 can function as a pacemaker. Prong 2206 can be shaped so that contact portion 2270 of prong 2206 contacts the right ventricle, left ventricle, right atrium, or left atrium of the heart. Subcutaneous device 2200 can function as a unipolar pacemaker, utilizing electrode 2272 on prong 2206. Further, subcutaneous device 2200 can function as a bipolar pacemaker, utilizing more than one prong 2206 and electrode 2272.

FIG. 54 is a top view of subcutaneous device 2200 positioned on xiphoid process X and/or sternum S. FIG. 55A is a perspective side view of subcutaneous device 2200 positioned on xiphoid process X and/or sternum S and showing a positioning of prong 2206 on heart H. FIG. 55B is a perspective side view of subcutaneous device 2200 positioned on xiphoid process X and/or sternum S and showing a positioning of prong 2206 on heart H. Subcutaneous device 2200 includes housing 2202, clip 2204, and prong 2206. Housing 2202 includes first side 2210 and bottom side 2216. Prong 2206 includes distal end 2262, arm portion 2268, contact portion 2270, electrode 2272, and sleeve 2274. FIGS. 54, 55A, and 55B also show xiphoid process X and sternum S. FIGS. 55A and 55B show heart H.

Subcutaneous device 2200 includes housing 2202, clip 2204, and prong 2206 as described above in reference to FIGS. 52-53F. In the embodiment shown in FIGS. 54-55B, subcutaneous device 2200 is configured to be a pacemaker used for cardiac monitoring, diagnostics, and/or therapeutics, such as subcutaneous device 100 described with respect to FIGS. 1-9C. In the embodiment shown in FIGS. 54-55B, subcutaneous device 2200 can be anchored to xiphoid process X and sternum S of a patient. Subcutaneous device 2200 can be implanted with a simple procedure where subcutaneous device 2200 is injected onto xiphoid process X and sternum S using a surgical instrument. For example, subcutaneous device 2200 can be deployed and anchored to xiphoid process X and sternum S using surgical instruments 1700, 1800, 1900, and 2000 and method 2100 described with respect to FIGS. 46A-51.

When subcutaneous device 2200 is anchored to xiphoid process X and sternum S via clip 2204, prong 2206 extends away from first side 2210 and bottom side 2216 of housing 2202. Contact portion 2270 extends away from bottom side 2216 and first side 2210 of housing 2202. As such, contact portion 2270 pushes down against heart H, and electrode 2272 at distal end 2262 of prong 2206 contacts heart H and maintains contact as heart H beats. Prong 2206 can be shaped so that prong 2206 contacts the right ventricle, left ventricle, right atrium, or left atrium of the heart. The overall desired stiffness of prong 2206 is achieved via structural tube 2282 and structural tube 2284 (described with respect to FIGS. 53A-53F) within sleeve 2274, which ensures that prong 2206 gently presses against heart H and moves up and down in contact with heart H as heart H beats, but is not stiff or sharp enough to pierce or tear the pericardial or epicardial tissue.

Prong 2206 is shaped to ensure prong 2206 is properly positioned against and will not lose contact with heart H. The surgical procedure for implanting subcutaneous device 2200 is less invasive than the surgical procedure required for more traditional pacemaker devices, as subcutaneous device is placed subcutaneously in the body. No leads need to be positioned in the vasculature of the patient, lowering the risk of thrombosis to the patient.

Subcutaneous Device 2300

FIG. 56 is a side view of subcutaneous device 2300 anchored to structural body component A. Subcutaneous device 2300 includes housing 2302, clip 2304, prong 2306, and prong 2306A.

Subcutaneous device 2300 is a medical device that is configured to be anchored to structural body component A, which may be a muscle, a bone, or a tissue of a patient. Subcutaneous device 2300 can be a monitoring device, a diagnostic device, a therapeutic device, or any combination thereof. For example, subcutaneous device 2300 can be a pacemaker device that is capable of monitoring a patient's heart rate, diagnosing an arrhythmia of the patient's heart, and providing therapeutic electrical stimulation to the patient's heart. Subcutaneous device 2300 includes housing 2302. Housing 2302 of subcutaneous device 2300 may include sensing circuitry 180, controller 182, memory 184, therapy circuitry 186, electrode(s) 188, sensor(s) 190, transceiver 192, and power source 194 as described with respect to FIG. 7 and/or any other component of a medical device.

Clip 2304 is attached to housing 2302. Clip 2304 is configured to anchor subcutaneous device 2300 to structural body component A. Clip 2304 moves vertically within housing 2302 between an open position and a closed position. Clip 2304 is moved vertically away from housing 2302 when clip 2304 is in an open position. Clip 2304 will be in an open position as it is advanced around structural body component A. Clip 2304 is an active clip. In addition to using the stiffness of clamping components to attach to the bone, the muscle, or the tissue, clip 2304 uses an active fixation method such as tines and/or screws, and/or any other suitable anchoring structure to secure clip 2304 to the bone, the muscle, or the tissue. Clip 2304 is moved vertically toward housing 2302 to change clip 2304 from an open position to a closed position. Clip 2304 is shown in FIG. 56 in a closed position around structural body component A to clamp around structural body component A and anchor subcutaneous device 2300 to structural body component A.

Prong 2306 and prong 2306A are connected to and extend away from housing 2302 of subcutaneous device 2300. In the embodiment shown in FIG. 56, prong 2306A is positioned above prong 2306 such that prong 2306A is between prong 2306 and housing 2302. In alternate embodiments, prong 2306A may be positioned next to prong 2306, as shown in FIG. 57G. Prong 2306 and prong 2306A are configured to contact remote body component B that is positioned away from structural body component A. In alternate embodiments, prong 2306A may be configured to contact a different remote body component B that is positioned away from structural body component A and remote body component B that prong 2306 contacts. Remote body component B may be an organ, a nerve, or tissue of the patient. For example, remote body component B can include a heart, a lung, or any other suitable organ in the body. Prong 2306 and prong 2306A each include an electrode that is capable of sensing an electrical activity or physiological parameter of remote body component B and/or providing therapeutic electrical stimulation to remote body component B.

In one example, subcutaneous device 2300 can be a pacemaker and the electrodes on prong 2306 and prong 2306A of subcutaneous device 2300 can sense the electrical activity of a heart. The sensed electrical activity can be transmitted to sensing circuitry and a controller in housing 2302 of subcutaneous device 2300. The controller can determine the heart rate of the patient and can detect whether an arrhythmia is present. If an arrhythmia is detected, the controller can send instructions to therapeutic circuitry to provide a therapeutic electrical stimulation to the heart. In this manner, subcutaneous device 2300 functions as a monitoring device, a diagnostic device, and a therapeutic device.

Subcutaneous device 2300 will be discussed in greater detail in relation to FIGS. 57A-58 below. Subcutaneous device 2300 will be discussed as a pacemaker that can be used for monitoring, diagnostics, and therapeutics in the discussion of FIGS. 57A-58 below. In this embodiment, subcutaneous device 2300 is a unipolar pacemaker. In alternate embodiments, subcutaneous device 2300 may be a bipolar pacemaker. Subcutaneous device 2300 can also be a monitoring device, a diagnostic device, an implantable cardioverter-defibrillator, a general organ/nerve/tissue stimulator, and/or a drug delivery device.

FIG. 57A is a perspective view of subcutaneous device 2300. FIG. 57B is a side view of subcutaneous device 2300. FIG. 57C is a top view of subcutaneous device 2300. FIG. 57D is a bottom view of subcutaneous device 2300. FIG. 57E is a back view of subcutaneous device 2300. FIG. 57F is a front view of subcutaneous device 2300. FIG. 57G is a perspective view of subcutaneous device 2300 showing prongs 2306 and 2306A positioned side-by-side. Subcutaneous device 2300 includes housing 2302, clip 2304, prong 2306, and prong 2306A. Housing 2302 includes first side 2310, second side 2312, top side 2314, bottom side 2316, front end 2318, back end 2320, housing latch 2322, and guide 2330. Clip 2304 includes top portion 2340, bottom portion 2342, and tines 2344. Prong 2306 includes proximal end 2360, distal end 2362, base portion 2364, arm portion 2368, contact portion 2370, electrode 2372, sleeve 2374 (which includes upper portion 2376 and lower portion 2378), wire 2380, structural tube 2382, and structural tube 2384. Prong 2306A includes proximal end 2360A, distal end 2362A, base portion 2364A, arm portion 2368A, contact portion 2370A, electrode 2372A, sleeve 2374A (which includes upper portion 2376A and lower portion 2378A), wire 2380A, structural tube 2382A, and structural tube 2384A.

Subcutaneous device 2300 includes housing 2302, clip 2304, prong 2306 and prong 2306A as described in reference to FIG. 56. Housing 2302 can be made out of stainless steel, titanium, nitinol, epoxy, silicone, polyurethane with metallic reinforcements, or any other material that is suitable for non-porous implants. Housing 2302 can also include an exterior coating. Clip 2304 can be made out of stainless steel, titanium, nitinol, epoxy, silicone, polyurethane with metallic reinforcements, or any other material that is suitable for non-porous implants. Prongs 2306 and 2306A can be made out of nickel titanium, also known as Nitinol. Nitinol is a shape memory alloy with superelasticity, allowing prongs 2306 and 2306A to go back to their original shapes and positions if prongs 2306 and/or 2306A are deformed as subcutaneous device 2300 is implanted into a patient. Prong 2306 and 2306A can also be made out of silicone, polyurethane, stainless steel, titanium, epoxy, polyurethane with metallic reinforcements, or any other material that is suitable for non-porous implants. As an example, prong 2306 and/or prong 2306A can be made out of a composite made of polyurethane and silicone and reinforced with metal to provide spring stiffness.

Housing 2302 includes first side 2310, second side 2312, top side 2314, bottom side 2316, front end 2318, back end 2320, housing latch 2322, and guide 2330. First side 2310 is opposite of second side 2312. Top side 2314 is a top of housing 2302 opposite of bottom side 2316, which is a bottom of housing 2302. Bottom side 2316 of housing 2302 may be shaped to form a channel that accepts prong 2306A (as shown in FIGS. 56-57F), or prong 2306A may be attached to bottom side 2316 of housing 2302 with a latch. Prongs 2306 and 2306A may also be positioned side-by-side and attached to bottom side 2316 of housing 2302 with a latch (as shown in FIG. 57G), or within a channel. Front end 2318 is opposite of back end 2320. Housing 2302 is substantially rectangular-shaped in the embodiment shown. In alternate embodiments, housing 2302 can be shaped as a cone, frustum, or cylinder. Housing 2302 can be made out of stainless steel, titanium, Nitinol, epoxy, silicone, polyurethane with metallic reinforcements, or any other material that is suitable for non-porous implants. Housing 2302 can also include an exterior coating.

Housing latch 2322 is connected to back end 2320 of housing 2302. Housing latch 2322 has a top portion that extends along back end 2320 of housing and a bottom portion that extends along bottom side 2316 of housing 2320. The top portion of housing latch 2322 is configured to engage with clip 2304. The bottom portion of housing latch 2322 is curved to accept prong 2306, and in some embodiments prong 2306A. For example, housing latch 2322 may accept prong 2306 and prong 2306A when prong 2306 and prong 2306A are positioned side-by-side, as shown in FIG. 57G. As such, housing latch 2322 engages with clip 2304 along back end 2320 of housing and with prong 2306, and sometimes prong 2306A, along bottom side 2316 of housing 2302. Housing latch 2322 is configured to attach prongs 2306 and 2306A to bottom side 2216 of housing 2302. Guide 2330 is an L-shaped rod that is connected to back end 2320 and first side 2310 of housing 2302. In this embodiment, guide 2330 is closer to top side 2314 than bottom side 2316 of housing 2302. Guide 2330 is configured to guide housing 2302 of subcutaneous device 2300 through a surgical instrument used to implant subcutaneous device 2300 into a patient.

Clip 2304 includes top portion 2340, bottom portion 2342, and tines 2344. Top portion 2340 is connected to bottom portion 2342. Top portion 2340 forms a top of clip 2304 and is a flat portion of clip 2304 that extends across top side 2314 of housing 2302. Bottom portion 2342 forms a bottom of clip 2304 and is a flat portion that extends along back end 2320 of housing 2302. Bottom portion 2342 of clip 2304 is configured to be attached to housing 2302 and mate with housing latch 2322. Bottom portion 2342 of clip 2304 has pins extending from a back end that are configured to engage with slots in the top portion of housing latch 2322. As such, clip 2304 is connected to housing 2302 via housing latch 2322. Tines 2344 extend from top portion 2340 of clip 2304. Tines 2344 have first ends connected to a center portion of top portion 2340 and second ends that extend away from top portion 2340 toward top side 2314 of housing 2302. Tines 2344 are curved and extend in different directions. Tines 2344 are thin and may be made of metal or any other suitable material. In this embodiment, clip 2304 has four tines 2344. In alternate embodiments, clip 2304 may have any number of tines 2344. Further, in alternate embodiments, any other suitable anchoring structures or active fixation methods may be used along with or instead of tines 2344. Tines 2344 are configured to pierce and anchor to structural body component A.

When clip 2304 is connected to back end 2320 of housing 2302, top portion 2340 of clip 2304 extends along top side 2314 of housing 2302. In this embodiment, top portion 2340 of clip 2304 extends at an angle to the length of housing 2302 from back end 2320 to front end 2318. In alternate embodiments, top portion 2340 of clip 2304 may extend at any angle to the length of housing 2302.

An opening is formed between top portion 2340 of clip 2304 and top side 2314 of housing 2302. Clip 2304 is movable between an open position and a closed position to change the height of the opening. When clip 2304 is in an open position, the opening is expanded and subcutaneous device 2300 is inserted into a patient such that the opening is positioned around the muscle, the bone, or the tissue. After subcutaneous device 2300 is positioned on the muscle, the bone, or the tissue, clip 2304 is moved into a closed position. When clip 2304 is in a closed position, the opening is reduced. Bottom portion 2342 of clip 2304 and housing latch 2322 form a ratchet mechanism to move clip 2304 into the open and closed positions. Top portion 2340 of clip 2304 is forced toward top side 2314 of housing 2302 and down onto the muscle, the bone, or the tissue. Tines 2344 attach to the muscle, the bone, or the tissue, which anchors clip 2304 to the muscle, the bone, or the tissue. Tines 2344 will pierce the muscle, the bone, or the tissue in response to pressure from the engagement of bottom portion 2342 of clip 2304 with housing latch 2322. Tines 2344 may contact top side 2314 of housing such that tines 2344 bend back around into the muscle, the bone, or the tissue and further secure and anchor clip 2304 and subcutaneous device 2300 to the muscle, the bone, or the tissue. Tines 2344 are also removable from the muscle, the bone, or the tissue, such that subcutaneous device 2300 is easily removable from structural body component A.

Prong 2306 includes proximal end 2360 and distal end 2362, which is opposite of proximal end 2360. Prong 2306 includes base portion 2364, arm portion 2368, and contact portion 2370. A first end of base portion 2364 is aligned with proximal end 2360 of prong 2306, and a second end of base portion 2364 is connected to a first end of arm portion 2368. Base portion 2364 is a straight, planar portion that is positioned against and extends along bottom side 2316 of housing 2302 and a bottom of prong 2306A when prong 2306A is positioned above prong 2306. Base portion 2364 is attached to housing 2302. Housing latch 2322 extends around base portion 2364 of prong 2306 to secure base portion 2364 of prong 2306 to housing 2302. Base portion 2364 extends through housing latch 2322. As such, proximal end 2360 of prong 2306 is attached to housing 2302. Base portion 2364 of prong 2306 is electrically connected to the internal components of housing 2302, for example with a feedthrough, to which prong 2306 is also connected.

The first end of arm portion 2368 is connected to the second end of base portion 2364, and a second end of arm portion 2368 is connected to a first end of contact portion 2370. As such, arm portion 2368 extends from base portion 2364 so as to define a first plane that includes opposite ends, or first end and second end, of arm portion 2368 and is perpendicular to the horizontal plane of housing 2302 such that the first plane is a vertical plane that bisects housing 1602 longitudinally from front end 1618 to back end 1620 and is perpendicular to top side 1614 and bottom side 1616. Arm portion 2368 also extends past front end 2318 of housing 2302 so that contact portion 2370 is positioned outwards from front end 2318 of housing 2302. In this embodiment, arm portion 2368 is a predominantly straight portion that is planar and aligned with base portion 2364. The first end of arm portion 2368 acts as a spring for prong 2306 and is under tension. Arm portion 2368 acts as a tension arm and the forces from the first end of arm portion 2368 translate to and push down on the second end of arm portion 2368. In alternate embodiments, arm portion 2368 of prong 2306 can extend from housing 2302 in any direction or directions.

The first end of contact portion 2370 is connected to the second end of arm portion 2368, and a second end of contact portion 2370 is aligned with distal end 2362 of prong 2306. As such, arm portion 2368 is between base portion 2364 and contact portion 2370. Arm portion 2368 extends beyond front end 2318 of housing 2302 so that contact portion 2370 is positioned beyond front end 2318 of housing 2302. Contact portion 2370 can be positioned such that distal end 2362 of prong 2306 contacts remote body component B (shown in FIG. 56). Contact portion 2370 is angled with respect to housing 2302 and arm portion 2368. Contact portion 2370 is angled away from the first plane defined with respect to arm portion 2368 and housing 2302. In this embodiment, contact portion 2370 is angled away from bottom side 2316 of housing 2302. Contact portion 2370 is also curved, or angled, away from first side 2310 of housing 2302. Contact portion 2370 extends away from bottom side 2316 of housing 2302 and extends away from first side 2310 of housing 2302 so that distal end 2362 of prong 2306 is positioned below and away from housing 2302 and arm portion 2368. In alternate embodiments, contact portion 2370 may be angled in any direction with respect to bottom side 2316 of housing and in any direction with respect to first side 2310 and second side 2312 of housing 2302 depending on the location of remote body component B with respect to structural body component A. Contact portion 2370 is angled toward remote body component B. For example, when remote body component B is a lung or a kidney, contact portion 2370 is angled toward the lung or the kidney. In this embodiment, a first portion of contact portion 2370 is angled about 90 degrees from bottom side 2316 of housing 2302 and arm portion 2368, and a second portion of contact portion 2370 is angled about 90 degrees from first side 2310 of housing 2302 and arm portion 2368. Contact portion 2370 may be angled about 45 degrees to about 60 degrees from the first vertical plane defined with respect to arm portion 2368 and housing 2302.

Prong 2306 further includes electrode 2372. Electrode 2372 is at distal end 2362 of prong 2306. As such, electrode 2372 makes up the second end of contact portion 2370. Electrode 2372 has a rounded end and has the same shape as electrode 1672A described in reference to FIGS. 42A and 42B. In alternate embodiments, electrode 2372 may have any suitable shape, such as any of the shapes of electrodes 1672, 1672B, and 1672C. Prong 2306 has a single electrode 2372 in the embodiment shown in FIGS. 57A-57F. Prong 2306 can have any number of electrodes in alternate embodiments. Electrode 2372 is positioned at distal end 2362 of prong 2306 to sense an electrical activity or physiological status of remote body component B. Electrode 2372 can also provide therapeutic electrical stimulation to remote body component B.

Sleeve 2374 is a hollow outer portion of prong 2306. Sleeve 2374 extends from proximal end 2360 of prong 2360 to contact portion 2370. A first end of sleeve 2374 is aligned with proximal end 2360 of prong 2306. Sleeve 2374 extends along base portion 2364, arm portion 2368, and a first portion of contact portion 2370. A second end of sleeve 2374 is within contact portion 2370. As such, sleeve 2374 makes up the outer portions of base portion 2364, arm portion 2368, and the first portion of contact portion 2370. Sleeve 2374 has upper portion 2376 opposite lower portion 2378. Upper portion 2376 and lower portion 2378 are flat, or planar, such that sleeve 2374 has a flat, or generally rectangular, cross-section. As such, a majority of prong 2306 has a flat, or generally rectangular, cross-section.

Wire 2380 extends through sleeve 2374, between upper portion 2376 and lower portion 2378, from proximal end 2360 of prong 2306 to contact portion 2370. Wire 2380 extends beyond the second end of sleeve 2374. A first end of wire 2380 is aligned with proximal end 2360 of prong 2306. Wire 2380 extends along base portion 2364, arm portion 2368, and contact portion 2370. A second end of wire 2380 is connected to electrode 2372. As such, contact portion 2370 of prong 2306 is made up of sleeve 2374, wire 2380, and electrode 2372. Wire 2380 has the same overall shape and angle as sleeve 2374 and extends beyond the second end of sleeve 2374. Wire 2380 extends away from the second end of sleeve 2374 and first side 2310 of housing 2302. In this embodiment, wire 2380 extends about 90 degrees away from the second end of sleeve 2374. As such, in this embodiment, wire 2380 is angled away from bottom side 2316 of housing 2302 along with sleeve 2374 and curved, or angled, away from first side 2310 of housing 2302 beyond sleeve 2374.

Structural tubes 2382 and 2384 may be configured like structural tubes 1682 and 1684 as shown in FIGS. 40A-40E. Structural tubes 2382 and 2384 extend through sleeve 2374, between upper portion 2376 and lower portion 2378 and along wire 2380. Structural tubes 2382 and 2384 extend from proximal end 2360 of prong 2360 to the second end of arm portion 2368. First ends of structural tubes 2382 and 2384 are aligned with proximal end 2360 of prong 2306. Structural tubes 2382 and 2384 extend along base portion 2364 and arm portion 2368. Second ends of structural tubes 2382 and 2384 are aligned with the second end of arm portion 2368. In alternate embodiments, structural tubes 2382 and 2384 may extend into contact portion 2370 to the second end of sleeve 2374 such that second ends of structural tubes 2382 and 2384 are aligned with the second end of sleeve 2374. Structural tubes 2382 and 2384 have the same overall shape as base portion 2364 and arm portion 2368. As such, in this embodiment, structural tubes 2382 and 2384 are planar.

First structural tube 2382 is on a first side of wire 2380, and second structural tube 2384 is on a second side of wire 2380 such that wire 2380 has structural tubes 2382 and 2384 on opposite sides of wire 2380. In alternate embodiments, prong 2306 may include any number of structural tubes 2382 and 2384 based on the desired stiffness of prong 2306. Structural tubes 2382 and 2384 may be hollow or solid. Structural tubes 2382 and 2384 can be any suitable size. For example, structural tubes 2382 and 2384 can have the same diameters as each other, can have the same diameter as wire 2380, or can have a smaller diameter than wire 2380. Structural tubes 2382 and 2384 can have any suitable thickness based on desired stiffness of prong 2306. Structural tubes 2382 and 2384 may be made of metal, polyurethane, silicone, any suitable plastic, a combination of metal and plastic, or any other suitable material. Structural tubes 2382 and 2384 are limited to an amount of metal that allows subcutaneous device 2300 to be MRI compatible. In alternate embodiments, prong 2306 may include any number of structural tubes 2382 and 2384. The size, shape, and material of structural tubes 2382 and 2384 may be selected based upon the desired stiffness of prong 2306. For example, prong 2306 may include five, seven, or any other suitable number of structural tubes 2382 and 2384 to make prong 2306 flatter and increase the stiffness of prong 2306.

Prong 2306A includes proximal end 2360A and distal end 2362A, which is opposite of proximal end 2360A. Prong 2306A includes base portion 2364A, arm portion 2368A, and contact portion 2370A. A first end of base portion 2364A is aligned with proximal end 2360A of prong 2306A, and a second end of base portion 2364A is connected to a first end of arm portion 2368A. Base portion 2364A is a straight, planar portion that is positioned against and extends along bottom side 2316A of housing 2302A, and base portion 2364 of prong 2306 when prong 2306A is positioned above prong 2306. Base portion 2364A is attached to housing 2302. Housing latch 2322A may extend around base portion 2364A of prong 2306A to secure base portion 2364A of prong 2306A to housing 2302A, such as when prong 2306 and prong 2306A are positioned side-by-side (as shown in FIG. 57G). As such, base portion 2364A extends through housing latch 2322A, and proximal end 2360A of prong 2306A is attached to housing 2302A. Base portion 2364A of prong 2306A is electrically connected to the internal components of housing 2302A, for example with a feedthrough, to which prong 2306A is also connected.

The first end of arm portion 2368A is connected to the second end of base portion 2364A, and a second end of arm portion 2368A is connected to a first end of contact portion 2370A. As such, arm portion 2368A extends from base portion 2364A so as to define a second plane that includes opposite ends, or first end and second end, of arm portion 2368A and is perpendicular to the horizontal plane of housing 2302 such that the second plane is a vertical plane that bisects housing 2302 longitudinally from front end 2318 to back end 2320 and is perpendicular to top side 2314 and bottom side 2316. Arm portion 2368A also extends past front end 2318A of housing 2302A so that contact portion 2370A is positioned outwards from front end 2318A of housing 2302A. Arm portion 2368A extends past arm portion 2368 of prong 2306. In this embodiment, arm portion 2368A is a predominantly straight portion that is planar and aligned with base portion 2364A. The first end of arm portion 2368A acts as a spring for prong 2306A and is under tension. Arm portion 2368A acts as a tension arm and the forces from the first end of arm portion 2368A translate to and push down on the second end of arm portion 2368A. In alternate embodiments, arm portion 2368A of prong 2306A can extend from housing 2302A in any direction or directions.

The first end of contact portion 2370A is connected to the second end of arm portion 2368A, and a second end of contact portion 2370A is aligned with distal end 2362A of prong 2306A. As such, arm portion 2368A is between base portion 2364A and contact portion 2370A. Arm portion 2368A extends beyond front end 2318A of housing 2302A so that contact portion 2370A is positioned beyond front end 2318A of housing 2302A. Further, arm portion 2368A extends beyond arm portion 2368 of prong 2306 so that contact portion 2370A extends beyond contact portion 2370 of prong 2306. Contact portion 2370A can be positioned such that distal end 2362A of prong 2306A contacts remote body component B (shown in FIG. 56). Contact portion 2370A is angled with respect to housing 2302A and arm portion 2368A. Contact portion 2370A is angled away from the second plane defined with respect to arm portion 2368A and housing 2302. In this embodiment, contact portion 2370A is angled away from bottom side 2316A of housing 2302A. Contact portion 2370A is also curved, or angled, away from first side 2310A of housing 2302A. Contact portion 2370A extends away from bottom side 2316A of housing 2302A and extends away from first side 2310A of housing 2302A so that distal end 2362A of prong 2306A is positioned below and away from housing 2302 and arm portion 2368A. In alternate embodiments, contact portion 2370A may be angled in any direction with respect to bottom side 2316A of housing and in any direction with respect to first side 2310A and second side 2312A of housing 2302A depending on the location of remote body component B with respect to structural body component A. Contact portion 2370A is angled toward remote body component B. For example, when remote body component B is a lung or a kidney, contact portion 2370A is angled toward the lung or the kidney. In this embodiment, a first portion of contact portion 2370A is angled about 90 degrees from bottom side 2316A of housing 2302A and arm portion 2368A, and a second portion of contact portion 2370A is angled about 90 degrees from first side 2310A of housing 2302A and arm portion 2368A. Contact portion 2370A may be angled about 45 degrees to about 60 degrees from the first vertical plane defined with respect to arm portion 2368A and housing 2302.

Prong 2306A further includes electrode 2372A. Electrode 2372A is at distal end 2362A of prong 2306A. As such, electrode 2372A makes up the second end of contact portion 2370A. Electrode 2372A has a rounded end and has the same shape as electrode 1672A described in reference to FIGS. 42A and 42B. In alternate embodiments, electrode 2372A may have any suitable shape, such as any of the shapes of electrodes 1672, 1672B, and 1672C. Prong 2306A has a single electrode 2372A in the embodiment shown in FIGS. 57A-57F. Prong 2306A can have any number of electrodes in alternate embodiments. Electrode 2372A is positioned at distal end 2362A of prong 2306A to sense an electrical activity or physiological status of remote body component B. Electrode 2372A can also provide therapeutic electrical stimulation to remote body component B.

Sleeve 2374A is a hollow outer portion of prong 2306A. Sleeve 2374A extends from proximal end 2360A of prong 2360A to contact portion 2370A. A first end of sleeve 2374A is aligned with proximal end 2360A of prong 2306A. Sleeve 2374A extends along base portion 2364A, arm portion 2368A, and a first portion of contact portion 2370A. A second end of sleeve 2374A is within contact portion 2370A. As such, sleeve 2374A makes up the outer portions of base portion 2364A, arm portion 2368A, and the first portion of contact portion 2370A. Sleeve 2374A has upper portion 2376A opposite lower portion 2378A. Upper portion 2376A and lower portion 2378A are flat, or planar, such that sleeve 2374A has a flat, or generally rectangular, cross-section. As such, a majority of prong 2306A has a flat, or generally rectangular, cross-section. Lower portion 2378A of sleeve 2374A of prong 2306A is adjacent upper portion 2376 of sleeve 2374 of prong 2306.

Wire 2380A extends through sleeve 2374A, between upper portion 2376A and lower portion 2378A, from proximal end 2360A of prong 2306A to contact portion 2370A. Wire 2380A extends beyond the second end of sleeve 2374A. A first end of wire 2380A is aligned with proximal end 2360A of prong 2306A. Wire 2380A extends along base portion 2364A, arm portion 2368A, and contact portion 2370A. A second end of wire 2380A is connected to electrode 2372A. As such, contact portion 2370A of prong 2306A is made up of sleeve 2374A, wire 2380A, and electrode 2372A. Wire 2380A has the same overall shape and angle as sleeve 2374A and extends beyond the second end of sleeve 2374A. Wire 2380A extends away from the second end of sleeve 2374A and first side 2310A of housing 2302A. In this embodiment, wire 2380A extends about 90 degrees away from the second end of sleeve 2374A. As such, in this embodiment, wire 2380A is angled away from bottom side 2316A of housing 2302A along with sleeve 2374A and curved, or angled, away from first side 2310A of housing 2302A beyond sleeve 2374A.

Structural tubes 2382A and 2384A may be configured like structural tubes 1682 and 1684 as shown in FIGS. 40A-40E. Structural tubes 2382A and 2384A extend through sleeve 2374A, between upper portion 2376A and lower portion 2378A and along wire 2380A. Structural tubes 2382A and 2384A extend from proximal end 2360A of prong 2360A to the second end of arm portion 2368A. First ends of structural tubes 2382A and 2384A are aligned with proximal end 2360A of prong 2306A. Structural tubes 2382A and 2384A extend along base portion 2364A and arm portion 2368A. Second ends of structural tubes 2382A and 2384A are aligned with the second end of arm portion 2368A. In alternate embodiments, structural tubes 2382A and 2384A may extend into contact portion 2370A to the second end of sleeve 2374A such that second ends of structural tubes 2382A and 2384A are aligned with the second end of sleeve 2374A. Structural tubes 2382A and 2384A have the same overall shape as base portion 2364A and arm portion 2368A. As such, in this embodiment, structural tubes 2382A and 2384A are planar.

First structural tube 2382A is on a first side of wire 2380A, and second structural tube 2384A is on a second side of wire 2380A such that wire 2380A has structural tubes 2382A and 2384A on opposite sides of wire 2380A. In alternate embodiments, prong 2306A may include any number of structural tubes 2382A and 2384A based on the desired stiffness of prong 2306A. Structural tubes 2382A and 2384A may be hollow or solid. Structural tubes 2382A and 2384A can be any suitable size. For example, structural tubes 2382A and 2384A can have the same diameters as each other, can have the same diameter as wire 2380A, or can have a smaller diameter than wire 2380A. Structural tubes 2382A and 2384A can have any suitable thickness based on desired stiffness of prong 2306A. Structural tubes 2382A and 2384A may be made of metal, polyurethane, silicone, any suitable plastic, a combination of metal and plastic, or any other suitable material. Structural tubes 2382A and 2384A are limited to an amount of metal that allows subcutaneous device 2300 to be MRI compatible. In alternate embodiments, prong 2306A may include any number of structural tubes 2382A and 2384A. The size, shape, and material of structural tubes 2382A and 2384A may be selected based upon the desired stiffness of prong 2306A. For example, prong 2306A may include five, seven, or any other suitable number of structural tubes 2382A and 2384A to make prong 2306A flatter and increase the stiffness of prong 2306A.

Prongs 2306 and 2306A are angled with respect to housing 2302 to improve contact of electrodes 2372 and 2372A, respectively, with remote body component B. Prongs 2306 and 2306A are angled so that contact portions 2370 and 2370A push down against remote body component B, such as the heart. Because contact portion 2370A extends beyond contact portion 2370, electrode 2372A is positioned beyond electrode 2372. Electrode 2372 at distal end 2362 of prong 2306 and electrode 2372A at distal end 2362A of prong 2306A contact the heart and different locations and bury into the cardiac tissue. Further, because prongs 2306 and 2306A are angled down toward heart, prongs 2306 and 2306A apply pressure to the heart as the heart beats and moves up and down, without increasing the stiffness of prongs 2306 and 2306A. As a result, electrodes 2372 and 2372A maintain contact with the heart without fixing electrodes 2372 and 2372A to the heart. For example, prongs 2306 and 2306A are prevented from bouncing off of the heart as the heart beats, which would cause intermittent contact that reduces functionality. Because electrode 2372 is on prong 2306 and electrode 2372A is on separate prong 2306A, electrodes 2372 and 2372A both maintain contact with the heart even if the different locations of the heart on which electrodes 2372 and 2372A are positioned move asynchronously, such as in different directions or at different rates. Additionally, contact portions 2370 and 2370A are angled away from bottom 2316 and first side 2310 of housing 2302 to ensure distal ends 2362 and 2362A of prongs 2306 and 2306A, respectively, are positioned on the heart when subcutaneous device 2300 is attached to a xiphoid and/or sternum of a patient. As such, subcutaneous device 2300 can be inserted and deployed into a patient without requiring cardiac catheterization labs. Thus, the procedure for inserting the device is simple and only requires local anesthesia, which means it can be carried out in various environments, such as in an ambulance.

Arm portions 2368 and 2368A of prongs 2306 and 2306A allows prongs 2306 and 2306A, respectively, to be flexible once they are positioned in the body. The pivot points of arm portion 2368 and 2368A, respectively, are adjacent the first end of arm portion 2368 and 2368A, respectively, which are connected to the second ends of base portions 2364 and 2364A, respectively, and slightly closer to proximal ends 2360 and 2360A than front end 2318 of housing 2302 is to proximal ends 2306 and 2306A, or where prongs 2306 and 2306A are secured to bottom side 2316 of housing 2302 by housing latch 2322. For example, if remote body component B is the heart of the patient and contact portion 2370 of prong 2306 and contact portion 2370A of prong 2306A are positioned against the heart, arm portions 2368 and 2368A of prongs 2306 and 2306A, respectively, allow prongs 2306 and 2306 to move up and down with the heart as the heart beats. Further, prong 2306 can move separately from prong 2306A such that electrode 2372 and electrode 2372A both maintain contact with the heart. This ensures that prongs 2306 and 2306A do not puncture or damage the heart while contact portions 2370 and 2370A of prongs 2306 and 2306A, respectively, maintain contact with the heart. In this embodiment, electrodes 2372 and 2372A at distal ends 2362 and 2362A of prongs 2306 and 2306A, respectively, each have a rounded end to further prevent prongs 2306 and 2306A from puncturing or damaging the heart when contact portions 2370 and 2370A of prongs 2306 and 2360A, respectively, are in contact with the heart. The overall axial stiffness of prongs 2306 and 2306A can be adjusted so that prongs 2306 and 2306A gently presses against the heart and move up and down in contact with the heart, sometimes separately, as the heart beats, but are not stiff or sharp enough to pierce or tear the pericardial or epicardial tissue. For example, the overall axial stiffness of prongs 2306 and 2306A can be adjusted by adjusting the material of prongs 2306 and 2306A, the spring bias or mechanical resistance of prongs 2306 and 2306A, the cross-sectional thicknesses of prongs 2306 and 2306A, the angle of incidence of prongs 2306 and 2306A on remote body component B, the outer profiles of prongs 2306 and 2306A where prongs 2306 and 2306A contact remote body component B, and/or any other suitable characteristic of prongs 2306 and 2306A.

The flat, or rectangular, cross-section of sleeves 2374 and 2372A created by planar upper portions 2376 and 2376A and planar lower portions 2378 and 2378A provide stiffness to prongs 2306 and 2306A, respectively, which makes prongs 2306 and 2306A more resistant to in-plane bending. Sleeves 2374 and 2374A also provide space for wires 2380 and 2380A to be surrounded by structural tubes 2382 and 2382A and structural tubes 2384 and 2384A, respectively. Structural tubes 2382, 2382A, 2384, and 2384A also provide the desired structural stiffness to prongs 2306 and 2306A, respectively. As a result, prongs 2306 and 2306A resist in-plane bending, or bending in any direction, to maintain positioning with respect to the heart, which ensures electrode 2372 and electrode 2372A maintain contact with the heart without requiring fluoroscopy or other visualization tools. In alternate embodiments, prongs 2306 and 2306A may include pre-shaped spines made of shape-memory material, such as nitinol, to provide stiffness along with or instead of structural tubes 2282, 2284, 2282A, and 2284A. In these embodiments, prongs 2306 and 2306A may have the shape shown in FIG. 56, for example, or other suitable shapes or configurations.

Subcutaneous device 2300 is described here as having two prongs 2306 and 2306A. As such, electrodes 2372 and 2372A can contact different locations of a remote body component, such as the heart, or different remote body components. In alternate embodiments, subcutaneous device 2300 can include prongs 2306 and 2306A that have any shape. For example, subcutaneous device 2300 can include any of the prongs shown and discussed in reference to FIGS. 1-37. Contact portions 2370 and 2370A can have any angle with respect to bottom side 2316, first side 2310, and second side 2312 of housing 2302.

Subcutaneous device 2300 can function as a pacemaker. Prongs 2306 and 2306A can be shaped so that contact portion 2370 of prong 2306 and contact portion 2370A of prong 2306A contact one or a combination of the right ventricle, left ventricle, right atrium, and left atrium of the heart. Subcutaneous device 2300 can function as a bipolar pacemaker, utilizing electrode 2372 on prong 2306 and electrode 2372A on prong 2306A.

FIG. 58 is a perspective view of subcutaneous device 2300 positioned on xiphoid process X and/or sternum S and showing a positioning of prongs 2306 and 2306A on heart H. Subcutaneous device 2300 includes housing 2302, clip 2304, prong 2306, and prong 2306A. Housing 2302 includes first side 2310 and bottom side 2316. Prong 2306 includes distal end 2362, arm portion 2368, contact portion 2370, electrode 2372, and sleeve 2374. Prong 2306A includes distal end 2362A, arm portion 2368A, contact portion 2370A, electrode 2372A, and sleeve 2374A. FIG. 58 also shows xiphoid process X, sternum S, and heart H.

Subcutaneous device 2300 includes housing 2302, clip 2304, prong 2306, and prong 2306A as described above in reference to FIGS. 56-57F. In the embodiment shown in FIG. 58, subcutaneous device 2300 is configured to be a pacemaker used for cardiac monitoring, diagnostics, and/or therapeutics, such as subcutaneous device 100 described with respect to FIGS. 1-9C. In the embodiment shown in FIG. 58, subcutaneous device 2300 can be anchored to xiphoid process X and sternum S of a patient. Subcutaneous device 2300 can be implanted with a simple procedure where subcutaneous device 2300 is injected onto xiphoid process X and sternum S using a surgical instrument. For example, subcutaneous device 2300 can be deployed and anchored to xiphoid process X and sternum S using surgical instruments 1700, 1800, 1900, and 2000 and method 2100 described with respect to FIGS. 46A-51.

When subcutaneous device 2300 is anchored to xiphoid process X and sternum S via clip 2304, prong 2306 and prong 2306A extend away from first side 2310 and bottom side 2316 of housing 2302. Contact portions 2370 and 2370A extend away from bottom side 2316 and first side 2310 of housing 2302. As such, contact portions 2370 and 2370A push down against heart H. Electrode 2372 at distal end 2362 of prong 2306 and electrode 2372A at distal end 2362A of prong 2306A contact heart H and maintain contact as heart H beats. Specifically, electrode 2372 at distal end 2362 of prong 2306 contacts heart H at a first location, such as the pericardium of the right ventricle, and electrode 2372A at distal end 2362A of prong 2306A contacts heart H at a second location, such as the pericardial layer of the left ventricle. Prongs 2306 and 2306A can be shaped so that prongs 2306 and 2306A contact the right ventricle, left ventricle, right atrium, or left atrium of the heart. Prongs 2306 and 2306A are separate such that arm portion 2368 of prong 2306 can move separately from arm portion 2368A of prong 2306A to enable electrodes 2372 and 2372A to each maintain contact with heart H even if the first location and the second location of heart H are moving asynchronously. The overall desired stiffness of prongs 2306 and 2306A is achieved via structural tubes 2382 and 2382A and structural tubes 2384 and 2384A (described with respect to FIGS. 57A-57F) within sleeves 2374 and 2374A, respectively, which ensures that prongs 2306 and 2306A gently press against heart H and move up and down in contact with heart H as heart H beats, but are not stiff or sharp enough to pierce or tear the pericardial or epicardial tissue.

Prongs 2306 and 2306A are shaped to ensure prongs 2306 and 2306A are properly positioned against and will not lose contact with heart H. The surgical procedure for implanting subcutaneous device 2300 is less invasive than the surgical procedure required for more traditional pacemaker devices, as subcutaneous device is placed subcutaneously in the body. No leads need to be positioned in the vasculature of the patient, lowering the risk of thrombosis to the patient.

Subcutaneous Device 2400

FIG. 59 is a side view of subcutaneous device 2400 anchored to structural body component A. Subcutaneous device 2400 includes body 2402, clip 2404 and prong 2406.

Subcutaneous device 2400 is a medical device that is configured to be anchored to structural body component A, which may be a muscle, a bone, or a tissue of a patient. Subcutaneous device 2400 can be a monitoring device, a diagnostic device, a therapeutic device, or any combination thereof. Subcutaneous device 2400 is connected to and works in conjunction with another subcutaneous device, such as any of subcutaneous devices 100, 400, 500, 600, 700, 800, 900, 1000, 1100, 1200, 1300, 1400, 1500, 1600, 2200, and 2300 shown in FIGS. 1-9C, 20-45, and 52-58. For example, subcutaneous device 2400 can be connected to and work in conjunction with a pacemaker device that is capable of monitoring a patient's heart rate, diagnosing an arrhythmia of the patient's heart, and providing therapeutic electrical stimulation to the patient's heart. As such, subcutaneous device 2400 acts as a secondary subcutaneous device to a primary subcutaneous device. Subcutaneous device 2400 does not include a housing. Rather, subcutaneous device 2400 is connected to the housing of the primary subcutaneous device. The housing of the primary subcutaneous device may include sensing circuitry 180, controller 182, memory 184, therapy circuitry 186, electrode(s) 188, sensor(s) 190, transceiver 192, and power source 194 as described with respect to FIG. 7 and/or any other component of a medical device.

Body 2402 connects clip 2404 to prong 2406. Clip 2404 is configured to anchor subcutaneous device 2400 to structural body component A. Clip 2404 will expand as it is advanced around structural body component A. In addition to using the stiffness of clamping components to attach to the bone, the muscle, or the tissue, clip 2404 uses an active fixation method such as tines and/or screws, and/or any other suitable anchoring structure to secure clip 2404 to the bone, the muscle, or the tissue. Clip 2404 has a spring bias that will put tension on structural body component A when it is expanded and fit onto structural body component A. The spring bias of clip 2404 and the active fixation method will anchor subcutaneous device 2400 to structural body component A.

Prong 2406 is connected to and extends away from clip 2404 of subcutaneous device 2400. Prong 2406 is configured to contact remote body component B that is positioned away from structural body component A. Remote body component B may be an organ, a nerve, or tissue of the patient. For example, remote body component B can include a heart, a lung, or any other suitable organ in the body. Prong 2406 includes an electrode that is capable of sensing an electrical activity or physiological parameter of remote body component B and/or providing therapeutic electrical stimulation to remote body component B.

In one example, subcutaneous device 2400 can work with another primary subcutaneous device to be a pacemaker, and the electrode on prong 2406 of subcutaneous device 2400 can sense the electrical activity of a heart. The sensed electrical activity can be transmitted to sensing circuitry and a controller in the housing of the primary subcutaneous device. The controller can determine the heart rate of the patient and can detect whether an arrhythmia is present. If an arrhythmia is detected, the controller can send instructions to therapeutic circuitry to provide a therapeutic electrical stimulation to the heart. In this manner, subcutaneous device 2400 functions as a monitoring device, a diagnostic device, and a therapeutic device.

Subcutaneous device 2400 will be discussed in greater detail in relation to FIGS. 60A-62E below. Subcutaneous device 2400 will be discussed in conjunction with subcutaneous device 2200, described with respect to FIGS. 52-55B, as a pacemaker that can be used for monitoring, diagnostics, and therapeutics in the discussion of FIGS. 60A-62E below. In this embodiment, subcutaneous device 2400 functions with another subcutaneous device to be a dual chamber or a triple chamber pacemaker. Subcutaneous device 2400 can also work with another primary subcutaneous device to be a monitoring device, a diagnostic device, an implantable cardioverter-defibrillator, a general organ/nerve/tissue stimulator, and/or a drug delivery device.

FIG. 60A is a top perspective view of subcutaneous device 2400. FIG. 60B is a side view of subcutaneous device 2400. FIG. 60C is a side view of subcutaneous device 2400. FIG. 60D is a top view of subcutaneous device 2400. Subcutaneous device 2400 includes body 2402, clip 2404, and prong 2406. Body 2402 includes first side 2410, second side 2412, top side 2414, bottom side 2416, front end 2418, and back end 2420. Clip 2404 includes top portion 2440, bottom portion 2442, spring portion 2444, and tines 2446. Prong 2406 includes proximal end 2460, distal end 2462, base portion 2464, arm portion 2468, contact portion 2470, electrode 2472, sleeve 2474 (which includes upper portion 2476 and lower portion 2478), wire 2480, structural tube 2482, and structural tube 2484.

Subcutaneous device 2400 includes body 2402, clip 2404, and prong 2406 as described in reference to FIG. 59. Body 2402 can be made out of stainless steel, titanium, nitinol, epoxy, silicone, polyurethane with metallic reinforcements, or any other material that is suitable for non-porous implants. Body 2402 can also include an exterior coating. Clip 2404 can be made out of stainless steel, titanium, nitinol, epoxy, silicone, polyurethane with metallic reinforcements, or any other material that is suitable for non-porous implants. Prong 2406 can be made out of nickel titanium, also known as Nitinol. Nitinol is a shape memory alloy with superelasticity, allowing prong 2406 to go back to its original shape and position if prong 2406 is deformed as subcutaneous device 2400 is implanted into a patient. Prong 2406 can also be made out of silicone, polyurethane, stainless steel, titanium, epoxy, polyurethane with metallic reinforcements, or any other material that is suitable for non-porous implants. As an example, prong 2406 can be made out of a composite made of polyurethane and silicone and reinforced with metal to provide spring stiffness.

Body 2402 includes first side 2410, second side 2412, top side 2414, bottom side 2416, front end 2418, back end 2420. First side 2410 is opposite of second side 2412. Top side 2414 is a top of body 2402 opposite of bottom side 2416, which is a bottom of housing 2402. Front end 2418 is opposite of back end 2420. Body 2402 is substantially cylindrical-shaped in the embodiment shown. In alternate embodiments, body 2402 can be shaped as a cone, frustum, or rectangular.

Body 2402 is configured to engage with clip 2404. Clip 2404 is rotatably connected to top side 2414 of body 2402. Body 2402 is configured to accept prong 2604. Prong 2604 extends into body 2402 from front end 2418 to back end 2420 between top side 2414 and bottom side 2416. As such, body 2402 engages with clip 2404 at top side 2414 of body 2402 and with prong 2406 between top side 2414 and bottom side 2416 of body 2402. Body 2402 is configured to accept prong 2406 and attach prong 2406 to clip 2404.

Clip 2404 includes top portion 2440, bottom portion 2442, spring portion 2444, and tines 2464. Top portion 2440 is connected to bottom portion 2442. Top portion 2440 is a flat portion that forms a top of clip 2404, and bottom portion 2442 is a flat portion that forms a bottom of clip 2404. Bottom portion 2442 is configured to be attached to top side 2414 of body 2402 of subcutaneous device 2400. Bottom portion 2442 extends beyond back end 2420 of body 2402. Bottom portion 2442 is configured to rotate with respect to body 2402, such that clip 2404 can rotate with respect to body 2402 and prong 2406. Spring portion 2444 is a curved portion positioned on a back end of clip 2404 that extends between and connects top portion 2440 to bottom portion 2442. Spring portion 2444 of clip 2404 is positioned beyond back end 2420 of housing 2404. Clip 2404 can be made out of stainless steel, titanium, nitinol, epoxy, silicone, polyurethane with metallic reinforcements, or any other material that is suitable for non-porous implants. Tines 2446 extend from top portion 2440 of clip 2404. Tines 2446 have first ends connected to a center portion of top portion 2440 and second ends that extend away from top portion 2440 toward bottom portion 2442 of clip 2404. Tines 2446 are curved and extend in different directions. Tines 2446 are thin and may be made of metal or any other suitable material. In this embodiment, clip 2404 has four tines 2446. In alternate embodiments, clip 2404 may have any number of tines 2446. Further, in alternate embodiments, any other suitable anchoring structures or active fixation methods may be used along with or instead of tines 2446. Tines 2446 are configured to pierce and anchor to structural body component A.

When clip 2404 is connected to body, top portion 2440 of clip 2404 extends at an angle to prong 2406. Clip 2404 is configured to rotate with respect to body 2402 such that clip 2404 rotates with respect to prong 2406. Clip 2404 may be configured to rotate 90 degrees and snap into place before being anchored to structural body component A. When clip 2404 is rotated, clip 2404 extends at an angle to prong 2406. Clip 2404 may be configured to rotate such that prong 2406 extends at any angle to clip 2404.

Spring portion 2444 acts as a spring for clip 2404 and is under tension. Top portion 2440 acts as a tension arm and the forces from spring portion 2444 translate to and push down on top portion 2440. In its natural state, a spring bias of spring portion 2444 forces the tip of top portion 2440, which is at the end of top portion 2440 positioned over top side 2414 of body 2402, towards bottom portion 2442 of clip 2404 and top side 2414 of body 2402. The tip of top portion 2440 of clip 2404 can be lifted up to expand clip 2404, and clip 2404 can be positioned on a muscle, a bone, or tissue of a patient. When clip 2404 is positioned on a muscle, a bone, or tissue of a patient, the tension in spring portion 2444 will force top portion 2440 down onto the muscle, the bone, or the tissue. This tension will anchor clip 2404 to the muscle, the bone, or the tissue.

After subcutaneous device 2400 is positioned on the muscle, the bone, or the tissue, tines 2446 attach to the muscle, the bone, or the tissue, which anchors clip 2404 to the muscle, the bone, or the tissue. Tines 2446 will pierce the muscle, the bone, or the tissue in response to tension in spring portion 2444 or additional pressure directed to top portion 2440 of clip 2404. Tines 2446 may contact bottom portion 2442 of clip 2404 such that tines 2446 bend back around into the muscle, the bone, or the tissue and further secure and anchor clip 2404 and subcutaneous device 2400 to the muscle, the bone, or the tissue. Tines 2446 are also removable from the muscle, the bone, or the tissue, such that subcutaneous device 2400 is easily removable from structural body component A.

Prong 2406 includes proximal end 2460 and distal end 2462, which is opposite of proximal end 2460. Prong 2406 includes base portion 2464, arm portion 2468, and contact portion 2470. A first end of base portion 2464 is aligned with proximal end 2460 of prong 2406, and a second end of base portion 2464 is connected to a first end of arm portion 2468. Base portion 2464 is a straight, planar portion that is positioned and extends within body 2402. Base portion 2464 is attached to body 2402. As such, proximal end 2460 of prong 2406 is attached to housing 2402. Base portion 2464 of prong 2406 is electrically connected to the internal components of a second primary subcutaneous device, such as subcutaneous device 2200, via a small cable with a first electrically active connector attached to proximal end 2460 of prong 2406 and a second electrically active connector attached to a header or feedthrough on the housing of the second primary subcutaneous device (as shown in FIG. 63).

The first end of arm portion 2468 is connected to the second end of base portion 2464, and a second end of arm portion 2468 is connected to a first end of contact portion 2470. As such, arm portion 2468 extends from base portion 2464 so as to define a first plane that includes opposite ends, or first end and second end, of arm portion 2468 and is perpendicular to the horizontal plane of body 2402 such that the first plane is a vertical plane that bisects body 2402 longitudinally from front end 2418 to back end 2420 and is perpendicular to top side 2414 and bottom side 2416. Arm portion 2468 also extends beyond clip 2404 so that contact portion 2470 is positioned outwards from clip 2404. In this embodiment, arm portion 2468 is a predominantly straight portion that is that is angled with respect to body 2402, clip 2404, and base portion 2464 of prong 2406. In this embodiment, arm portion 2468 is angled away, or extends away, from bottom side 2416 of body 2402 and bottom portion 2442 of clip 2404. The first end of arm portion 2468 acts as a spring for prong 2406 and is under tension. Arm portion 2468 acts as a tension arm and the forces from the first end of arm portion 2468 translate to and push down on the second end of arm portion 2468. In its natural state, a spring bias of arm portion 2468 forces distal end 2462 of prong 2406 away from bottom side 2416 of body 2402 and bottom portion 2442 of clip 2404. In alternate embodiments, arm portion 2468 of prong 2406 can extend in any direction or directions.

The first end of contact portion 2470 is connected to the second end of arm portion 2468, and a second end of contact portion 2470 is aligned with distal end 2462 of prong 2406. As such, arm portion 2468 is between base portion 2464 and contact portion 2470. Arm portion 2468 extends beyond clip 2404 so that contact portion 2470 is positioned beyond clip 2404. Contact portion 2470 can be positioned such that distal end 2462 of prong 2406 contacts remote body component B (shown in FIG. 59). Contact portion 2470 is angled with respect to body 2402 and arm portion 2468. Contact portion 2470 is angled away from the first plane defined with respect to arm portion 2468 and body 2402. In this embodiment, contact portion 2470 is further angled away from bottom side 2416 of body 2402. Contact portion 2470 is also curved, or angled, away from first side 2410 of body 2402. Contact portion 2470 extends away from bottom side 2416 of body 2402 and extends away from first side 2410 of body 2402 so that distal end 2462 of prong 2406 is positioned below and away from body 2402 and arm portion 2468. In alternate embodiments, contact portion 2470 may be angled in any direction with respect to bottom side 2416 of body 2402 and in any direction with respect to first side 2410 and second side 2412 of body 2402 depending on the location of remote body component B with respect to structural body component A. Contact portion 2470 is angled toward remote body component B. For example, when remote body component B is a lung or a kidney, contact portion 2470 is angled toward the lung or the kidney. In this embodiment, a first portion of contact portion 2470 is angled about 90 degrees from bottom side 2416 of body 2402 and arm portion 2468, and a second portion of contact portion 2470 is angled about 90 degrees from first side 2410 of body 2402 and arm portion 2468. Contact portion 2470 may be angled about 45 degrees to about 60 degrees from the first vertical plane defined with respect to arm portion 2468 and body 2402.

Prong 2406 further includes electrode 2472. Electrode 2472 is at distal end 2462 of prong 2406. As such, electrode 2472 makes up the second end of contact portion 2470. Electrode 2472 has a rounded end and has the same shape as electrode 1672A described in reference to FIGS. 42A and 42B. In alternate embodiments, electrode 2472 may have any suitable shape, such as any of the shapes of electrodes 1672, 1672B, and 1672C. Prong 2406 has a single electrode 2472 in the embodiment shown in FIGS. 60A-60D. Prong 2406 can have any number of electrodes in alternate embodiments. Electrode 2472 is positioned at distal end 2462 of prong 2406 to sense an electrical activity or physiological status of remote body component B. Electrode 2472 can also provide therapeutic electrical stimulation to remote body component B.

Sleeve 2474 is a hollow outer portion of prong 2406. Sleeve 2474 extends from proximal end 2460 of prong 2460 to contact portion 2470. A first end of sleeve 2474 is aligned with proximal end 2460 of prong 2406. Sleeve 2474 extends along base portion 2464, arm portion 2468, and a first portion of contact portion 2470. A second end of sleeve 2474 is within contact portion 2470. As such, sleeve 2474 makes up the outer portions of base portion 2464, arm portion 2468, and the first portion of contact portion 2470. Sleeve 2474 has upper portion 2476 opposite lower portion 2478. Upper portion 2476 and lower portion 2478 are flat, or planar, such that sleeve 2474 has a flat, or generally rectangular, cross-section. As such, a majority of prong 2406 has a flat, or generally rectangular, cross-section.

Wire 2480 extends through sleeve 2474, between upper portion 2476 and lower portion 2478, from proximal end 2460 of prong 2406 to contact portion 2470. Wire 2480 extends beyond the second end of sleeve 2474. A first end of wire 2480 is aligned with proximal end 2460 of prong 2406. Wire 2480 extends along base portion 2464, arm portion 2468, and contact portion 2470. A second end of wire 2480 is connected to electrode 2472. As such, contact portion 2470 of prong 2406 is made up of sleeve 2474, wire 2480, and electrode 2472. Wire 2480 has the same overall shape and angle as sleeve 2474 and extends beyond the second end of sleeve 2474. Wire 2480 extends away from the second end of sleeve 2474 and first side 2410 of body 2402. In this embodiment, wire 2480 extends about 90 degrees away from the second end of sleeve 2474. As such, in this embodiment, wire 2480 is angled away from bottom side 2416 of body 2402 along with sleeve 2474 and curved, or angled, away from first side 2410 of body 2402 beyond sleeve 2474.

Structural tubes 2482 and 2484 may be configured like structural tubes 1682 and 1684 as shown in FIGS. 40A-40E. Structural tubes 2482 and 2484 extend through sleeve 2474, between upper portion 2476 and lower portion 2478 and along wire 2480. Structural tubes 2482 and 2484 extend from proximal end 2460 of prong 2460 to the second end of arm portion 2468. First ends of structural tubes 2482 and 2484 are aligned with proximal end 2460 of prong 2406. Structural tubes 2482 and 2484 extend along base portion 2464 and arm portion 2468. Second ends of structural tubes 2482 and 2484 are aligned with the second end of arm portion 2468. In alternate embodiments, structural tubes 2482 and 2484 may extend into contact portion 2470 to the second end of sleeve 2474 such that second ends of structural tubes 2482 and 2484 are aligned with the second end of sleeve 2474. Structural tubes 2482 and 2484 have the same overall shape as base portion 2464 and arm portion 2468. As such, in this embodiment, structural tubes 2482 and 2484 are planar.

First structural tube 2482 is on a first side of wire 2480, and second structural tube 2484 is on a second side of wire 2480 such that wire 2480 has structural tubes 2482 and 2484 on opposite sides of wire 2480. In alternate embodiments, prong 2406 may include any number of structural tubes 2482 and 2484 based on the desired stiffness of prong 2406. Structural tubes 2482 and 2484 may be hollow or solid. Structural tubes 2482 and 2484 can be any suitable size. For example, structural tubes 2482 and 2484 can have the same diameters as each other, can have the same diameter as wire 2480, or can have a smaller diameter than wire 2480. Structural tubes 2482 and 2484 can have any suitable thickness based on desired stiffness of prong 2406. Structural tubes 2482 and 2484 may be made of metal, polyurethane, silicone, any suitable plastic, a combination of metal and plastic, or any other suitable material. Structural tubes 2482 and 2484 are limited to an amount of metal that allows subcutaneous device 2400 to be MRI compatible. In alternate embodiments, prong 2406 may include any number of structural tubes 2482 and 2484. The size, shape, and material of structural tubes 2482 and 2484 may be selected based upon the desired stiffness of prong 2406. For example, prong 2406 may include five, seven, or any other suitable number of structural tubes 2482 and 2484 to make prong 2406 flatter and increase the stiffness of prong 2406.

Prong 2406 is angled with respect to body 2402 and clip 2404 to improve contact of electrode 2472 with remote body component B. Prong 2406 is angled so that contact portion 2470 pushes down against remote body component B, such as the heart. Electrode 2472 at distal end 2462 of prong 2406 contacts the heart and buries into the cardiac tissue. Further, because prong 2406 is angled down toward heart, prong 2406 applies pressure to the heart as the heart beats and moves up and down, without increasing the stiffness of prong 2406. As a result, electrode 2472 maintains contact with the heart without fixing electrode 2472 to the heart. For example, prong 2406 is prevented from bouncing off of the heart as the heart beats, which would cause intermittent contact that reduces functionality. Additionally, contact portion 2470 is angled away from bottom 2416 and first side 2410 of body 2402 to ensure distal end 2462 of prong 2406 is positioned on the heart when subcutaneous device 2400 is attached to a xiphoid and/or sternum of a patient. As such, subcutaneous device 2400 can be inserted and deployed into a patient without requiring cardiac catheterization labs. Thus, the procedure for inserting the device is simple and only requires local anesthesia, which means it can be carried out in various environments, such as in an ambulance.

Arm portion 2468 of prong 2406 allows prong 2406 to be flexible once it is positioned in the body. The pivot point of arm portion 2468 is at the first end of arm portion 2468, which is connected to the second end of base portion 2464. For example, if remote body component B is the heart of the patient and contact portion 2470 of prong 2406 is positioned against the heart, arm portion 2468 of prong 2406 allows prong 2406 to move up and down with the heart as the heart beats. This ensures that prong 2406 does not puncture or damage the heart while contact portion 2470 of prong 2406 maintains contact with the heart. In this embodiment, electrode 2472 at distal end 2462 of prong 2406 has a rounded end to further prevent prong 2406 from puncturing or damaging the heart when contact portion 2470 of prong 2406 is in contact with the heart. The overall axial stiffness of prong 2406 can be adjusted so that prong 2406 gently presses against the heart and moves up and down in contact with the heart as the heart beats, but is not stiff or sharp enough to pierce or tear the pericardial or epicardial tissue. For example, the overall axial stiffness of prong 2406 can be adjusted by adjusting the material of prong 2406, the spring bias or mechanical resistance of prong 2406, the cross-sectional thickness of prong 2406, the angle of incidence of prong 2406 on remote body component B, the outer profile of prong 2406 where prong 2406 contacts remote body component B, and/or any other suitable characteristic of prong 2406.

The flat, or rectangular, cross-section of sleeve 2474 created by planar upper portion 2476 and planar lower portion 2478 provides stiffness to prong 2406, which makes prong 2406 more resistant to in-plane bending. Sleeve 2474 also provides space for wire 2480 to be surrounded by structural tubes 2482 and 2484. Structural tubes 2482 and 2484 also provide the desired structural stiffness to prong 2406. As a result, prong 2406 resists in-plane bending, or bending in any direction, to maintain positioning with respect to the heart, which ensures electrode 2472 maintains contact with the heart without requiring fluoroscopy or other visualization tools. In alternate embodiments, prong 2406 may include a pre-shaped spine made of shape-memory material, such as nitinol, to provide stiffness along with or instead of structural tubes 2482 and 2484. In these embodiments, prong 2406 may have the shape shown in FIG. 59, for example, or other suitable shapes or configurations.

Subcutaneous device 2400 is described here as having a single prong 2406. In alternate embodiments, subcutaneous device 2400 can include any number of prongs and those prongs can have any shape. For example, subcutaneous device 2400 can include any of the prongs shown and discussed in reference to FIGS. 1-37. Contact portion 2470 can have any angle with respect to bottom side 2416, first side 2410, and second side 2412 of body 2402.

Subcutaneous device 2400 works in conjunction with another subcutaneous device. As such, subcutaneous device 2400 acts as a secondary device. For example, subcutaneous device 2400 can be connected to and work with another subcutaneous device to function as a pacemaker. Clip 2404 rotates with respect to body 2402 and prong 2406 so that prong 2406 is not limited to only reaching organs that are coaxial with body 2402. Prong 2406 can be shaped so that contact portion 2470 of prong 2406 contacts the right ventricle, left ventricle, right atrium, or left atrium of the heart. Subcutaneous device 2400 can function with another primary subcutaneous device as a bipolar pacemaker, utilizing electrode 2472 on prong 2406 along with the electrode on the primary subcutaneous device. Further, in alternate embodiments, subcutaneous device 2400 can utilize more than one prong 2406 and electrode 2472.

FIG. 61A is a top view of subcutaneous device 2400 and subcutaneous device 2200 positioned on xiphoid process X and/or sternum S. FIG. 61B is a perspective side view of subcutaneous device 2400 and subcutaneous device 2200 positioned on xiphoid process X and/or sternum S. FIG. 62A is a perspective side view of subcutaneous device 2400 and subcutaneous device 2200 positioned on xiphoid process X and/or sternum S and showing a positioning of prongs 2406 and 2206 on heart H. FIG. 62B is a perspective side view of subcutaneous device 2400 and subcutaneous device 2200 positioned on xiphoid process X and/or sternum S and showing a positioning of prongs 2406 and 2206 on heart H. FIG. 62C is a perspective side view of subcutaneous device 2400 and subcutaneous device 2200 positioned on xiphoid process X and/or sternum S and showing a positioning of prongs 2406 and 2206 on heart H. FIG. 62D is a perspective end view of subcutaneous device 2400 and subcutaneous device 2200 positioned on xiphoid process X and/or sternum S and showing a positioning of prongs 2406 and 2206 on heart H. FIG. 62E is a front cut away view of subcutaneous device 2400 and subcutaneous device 2200 positioned on xiphoid process X and sternum S and showing a positioning of prongs 2406 and 2206 on heart H. FIG. 63 is a perspective view of subcutaneous device 2400 connected to subcutaneous device 2200.

Subcutaneous device 2200 includes housing 2202, clip 2204, and prong 2206. Prong 2206 includes electrode 2272. Subcutaneous device 2400 includes body 2402, clip 2404, prong 2406, and cable 2486. Prong 2406 includes electrode 2472. Cable 2486 includes first connector 2488 and second connector 2490. FIGS. 61A and 61B also show xiphoid process X and sternum S. FIGS. 62A-62E show heart H.

Subcutaneous device 2200 is the same as was described with respect to FIGS. 52-55B. Subcutaneous device 2400 includes body 2402, clip 2404, and prong 2406 as described above in reference to FIGS. 59-60D. Subcutaneous device 2400 also includes cable 2486, which has first connector 2488 on a first end and second connector 2490 on a second end. Cable 2486 connects subcutaneous device 2400 to subcutaneous 2200. First connector 2488 and second connector 2490 are electrically active connectors. First connector 2488 is attached to proximal end 2460 of prong 2406. Second connector 2490 is attached to a header or feedthrough on housing 2202 of subcutaneous device 2200. Cable 2486 electrically connects prong 2406 of subcutaneous device 2400 to circuitry within housing 2202 of subcutaneous device 2200. In the embodiment shown in FIGS. 61A-63, subcutaneous device 2200 and subcutaneous device 2400 are configured to function together as a pacemaker used for cardiac monitoring, diagnostics, and/or therapeutics, such as subcutaneous device 100 described with respect to FIGS. 1-9C. In the embodiment shown in FIGS. 61A-63, subcutaneous device 2200 and subcutaneous device 2400 can be anchored to xiphoid process X and sternum S of a patient. Subcutaneous device 2200 can be implanted with a simple procedure where subcutaneous device 2200 is injected onto xiphoid process X and sternum S using a surgical instrument. For example, subcutaneous device 2200 can be deployed and anchored to xiphoid process X and sternum S using surgical instruments 1700, 1800, 1900, and 2000 and method 2100 described with respect to FIGS. 46A-51.

Subcutaneous device 2400 can be implanted following the deployment of subcutaneous device 2200. For example, subcutaneous device 2400 can be deployed and anchored to xiphoid process X and sternum S using one or more of surgical instruments 1700, 1800, 1900, and 2000 and method 2100 described with respect to FIGS. 46A-51. However, surgical instruments 1700, 1800, 1900, and 2000 may be directed to a different location in the patient, such as to the left of the sternum so that subcutaneous device 2400 is injected adjacent and to the left of subcutaneous device 2200 onto xiphoid process X and sternum S. Subcutaneous device 2400 is physically and electrically connected to subcutaneous device 2200 via cable 2486.

When subcutaneous devices 2200 and 2400 are anchored to xiphoid process X and sternum S via clips 2204 and 2404, respectively, prongs 2206 and 2406 extend away from first side 2210 and bottom side 2216 of housing 2202 and first side 2410 and bottom side 2416 of body 2402, respectively. As such, prongs 2200 and 2400 push down against heart H, and electrodes 2272 and 2472 contact heart H and maintain contact as heart H beats. Specifically, electrode 2272 contacts heart H at a first location, and electrode 2472 contacts heart H at a second location. For example, electrode 2272 on prong 2206 may contact the left ventricle and electrode 2474 on prong 2406 may contact the right ventricle of the heart. Prongs 2206 and 2406 can be shaped so that prongs 2206 and 2406 contact the right ventricle, left ventricle, right atrium, or left atrium of the heart. The overall desired stiffness of prongs 2206 and 2406 is achieved via structural tubes 2282 and 2482 and structural tubes 2284 and 2482 within sleeves 2274 and 2474, respectively, which ensures that prongs 2206 and 2406 gently press against heart H and move up and down in contact with heart H as heart H beats, but is not stiff or sharp enough to pierce or tear the pericardial or epicardial tissue.

Prongs 2206 and 2406 are shaped to ensure prongs 2206 and 2406 are properly positioned against and will not lose contact with heart H. The surgical procedure for implanting subcutaneous device 2400 is less invasive than the surgical procedure required for more traditional pacemaker devices, as subcutaneous device is placed subcutaneously in the body. No leads need to be positioned in the vasculature of the patient, lowering the risk of thrombosis to the patient.

Subcutaneous devices 100, 400, 500, 600, 700, 800, 900, 1000, 1100, 1200, 1300, 1400, 1500, 1600, 2200, 2300, and 2400 disclose various embodiments of the subcutaneous devices, including: a single prong cardiac monitoring device, a multi-prong cardiac monitoring device, a pulmonary monitoring device, a single chamber pacemaker, a dual chamber pacemaker, a triple chamber pacemaker, an atrial defibrillator, a single-vector ventricular defibrillator, a multi-vector ventricular defibrillator, and an implantable drug pump and/or drug delivery device. Each of the pacemaker embodiments can also function as a monitoring and diagnostic device and/or a drug delivery device; each of the defibrillator embodiments can also function as a monitoring and diagnostic device, a pacemaker device, and/or a drug delivery device; and each of the drug delivery embodiments can also function as a monitoring and diagnostic device, a pacemaker device, and/or a defibrillator device. Further, the features of each embodiment may be combined and/or substituted with features of any other embodiment, unless explicitly disclosed otherwise. For example, each embodiment may provide therapeutic and/or diagnostic capabilities including electric stimulation, pacing, electric shock-delivery, drug delivery, electric signal sensing (which incorporates photo receptors), acoustic and vibration sensing (which incorporates microphones), and magnetic field sensing (which incorporates magnetometers), unless explicitly disclosed otherwise. Additionally, in some or all of the embodiments described and shown, any of the clip designs that are disclosed may be substituted for any other clip design disclosed herein or in U.S. application Ser. No. 17/020,356, filed on Sep. 14, 2020, entitled CLIP DESIGN FOR A SUBCUTANEOUS DEVICE, which is incorporated by reference.

DISCUSSION OF POSSIBLE EMBODIMENTS

The following are non-exclusive descriptions of possible embodiments of the present invention.

A subcutaneously implantable device includes a housing that is implantable into a body of a patient, a prong, and an electrode. The prong is attached to the housing at a proximal end of the prong, and has a contact portion at or adjacent to a distal end of the prong that is configured to contact an organ, a nerve, a first tissue and/or a second tissue of the patient. The prong is constructed to apply pressure to the organ, the nerve, the first tissue and/or the second tissue so as to maintain contact between the contact portion and the organ, the nerve, the first tissue and/or the second tissue without fixing the contact portion to the organ, the nerve, the first tissue and/or the second tissue. The electrode is provided at the contact portion of the prong, is configured to contact the organ, the nerve, the first tissue and/or the second tissue, and is electrically coupled or couplable with circuitry that is configured to provide monitoring, therapeutic, and/or diagnostic capabilities with respect to the organ, the nerve, the first tissue and/or the second tissue.

The device of the preceding paragraph can optionally include, additionally and/or alternatively, any one or more of the following features, configurations and/or additional components:

A clip attached to the housing that is configured to anchor the device to a muscle, a bone, and/or the first tissue.

The clip is configured to attach the device to a xiphoid process and/or a sternum of the patient.

The prong is constructed to provide spring action in the application of pressure to the organ, the nerve, the first tissue and/or the second tissue.

The prong is configured for the contact portion to contact a heart, and the spring action of the prong permits the contact portion to maintain contact with the heart as the heart beats.

The prong is angled away from the housing to apply pressure to the heart, and the contact portion is configured to bury into cardiac tissue.

The contact portion is angled away from the housing toward the organ, the nerve, the first tissue, and/or the second tissue.

The prong comprises a base portion attached to the housing, and an arm portion extending from the base portion away from the housing, wherein the contact portion is located at a distal end of the arm portion opposite the base portion.

The arm portion extends away from the housing so as to define a first plane that includes opposite ends of the arm portion and is perpendicular to a horizontal plane of the housing, and the contact portion is angled away from the first plane.

The prong further comprises a spring portion between the base portion and the arm portion.

The prong comprises a spine made of shape-memory material.

The device is configured to be implanted in the body at a location proximate to a lung of the patient, and the prong is configured to contact the lung.

The device is configured to be implanted in the body at a location proximate to a nerve of the patient, at the prong is configured to contact the nerve.

The prong is constructed to apply pressure to the organ, the nerve, the first tissue and/or the second tissue in a preconfigured magnitude and direction, which are controlled based on at least one of (a) a material of the prong, (b) a mechanical resistance of the prong, (c) a cross-sectional thickness of the prong, (d) an angle of incidence of the prong on the organ, the nerve, the first tissue and/or the second tissue, or (e) an outer profile of the contact portion of the prong.

The electrode is electrically coupled or couplable with the circuitry in order to provide electrical stimulation to the organ, the nerve, the first tissue and/or the second tissue.

The electrode is electrically coupled or couplable with the circuitry in order to deliver an electric shock to the organ, the nerve, the first tissue and/or the second tissue.

The prong is configured for the contact portion to contact a heart, and the electrode is electrically coupled or couplable with the circuitry in order to deliver pacing signals to the heart.

The electrode is electrically coupled or couplable with the circuitry in order to provide drug delivery to the organ, the nerve, the first tissue and/or the second tissue.

The electrode is electrically coupled or couplable with the circuitry in order to provide signals to the circuitry from at least one of an electric signal sensor, an acoustic vibration sensor, or a magnetic field sensor provided on the contact portion of the prong.

The circuitry is located within the housing.

A subcutaneously implantable device includes a clip that is configured to be anchored to a muscle, a bone, and/or a first tissue of a patient, a prong, and an electrode. The prong has a proximal end secured adjacent to the clip, and has a contact portion at or adjacent to a distal end of the prong that is configured to contact an organ, a nerve, the first tissue, and/or a second tissue. The prong is constructed to apply pressure to the organ, the nerve, the first tissue and/or the second tissue so as to maintain contact between the contact portion and the organ, the nerve, the first tissue and/or the second tissue without fixing the contact portion to the organ, the nerve, the first tissue and/or the second tissue. The electrode is provided at the contact portion of the prong, is configured to contact the organ, the nerve, the first tissue, and/or the second tissue, and is configured for electrical communication with circuitry for providing monitoring, therapeutic, and/or diagnostic capabilities with respect to the organ, the nerve, the first tissue, and/or the second tissue.

The device of the preceding paragraph can optionally include, additionally and/or alternatively, any one or more of the following features, configurations and/or additional components:

The prong is constructed to provide spring action in the application of pressure to the organ, the nerve, the first tissue and/or the second tissue.

The prong is configured for the contact portion to contact a heart, and the spring action of the prong permits the contact portion to maintain contact with the heart as the heart beats.

The contact portion is configured to bury into cardiac tissue.

The prong comprises a base portion secured adjacent to the clip, and an arm portion extending from the base portion, wherein the contact portion is located at a distal end of the arm portion opposite the base portion.

The prong further comprises a spring portion between the base portion and the arm portion.

The prong comprises a spine made of shape-memory material.

The clip is configured to attach the device to a xiphoid process and/or a sternum of the patient.

The prong is constructed to apply pressure to the organ, the nerve, the first tissue and/or the second tissue in a preconfigured magnitude and direction, which are controlled based on at least one of (a) a material of the prong, (b) a mechanical resistance of the prong, (c) a cross-sectional thickness of the prong, (d) an angle of incidence of the prong on the organ, the nerve, the first tissue and/or the second tissue, or (e) an outer profile of the contact portion of the prong.

The electrode is electrically coupled or couplable with the circuitry in order to: provide electrical stimulation to the organ, the nerve, the first tissue and/or the second tissue; deliver an electric shock to the organ, the nerve, the first tissue and/or the second tissue; deliver pacing signals to a heart; provide drug delivery to the organ, the nerve, the first tissue and/or the second tissue; and/or provide signals to the circuitry from at least one of an electric signal sensor, an acoustic vibration sensor, or a magnetic field sensor provided on the contact portion of the prong.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A subcutaneously implantable device comprising:
   a housing that is implantable into a body of a patient and is securable to a muscle, a bone and/or a first tissue of the patient underneath the patient's skin and outside of an organ of the patient that is targeted for monitoring, therapy, and/or diagnosis;
   a prong attached to the housing at a proximal end of the prong, the prong having a contact portion at or adjacent to a distal end of the prong that is configured to contact the organ, wherein the prong is constructed to apply pressure to the organ with spring action so as to maintain contact between the contact portion and the organ without fixing the contact portion to the organ;
   an electrode at the contact portion of the prong, the electrode being configured to contact the organ and being electrically coupled or couplable with circuitry that is configured to provide monitoring, therapeutic, and/or diagnostic capabilities with respect to the organ.

2. The device of claim 1, further comprising a clip attached to the housing that is configured to anchor the device to the muscle, the bone, and/or the first tissue.

3. The device of claim 2, wherein the clip is configured to attach the device to a xiphoid process and/or a sternum of the patient.

4. The device of claim 1, wherein the prong is configured for the contact portion to contact a heart, and the spring action of the prong permits the contact portion to maintain contact with the heart as the heart beats.

5. The device of claim 4, wherein the prong is angled away from the housing to apply pressure to the heart, and the contact portion is configured to bury into cardiac tissue.

6. The device of claim 1, wherein the contact portion is angled away from the housing toward the organ and is configured to bury into the organ.

7. The device of claim 1, wherein the prong comprises a base portion attached to the housing, and an arm portion extending from the base portion away from the housing, wherein the contact portion is located at a distal end of the arm portion opposite the base portion.

8. The device of claim 7, wherein the arm portion extends away from the housing so as to define a first plane that includes opposite ends of the arm portion and is perpendicular to a horizontal plane of the housing, and the contact portion is angled away from the first plane.

9. The device of claim 7, wherein the prong further comprises a spring portion between the base portion and the arm portion.

10. The device of claim 1, wherein the prong comprises a spine made of shape-memory material.

11. The device of claim 1, wherein the device is configured to be implanted in the body at a location proximate to a lung of the patient, and the prong is configured to contact the lung.

12. The device of claim 1, wherein the prong is constructed to apply pressure to the organ in a preconfigured magnitude and direction, which are controlled based on at least one of (a) a material of the prong, (b) a mechanical resistance of the prong, (c) a cross-sectional thickness of the prong, (d) an angle of incidence of the prong on the organ, or (e) an outer profile of the contact portion of the prong.

13. The device of claim 1, wherein the electrode is electrically coupled or couplable with the circuitry in order to provide electrical stimulation to the organ.

14. The device of claim 1, wherein the electrode is electrically coupled or couplable with the circuitry in order to deliver an electric shock to the organ.

15. The device of claim 1, wherein the prong is configured for the contact portion to contact a heart, and the electrode is electrically coupled or couplable with the circuitry in order to deliver pacing signals to the heart.

16. The device of claim 1, wherein the circuitry is configured to control a drug pump to provide drug delivery to the organ.

17. The device of claim 1, wherein the electrode is electrically coupled or couplable with the circuitry in order to provide signals to the circuitry from at least one of an electric signal sensor, an acoustic vibration sensor, or a magnetic field sensor provided on the contact portion of the prong.

18. The device of claim 1, wherein the circuitry is located within the housing.

19. A subcutaneously implantable device comprising:
a clip that is configured to be anchored to a muscle, a bone, and/or a first tissue of a patient;
a prong having a proximal end secured adjacent to the clip, the prong having a contact portion at or adjacent to a distal end of the prong that is configured to contact an organ, a nerve, the first tissue, or a second tissue from outside of the organ, the nerve, the first tissue, or the second tissue, wherein the prong is constructed to apply pressure to the organ, the nerve, the first tissue or the second tissue so as to maintain contact between the contact portion and the organ, the nerve, the first tissue or the second tissue without fixing the contact portion to the organ, the nerve, the first tissue or the second tissue; and
an electrode at the contact portion of the prong, the electrode being configured to contact the organ, the nerve, the first tissue, or the second tissue, and being configured for electrical communication with circuitry for providing monitoring, therapeutic, and/or diagnostic capabilities with respect to the organ, the nerve, the first tissue, or the second tissue.

20. The device of claim 19, wherein the prong is constructed to provide spring action in the application of pressure to the organ, the nerve, the first tissue or the second tissue.

21. The device of claim 19, wherein the prong is configured for the contact portion to contact a heart, and the spring action of the prong permits the contact portion to maintain contact with the heart as the heart beats.

22. The device of claim 21, wherein the contact portion is configured to bury into cardiac tissue.

23. The device of claim 19, wherein the prong comprises a base portion secured adjacent to the clip, and an arm portion extending from the base portion, wherein the contact portion is located at a distal end of the arm portion opposite the base portion.

24. The device of claim 23, wherein the prong further comprises a spring portion between the base portion and the arm portion.

25. The device of claim 19, wherein the prong comprises a spine made of shape-memory material.

26. The device of claim 19, wherein the clip is configured to attach the device to a xiphoid process and/or a sternum of the patient.

27. The device of claim 19, wherein the prong is constructed to apply pressure to the organ, the nerve, the first tissue and/or the second tissue in a preconfigured magnitude and direction, which are controlled based on at least one of (a) a material of the prong, (b) a mechanical resistance of the prong, (c) a cross-sectional thickness of the prong, (d) an angle of incidence of the prong on the organ, the nerve, the first tissue and/or the second tissue, or (e) an outer profile of the contact portion of the prong.

28. The device of claim 19, wherein the electrode is electrically coupled or couplable with the circuitry in order to:
provide electrical stimulation to the organ, the nerve, the first tissue and/or the second tissue;
deliver an electric shock to the organ, the nerve, the first tissue and/or the second tissue;
deliver pacing signals to a heart;
provide drug delivery to the organ, the nerve, the first tissue and/or the second tissue; and/or
provide signals to the circuitry from at least one of an electric signal sensor, an acoustic vibration sensor, or a magnetic field sensor provided on the contact portion of the prong.

* * * * *